United States Patent
Tanaka et al.

(10) Patent No.: US 12,391,971 B2
(45) Date of Patent: Aug. 19, 2025

(54) METHOD FOR SYNTHESIZING PEPTIDES IN CELL-FREE TRANSLATION SYSTEM

(71) Applicant: Chugai Seiyaku Kabushiki Kaisha, Tokyo (JP)

(72) Inventors: Shota Tanaka, Kanagawa (JP); Atsushi Ohta, Kanagawa (JP); Tetsuo Kojima, Kanagawa (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 1000 days.

(21) Appl. No.: 16/479,736

(22) PCT Filed: Jan. 30, 2018

(86) PCT No.: PCT/JP2018/002831
§ 371 (c)(1),
(2) Date: Jul. 22, 2019

(87) PCT Pub. No.: WO2018/143145
PCT Pub. Date: Aug. 9, 2018

(65) Prior Publication Data
US 2020/0040372 A1 Feb. 6, 2020

(30) Foreign Application Priority Data
Jan. 31, 2017 (JP) ................. 2017-015201

(51) Int. Cl.
| | | |
|---|---|---|
| C07K 1/06 | (2006.01) | |
| C07H 21/02 | (2006.01) | |
| C07K 17/00 | (2006.01) | |
| C12P 21/02 | (2006.01) | |

(52) U.S. Cl.
CPC .............. *C12P 21/02* (2013.01); *C07H 21/02* (2013.01); *C07K 1/061* (2013.01); *C07K 17/00* (2013.01)

(58) Field of Classification Search
CPC ......... C12P 21/02; C07H 21/02; C07K 1/061; C07K 17/00
See application file for complete search history.

(56) References Cited

U.S. PATENT DOCUMENTS

| | | |
|---|---|---|
| 4,859,736 A | 8/1989 | Rink |
| 5,057,415 A | 10/1991 | Schuetz et al. |
| 5,059,679 A | 10/1991 | Yajima et al. |
| 7,288,372 B2 | 10/2007 | Olejnik et al. |
| 7,439,222 B2 | 10/2008 | Guinn et al. |
| 8,518,666 B2 | 8/2013 | Wang et al. |
| 8,809,280 B2 | 8/2014 | Strom et al. |
| 9,133,245 B2 | 9/2015 | Gao et al. |
| 9,409,952 B2 | 8/2016 | Kariyuki et al. |
| 9,701,993 B2 | 7/2017 | Suga et al. |
| 10,711,268 B2 | 7/2020 | Murakami et al. |
| 10,815,489 B2 | 10/2020 | Ohta et al. |
| 11,492,369 B2 | 11/2022 | Nomura et al. |
| 11,542,299 B2 | 1/2023 | Nomura et al. |
| 11,732,002 B2 | 8/2023 | Iwasaki et al. |
| 11,787,836 B2 | 10/2023 | Nomura et al. |
| 11,891,457 B2 | 2/2024 | Kariyuki et al. |
| 12,071,396 B2 | 8/2024 | Wadamoto |
| 2003/0219780 A1 | 11/2003 | Olejnik et al. |
| 2005/0026994 A1* | 2/2005 | France .................. A61P 35/00 514/616 |
| 2005/0165217 A1 | 7/2005 | Guinn et al. |
| 2006/0252051 A1* | 11/2006 | Merryman ............. C07H 21/00 435/6.12 |
| 2008/0044854 A1 | 2/2008 | Wang et al. |
| 2008/0221303 A1 | 9/2008 | Katzhendler et al. |
| 2010/0137561 A1 | 6/2010 | Chen |
| 2010/0292435 A1 | 11/2010 | Chen et al. |
| 2013/0035296 A1 | 2/2013 | Strom et al. |
| 2013/0217253 A1 | 8/2013 | Suga et al. |
| 2014/0194369 A1 | 7/2014 | Gao et al. |
| 2015/0080549 A1 | 3/2015 | Kariyuki et al. |

(Continued)

FOREIGN PATENT DOCUMENTS

| | | |
|---|---|---|
| EP | 1277755 A1 | 1/2003 |
| EP | 1424395 A1 | 6/2004 |

(Continued)

OTHER PUBLICATIONS

Machine translation of WO-2015019999-A1, Murakami, Hiroshi (Year: 2015).*
Merriam-Webster Dictionary Definition of peptide. (downloaded Jul. 2022). (Year: 2022).*
Steward Dissertation, 1996 (University of California, Irvine). (Year: 1996).*
Hendrickson et al "Incorporation of Nonnatural Amino Acids Into Proteins" (Annu. Rev. Biochem. 2004. vol. 73: pp. 147-176). (Year: 2004).*

(Continued)

*Primary Examiner* — Catherine S Hibbert
(74) *Attorney, Agent, or Firm* — Nixon & Vanderhye P.C.

(57) ABSTRACT

An objective of the present invention is to provide methods of synthesizing peptides containing structurally diverse amino acids using cell-free translation systems, which can accomplish excellent translational efficiency as compared to conventional techniques (the conventional techniques being methods which involve preparing aminoacyl-tRNAs which do not have protecting groups outside the translation systems without using ARS, and then adding the prepared aminoacyl-tRNAs into translation systems). In the present invention, it was found that amino acid-containing peptides can be synthesized efficiently by protecting an amino acid linked to tRNA with an appropriate protecting group, and then performing the step of deprotecting the protecting group of the amino acid linked to tRNA and the step of peptide translation from a template nucleic acid in a cell-free translation system in parallel.

17 Claims, 13 Drawing Sheets
Specification includes a Sequence Listing.

(56) References Cited

U.S. PATENT DOCUMENTS

| | | |
|---|---|---|
| 2015/0218221 A1 | 8/2015 | Van Der Laan et al. |
| 2016/0272964 A1 | 9/2016 | Murakami et al. |
| 2016/0289668 A1* | 10/2016 | Murakami ......... G01N 33/5308 |
| 2016/0311858 A1 | 10/2016 | Kariyuki et al. |
| 2018/0127761 A1 | 5/2018 | Ohta et al. |
| 2019/0338050 A1 | 11/2019 | Nakano et al. |
| 2020/0131669 A1 | 4/2020 | Muraoka et al. |
| 2020/0277327 A1 | 9/2020 | Nomura et al. |
| 2020/0339623 A1 | 10/2020 | Nomura et al. |
| 2021/0061860 A1 | 3/2021 | Kariyuki et al. |
| 2021/0087572 A1 | 3/2021 | Ohta et al. |
| 2022/0017456 A1 | 1/2022 | Ishizawa |
| 2022/0024972 A1 | 1/2022 | Iwaskai et al. |
| 2022/0144762 A1 | 5/2022 | Wadamoto |
| 2022/0205009 A1 | 6/2022 | Shinohara et al. |
| 2023/0069218 A1 | 3/2023 | Yoshii et al. |
| 2023/0096766 A1 | 3/2023 | Muraoka et al. |
| 2023/0108274 A1 | 4/2023 | Kagotani et al. |
| 2023/0138226 A1 | 5/2023 | Nomura et al. |
| 2023/0151060 A1 | 5/2023 | Tanada et al. |
| 2023/0303619 A1 | 9/2023 | Iwasaki et al. |
| 2023/0406879 A1 | 12/2023 | Nomura et al. |
| 2024/0052340 A1 | 2/2024 | Nishimura et al. |
| 2024/0158446 A1 | 5/2024 | Kawada et al. |
| 2024/0166689 A1 | 5/2024 | Kariyuki et al. |

FOREIGN PATENT DOCUMENTS

| | | |
|---|---|---|
| EP | 1964916 A1 | 9/2008 |
| EP | 2088202 A1 | 8/2009 |
| EP | 2141175 A1 | 1/2010 |
| EP | 2177533 A1 | 4/2010 |
| EP | 2380596 A1 | 10/2011 |
| EP | 2492344 A1 | 8/2012 |
| EP | 2610348 A1 | 7/2013 |
| EP | 2615455 A1 | 7/2013 |
| EP | 2647720 A1 | 10/2013 |
| EP | 2813512 A1 | 12/2014 |
| EP | 2492344 B1 | 4/2016 |
| EP | 3031915 A1 | 6/2016 |
| EP | 2141175 B1 | 7/2016 |
| EP | 2813512 B1 | 3/2021 |
| JP | S57159747 A | 10/1982 |
| JP | S60169451 A | 9/1985 |
| JP | S62289 A | 1/1987 |
| JP | S62143698 A | 6/1987 |
| JP | S63260946 A | 10/1988 |
| JP | H01222795 A | 9/1989 |
| JP | H0259146 B2 | 12/1990 |
| JP | 2513775 B2 | 7/1996 |
| JP | 2003508408 A | 3/2003 |
| JP | 2003531199 A | 10/2003 |
| JP | 2005095013 A | 4/2005 |
| JP | 2007319064 A | 12/2007 |
| JP | 2009096791 A | 5/2009 |
| JP | 2009528824 A | 8/2009 |
| JP | 4490663 B2 | 6/2010 |
| JP | 2011139667 A | 7/2011 |
| JP | 2012506909 A | 3/2012 |
| JP | 2012510486 A | 5/2012 |
| JP | 2012525348 A | 10/2012 |
| JP | 5808882 B2 | 11/2015 |
| JP | 2017043615 A | 3/2017 |
| WO | WO-9831700 A1 | 7/1998 |
| WO | WO-9854577 A1 | 12/1998 |
| WO | WO-0181325 A2 | 11/2001 |
| WO | WO-02085923 A2 | 10/2002 |
| WO | WO-03014354 A1 | 2/2003 |
| WO | WO-03/068990 A1 | 8/2003 |
| WO | WO-03089454 A2 | 10/2003 |
| WO | WO-2005063791 A2 | 7/2005 |
| WO | WO-2007/066627 A1 | 6/2007 |
| WO | WO-2007/103307 A2 | 9/2007 |
| WO | WO-2007120614 A2 | 10/2007 |
| WO | WO-2008117833 A1 | 10/2008 |
| WO | WO-2010053050 A1 | 5/2010 |
| WO | WO-2010062590 A2 | 6/2010 |
| WO | WO-2010063604 A1 | 6/2010 |
| WO | WO-2010125079 A2 | 11/2010 |
| WO | WO-2011049157 A1 | 4/2011 |
| WO | WO-2011051692 A1 | 5/2011 |
| WO | WO-2011058122 A1 | 5/2011 |
| WO | WO-2012/026566 A1 | 3/2012 |
| WO | WO-2012033154 A1 | 3/2012 |
| WO | WO-2012074130 A1 | 6/2012 |
| WO | WO-2012122059 A1 | 9/2012 |
| WO | WO-2013100132 A1 | 7/2013 |
| WO | WO-2014033466 A1 | 3/2014 |
| WO | WO-2014181888 A1 | 11/2014 |
| WO | WO-2015019192 A2 | 2/2015 |
| WO | WO-2015019999 A1 * | 2/2015 | ............... C07K 7/06 |
| WO | WO-2015155676 A1 | 10/2015 |
| WO | WO-2015179434 A1 | 11/2015 |
| WO | WO-2015185162 A1 | 12/2015 |
| WO | WO-2016115168 A1 | 7/2016 |
| WO | WO-2016148044 A1 | 9/2016 |
| WO | WO-2016154675 A1 | 10/2016 |
| WO | WO-2017136708 A1 | 8/2017 |
| WO | WO-2017150732 A1 | 9/2017 |
| WO | WO-2017181061 A1 | 10/2017 |
| WO | WO-2018100561 A1 | 6/2018 |
| WO | WO-2018143145 A1 | 8/2018 |
| WO | WO-2018225851 A1 | 12/2018 |
| WO | WO-2018225864 A1 | 12/2018 |
| WO | WO-2019117274 A1 | 6/2019 |
| WO | WO-2020095983 A1 | 5/2020 |
| WO | WO-2020111238 A1 | 6/2020 |
| WO | WO-2020122182 A1 | 6/2020 |
| WO | WO-2020138336 A1 | 7/2020 |
| WO | WO-2020189540 A1 | 9/2020 |
| WO | WO2021090855 A1 | 5/2021 |
| WO | WO2021117848 A1 | 6/2021 |
| WO | WO2021132546 A1 | 7/2021 |
| WO | WO2021261577 A1 | 12/2021 |
| WO | WO2022234853 A1 | 11/2022 |
| WO | WO2023214576 A1 | 11/2023 |

OTHER PUBLICATIONS

Lodder PhD Dissertation (University of Virginia, 2000). (Year: 2000).*
Karginov et al in "Facile characterization of translation initiation via nonsense codon suppression" (Nucleic Acids Research vol. 27, No. 16: 3283. Aug. 1999). (Year: 1999).*
Arif 2018 publication "Engineering amidases for peptide C-terminal modification". (Year: 2018).*
Andrusiak Dissertation, University of Toronto, 2009. (Year: 2009).*
Chen et al (J Am Chem Soc 2017, vol. 139: pp. 14098-14108). (Year: 2017).*
Ohtsuki et al Nature Comm pub Aug. 17, 2016 (Year: 2016).*
Lodder et al "The N-pentenoyl protecting group for aminoacyl-tRNAs" (Methods Jul. 2005 vol. 36 No. 3: pp. 245-251) (Year: 2005).*
Beck, J.G., "Intestinal Permeability of Cyclic Peptides: Common Key Backbone Motifs Identified," Journal of the American Chemical Society, 2012, vol. 134, pp. 12125-12133.
Doi, Yoshio, et al., "Elongation Factor Tu Mutants Expand Amino Acid Tolerance of Protein Biosynthesis System," Journal of the American Chemical Society, 2007, vol. 129, pp. 14458-14462.
Fujino, Tomoshige, et al., "Reevaluation of the D-Amino Acid Compatibility with the Elongation Event in Translation," Journal of the American Chemical Society, 2013, vol. 135, pp. 1830-1837.
Fujino, Tomoshige, et al., "Ribosomal Synthesis of Peptides with Multiple β-Amino Acids," Journal of the American Chemical Society, 2016, vol. 138, pp. 1962-1969.
Hartman, Matthew C.T., et al., "An Expanded Set of Amino Acid Analogs for the Ribosomal Translation of Unnatural Peptides," PLos One, Oct. 2007, Issue 10, pp. 1-15.
Hecht, Sidney M., et al., "Chemical Aminoacylation of tRNA's," The Journal of Biological Chemistry, vol. 253, No. 13, Jul. 10, 1978, pp. 4517-4520.

(56) References Cited

OTHER PUBLICATIONS

Kawakami, Takashi, et al., "Messenger RNA-Programmed Incorporation of Multiple N-Methyl-Amino Acids into Linear and Cyclic Peptides," Chemistry & Biology, vol. 15, pp. 32-42, Jan. 2008.
Kawakami, Takashi, et al., "Ribosomal Synthesis of Polypeptides and Peptoid-Peptide Hybrids," Journal of American Chemical Society, 2008, vol. 130, pp. 16861-16863.
Maini Rumit, et al., "Protein Synthesis with Ribosomes Selected for the Incorporation of β-Amino Acids," Biochemistry, 2015, vol. 54, 3694-3706.
Maini, Rumit, et al., "Ribosome-mediated synthesis of natural product-like peptides via cell-free translation," Current Opinion in Chemical Biology, 2016, vol. 34, pp. 44-52.
Millward, Steven W., et al., "A General Route for Post-Translational Cyclization of mRNA Display Libraries," Journal of American Chemical Society, 2005, vol. 127, pp. 14142-14143.
Subtelny, Alexander O., et al., "Ribosomal Synthesis of N-Methyl Peptides," Journal of American Chemical Society, 2008, vol. 130, pp. 6131-6136.
Subtelny, Alexander O., et al., Optimal Codon Choice can Improve the Efficiency and Fidelity of N-Methyl Amino Acid Incorporation into Peptides by In Vitro Translation, Angew Chemical Int. Ed Engl., Mar. 28, 2011; vol. 50(14), pp. 3164-3167.
Wang, Jinfan, et al., "Kinetics of Ribosome-Catalyzed Polymerization Using Artificial Aminoacyl-tRNA Substrates Clarifies Inefficiencies and Improvements," ACS Chemical Biology, 2015, vol. 10, pp. 2187-2192.
White, Tina R., "On-resin N-methylation of cyclic peptides for discovery of orally bioavailable scaffolds," Nature Chemical Biology, Nov. 2011, vol. 7, pp. 810-817.
Yamagishi, Yusuke, et al., "Natural Product-Like Macrocyclic N-Methyl-Peptide Inhibitors against a Ubiquitin Ligase Uncovered from a Ribosome-Expressed De Novo Library," Chemistry & Biology, Dec. 23, 2011, vol. 18, pp. 1562-1570.
Loos, Patrick, et al., "Unified Azoline and Azole Syntheses by Optimized Aza-Wittig Chemistry," European Journal Organic Chemistry, 2013, pp. 3210-3315.
Lundquist, Joseph T., et al., "Improved Solid-Phase Peptide Synthesis Method Utilizing α-Azide-Protected Amino Acids," Organic Letters, 2001, vol. 3, No. 5, pp. 781-783.
Abdalla, M.A., et al., "Natural Cyclic Peptides as an Attractive Modality for Therapeutics: A Mini Review," Molecules, 23(8):2080 (2018).
Afonso, A., et al., "Solid-Phase Synthesis of Biaryl Cyclic Peptides Containing a 3-Aryltyrosine," European Journal of Organic Chemistry, 2012(31):6204-6211 (2012).
Alakhov, Y.B., et al., "Butylation of the Tryptophan Indole Ring: A Side Reaction During the Removal of t-butyloxycarbonyl and t-butyl Protecting Groups in Peptide Synthesis," Journal of the Chemical Society D: Chemical Communications, 7:406b-407 (1970).
Albericio, F., et al., "Fmoc Methodology: Cleavage from the Resin and Final Deprotection," Amino Acids, Peptides and Proteins in Organic Chemistry, 3:349-369 (2011).
Alex, A., et al., "Intramolecular Hydrogen Bonding to Improve Membrane Permeability and Absorption in Beyond Rule of Five Chemical Space," Medicinal Chemistry Communication, 2(7):669-674 (2011).
Alvaro, et al., "A Novel Activity of Immobilized Penicillin G Acylase: Removal of Benzyloxycarbonyl Amino Protecting Group," Biocatalysis and Biotransformation, 18(3):253-258 (2000).
Van Der Auwera, C.V.D., et al., "Easy Cleavage of C'-Terminal Iminoacids from Peptide Acids through Acidic Hydrolysis," International Journal of Peptide and Protein Research, 31(2):186-191 (1988).
Bastiaans, et al., "Flexible and Convergent Total Synthesis of Cyclotheonamide B," The Journal of Organic Chemistry, 62(12):3880-3889 (1997).
Behrendt, R., et al., "Advances in Fmoc Solid-Phase Peptide Synthesis," Journal of Peptide Science, 22(1):4-27 (2016).

Bock, J.E., et al., "Getting in Shape: Controlling Peptide Bioactivity and Bioavailability Using Conformational Constraints," ACS Chemical Biology, 8(3):488-499 (2013).
Bockus, A.T., et al., "Form and Function in Cyclic Peptide Natural Products: A Pharmacokinetic Perspective," Current Topics in Medicinal Chemistry, 13(7):821-836 (2013).
Bolek, et al., Journal of Fluorine Chemistry, 27:13-21 (2019).
Brunner, J., Chemical Society Reviews, 22(3):183-189 (1993).
Burkholder, et al., Bioorganic & Medicinal Chemistry Letters, 2(6):579-582 (1992).
Carpino, L.A., et al., "Dramatically Enhanced N-→O Acyl Migration During the Trifluoroacetic Acid-based Deprotection Step in Solid Phase Peptide Synthesis," Tetrahedron Letters, 46(8):1361-1364 (2005).
Chatterjee, J., et al., "N-Methylation of Peptides: A New Perspective in Medicinal Chemistry," Accounts of Chemical Research, 41(10):1331-1342 (2008).
Chen, C.C., et al., "A Mild Removal of Fmoc Group Using Sodium Azide," Amino Acids, 46(2):367-374 (2014).
Chen, J.F., et al., "Effect of Alanine-293 Replacement on the Activity, ATP Binding, and Editing of *Escherichia coli* Leucyl-tRNA Synthetase," Biochemistry, 40(5):1144-1149 (2001).
Chen, S., et al., "Structurally Diverse Cyclisation Linkers Impose Different Backbone Conformations in Bicyclic Peptides," Chembiochem, 13(7):1032-1038 (2012).
Coppins, R.L., "Cyclic Antibiotic Peptide Design: Structure and Membrane Interaction," Cyclic Antibiotic Peptide Design: Structure and Membrane Interaction, pp. 1-8 (2001).
Cornella, J., et al., "Practical Ni-Catalyzed Aryl-Alkyl Cross-Coupling of Secondary Redox-Active Esters," Journal of the American Chemical Society, 138(7):2174-2177 (2016).
Cox, A.D., et al., "Drugging the Undruggable RAS: Mission Possible?," Nature Reviews Drug Discovery, 13(11):828-851 (2014).
Creighton, C.J., et al., "Mechanistic Studies of an Unusual Amide Bond Scission," Journal of the American Chemical Society, 121(29):6786-6791 (1999).
Cudic, M. and Fields, G.B., "Solid-Phase Peptide Synthesis," Molecular Biomethods Handbook, 515-546 (2008).
Cusack, S., et al., "The 2 A Crystal Structure of Leucyl-tRNA Synthetase and Its Complex With a Leucyl-Adenylate Analogue," The EMBO Journal, 19(10):2351-2361 (2000).
Dailler, et al., "Divergent Synthesis of Aeruginosa Based on a C(sp(3))-H Activation Strategy," Chemistry, 21(26):9370-9379 (2015).
Dawson, P.E., et al., "Synthesis of Proteins by Native Chemical Ligation," Science, 266(5186):776-779 (1994).
Doublie, S., et al., "Tryptophanyl-tRNA Synthetase Crystal Structure Reveals an Unexpected Homology to Tyrosyl-tRNA Synthetase," Structure, 3(1):17-31 (1995).
Eberhard, H. and Seitz, O., "N—O-Acyl Shift in Fmoc-Based Synthesis of Phosphopeptides," Organic & Biomolecular Chemistry, 6(8):1349-1355 (2008).
Falanga, A., et al., "Cyclic Peptides as Novel Therapeutic Microbicides: Engineering of Human Defensin Mimetics," Molecules, 22(7):1217 (2017).
Fang, W.J., et al., "Deletion of Ac—NMePhe(1) from [NMePhe(1)]arodyn Under Acidic Conditions, Part 1: Effects of Cleavage Conditions and N-terminal Functionality," Biopolymers 96(1):97-102 (2011).
Frankel, A., et al, "Encodamers: Unnatural Peptide Oligomers Encoded in RNA," Chemistry & Biology, 10(11):1043-1050 (2003).
Fujii, N., et al., "Trimethylsilyl Trifluoromethanesulphonate as a Useful Deprotecting Reagent in Both Solution and Solid Phase Peptide Syntheses," Journal of the Chemical Society, 4:274-275 (1987).
Fujino, M., et al., "Further Studies on the Use of Multi-substituted Benzenesulfonyl Groups for Protection of the Guanidino Function of Arginine," Chemical and Pharmaceutical Bulletin, 29(10):2825-2831 (1981).
Fukai, S., et al., "Mechanism of Molecular Interactions for tRNA(Val) Recognition by Valyl-tRNA Synthetase," RNA, 9(1):100-111 (2003).
Fukai, S., et al., "Structural Basis for Double-Sieve Discrimination of L-Valine From L-Isoleucine and L-Threonine by the Complex of tRNA(Val) and Valyl-tRNA Synthetase," Cell, 103(5):793-803 (2000).

(56) References Cited

OTHER PUBLICATIONS

Fukunaga, R. and Yokoyama, S., "Structural Basis for Non-Cognate Amino Acid Discrimination by the Valyl-tRNA Synthetase Editing Domain," The Journal of Biological Chemistry, 280(33):29937-29945 (2005).
Ganesan, A., "The Impact of Natural Products Upon Modern Drug Discovery," Current Opinion in Chemical Biology, 12(3):306-317 (2008).
GenBank, "Valine-tRNA ligase [*Thermus thermophilus*]," Accession No. P96142, accessed on Jan. 27, 2021.
Gilon, C., et al., "Backbone Cyclization: A New Method for Conferring Conformational Constraint on Peptides," Biopolymers, 31(6):745-750 (1991).
Goto, et al., "Ribosomal Synthesis of Combinatorial Polypeptides Containing Unusual Amino Acid Blocks," Kagaku Kogyo, 58(4):255-262 (2007).
Goto, Y. and Suga, H., "Translation Initiation With Initiator tRNA Charged With Exotic Peptides," Journal of the American Chemical Society, 131(14):5040-5041 (2009).
Goto, Y., et al., "Flexizymes for Genetic Code Reprogramming," Nature Protocols, 6(6):779-790 (2011).
Gracia, S.R., et al., "Synthesis of Chemically Modified Bioactive Peptides: Recent Advances, Challenges and Developments for Medicinal Chemistry," Future Medicinal Chemistry, 1(7):1289-1310 (2009).
Gravestock, et al., "Novel branched isocyanides as useful building blocks in the Passerini-amine deprotection-acyl migration (PADAM) synthesis of potential HIV-1 protease inhibitors," Tetrahedron Letters, 53(26):3225-3229 (2012).
Grosjean, H. and Bjork, G.R., "Enzymatic Conversion of Cytidine to Lysidine in Anticodon of Bacterial Isoleucyl-tRNA-an Alternative Way of RNA Editing," Trends in Biochemical Sciences, 29(4):165-168 (2004).
Hartman, M.C.T., et al., "Enzymatic Aminoacylation of tRNA With Unnatural Amino Acids," Proceedings of the National Academy of Sciences of the United States of America, 103(12):4356-4361 (2006).
Hayashi, G., et al., "Ribosomal Synthesis of Nonstandard Cyclic Peptides and Its Application to Drug Discovery," The Journal of Japanese Biochemical Society, 82(6):505-514 (2010).
Heinis, C., et al., "Phage-Encoded Combinatorial Chemical Libraries Based on Bicyclic Peptides," Nature Chemical Biology, 5(7):502-507 (2009).
Higuchi, T. and Suga, H., "Programmed Synthesis of Natural Product-Like Non-Standard Peptides Using the Translation System and Its Application," Journal of Synthetic Organic Chemistry, 68(3):217-227 (2010).
Hoogenboom, H.R., "Selecting and Screening Recombinant Antibody Libraries," Nature Biotechnology, 23(9):1105-1116 (2005).
Hountondji, C., et al., "Crucial Role of Conserved Lysine 277 in the Fidelity of tRNA Aminoacylation by *Escherichia coli* Valyl-tRNA Synthetase," Biochemistry, 41(50):14856-14865 (2002).
Hountondji, C., et al., "Valyl-tRNA Synthetase From *Escherichia coli* MALDI-MS Identification of the Binding Sites for L-Valine or for Noncognate Amino Acids Upon Qualitative Comparative Labeling With Reactive Amino-Acid Analogs," European Journal of Biochemistry, 267(15):4789-4798 (2000).
Hruby, V.J., et al., "Emerging Approaches in the Molecular Design of Receptor-Selective Peptide Ligands: Conformational, Topographical and Dynamic Considerations," The Biochemical Journal, 268(2):249-262 (1990).
Huihui, K.M.M., et al., "Decarboxylative Cross-Electrophile Coupling of N-Hydroxyphthalimide Esters With Aryl Iodides," Journal of the American Chemical Society, 138(15):5016-5019 (2016).
Ikeuchi, Y., et al., "Agmatine-conjugated Cytidine in a tRNA Anticodon is Essential for AUA Decoding in Archaea," Nature Chemical Biology, 6(4):277-282 (2010).
Ikeuchi, Y., et al., "Molecular Mechanism of Lysidine Synthesis That Determines tRNA Identity and Codon Recognition," Molecular Cell, 19(2):235-246 (2005).

Isidro-Llobet, A., et al., "Amino Acid-Protecting Groups," Chemical Reviews, 109(6):2455-2504 (2009).
Itoh, Y., et al., "Crystallographic and Mutational Studies of Seryl-tRNA Synthetase From the Archaeon Pyrococcus Horikoshii," RNA Biology, 5(3):169-177 (2008).
Iwane, Y., et al., "Expanding the Amino Acid Repertoire of Ribosomal Polypeptide Synthesis via the Artificial Division of Codon Boxes," Nature Chemistry, 8(4):317-325 (2016).
Jaradat, D.M.M., "Thirteen Decades of Peptide Synthesis: Key Developments in Solid Phase Peptide Synthesis and Amide Bond Formation Utilized in Peptide Ligation," Amino Acids, 50(1):39-68 (2018).
Jones, A.B., et al., "A Formal Synthesis of FK-506. Exploration of Some Alternatives to Macrolactamization," The Journal of Organic Chemistry, 55(9):2786-2797 (1990).
Josephson, K., et al., "mRNA Display: From Basic Principles to Macrocycle Drug Discovery," Drug Discovery Today, 19(4):388-399 (2014).
Josephson, K., et al., "Ribosomal Synthesis of Unnatural Peptides," Journal of the American Chemical Society, 127(33):11727-11735 (2005).
Kato, et al., "Enzymes Involved in Drug Metabolism and Reaction Mechanisms Thereof," Yakubutsutaishagaku, 2nd edition, pp. 9-13 (2000).
Kato, et al., "Enzymes Involved in Drug Metabolism and Reaction Mechanisms Thereof," Yakubutsutaishagaku, 3rd edition, pp. 43-46 (2010).
Katoh, T., et al., "Ribosomal Synthesis of Backbone Macrocyclic Peptides," Chemical Communications, 47(36):9946-9958 (2011).
Kawakami, T. and Aimoto, S., "Sequential Peptide Ligation by Using a Controlled Cysteinyl Prolyl Ester (CPE) Autoactivating Unit," Tetrahedron Letters, 48(11):1903-1905 (2007).
Kawakami, T., et al., "Diverse Backbone-Cyclized Peptides via Codon Reprogramming," Nature Chemical Biology, 5(12):888-890 (2009).
Kawakami, T., et al., "In Vitro Selection of Multiple Libraries Created by Genetic Code Reprogramming to Discover Macrocyclic Peptides That Antagonize VEGFR2 Activity in Living Cells," ACS Chemical Biology, 8(6):1205-1214 (2013).
Kawakami, T., et al., "Incorporation of Electrically Charged N-alkyl Amino Acids Into Ribosomally Synthesized Peptides via Post-translational Conversion," Chemical Science, 5(3):887-893 (2014).
Kiho, T., et al., "Total Synthesis of Pleofugin A, a Potent Inositol Phosphorylceramide Synthase Inhibitor," Organic Letters, 20(15):4637-4640 (2018).
Kleineweischede, R. and Hackenberger, C.P., "Chemoselective Peptide Cyclization by Traceless Staudinger Ligation," Angewandte Chemie (International ed. in English), 47(32):5984-5988 (2008).
Kobayashi, T., et al., "Recognition of Non-Alpha-Amino Substrates by pyrrolysyl-tRNA Synthetase," Journal of Molecular Biology, 385(5):1352-1360 (2009).
Kopina, B.J. and Lauhon, C.T., "Efficient Preparation of 2,4-diaminopyrimidine Nucleosides: Total Synthesis of Lysidine and Agmatidine," Organic Letters, 14(16):4118-4121 (2012).
Kuhn, B., et al., "Intramolecular Hydrogen Bonding in Medicinal Chemistry," Journal of Medicinal Chemistry, 53(6):2601-2611 (2010).
Lajoie, M.J., et al., "Overcoming Challenges in Engineering the Genetic Code," Journal of Molecular Biology, 428(5PtB):1004-1021 (2016).
Lassak, J., et al., "Stall No More at Polyproline Stretches With the Translation Elongation Factors EF-P and IF-5A," Molecular Microbiology, 99(2):219-235 (2016).
Laufer, B., et al., "The Impact of Amino Acid Side Chain Mutations in Conformational Design of Peptides and Proteins," Chemistry, 16(18):5385-5390 (2010).
Lee, K.W. and Briggs, J.M., "Molecular Modeling Study of the Editing Active Site of *Escherichia coli* Leucyl-tRNA Synthetase: Two Amino Acid Binding Sites in the Editing Domain," Proteins, 54(4):693-704 (2004).
Lejeune, V., et al., "Towards a Selective Boc Deprotection on Acid Cleavable Wang Resin," Tetrahedron Letters, 44(25):4757-4759 (2003).

(56) References Cited

OTHER PUBLICATIONS

Lenzi, A., et al., "Synthesis of N-Boc-α-amino Acids With Nucleobase Residues as Building Blocks for the Preparation of Chiral PNA (Peptidic Nucleic Acids)," Tetrahedron Letters, 36(10):1713-1716 (1995).

Li, H., et al., "Ni-Catalyzed Electrochemical Decarboxylative C-C Couplings in Batch and Continuous Flow," Organic Letters, 20(5):1338-1341 (2018).

Li, S., et al., "In Vitro Selection of mRNA Display Libraries Containing an Unnatural Amino Acid," Journal of the American Chemical Society, 124(34):9972-9973 (2002).

Li, X., et al., "Salicylaldehyde Ester-Induced Chemoselective Peptide Ligations: Enabling Generation of Natural Peptidic Linkages at the Serine/Threonine Sites," Organic Letters, 12(8):1724-1727 (2010).

Liniger, M., et al., "Total Synthesis and Characterization of 7-Hypoquinuclidonium Tetrafluoroborate and 7-Hypoquinuclidone BF3 Complex," Journal of the American Chemical Society, 138(3):969-974 (2016).

Liu, D.R., et al., "Engineering a tRNA and aminoacyl-tRNA Synthetase for the Site-Specific Incorporation of Unnatural Amino Acids Into Proteins in Vivo," Proceedings of the National Academy of Sciences of the United States of America, 94(19):10092-10097 (1997).

Liu, T., et al., "Synthesis and Screening of a Cyclic Peptide Library: Discovery of Small-Molecule Ligands Against Human Prolactin Receptor," Bioorganic and Medicinal Chemistry, 17(3):1026-1033 (2009).

Liu, Z., et al., "N-Boc Deprotection and Isolation Method for Water-soluble Zwitterionic Compounds," The Journal of Organic Chemistry, 79(23):11792-11796 (2014).

Lodder, M., et al., "The N-Pentenoyl Protecting Group for Aminoacyl-tRNAs," Methods, 36(3):245-251 (2005).

Low, K.E., et al., "Rational Design of Calpain Inhibitors Based on Calpastatin Peptidomimetics," Journal of Medicinal Chemistry, 59(11):5403-5415 (2016).

Luo, D., et al., "Total Synthesis of the Potent Marine-Derived Elastase Inhibitor Lyngbyastatin 7 and in Vitro Biological Evaluation in Model Systems for Pulmonary Diseases," The Journal of Organic Chemistry, 81(2):532-544 (2016).

Malhotra, R., et al., "Efficient Asymmetric Synthesis of N-Protected-B-Aryloxyamino Acids Via Regioselective Ring Opening of Serine Sulfamidate Carboxylic Acid," Organic & Biomolecular Chemistry, 12(33):6507-6515 (2014).

Manfredini, S., et al., "Design and Synthesis of Phosphonoacetic Acid (PPA) Ester and Amide Bioisosters of Ribofuranosylnucleoside Diphosphates as Potential Ribonucleotide Reductase Inhibitors and Evaluation of Their Enzyme Inhibitory, Cytostatic and Antiviral Activity," Antiviral Chemistry and Chemotherapy, 14(4):183-194 (2003).

Mangold, S.L., et al., "Z-Selective Olefin Metathesis on Peptides: Investigation of Side-Chain Influence, Preorganization, and Guidelines in Substrate Selection," Journal of the American Chemical Society, 136(35):12469-12478 (2014).

Marcucci, E., et al., "Solid-Phase Synthesis of NMe-IB-01212, a Highly N-Methylated Cyclic Peptide," Organic Letters, 14(2):612-615 (2012).

Mas-Moruno, C., et al., "Cilengitide: The First Anti-Angiogenic Small Molecule Drug Candidate Design, Synthesis, and Clinical Evaluation," Anti-Cancer Agents in Medicinal Chemistry, 10(10):753-768 (2010).

Meinnel, T., et al., "Methionine as Translation Start Signal: A Review of the Enzymes of the Pathway in *Escherichia coli*," Biochimie, 75(12):1061-1075 (1993).

Mermershtain, I., et al., "Idiosyncrasy and Identity in the Prokaryotic Phe-system: Crystal Structure of *E. coli* phenylalanyl-tRNA Synthetase Complexed With Phenylalanine and AMP," Protein Science, 20(1):160-167 (2011).

Merryman, C. and Green, R., "Transformation of Aminoacyl tRNAs for the in Vitro Selection of "Drug-Like" Molecules," Chemistry & Biology, 11(4):575-582 (2004).

Millward, S.W., et al., "Design of Cyclic Peptides That Bind Protein Surfaces With Antibody-Like Affinity," ACS Chemical Biology, 2(9):625-634 (2007).

Miyake, A., et al., "Design and Synthesis of N-[N-[(S)-1-ethoxycarbonyl-3-phenylpropyl]-I-alanyl]-N-(Indan-2-yl)glycine (CV-3317), a New, Potent Angiotensin Converting Enzyme Inhibitor," Chemical and Pharmaceutical Bulletin, 34(7):2852-2858 (1986).

Montalbetti, C.A.G.N. and Falque, V., "Amide Bond Formation and Peptide Coupling," Tetrahedron, 61(46):10827-10852 (2005).

Morieux, P., et al., "The Structure-Activity Relationship of the 3-Oxy Site in the Anticonvulsant (R)-N-Benzyl 2-Acetamido-3-Methoxypropionamide," Journal of Medicinal Chemistry, 53(15):5716-5726 (2010).

Muramatsu, T., et al., "A Novel Lysine-Substituted Nucleoside in The First Position of the Anticodon of Minor Isoleucine tRNA from *Escherichia coli*," The Journal of Biological Chemistry, 263(19):9261-9267 (1988).

Murashige, R., et al., "Asymmetric and Efficient Synthesis of Homophenylalanine Derivatives via Friedel-Crafts Reaction With Trifluoromethanesulfonic Acid," Tetrahedron Letters, 49(46):6566-6568 (2008).

Navo, C.D., et al., "Oxygen by Carbon Replacement at the Glycosidic Linkage Modulates the Sugar Conformation in Tn Antigen Mimics," ACS Omega, 3(12):18142-18152 (2018).

Niida, A., et al., "Investigation of the Structural Requirements of K-Ras(G12D) Selective Inhibitory Peptide KRpep-2d Using Alanine Scans and Cysteine Bridging," Bioorganic & Medicinal Chemistry Letters, 27(12):2757-2761 (2017).

Ohta, A., et al., "Synthesis of Polyester by Means of Genetic Code Reprogramming," Chemistry & Biology, 14(12):1315-1322 (2007).

Ohtsuki, T., et al., "Phototriggered Protein Syntheses by Using (7-diethylaminocoumarin-4-yl) Methoxycarbonyl-Caged Aminoacyl tRNAs," Nature communications, 7:12501 (2016).

Ohwada, T., et al., "On the Planarity of Amide Nitrogen. Intrinsic Pyramidal Nitrogen of N-acyl-7-azabicyclo[2.2.1]heptanes," Tetrahedron Letters, 39(8):865-868 (1998).

Orain, D., et al., "Protecting Groups in Solid-Phase Organic Synthesis," Journal of Combinatorial Chemistry, 4(1):1-16 (2002).

Osawa, T., et al., "Structural Basis of tRNA Agmatinylation Essential for AUA Codon Decoding," Nature Structural & Molecular Biology, 18(11):1275-1280 (2011).

Ostrem, J.M.L., et al., "Direct Small-Molecule Inhibitors of KRAS: From Structural Insights to Mechanism-Based Design," Nature Reviews Drug discovery, 15(11):771-785 (2016).

Ovadia, O., et al., "Improvement of Drug-Like Properties of Peptides: The Somatostatin Paradigm," Expert Opinion on Drug Discovery, 5(7):655-671 (2010).

Ovadia, O., et al., "The Effect of Multiple N-Methylation on Intestinal Permeability of Cyclic Hexapeptides," Molecular Pharmaceutics, 8(2):479-487 (2011).

Parthasarathy, R., et al., "Sortase A as a Novel Molecular "Stapler" for Sequence-Specific Protein Conjugation," Bioconjugate Chemistry, 18(2):469-476 (2007).

Peacock, J.R., et al., "Amino Acid-Dependent Stability of the Acyl Linkage in aminoacyl-tRNA," RNA, 20(6):758-764 (2014).

Perona, J.J. and Hadd, A., "Structural Diversity and Protein Engineering of the aminoacyl-tRNA Synthetases," Biochemistry, 51(44):8705-8729 (2012).

Peschke, B., et al., "New Highly Potent Dipeptidic Growth Hormone Secretagogues with Low Molecular Weight," European Journal of Medicinal Chemistry, 35(6):599-618 (2000).

Piszkiewicz, D., et al., "Anomalous Cleavage of Aspartyl-Proline Peptide Bonds During Amino Acid Sequence Determinations," Biochemical and Biophysical Research Communications, 40(5):1173-1178 (1970).

Rader, A.F.B., et al., "Orally Active Peptides: Is There a Magic Bullet?," Angewandte Chemie, 57(44):14414-14438 (2018).

Rafi, S.B., et al., "Predicting and Improving The Membrane Permeability of Peptidic Small Molecules," Journal of Medicinal Chemistry, 55(7):3163-3169 (2012).

Rand, A.C., et al., "Optimizing PK Properties of Cyclic Peptides: The Effect of Side Chain Substitutions on Permeability and Clearance," Med Chem Commun., 3(10):1282-1289 (2012).

(56) References Cited

OTHER PUBLICATIONS

Reddy, P.R., et al., "Synthesis of Small Cyclic Peptides via Intramolecular Heck Reactions," Tetrahedron Letters, 44(2):353-356 (2003).
Rezai, T., et al., "Testing the Conformational Hypothesis of Passive Membrane Permeability Using Synthetic Cyclic Peptide Diastereomers," Journal of the American Chemical Society, 128(8):2510-2511 (2006).
Rodriguez, H., et al., "A Convenient Microwave-Enhanced Solid-phase Synthesis of Short Chain N-Methyl-Rich Peptides," Journal of Peptide Science, 16(3):136-140 (2010).
Roodbeen, R., et al., "Microwave Heating in the Solid-Phase Synthesis of N-Methylated Peptides: When is Room Temperature Better?," European Journal of Organic Chemistry, 2012(36):7106-7111 (2012).
Sakamoto, K., et al., "K-Ras(G12D)-Selective Inhibitory Peptides Generated by Random Peptide T7 Phage Display Technology," Biochemical and Biophysical Research Communications, 484(3):605-611 (2017).
Salowe, S.P., et al., "The Catalytic Flexibility of Trnaile-Lysidine Synthetase Can Generate Alternative tRNA Substrates for Isoleucyl-tRNA Synthetase," The Journal of Biological Chemistry, 284(15):9656-9662 (2009).
Samatar, A.A., et al., "Targeting RAS-ERK Signalling in Cancer: Promises and Challenges," Nature reviews. Drug Discovery, 13(12):928-942 (2014).
Sang-Aroon, W., et al., "Theoretical Study on Isomerization and Peptide Bond Cleavage at Aspartic Residue," Journal of Molecular Modeling, 19(9):3627-3636 (2013).
Sankaranarayanan, R., et al., "The Structure of threonyl-tRNA synthetase-tRNA(Thr) Complex Enlightens Its Repressor Activity and Reveals an Essential Zinc Ion in the Active Site," Cell, 97(3):371-381 (1999).
Satyanarayanajois, S.D. and Hill, R.A., "Medicinal Chemistry for 2020," Future Medicinal Chemistry, 3(14):1765-1786 (2011).
Schlippe, Y.V.G., et al., "In Vitro Selection of Highly Modified Cyclic Peptides That Act as Tight Binding Inhibitors," Journal of the American Chemical Society, 134(25):10469-10477 (2012).
Sever, S., et al., "*Escherichia coli* tryptophanyl-tRNA Synthetase Mutants Selected for Tryptophan Auxotrophy Implicate the Dimer Interface in Optimizing Amino Acid Binding," Biochemistry, 35(1):32-40 (1996).
Shimizu, Y., et al., "Cell-Free Translation Reconstituted With Purified Components," Nature Biotechnology, 19(8):751-755 (2001).
Shukla, G.S. and Krag, D.N., "Phage-Displayed Combinatorial Peptide Libraries in Fusion to Beta-Lactamase as Reporter for an Accelerated Clone Screening: Potential Uses of Selected Enzyme-Linked Affinity Reagents in Downstream Applications," Combinatorial Chemistry & High Throughput Screening, 13(1):75-87 (2010).
Sogabe, S., et al., "Crystal Structure of a Human K-Ras G12D Mutant in Complex with GDP and the Cyclic Inhibitory Peptide KRpep-2d," ACS Medicinal Chemistry Letters, 8(7):732-736 (2017).
Starosta, A.L., et al., "A Conserved Proline Triplet in Val-tRNA Synthetase and the Origin of Elongation Factor P," Cell Reports, 9(2):476-483 (2014).
Stetsenko, D.A., et al., "Removal of Acid-Labile Protecting or Anchoring Groups in the Presence of Polyfluorinated Alcohol: Application to Solid-Phase Peptide Synthesis," Russian Journal of Bioorganic Chemistry, 42(2):143-152 (2016).
Struck, A., et al., "An Enzyme Cascade for Selective Modification of Tyrosine Residues in Structurally Diverse Peptides and Proteins," Journal of the American Chemical Society, 138(9):3038-3045 (2016).
Suenaga, K., et al., "Aurilide, A Cytotoxic Depsipeptide From the Sea Hare Dolabella Auricularia: Isolation, Structure Determination, Synthesis, and Biological Activity," Tetrahedron, 60(38):8509-8527 (2004).
Suenaga, K., et al., "Synthesis and Cytotoxicity of Aurilide Analogs," Bioorganic & Medicinal Chemistry Letters, 18(14):3902-3905 (2008).

Suzuki, T., et al., "Discovery and Characterization of tRNAIle Lysidine Synthetase (TilS)," FEBS Letters, 584(2):272-277 (2010).
Suzuki, T., "The Genetic Code Deciphering Mechanism in Archaea—Biosynthesis of Agmatidine and Decoding of the AUA Codon," Kagaku to Seibutsu, 50(1):36-43 (2012).
Takahashi, T., et al., "Solid Phase Library Synthesis of Cyclic Depsipeptides: Aurilide and Aurilide Analogues," Journal of Combinatorial Chemistry, 5(4):414-428 (2003).
Tam, J.P., et al., "Cyclohexyl Ester as a New Protecting Group for Aspartyl Peptides to Minimize Aspartimide Formation in Acidic and Basic Treatments," Tetrahedron Letters, 20(42):4033-4036 (1979).
Tan, Z., et al., "Amino Acid Backbone Specificity of the *Escherichia coli* Translation Machinery," Journal of the American Chemical Society, 126(40):12752-12753 (2004).
Teixido, M., et al., "Solid-Phase Synthesis and Characterization of N-Methyl-Rich Peptides," The Journal of Peptide Research, 65(2):153-166 (2005).
Terasaka, et al., "Construction of Nonstandard Peptide Library by Genetic Code Reprogramming and Bioactive Peptide Discovery," Experimental Medicine, 29(7):1063-1070 (2011).
Terasaka, N., et al., "Recent Developments of Engineered Translational Machineries for the Incorporation of Non-Canonical Amino Acids Into Polypeptides," International Journal of Molecular Sciences, 16(3):6513-6531 (2015).
Toriyama, F., et al., "Redox-Active Esters in Fe-catalyzed C-C Coupling," Journal of the American Chemical Society, 138(35):11132-11135 (2016).
Tsuda, et al., "Amino Acids, Peptides and Proteins in Organic Chemistry," 3:201-406, 495-517, 549-569 (2011).
Tsukiji, S. and Nagamune, T., "Sortase-mediated Ligation: A Gift From Gram-positive Bacteria to Protein Engineering," Chembiochem, 10(5):787-798 (2009).
Urban, J., et al., "Lability of N-alkylated Peptides Towards TFA Cleavage," International Journal of Peptide and Protein Research, 47(3):182-189 (1996).
Vaisar, T. and Urban, J., "Gas-Phase Fragmentation of Protonated Mono-n-Methylated Peptides. Analogy With Solution-Phase Acid-Catalyzed Hydrolysis," Journal of Mass Spectrometry, 33(6):505-524 (1998).
Villar, E.A., et al., "How Proteins Bind Macrocycles," Nature Chemical Biology, 10(9):723-731 (2014).
Wang, S., et al., "Iridium/f-Amphox-Catalyzed Asymmetric Hydrogenation of Styrylglyoxylamides," Synlett, 29(16):2203-2207 (2018).
Wang, T., et al., "Revisiting Oxytocin through the Medium of Isonitriles," Journal of the American Chemical Society, 134(32):13244-13247 (2012).
Watanabe, E., et al., "A Practical Method for Continuous Production of Sp3-Rich Compounds From (Hetero) Aryl Halides and Redox-Active Esters," Chemistry, 26(1):186-191 (2020).
Weber, F., et al., "A Potato Mitochondrial Isoleucine tRNA is Coded for by a Mitochondrial Gene Possessing a Methionine Anticodon," Nucleic Acids Research, 18(17):5027-5030 (1990).
Wells, J.A. and McClendon, C.L., "Reaching for High-Hanging Fruit in Drug Discovery at Protein-Protein Interfaces," Nature, 450(7172):1001-1009 (2007).
Wenschuh, H., et al., "Stepwise Automated Solid Phase Synthesis of Naturally Occurring Peptaibols Using FMOC Amino Acid Fluorides," The Journal of Organic Chemistry, 60(2):405-410 (1995).
Wermuth, C. G., editor, "The Practice of Medicinal Chemistry," 2nd Edition, Academic Press, pp. 52-53 (2003), English translation of Wermuth, C. G., editor, "The Practice of Medicinal Chemistry," 2nd Edition, vol. 1, p. 87 (2003).
White, C.J. and Yudin, A.K., "Contemporary Strategies for Peptide Macrocyclization," Nature Chemistry, 3(7):509-524 (2011).
Wu, J., et al., "Intrinsic Basicity of Oligomeric Peptides that Contain Glycine, Alanine, and Valine—the Effects of the Alkyl Side Chain on Proton Transfer Reactions," Journal of the American Society for Mass Spectrometry, 6(2):91-101 (1995).
Wu, N., et al., "A Genetically Encoded Photocaged Amino Acid," Journal of the American Chemical Society, 126(44):14306-14307 (2004).
Yajima, et al., "New Strategy for the Chemical Synthesis of Proteins," Tetrahedron, 44(3):805-819 (1988).

(56) References Cited

OTHER PUBLICATIONS

Yamanoi, K., et al., "Synthesis of Trans and cis-α-(carboxycyclopropyl) Glycines Novel Neuroinhibitory Amino Acids as L-Glutamate Analogue," Tetrahedron Letters, 29(10):1181-1184 (1988).
Yanagisawa, T., et al., "Multistep Engineering of Pyrrolysyl-tRNA Synthetase to Genetically Encode N(epsilon)-(o-azidobenzyloxycarbonyl) Lysine for Site-Specific Protein Modification," Chemistry & Biology, 15(11):1187-1197 (2008).
Yang, Y., "Side Reactions in Peptide Synthesis," pp. 1-31 (2015).
Yang, Y., Side Reactions in Peptide Synthesis, pp. 246 (2016).
Yao, G., et al., "Efficient Synthesis and Stereochemical Revision of Coibamide A," Journal of American Chemical Society, 137(42):13488-13491 (2015).
Zhai, Y. and Martinis, S.A., "Two Conserved Threonines Collaborate in the *Escherichia coli* Leucyl-tRNA Synthetase Amino Acid Editing Mechanism," Biochemistry, 44(47):15437-15443 (2005).
Zhang, A.J., et al., "A Method for Removal of N-BOC Protecting Groups from Substrates on TFA-Sensitive Resins," Tetrahedron Letters, 39(41):7439-7442 (1998).
Zhang, B., et al., "Specificity of Translation for N-Alkyl Amino Acids," Journal of the American Chemical Society, 129(37):11316-11317 (2007).
Zhang, K., et al., "Ab Initio Studies of Neutral and Protonated Triglycines: Comparison of Calculated and Experimental Gas-Phase Basicity," Journal of the American Chemical Society, 116(25):11512-11521 (1994).
U.S. Appl. No. 07/171,049, filed Mar. 21, 1988, Rink, et al.
U.S. Appl. No. 07/331,292, filed Mar. 30, 1989, Yajima et al.
U.S. Appl. No. 10/345,664, filed Jan. 16, 2003, Olejnik et al.
U.S. Appl. No. 11/682,272, filed Mar. 5, 2007, Wang et al.
U.S. Appl. No. 13/505,625, filed Oct. 22, 2012, Strom et al.
U.S. Appl. No. 13/816,911, filed Aug. 26, 2011, Suga et al.
U.S. Appl. No. 14/125,906, filed Mar. 10, 2014, Gao et al.
U.S. Appl. No. 14/368,564, filed Jun. 25, 2014, Kariyuki et al., related application.
U.S. Appl. No. 14/428,804, filed Sep. 20, 2013, Van et al.
U.S. Appl. No. 14/889,868, filed May 12, 2014, Murakami et al.
U.S. Appl. No. 15/166,550, filed May 27, 2016, Kariyuki et al., related application.
U.S. Appl. No. 15/557,532, filed Sep. 12, 2017, Ohta et al., related application.
U.S. Appl. No. 16/081,522, filed Jul. 8, 2019, Nakano et al., related application.
U.S. Appl. No. 16/619,014, filed Dec. 3, 2019, Muraoka et al., related application.
U.S. Appl. No. 16/619,388, filed Dec. 4, 2019, Nomura et al., related application.
U.S. Appl. No. 16/771,335, filed Jun. 10, 2020, Nomura et al., related application.
U.S. Appl. No. 17/011,815, filed Sep. 3, 2020, Kariyuki et al., related application.
U.S. Appl. No. 17/024,944, filed Sep. 18, 2020, Ohta et al., related application.
U.S. Appl. No. 17/291,099, filed Jun. 3, 2021, Ishizawa, related application.
U.S. Appl. No. 17/297,231, filed May 26, 2021, Iwasaki et al., related application.
U.S. Appl. No. 17/312,296, filed Jun. 9, 2021, Muraoka et al., related application.
U.S. Appl. No. 17/417,822, filed Jun. 24, 2021, Shinohara et al., related application.
U.S. Appl. No. 17/437,535, filed Sep. 9, 2021, Wadamoto et al., related application.
U.S. Appl. No. 17/773,733, filed May 2, 2022, Tanada et al., related application.
U.S. Appl. No. 17/783,076, filed Jun. 7, 2022, Yoshii et al., related application.
U.S. Appl. No. 17/787,809, filed Jun. 21, 2022, Kagotani et al., related application.
U.S. Appl. No. 17/976,942, filed Oct. 31, 2022, Nomura et al., related application.
U.S. Appl. No. 18/010,608, filed Dec. 15, 2022, Nishimura et al., related application.
U.S. Appl. No. 18/203,371, filed May 30, 2023, Iwasaki et al., related application.
U.S. Appl. No. 18/289,592, filed Nov. 6, 2023, Kawada et al., related application.
U.S. Appl. No. 18/459,998, filed Sep. 1, 2023, Nomura et al., related application.
U.S. Appl. No. 18/460,300, filed Sep. 1, 2023, Kariyuki et al., related application.
U.S. Appl. No. 18/773,066, filed Jul. 15, 2024, Tanada et al., related application.
U.S. Appl. No. 18/781,112, filed Jul. 23, 2024, Wadamoto, related application.
U.S. Appl. No. 18/829,566, filed Sep. 10, 2024, Kawada et al., related application.

\* cited by examiner

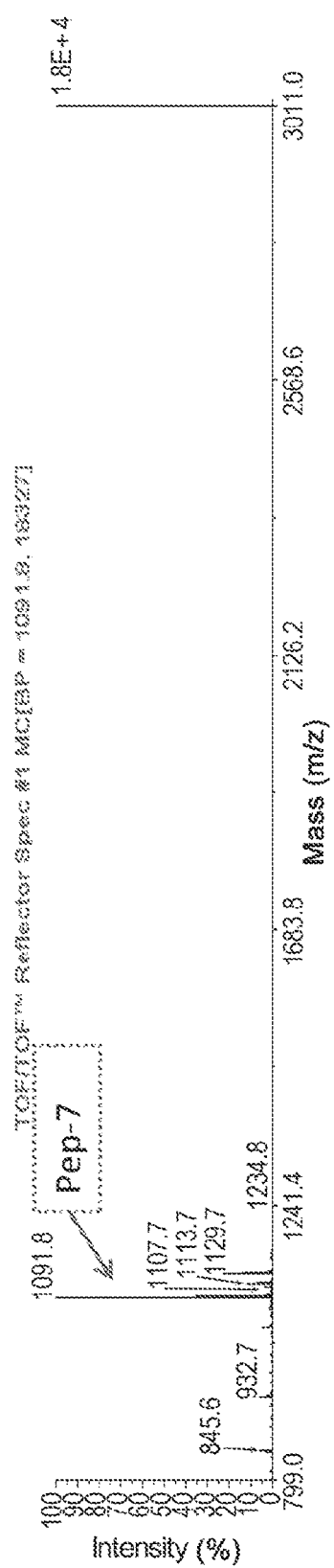
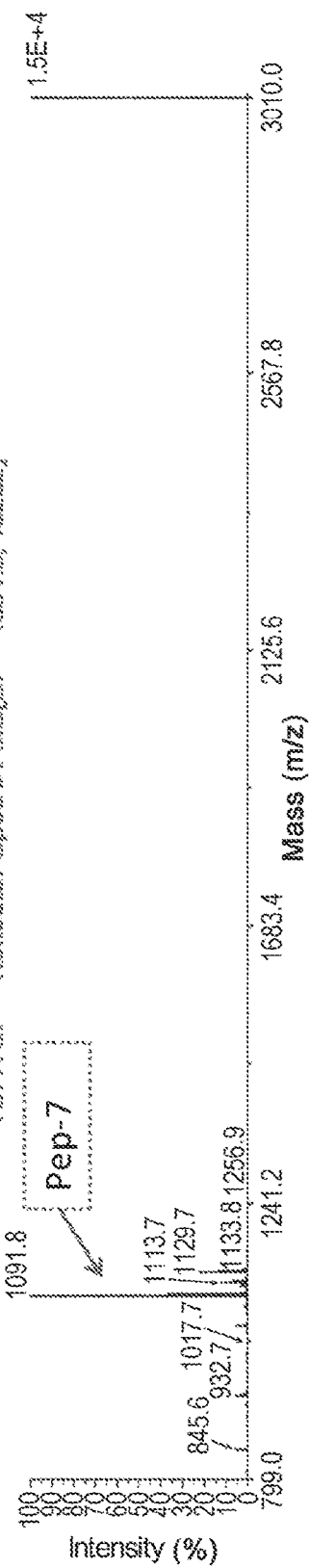
FIG. 1-4

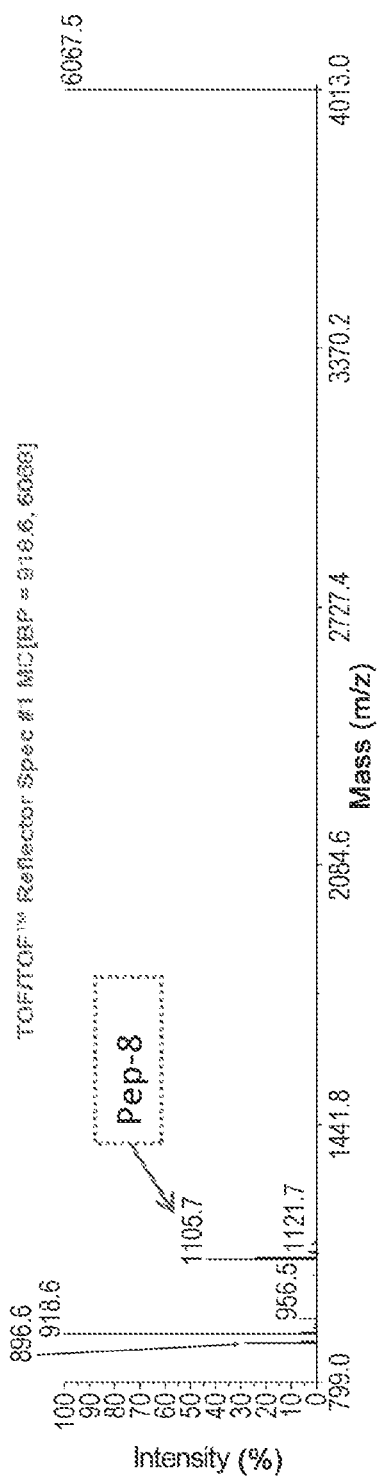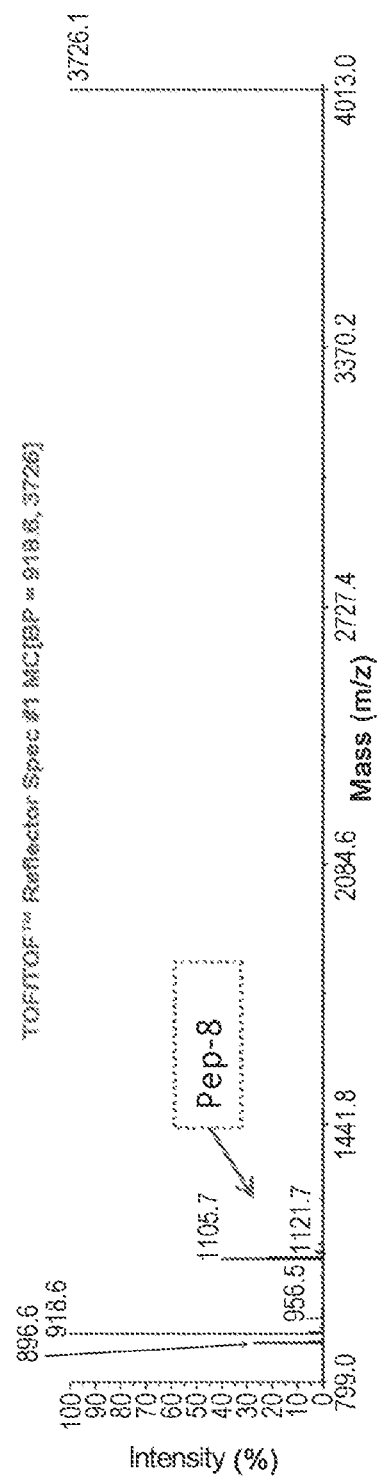
FIG. 1-5

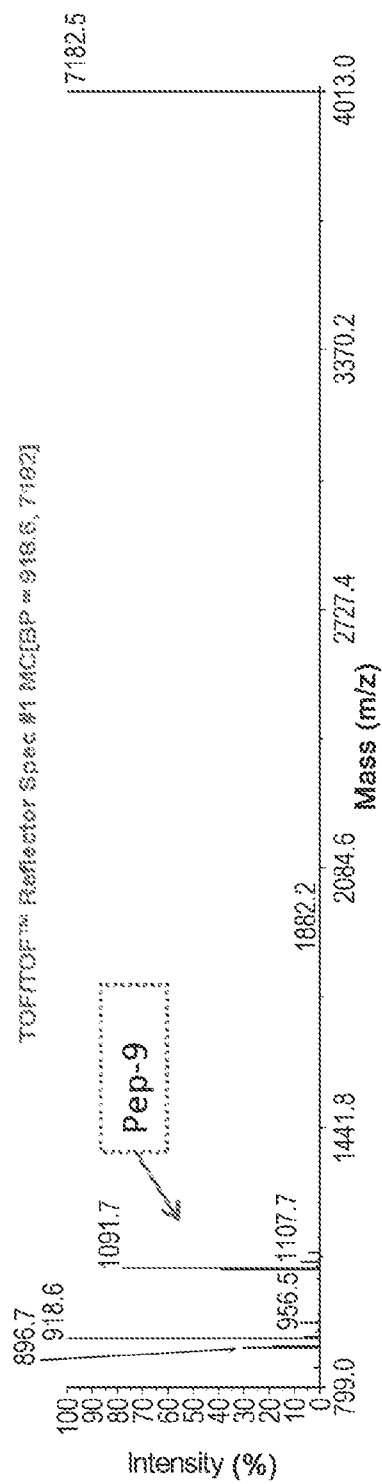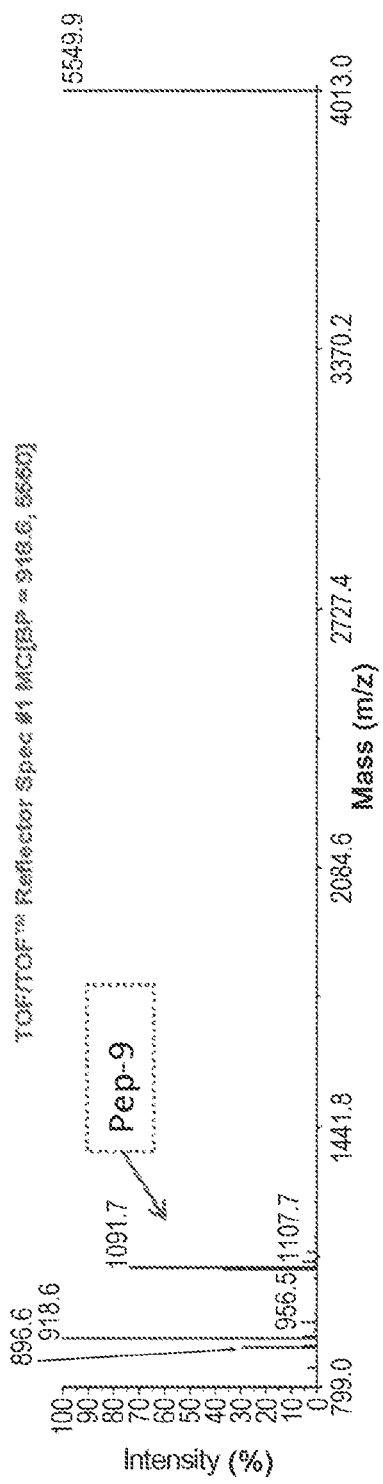
FIG. 1-6

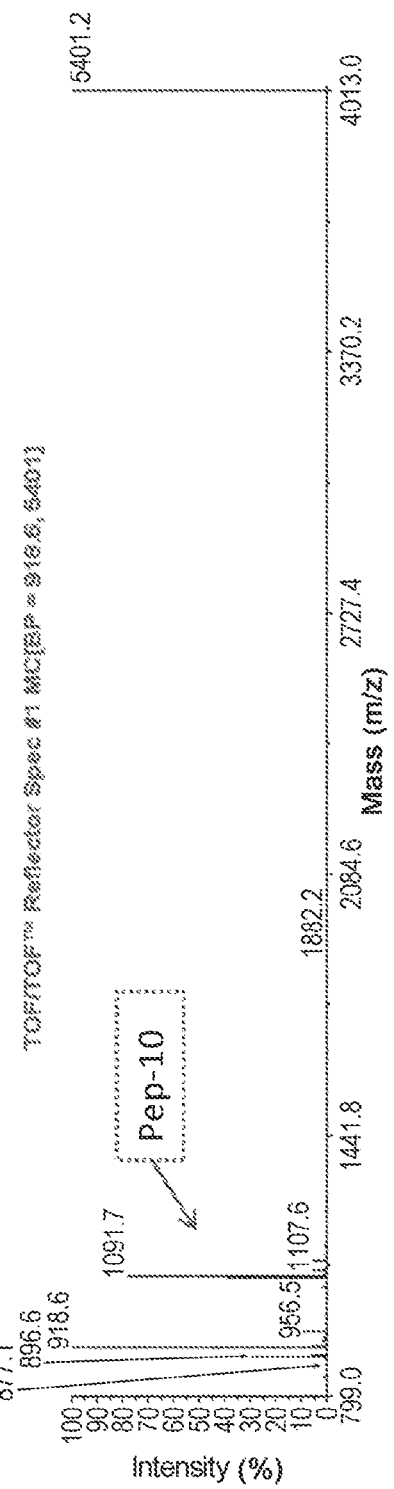
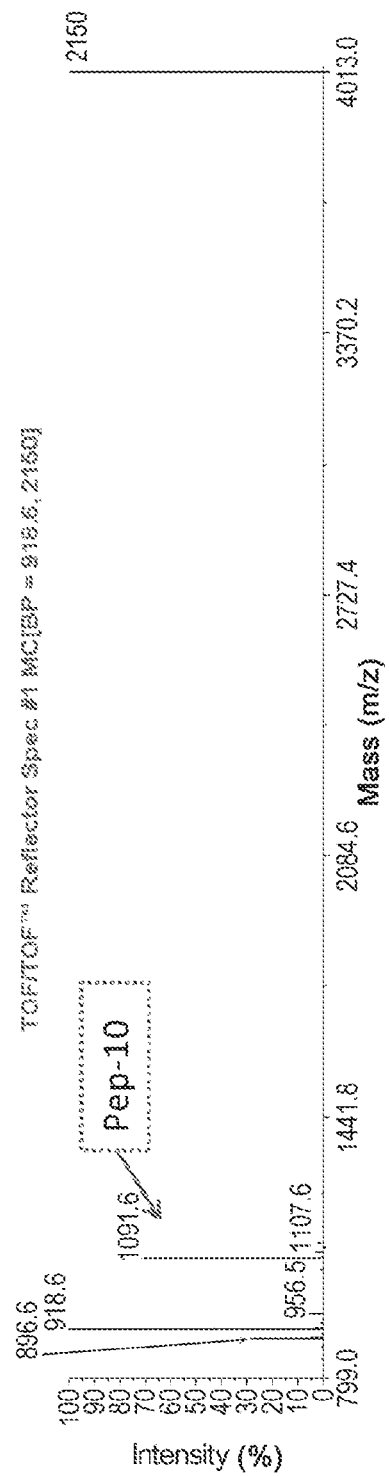
FIG. 1-7

Translated Sequence   fM S X K P F A R V G
Peptide Sequence Number Pep-11   X=Hph   SEQ ID NO: 5
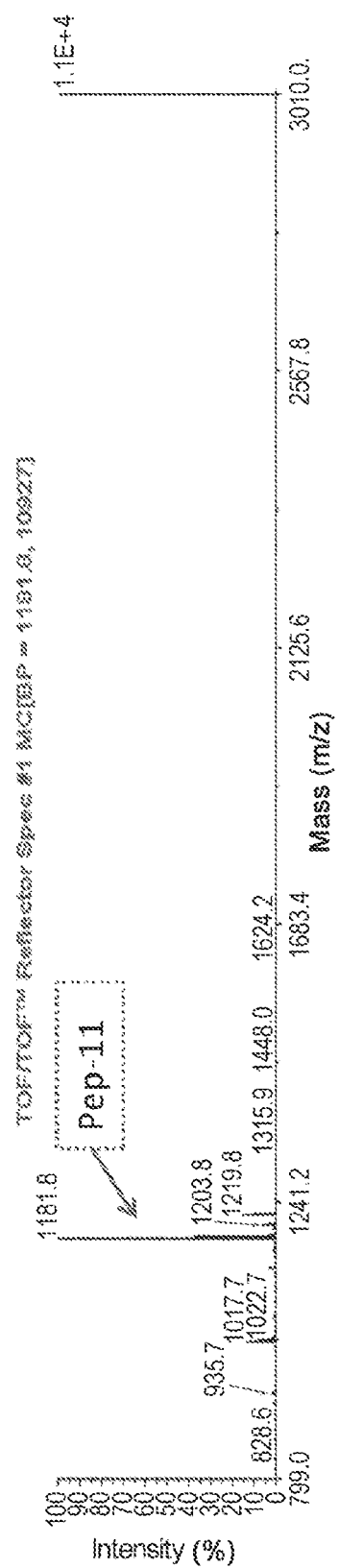
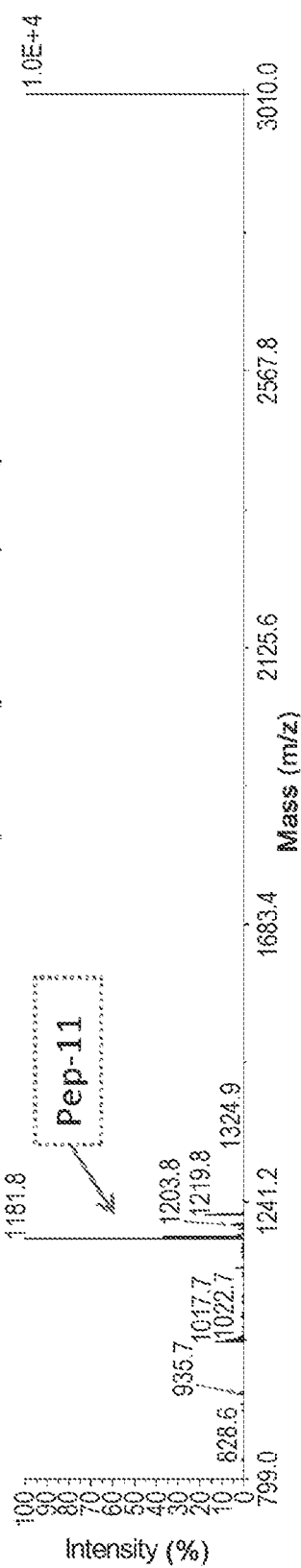
FIG. 1-8

Translated Sequence     fM  S  L  K  P  F  A  X  V  G
Peptide Sequence Number Pep-12   X=Hph   SEQ ID NO: 11
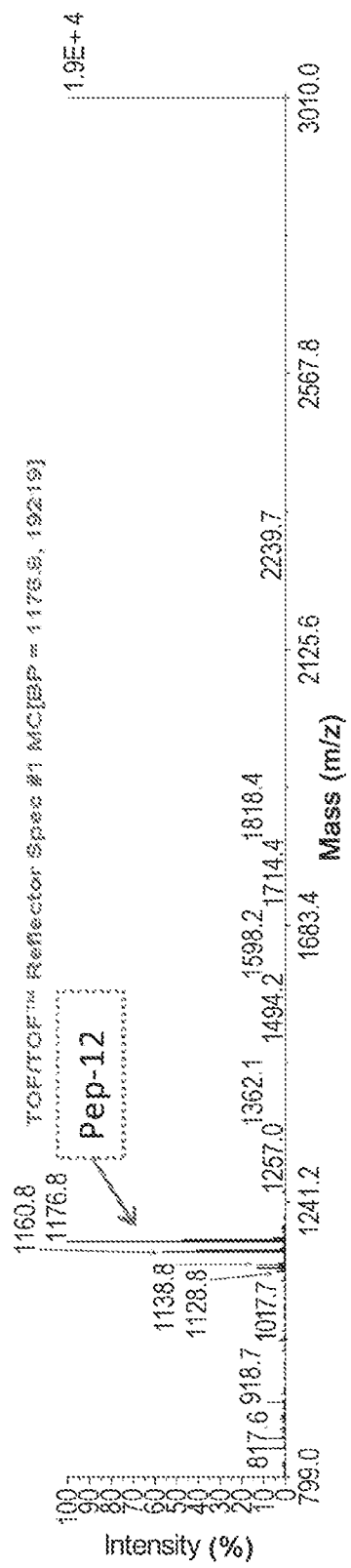
FIG. 1-9

Peptide Sequence
fMSXKPFARVGDDD (SEQ ID NO. 8)

| X | Peptide Sequence Number |
|---|---|
| Aze(2) | Pep-4 |
| nBuG | Pep-5 |
| Ala(3-Pyr) | Pep-6 |

Peptide Sequence
fMS<u>X</u>KPFARVGDDD (SEQ ID NO. 8)

| X | Peptide Sequence Number |
|---|---|
| Hph | Pep-17 |

Pep-18

AAtR No.   15   21

100 | 115

Peptide Sequence
fMSLKPFAXVGDDD (SEQ ID NO. 12)

| X | Peptide Sequence Number |
|---|---|
| Hph | Pep-18 |

…

METHOD FOR SYNTHESIZING PEPTIDES IN CELL-FREE TRANSLATION SYSTEM

CROSS-REFERENCE TO RELATED APPLICATIONS

This application is a U.S. National Phase of PCT Application No. PCT/JP2018/002831, filed Jan. 31, 2018, which claims the benefit of Japanese Patent Application No. 2017-015201, filed Jan. 31, 2017, each of which is incorporated herein by reference in its entirety.

REFERENCE TO SEQUENCE LISTING SUBMITTED ELECTRONICALLY

The content of the electronically submitted sequence listing (Name: 6663_0117_Sequence_Listing.txt; Size: 3.83 kilobytes; and Date of Creation: Jul. 22, 2019) filed with the application is incorporated herein by reference in its entirety.

TECHNICAL FIELD

The present invention relates to methods for synthesizing peptides using cell-free translation systems.

BACKGROUND ART

Attention has been given to middle molecular-weight compounds (a molecular weight of 500 to 2000), since they have possibilities of achieving things which are difficult for small molecules for the compound's ability to access tough targets and things which are difficult for antibodies for the compound's ability to transfer into cells (which ability allows for the development as intracellularly-targeted drugs and drugs for oral administration). Molecular species representative of middle molecular-weight compounds are peptides. The natural product cyclosporine A is a representative example, and it is a peptide which can be orally administered and inhibits an intracellular target cyclophilin.

Features of cyclosporine A include that it is a cyclic peptide comprising an unnatural amino acid as its constituents. Stemming from this, there have been a number of reports on studies that introduce unnatural amino acids into peptides to increase the drug-likeness of the peptides, and further apply them to drug discovery (NPLs 5, 6, and 7). It is now known that introduction of such unnatural amino acids leads to the decrease in hydrogen-bond donor hydrogens, acquisition of protease resistance, and fixing of conformation, thereby contributing to membrane permeability and metabolic stability (NPLs 5 and 8, and PTL 3).

From the above, drug discovery methods which select candidate substances for pharmaceuticals from a library of various peptides containing a number of unnatural amino acids have been considered. In particular, in terms of diversity and convenience of screening, mRNA display libraries of peptides containing unnatural amino acids, which use cell-free translation systems, are much anticipated (NPLs 9 and 10, PTL 2).

Generally in organisms on earth, information stored in DNAs (=information-storing substances) defines, via RNAs (=information-transmitting substances), the structures of proteins (=functioning substances) and functions resulting from those structures. A polypeptide or protein is composed of 20 types of amino acids. Information in DNA which is composed of four types of nucleotides is transcribed into RNA and then that information is translated into amino acids which constitute the polypeptide or protein.

During translation, tRNAs play the role as an adaptor that matches a stretch of three-letter sequence of nucleotides to one type of amino acid. Furthermore, aminoacyl-tRNA synthetases (ARSs) are involved in linking between a tRNA and an amino acid. An ARS is an enzyme that specifically links an amino acid to a tRNA. In every biological species, with a few exceptions, there are 20 types of ARSs, each corresponding to each of the 20 types of amino acids present in nature. ARS accurately acylates a tRNA with a particular amino acid from the 20 types of proteinous amino acids assigned to the codon of the tRNA.

It has been reported that unnatural aminoacyl-tRNAs, which are essential for the synthesis of peptides containing unnatural amino acids by mRNA translation, can be prepared by using the above-described ARSs (NPL 1). However, natural ARSs have high substrate specificity, and the structures of amino acids which ARSs can acylate are limited to amino acid structures similar to those of natural amino acids. Therefore, preparing unnatural aminoacyl-tRNAs using ARSs would not be a highly versatile method. In recent years, some modified ARSs with modified substrate specificity have been prepared, accomplishing improvement of aminoacylation efficiency to some unnatural amino acids (PTL 1). However, when this method is used, a modified ARS needs to be prepared for each of the amino acids, which requires a lot of time and efforts.

In this way, it is not easy to aminoacylate structurally-diverse unnatural amino acids using ARSs. Under such circumstances, methods for preparing structurally-diverse unnatural aminoacyl-tRNAs which do not use ARSs (defined as non-ARS methods) are known. Representative examples include the following methods.

First, in the pdCpA method developed by Hecht et al. (NPL 2), pdCpA (5'-phospho-2'-deooxyribocytidylriboadenosine) acylated with a chemically-synthesized unnatural amino acid and tRNA lacking 3'-end CA obtained by transcription can be ligated using a T4 RNA ligase. In this method, theoretically, the structures are not limited as long as unnatural amino acids can be chemically synthesized, and tRNAs aminoacylated with arbitrary unnatural amino acids can be prepared. Furthermore, Forster et al. have reported the pCpA method which uses pCpA (5'-phospho-ribocytidylriboadenosine) instead of pdCpA (NPL 3).

As another method, Suga et al. have reported a method of aminoacylating tRNAs with unnatural amino acids activated in advance by esterification, using artificial RNA catalysts (Flexizymes) (PTL 2). This method is also considered applicable to prepare tRNAs aminoacylated with arbitrary unnatural amino acids.

These non-ARS methods are methods that synthesize peptides by adding unnatural aminoacyl-tRNAs prepared outside translation systems to translation reaction solutions.

Structurally diverse unnatural aminoacyl-tRNAs can be prepared by using any of the above-mentioned methods. Although it may not necessarily be the case that any desired types of unnatural amino acids can be introduced into peptides by translation, introduction of various α-amino acids, N-alkyl amino acids, β-amino acids, D-amino acids, and such into peptides by translation have been examined and reported (NPL 4).

Furthermore, by utilizing post-translational modification, Kawakami et al. have succeeded in synthesizing peptides containing an N-alkyl amino acid with a positively- or negatively-charged substituent group on its side chain, which had previously been impossible to introduce by translation (NPL 14). Although this is not an example of directly improving translation efficiency, the method is considered to be one of effective methods for synthesizing peptides containing structurally-diverse unnatural amino acids.

Modification of ribosome (NPL 15) and modification of EF-Tu (NPL 16) have been reported as techniques that improved the peptide translation efficiency when synthesizing peptides using unnatural aminoacyl-tRNAs. Techniques that use these modified forms involve changing substrate specificity to unnatural amino acids having the structure of interest. Therefore, unnatural aminoacyl-tRNAs must be prepared structure by structure, which require a lot of efforts. Highly versatile techniques having effects of improving translation efficiency for structurally diverse unnatural amino acids have not been reported to the best of the inventors' knowledge.

Addition of large amounts of tRNAs to cell-free translation systems is known to be a causative factor for decreasing peptide yield (NPL 17). Therefore, there was a possibility that addition of a component that does not exist in nature to a cell-free translation system disturbs translational synthesis (ribosomal synthesis) of peptides, thus affecting the yield.

PATENT LITERATURE

[PTL 1] WO 2007/103307
[PTL 2] WO 2007/066627
[PTL 3] WO 2013/100132
[NPL 1] M. C. T. Hartman et al., PLoS one, 2007, 10, e972.
[NPL 2] S. M. Hecht et al., J. Biol. Chem. 253 (1978) 4517-4520.
[NPL 3] J. Wang et al., ACS. Chem. Biol. 2015, 10, 2187-2192.
[NPL 4] R. Maini et al., Curr. Opin. Chem. Biol. 2016, 34, 44-52.
[NPL 5] R. S. Lokey et al., Nat. Chem. Biol. 2011, 7(11), 810-817.
[NPL 6] J. W. Szostak et al., J. Am. Chem. Soc. 2008, 130, 6131-6136.
[NPL 7] T. Kawakami et al., Chemistry & Biology, 2008, Vol. 15, 32-42.
[NPL 8] H. Kessler et al., J. Am. Chem. Soc. 2012, 134, 12125-12133.
[NPL 9] S. W. Millward et al., J. Am. Chem. Soc., 2005, 127, 14142-14143.
[NPL 10] Y. Yamagishi et al., Chem. Biol., 18, 1562-1570, 2011.
[NPL 11] T. Fujino et al., J. Am. Chem. Soc. 2013, 135, 1830-1837.
[NPL 12] T. Fujino et al., J. Am. Chem. Soc. 2016, 138, 1962-1969.
[NPL 13] T. Kawakami et al., J. Am. Chem. Soc. 2008, 130, 16861-16863.
[NPL 14] T. Kawakami et al., Chem. Sci., 2014, 5, 887-893.
[NPL 15] R. Maini et al., Biochemistry. 2015, 54, 3694-3706.
[NPL 16] Y. Doi et al., J. Am. Chem. Soc. 2007, 129, 14458-14462.
[NPL 17] A. O. Subtelny et al., Angew Chem Int Ed 2011 50 3164.

SUMMARY OF THE INVENTION

Problems to be Solved by the Invention

In order to increase the probability of obtaining middle molecular-weight cyclic peptides having desired activities, the present inventors have so far constructed peptide display libraries with a focus on structural diversity, such as carrying a linear portion. Through the examination, the inventors reached the idea that for further greatly increasing the probability of obtaining peptides binding to various targets, introducing many types of amino acids carrying side chains with different properties is also important. Based on this idea, structurally-diverse natural amino acids and amino acid analogs which have no report on the introduction by ribosomal synthesis were synthesized, and translational introduction of natural amino acids and amino acid analogs using aminoacyl-tRNAs prepared by the pCpA method were tried. However, there were many cases where translation did not occur or was insufficient. The present inventors concluded that preparing modified forms (for example, of ribosomes, but are not limited thereto) that correspond to all of such natural amino acids and amino acid analogs is not realistic, since their structures are so diverse.

The present invention was achieved in view of these circumstances. An objective of the present invention is to provide methods of synthesizing peptides for structurally-diverse natural amino acids and amino acid analogs using cell-free translation systems, which accomplish excellent translational efficiency as compared to conventional methods (i.e., methods which involve preparing unprotected aminoacyl-tRNAs outside the translation systems by a technique that does not use ARSs, and then adding the prepared aminoacyl-tRNAs into the translation systems).

Means for Solving the Problems

As a result of carrying out examinations to solve the above-mentioned problems, the present inventors discovered that translation efficiency of peptides containing structurally-diverse natural amino acids and amino acid analogs can be improved as compared with conventional methods. Specifically, the inventors succeeded in establishing a means which involves adding to a cell-free translation system aminoacyl-tRNAs to which protecting group-bearing natural amino acids or protecting group-bearing amino acid analogs are linked, and performing deprotection and peptide translation in parallel in the system.

When the present inventors conceived this means, the focus was on the hydrolysis of aminoacyl-tRNA, and the inventors hypothesized that translation efficiency can be improved by minimizing the hydrolysis. It is known that in a translation system, aminoacyl-tRNAs come to have increased stability against hydrolysis when forming a complex with EF-tu. However, since the original substrate of EF-tu is natural aminoacyl-tRNAs, the ability of structurally-diverse unnatural aminoacyl-tRNAs to form complexes with EF-tu may be weaker than those of the natural types. Stating differently, while varying in degree depending on the structure, unnatural aminoacyl-tRNAs may be less susceptible to this stabilizing effect. Based on this presumption, first, the present inventors considered increasing the stability of unnatural aminoacyl-tRNAs against hydrolysis by increasing the concentration of EF-tu and examined. However, improvement of translation efficiency was insufficient. In addition to this, the present inventors found that in the conventional methods, which prepare unprotected aminoacyl-tRNAs outside a cell-free translation system and then add them to the systems as described above, hydrolysis does progress substantially during the preparation. Taken together, two factors, which are hydrolysis of aminoacyl-tRNA by itself outside the translation systems and hydrolysis in the translation systems for their being aminoacyl-tRNAs of amino acid analogs, were presumed to be the factors causing decrease in translation efficiency of the amino acid analogs. On the other hand, the present inventors have found that aminoacyl-tRNAs to which a nitrogen-atom-protected amino acid analog is linked have improved stability against hydrolysis when compared to unprotected aminoacyl-tRNAs.

From the above-mentioned findings, the present inventors considered that the two hydrolysis influences mentioned above can be minimized if a method is developed to add a nitrogen-atom-protected amino acid analog-bearing aminoacyl-tRNA to a translation system and perform deprotection in the translation system. Based on such consideration, the present inventors performed various examinations, found appropriate protecting groups, and completed the present invention which enables more efficient translation with structurally-diverse natural amino acids and amino acid analogs, as compared with conventional methods.

The present invention is based on such findings, and specifically provides the inventions of [1] to [18] below:

[1] a method of synthesizing a peptide containing at least one amino acid, wherein the method comprises a step of deprotecting a protecting group of an amino acid having the protecting group and a translation step, the protecting and translation being performed in a cell-free translation system that comprises tRNA to which the amino acid having the protecting group is linked, wherein the deprotecting and translation steps are performed in parallel;

[2] the method of [1], wherein the protecting group of the amino acid is deprotected by one or more selected from the group consisting of an enzyme, a reducing agent, and a photoreaction;

[3] the method of [2], wherein the enzyme is a hydrolytic enzyme;

[4] the method of [3], wherein the enzyme is a penicillin amidohydrolase, an esterase, or an aminopeptidase;

[5] the method of [4], wherein the protecting group is a group represented by the following general formula (I), (II), (III), or (XII):

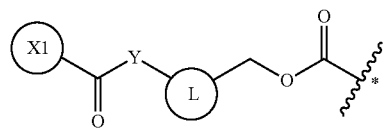

(I)

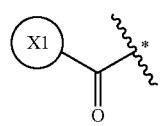

(II)

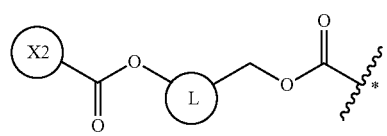

(III)

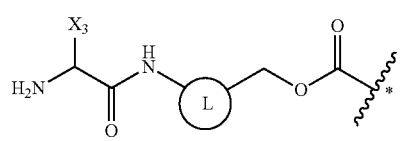

(XII)

(wherein
X1 is a moiety recognized by a penicillin amidohydrolase;
Y is NH or an oxygen atom;
X2 is a moiety recognized by an esterase;
X3 is a moiety recognized by an aminopeptidase; and
L is a single bond, an arylene, or a heteroarylene);

[6] the method of [5], wherein X1 in the above-mentioned formula (I) is a group represented by the following general formula (IV) or a 2-thienylmethyl, or wherein X2 in the above-mentioned formula (III) is an optionally substituted alkyl, an optionally substituted aralkyl, or an optionally substituted cycloalkyl:

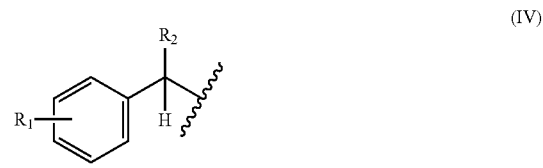

(IV)

(wherein $R_1$ and $R_2$ each independently are a hydrogen atom, a hydroxyl, a fluoro, a chloro, a bromo, an amino, a nitro, or a methoxy);

[7] the method of [5], wherein the above-mentioned formula (XII) is a group represented by the following general formula (XIII):

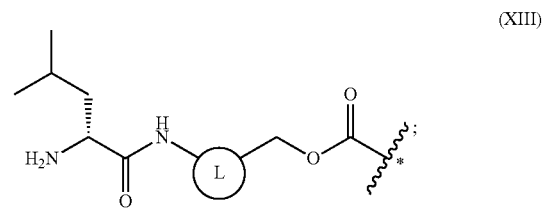

(XIII)

[8] the method of [2], wherein the reducing agent is tris(2-carboxyethyl)phosphine (TCEP);

[9] the method of [8], wherein the protecting group is a group represented by the following general formula (V), or an azido group formed together with a main chain amino group:

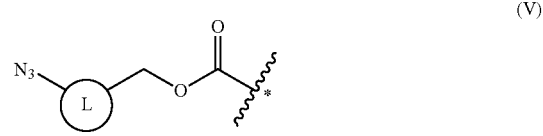

(V)

(wherein L is a single bond, an arylene, or a heteroarylene);

[10] the method of [9], wherein the protecting group is a 4-azidobenzyloxycarbonyl group (Acbz) or an azidomethyloxycarbonyl group (Azoc);

[11] the method of any one of [1] to [10], wherein the amino acid is an amino acid analog;

[12] the method of [11], wherein the amino acid analog is one or more types of translatable amino acid analogs selected from the group consisting of cyclic amino acid-containing N-alkyl amino acids, aliphatic amino acids, aromatic amino acids, β-amino acids, D-amino acids, and α-dialkylamino acids;

[13] the method of [12], wherein the amino acid analog is represented by the following general formula (VI) or (VII):

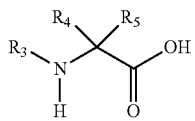
(VI)

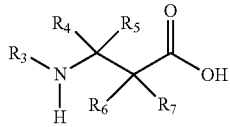
(VII)

(wherein
R$_3$, R$_4$, and R$_5$ each independently are a hydrogen atom, an alkyl, an alkenyl, an alkynyl, an aryl, a heteroaryl, an aralkyl, or a cycloalkyl group, each of which are optionally substituted; or R$_3$ and R$_4$, or R$_3$ and R$_5$, may form a ring together with an atom to which they are bonded; and R$_6$ and R$_7$ each independently are a hydrogen atom or a methyl);

[14] the method of any one of [1] to [13], wherein the protecting group is a protecting group deprotected by a reaction condition orthogonal to a reaction condition used for post-translational modification;

[15] the method of [14], wherein the protecting group is a protecting group orthogonal to a protecting group used in an initiation suppression (iSP) method;

[16] a compound having a protecting group P$_1$ on a main-chain amino group of an amino acid analog, wherein the compound is represented by the following general formula (VIII) or (IX):

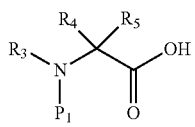
(VIII)

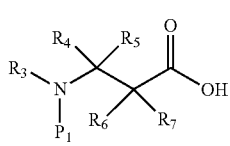
(IX)

(wherein each of R$_3$ to R$_7$ is as defined in [13] and P$_1$ is the protecting group described in any one of [5] to [7]);

[17] a compound formed by linking the compound of [16] with pCpA or pdCpA, wherein the compound is represented by the following general formula (X) or (XI):

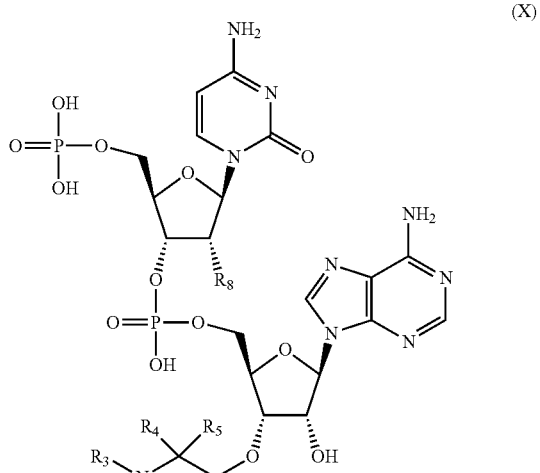
(X)

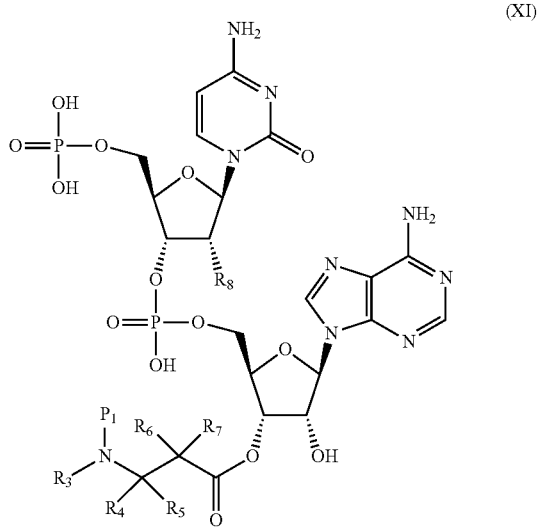
(XI)

(wherein each of R$_3$ to R$_7$ is as defined in [13], R$_8$ is a hydrogen atom or a hydroxyl, and P$_1$ is the protecting group described in any one of [5] to [7]); and

[18] an aminoacyl-tRNA formed by linking the compound of [16] with tRNA. The present invention further provides the inventions of [2-1] to [2-13] below:

[2-1] a method of synthesizing a peptide, which comprises a step of deprotecting one or more types of protecting group-bearing constituents of a cell-free translation system and a translation step, the deprotecting and translation being performed in the cell-free translation system, wherein the deprotecting and translation steps are performed in parallel;

[2-2] a method of synthesizing a peptide, which comprises a step of deprotecting one or more types of protecting group-bearing constituents of a cell-free translation system by an enzyme, a reducing agent, or a photoreaction and a translation step, the deprotecting and translation being performed in the cell-free translation system, wherein the deprotecting and translation steps are performed in parallel;

[2-3] a method of synthesizing a peptide, which comprises a step of deprotecting a protecting group of an amino acid having the protecting group by an enzyme, a reducing agent, or a photoreaction and a translation step, the deprotecting and translation being performed in a cell-free translation system that comprises a tRNA to which the amino acid is linked;

[2-4] the method of [2-3], wherein the translating step is initiated after the protecting group of the amino acid is deprotected in the cell-free translation system;

[2-5] a method of producing a complex of a peptide which comprises one or more types of amino acid residues and has a cyclic portion and a nucleic acid which encodes the peptide, or a library comprising the complexes, wherein the method comprises a step of synthesizing the peptide by the method of [2-1] to [2-4], and a step of cyclizing the synthesized peptide;

[2-6] the method of [2-5], wherein the peptide is cyclized by an amide bond, a thioether bond, a disulfide bond, an ether bond, an ester bond, a thioester bond, or a carbon-carbon bond;

[2-7] use of a protecting group which is deprotected by an enzyme, a reducing agent, or a photoreaction in a peptide synthesis method, wherein the method comprises a step of deprotecting one or more types of protecting group-bearing constituents of a cell-free translation system and a translation step, the deprotecting and translation being performed in the cell-free translation system, wherein the deprotecting and translation steps are performed in parallel;

[2-8] use of a protecting group which is deprotected by an enzyme, a reducing agent, or a photoreaction in a peptide synthesis method, wherein the method comprises a step of deprotecting the protecting group of an amino acid and a translation step, the deprotecting and translation being performed in a cell-free translation system that comprises a tRNA linked to the amino acid comprising the protecting group, wherein the deprotecting and translation steps are performed in parallel;

[2-9] a method of increasing yield of a synthesized peptide, which comprises a step of deprotecting one or more types of protecting group-bearing constituents of a cell-free translation system and a translation step, the deprotecting and translation being performed in the cell-free translation system, wherein the deprotecting and translation steps are performed in parallel;

[2-10] a method of increasing yield of a synthesized peptide, which comprises a step of deprotecting a protecting group of an amino acid and a translation step, the deprotecting and translation being performed in a cell-free translation system that comprises a tRNA linked to the amino acid comprising the protecting group, wherein the deprotecting and translation steps are performed in parallel;

[2-11] a protecting group for use in a peptide synthesis method, wherein the protecting group is deprotected by an enzyme, a reducing agent, or a photoreaction, wherein the method comprises a step of deprotecting one or more types of protecting group-bearing constituents of a cell-free translation system and a translation step, the deprotecting and translation being performed in the cell-free translation system, wherein the deprotecting and translation step are performed in parallel;

[2-12] a protecting group for use in a peptide synthesis method, wherein the protecting group is deprotected by an enzyme, a reducing agent, or a photoreaction, wherein the method comprises a step of deprotecting the protecting group of an amino acid and a translation step, the deprotecting and translation being performed in a cell-free translation system that comprises a tRNA linked to the amino acid comprising the protecting group, wherein the deprotecting and translation steps are performed in parallel; and

[2-13] the method of any one of [2-3] to [2-6] and [2-10], the use of [2-8], or the protecting group of [2-12], wherein the amino acid is an amino acid analog.

Effects of the Invention

In the present invention, protecting groups of amino acids constituting aminoacyl-tRNAs are deprotected in parallel with the translation step in cell-free translation systems. The present invention provides peptide synthesis methods with improved translation efficiency as compared with the conventional pCpA method which carries out the deprotection outside the cell-free translation systems.

BRIEF DESCRIPTION OF THE DRAWINGS

FIG. 1-2 shows the experimental results of identifying the molecular weights of major products among ribosomally-synthesized peptides using AAtR-2, AAtR-5, and AAtR-8 by MALDI-TOF MS.

FIG. 1-3 shows the experimental results of identifying the molecular weights of major products among ribosomally-synthesized peptides using AAtR-3, AAtR-6, and AAtR-9 by MALDI-TOF MS.

FIG. 1-4 shows the experimental results of identifying the molecular weights of major products among ribosomally-synthesized peptides using AAtR-10 and AAtR-16 by MALDI-TOF MS.

FIG. 1-5 shows the experimental results of identifying the molecular weights of major products among ribosomally-synthesized peptides using AAtR-11 and AAtR-17 by MALDI-TOF MS.

FIG. 1-6 shows the experimental results of identifying the molecular weights of major products among ribosomally-synthesized peptides using AAtR-12 and AAtR-18 by MALDI-TOF MS.

FIG. 1-7 shows the experimental results of identifying the molecular weights of major products among ribosomally-synthesized peptides using AAtR-13 and AAtR-19 by MALDI-TOF MS.

FIG. 1-8 shows the experimental results of identifying the molecular weights of major products among ribosomally-synthesized peptides using AAtR-14 and AAtR-20 by MALDI-TOF MS.

FIG. 1-9 shows the experimental results of identifying the molecular weights of major products among ribosomally-synthesized peptides using AAtR-15 and AAtR-21 by MALDI-TOF MS.

FIG. 2-1 shows the experimental results of checking the translation levels of the ribosomally-synthesized peptides using AAtR-1 to AAtR-9 by electrophoresis (relative values are given for Pep-4, Pep-5, and Pep-6 using the translation levels for the peptides synthesized using AAtR-1, AAtR-2, and AAtR-3, respectively, as the basal level (100)).

FIG. 2-2 shows the experimental results of checking the translation levels of the ribosomally-synthesized peptides using AAtR19 to AAtR-16 and AAtR-16 to AAtR-19 by electrophoresis (relative values are given for Pep-14, Pep-15, Pep-16, and Pep-13 using the translation levels for the peptides synthesized using AAtR-11, AAtR-12, AAtR-13, and AAtR-10, respectively, as the basal level (100)).

FIG. 2-3 shows the experimental results of checking the translation levels of the ribosomally-synthesized peptides using AAtR-14 and AAtR-20 by electrophoresis (relative value is given for Pep-17 using the translation level for the peptide synthesized using AAtR-14 as the basal level (100)).

FIG. 2-4 shows the experimental results of checking the translation levels of the ribosomally-synthesized peptides using AAtR-15 and AAtR-21 by electrophoresis (relative value is given for Pep-18 using the translation level for the peptide synthesized using AAtR-15 as the basal level (100)).

MODE FOR CARRYING OUT THE INVENTION

Definition of Substituent Groups and Such

Figure 1:
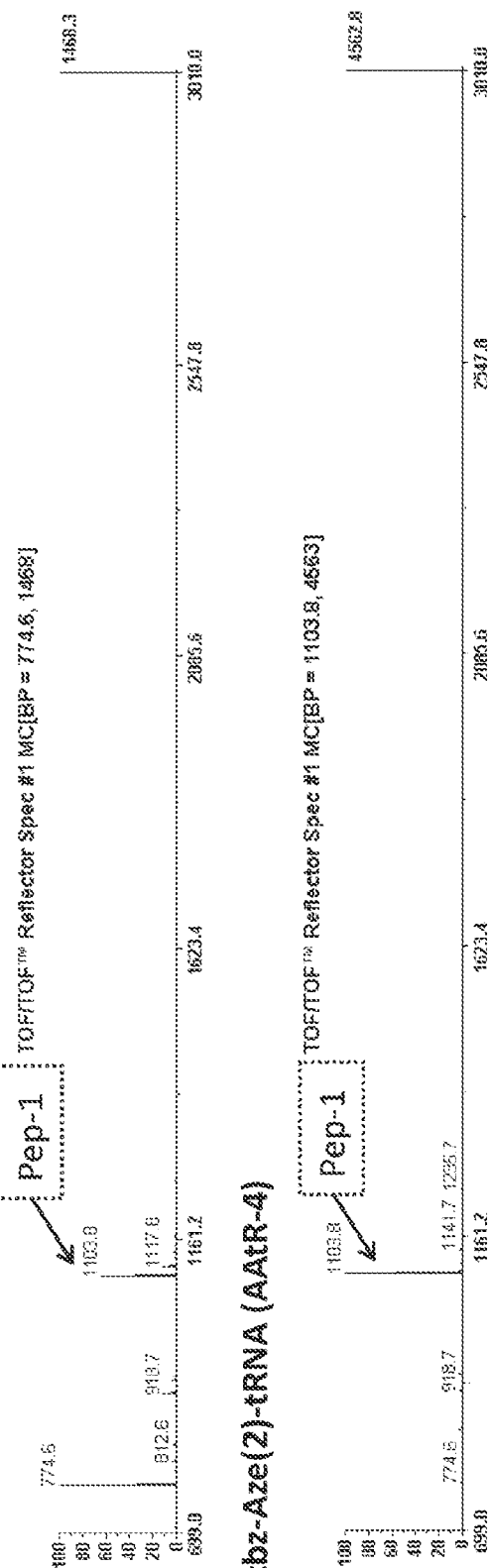
FIG. 1-1 shows the experimental results of identifying the molecular weights of major products among ribosomally-synthesized (translationally-synthesized) peptides using AAtR-1, AAtR-4, and AAtR-7 by MALDI-TOF MS.

Herein, the term "alkyl" refers to a monovalent group derived from aliphatic hydrocarbon by removal of one arbitrary hydrogen atom and has a subset of a hydrocarbyl or hydrocarbon group structure containing neither heteroatoms nor unsaturated carbon-carbon bonds in the backbone and containing hydrogen and carbon atoms. Its carbon chain length n is in the range of one to 20, and "alkyl" is preferably C2-C10 alkyl. Examples of alkyl include "C1-C6 alkyl" and specifically include methyl, ethyl, propyl, butyl, pentyl, hexyl, isopropyl, t-butyl group, sec-butyl group, 1-methylpropyl group, 1,1-dimethylpropyl group, 2,2-dimethylpropyl, 1,2-dimethylpropyl, 1,1,2-trimethylpropyl, 1,2,2-trimethylpropyl, 1,1,2,2-tetramethylpropyl, 1-methylbutyl, 2-methylbutyl, 3-methylbutyl, 1,1-dimethylbutyl, 1,2-dimethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, isopentyl, and neopentyl.

Herein, the term "alkenyl" refers to a monovalent group having at least one double bond (two adjacent SP2 carbon atoms). The double bond can assume entgegen (E) or zusammen (Z) and cis or trans geometric forms depending on the arrangement of the double bond and substituents (if they exist). Examples of alkenyl include linear or branched chains, including straight chains containing internal olefins. Preferred examples thereof include C2-C10 alkenyl, and more preferably C2-C6 alkenyl.

Specific examples of alkenyl include vinyl, allyl, 1-propenyl, 2-propenyl, 1-butenyl, 2-butenyl (including cis and trans forms), 3-butenyl, pentenyl, and hexenyl.

Herein, the term "alkynyl" refers to a monovalent group having at least one triple bond (two adjacent SP carbon atoms). Examples thereof include linear or branched chain alkynyl including internal alkylene. Preferred examples thereof include C2-C10 alkynyl, and more preferably C2-C6 alkynyl.

Specific examples of alkynyl include ethynyl, 1-propynyl, propargyl, 3-butynyl, pentynyl, hexynyl, 3-phenyl-2-propynyl, 3-(2'-fluorophenyl)-2-propynyl, 2-hydroxy-2-propynyl, 3-(3-fluorophenyl)-2-propynyl, and 3-methyl-(5-phenyl)-4-pentynyl.

Herein, the term "cycloalkyl" means a saturated or partially saturated cyclic monovalent aliphatic hydrocarbon group containing a single ring, bicyclo ring, or spiro ring. Preferred examples thereof include C3-C10 cycloalkyl. Specific examples of cycloalkyl include cyclopropyl, cyclobutyl, cyclopentyl, cyclohexyl, cycloheptyl, cyclooctyl, and bicyclo[2.2.1]heptyl.

Herein, the term "aryl" means a monovalent aromatic hydrocarbon ring. Preferred examples thereof include C6-C10 aryl. Specific examples of aryl include phenyl and naphthyl (e.g., 1-naphthyl and 2-naphthyl).

Herein, the term "heteroaryl" means an aromatic cyclic monovalent group containing preferably one to five heteroatoms among ring-constituting atoms and may be partially saturated. The ring may be a single ring or bicyclic condensed ring (e.g., bicyclic heteroaryl formed by condensation with benzene or a monocyclic heteroaryl). The number of ring-constituting atoms is preferably five to ten (five- to ten-membered heteroaryl).

Specific examples of heteroaryl include furyl, thienyl, pyrrolyl, imidazolyl, pyrazolyl, thiazolyl, isothiazolyl, oxazolyl, isooxazolyl, oxadiazolyl, thiadiazolyl, triazolyl, tetrazolyl, pyridyl, pyrimidyl, pyridazinyl, pyrazinyl, triazinyl, benzofuranyl, benzothienyl, benzothiadiazolyl, benzothiazolyl, benzoxazolyl, benzoxadiazolyl, benzimidazolyl, indolyl, isoindolyl, indazolyl, quinolyl, isoquinolyl, cinnolinyl, quinazolinyl, quinoxalinyl, benzodioxolyl, indolizinyl, and imidazopyridyl.

Herein, the term "arylalkyl (aralkyl)" means a group containing both an aryl and an alkyl, for example, a group derived from the above-mentioned alkyl by replacement of at least one hydrogen atom with an aryl. Preferred examples thereof include "C5-C10 aryl-C1-C6 alkyl", such as benzyl.

Herein, the term "arylene" means a divalent group derived from the above-mentioned aryl by removing another single arbitrary hydrogen atom. An arylene may be a single ring or a condensed ring. The number of ring-constituting atoms is not particularly limited, but is preferably six to ten (C6-10 arylene). Specific examples of arylene include phenylene and naphthylene.

Herein, the term "heteroarylene" means a divalent group derived from the above-mentioned heteroaryl by removing another single arbitrary hydrogen atom. A heteroarylene may be a single ring or a condensed ring. The number of ring-constituting atoms is not particularly limited but is preferably five to ten (five- to ten-membered heteroarylene). Specific examples of heteroarylene include pyroldiyl, imidazoldiyl, pyrazoldiyl, pyridindiyl, pyridazindiyl, pyrimidindiyl, pyrazindiyl, triazoldiyl, triazindiyl, isooxazoldiyl, oxazoldiyl, oxadiazoldiyl, isothiazoldiyl, thiazoldiyl, thiadiazoldiyl, furandiyl, and thiophendiyl.

In the present invention, "amino acids" constituting the peptides may be "natural amino acids" or "amino acid analogs". The "amino acids", "natural amino acids", and "amino acid analogs" are also referred to as "amino acid residues", "natural amino acid residues", and "amino acid analog residues", respectively.

"Natural amino acids" are α-aminocarboxylic acids (α-amino acids), and refer to the 20 types of amino acids contained in proteins. Specifically, they refer to Gly, Ala, Ser, Thr, Val, Leu, Ile, Phe, Tyr, Trp, His, Glu, Asp, Gln, Asn, Cys, Met, Lys, Arg and Pro.

"Amino acid analogs" are not particularly limited, and include β-amino acids, γ-amino acids, D-amino acids, N-substituted amino acids, α,α-disubstituted amino acids, hydroxycarboxylic acids, and unnatural amino acids (amino acids whose side chains are different from those of natural amino acids: for example, unnatural α-amino acids, β-amino acids, and γ-amino acids). An α-amino acid may be a D-amino acid, or an α,α-dialkylamino acid. In a similar manner to an α-amino acid, a β-amino acid and a γ-amino acid are also allowed to have any configuration. A side chain (with the main chain being methylene) of the amino acid analogs is not particularly limited, and may have, besides hydrogen atoms, for example, an alkyl, an alkenyl, an alkynyl, an aryl, a heteroaryl, an aralkyl, or a cycloalkyl.

Each of these may have one or more substituents, and these substituents can be selected from any functional group containing, for example, a halogen atom, an N atom, an O atom, an S atom, a B atom, a Si atom, or a P atom. For example, herein, "C1-C6 alkyl optionally substituted with halogen" means "C1-C6 alkyl" substituted with one or more halogen atoms, and specific examples include trifluoromethyl, difluoromethyl, fluoromethyl, pentafluoroethyl, tetrafluoroethyl, trifluoroethyl, difluoroethyl, fluoroethyl, trichloromethyl, dichloromethyl, chloromethyl, pentachloroethyl, tetrachloroethyl, trichloroethyl, dichloroethyl, and chloroethyl. Furthermore, for example, "optionally substituted C5-C10 aryl C1-C6 alkyl" means that in which at least one hydrogen atom of the aryl and/or alkyl of "C5-C10 aryl C1-C6 alkyl" has been substituted with a substituent. Furthermore, "cases having two or more substituents" include cases having an S atom-containing functional group, which further has functional groups such as an amino or a halogen.

The main chain amino group of an amino acid analog may be unsubstituted (a NH2 group), or it may be substituted (that is, an NHR group; in which R represents an alkyl, an alkenyl, an alkynyl, an aryl, a heteroaryl, an aralkyl, or a cycloalkyl, each of which optionally has a substituent; or a carbon chain bonded to the N atom and a carbon atom at the □ position may form a ring as in proline. The substituent is similar to the substituent of the side chain, and examples include a halogen, an oxy, and a hydroxy.). Furthermore, for "an alkyl, an alkenyl, an alkynyl, an aryl, a heteroaryl, an aralkyl, or a cycloalkyl" in the definition of these substituents, the above-mentioned definitions for these functional groups are applied. For example, herein, "alkoxy" means a group in which a hydrogen atom in a hydroxy group is replaced with the above-mentioned alkyl group. Preferred examples thereof include "C1-C6 alkoxy".

Examples of halogen-derived substituents include fluoro (—F), chloro (—Cl), bromo (—Br), and iodo (—I).

Examples of 0 atom-derived substituents include hydroxyl (—OH), oxy (—OR), carbonyl (—C=O—R), carboxyl (—CO2H), oxycarbonyl (—C=O—OR), carbonyloxy (—O—C=O—R), thiocarbonyl (—C=O—SR), carbonylthio group (—S—C=O—R), aminocarbonyl (—C=O—NHR), carbonylamino (—NH—C=O—R), oxycarbonylamino (—NH—C=O—OR), sulfonylamino (—NH—SO2-R), aminosulfonyl (~SO2-NHR), sulfamoylamino (—NH—SO2-NHR), thiocarboxyl (—C(=O)—SH), and carboxylcarbonyl (—C(=O)—CO2H).

Examples of oxy (—OR) include alkoxy, cycloalkoxy, alkenyloxy, alkynyloxy, aryloxy, heteroaryloxy, and aralkyloxy.

Examples of carbonyl (—C=O—R) include formyl (—C=O—H), alkylcarbonyl, cycloalkylcarbonyl, alkenylcarbonyl, alkynylcarbonyl, arylcarbonyl, heteroarylcarbonyl, and aralkylcarbonyl.

Examples of oxycarbonyl (—C=O—OR) include alkyloxycarbonyl, cycloalkyloxycarbonyl, alkenyloxycarbonyl, alkynyloxycarbonyl, aryloxycarbonyl, heteroaryloxycarbonyl, and aralkyloxycarbonyl.

(—C=O—OR)

Examples of carbonyloxy (—O—C=O—R) include alkylcarbonyloxy, cycloalkylcarbonyloxy, alkenylcarbonyloxy, alkynylcarbonyloxy, arylcarbonyloxy, heteroarylcarbonyloxy, and aralkylcarbonyloxy.

Examples of thiocarbonyl (—C=O—SR) include alkylthiocarbonyl, cycloalkylthiocarbonyl, alkenylthiocarbonyl, alkynylthiocarbonyl, arylthiocarbonyl, heteroarylthiocarbonyl, and aralkylthiocarbonyl.

Examples of carbonylthio (—S—C=O—R) include, alkylcarbonylthio, cycloalkylcarbonylthio, alkenylcarbonylthio, alkynylcarbonylthio, arylcarbonylthio, heteroarylcarbonylthio, and aralkylcarbonylthio.

Examples of aminocarbonyl (—C=O—NHR) include alkylaminocarbonyl, cycloalkylaminocarbonyl, alkenylaminocarbonyl, alkynylaminocarbonyl, arylaminocarbonyl, heteroarylaminocarbonyl, and aralkylaminocarbonyl. Additional examples include compounds produced by further substitution of an alkyl, a cycloalkyl, an alkenyl, an alkynyl, an aryl, a heteroaryl, or an aralkyl for the H atom bonded to the N atom in —C=O—NHR.

Examples of carbonylamino (—NH—C=O—R) include alkylcarbonylamino, cycloalkylcarbonylamino, alkenylcarbonylamino, alkynylcarbonylamino, arylcarbonylamino, heteroarylcarbonylamino, and aralkylcarbonylamino. Additional examples include compounds produced by further substitution of an alkyl, a cycloalkyl, an alkenyl, an alkynyl, an aryl, a heteroaryl, or an aralkyl for the H atom bonded to the N atom in —NH—C=O—R.

Examples of oxycarbonylamino (—NH—C=O—OR) include alkoxycarbonylamino, cycloalkoxycarbonylamino, alkenyloxycarbonylamino, alkynyloxycarbonylamino, aryloxycarbonylamino, heteroaryloxycarbonylamino, and aralkyloxycarbonylamino. Additional examples include compounds produced by further substitution of an alkyl, a cycloalkyl, an alkenyl, an alkynyl, an aryl, a heteroaryl, or an aralkyl for the H atom bonded to the N atom in —NH—C=O—OR.

Examples of sulfonylamino (—NH—SO2-R) include alkylsulfonylamino, cycloalkylsulfonylamino, alkenylsulfonylamino, alkynylsulfonylamino, arylsulfonylamino, heteroarylsulfonylamino, and aralkylsulfonylamino. Additional examples include compounds produced by further substitution of an alkyl, a cycloalkyl, an alkenyl, an alkynyl, an aryl, a heteroaryl, or an aralkyl for the H atom bonded to the N atom in —NH—SO2-R.

Examples of aminosulfonyl (~SO2-NHR) include alkylaminosulfonyl, cycloalkylaminosulfonyl, alkenylaminosulfonyl, alkynylaminosulfonyl, arylaminosulfonyl, heteroarylaminosulfonyl, and aralkylaminosulfonyl. Additional examples include compounds produced by further substitution of an alkyl, a cycloalkyl, an alkenyl, an alkynyl, an aryl, a heteroaryl, or an aralkyl for the H atom bonded to the N atom in —SO2-NHR.

Examples of sulfamoylamino (—NH—SO2-NHR) include alkylsulfamoylamino, cycloalkylsulfamoylamino, alkenylsulfamoylamino, alkynylsulfamoylamino, arylsulfamoylamino, heteroarylsulfamoylamino, and aralkylsulfamoylamino. Additionally, the two H atoms bonded to the N atoms in —NH—SO2-NHR may be substituted with a substituent independently selected from the group consisting of an alkyl, a cycloalkyl, an alkenyl, an alkynyl, an aryl, a heteroaryl, and an aralkyl; or these two substituents may form a ring.

For S atom-derived substituents, examples include thiol (—SH), thio (—S—R), sulfinyl (—S=O—R), sulfonyl (—S(O)2-R), and sulfo (—SO3H).

Examples of thio (—S—R) are selected from among alkylthio, cycloalkylthio, alkenylthio, alkynylthio, arylthio, heteroarylthio, aralkylthio, and such.

Examples of sulfinyl (—S=O—R) include alkylfulfinyl, cycloalkylsulfinyl, alkenylsulfinyl, alkynylsulfinyl, arylsulfinyl, heteroarylsulfinyl, and aralkylsulfinyl.

Examples of sulfonyl (—S(O)2-R) include alkylsulfonyl, cycloalkylsulfonyl, alkenylsulfonyl, alkynylsulfonyl, arylsulfonyl, heteroarylsulfonyl, and aralkylsulfonyl.

For N atom-derived substituents, examples include azide (—N3, also called "azido group"), cyano (—CN), primary amino (—NH2), secondary amino (—NH—R), tertiary amino (—NR(R')), amidino (—C(=NH)—NH2), substituted amidino (—C(=NR)—NR'R"), guanidino (—NH—C(=NH)—NH2), substituted guanidino (—NR—C(=NR''')—NR'R"), and aminocarbonylamino (—NR—CO—NR'R").

Examples of secondary amino (—NH—R) include alkylamino, cycloalkylamino, alkenylamino, alkynylamino, arylamino, heteroarylamino, and aralkylamino.

Examples of tertiary amino (—NR(R')) include amino groups, such as alkyl(aralkyl)amino, having any two substituents each independently selected from alkyl, cycloalkyl, alkenyl, alkynyl, aryl, heteroaryl, and aralkyl; and these two arbitrary substituents may form a ring.

Examples of substituted amidino (—C(=NR)—NR'R") include groups in which each of the three substituents R, R', and R" on the N atoms is independently selected from among alkyl, cycloalkyl, alkenyl, alkynyl, aryl, heteroaryl, and aralkyl; and such examples include alkyl(aralkyl)(aryl)amidino.

Examples of substituted guanidino (—NR—C(=NR''')—NR'R") include groups in which each of R, R', R", and R''' is independently selected from alkyl, cycloalkyl, alkenyl, alkynyl, aryl, heteroaryl, and aralkyl; or groups in which they form a ring.

Examples of aminocarbonylamino (—NR—CO—NR'R") include groups in which each of R, R', and R" is independently selected from a hydrogen atom, alkyl, cycloalkyl, alkenyl, alkynyl, aryl, heteroaryl, and aralkyl; or groups in which they form a ring.

Examples of B atom-derived substituents include boryl (—BR(R')) and dioxyboryl (—B(OR)(OR')). These two substituents, R and R', are each independently selected from alkyl, cycloalkyl, alkenyl, alkynyl, aryl, heteroaryl, and aralkyl; or they may form a ring.

At least one atom constituting an "amino acid" constituting the peptide may be an atom (isotope) of the same atomic number (number of protons) and different mass number (total number of protons and neutrons). Examples of the isotope contained in the "amino acid" constituting the peptide include a hydrogen atom, a carbon atom, a nitrogen atom, an oxygen atom, a phosphorus atom, a sulfur atom, a fluorine atom, and a chlorine atom, including 2H, 3H, 13C, 14C, 15N, 17O, 18O, 31P, 32P, 35S, 18F and 36Cl.

Without wishing to be bound by a specific theory, features of amino acids which would receive large improvement effect on peptide translation efficiency by the present invention may include amino acids whose aminoacyl-tRNA is rapidly hydrolyzed by itself and has low affinity to EF-tu.

On the other hand, without wishing to be bound by a specific theory, features of amino acids of which improvement effect on translation efficiency in the present invention is predicted not to be large include amino acids whose aminoacyl-tRNA is slowly hydrolyzed by itself (in particular, the hydrolysis is slow enough to be negligible when considering the time required for translation), and/or has sufficiently high affinity to EF-tu. Such amino acids can also be used in a range that the effects of the present invention are not impaired.

In the present invention, exemplary amino acid analogs that can be used for the synthesis of the peptide of the present invention are shown below; however, the amino acid analogs are not limited thereto. Many of these amino acid analogs can be purchased with their side chains protected or unprotected and their amine moieties protected or unprotected. Those that cannot be purchased can be synthesized by known methods.

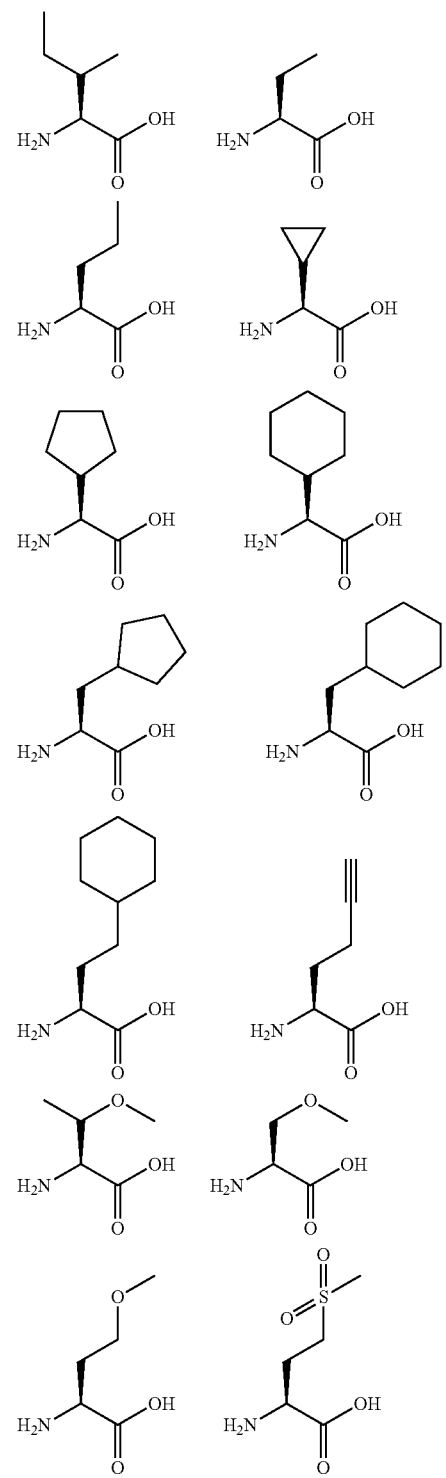

-continued
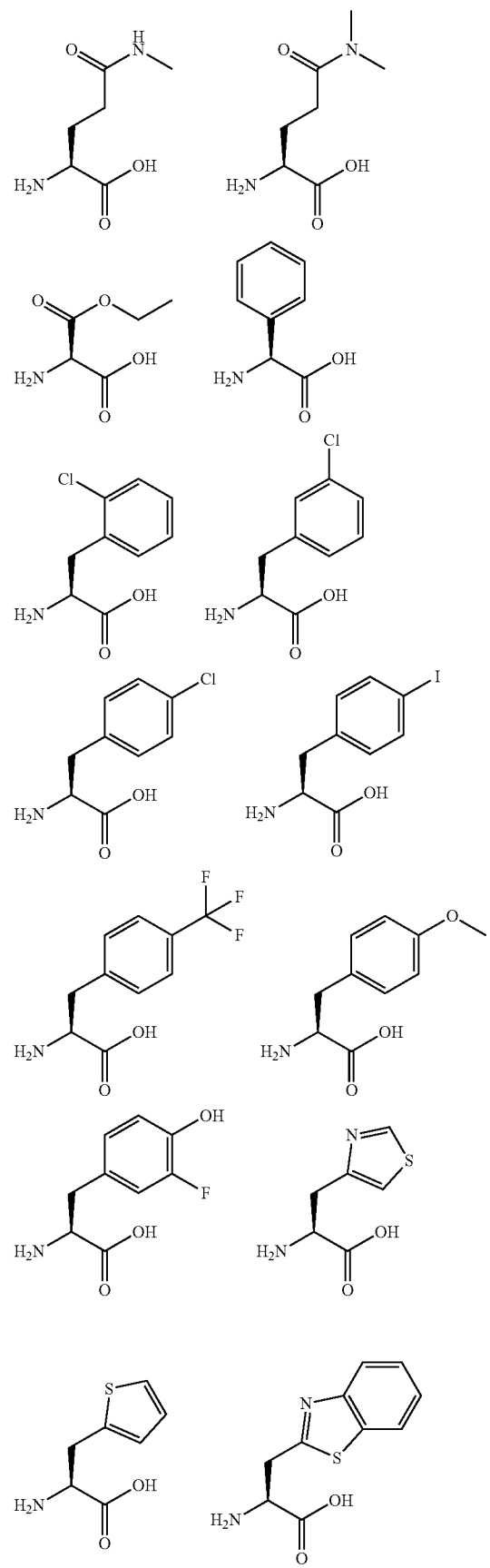 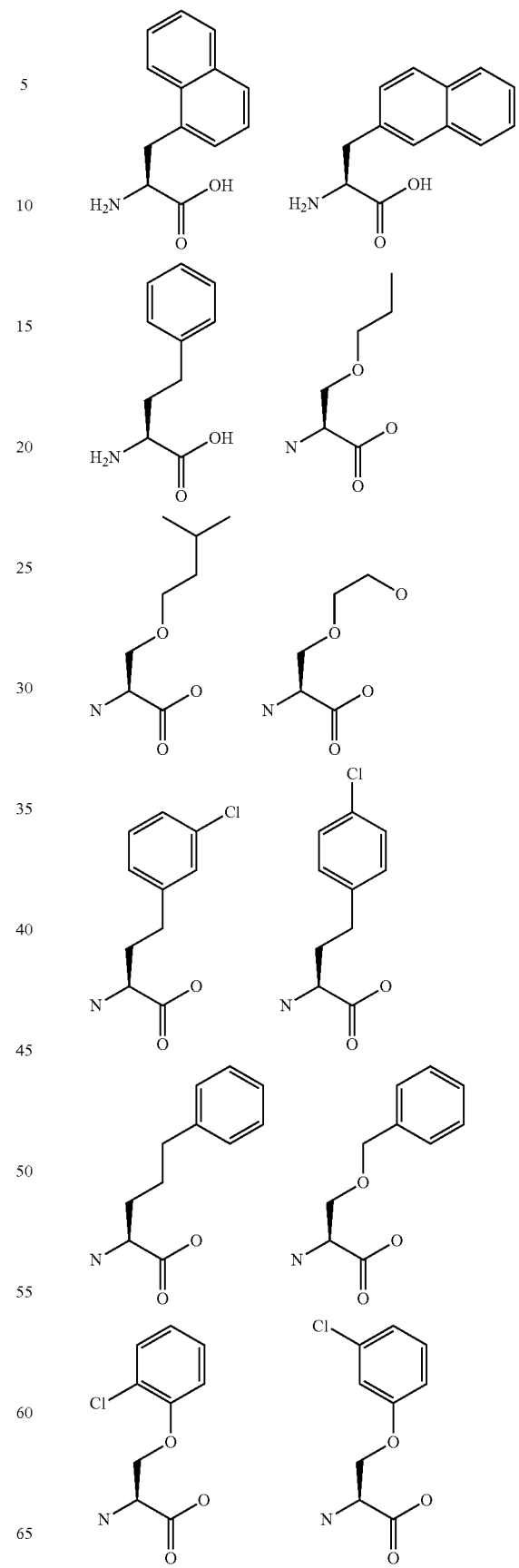

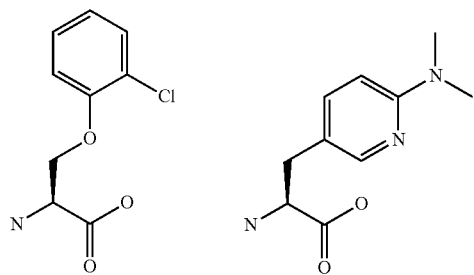

The following N-Me amino acids can be used as the amino acid analogs: N-methylalanine; N-methylglycine; N-methylphenylalanine; N-methyltyrosine; N-methyl-3-chlorophenylalanine; N-methyl-4-chlorophenylalanine; N-methyl-4-methoxyphenylalanine; N-methyl-4-thiazolalanine; N-methylhistidine; N-methylserine; and N-methylaspartic acid.

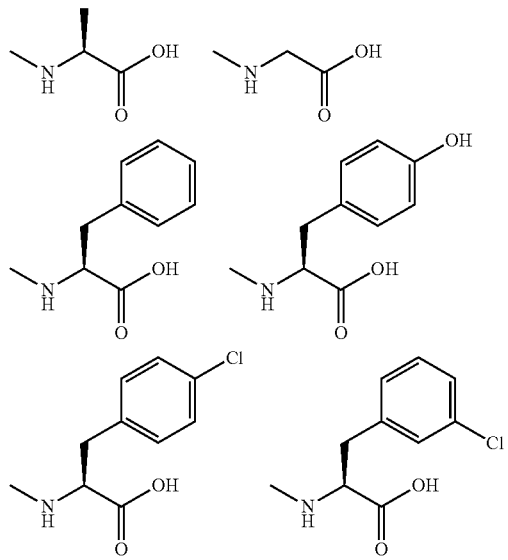

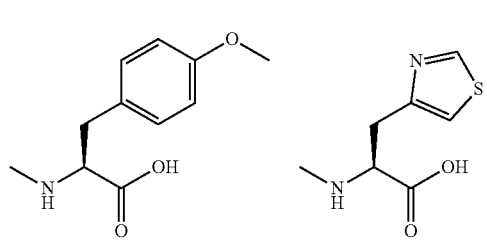

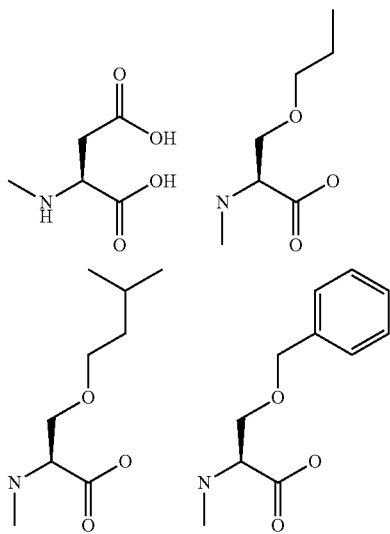

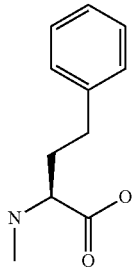

The following N-alkylamino acids may also be used as the amino acid analogs.

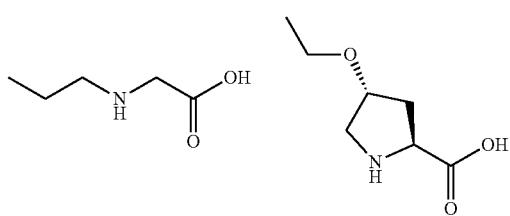

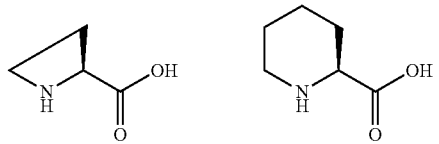

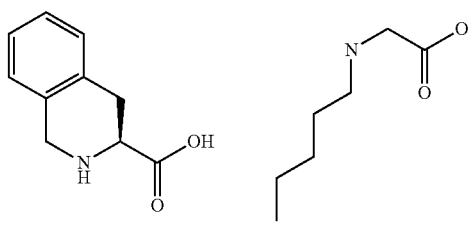

-continued

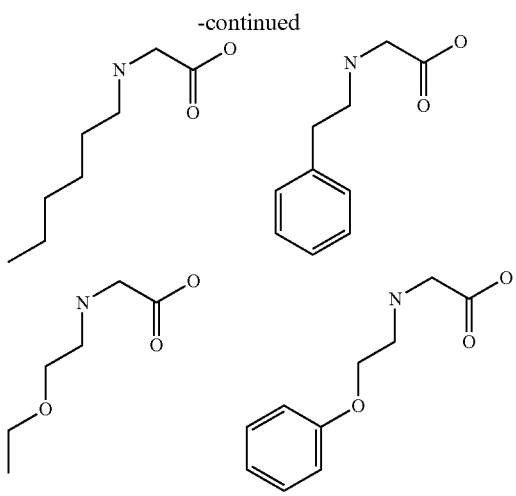

The following D-amino acid can also be used as the amino acid analog.

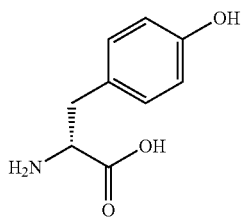 [SMILES: N[C@H](Cc1ccc(O)cc1)C(=O)O]

The following α,α-dialkylamino acid can also be used as the amino acid analog.

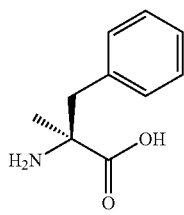

The following amino acid may also be used as the amino acid analog.

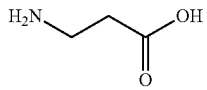

In a non-limiting embodiment, one or more types of translatable amino acid analogs selected from the group consisting of cyclic amino acid-containing N-alkyl amino acids, aliphatic amino acids, aromatic amino acids, β-amino acids, D-amino acids, and α-dialkylamino acids can be selected as amino acid analogs used in peptide synthesis in the present invention.

While not being limited to the following, whether an amino acid analog used in the above-mentioned embodiment is translatable can be evaluated by techniques known to those skilled in the art, such as MALDI-TOF MS for mass spectrometric analysis of peptides ribosomally synthesized in cell-free translation systems and detection of peptides using radioisotope-labeled amino acids by electrophoresis.

In a non-limiting embodiment, a protecting group-containing amino acid which can be used for peptide synthesis in the present invention is preferably introduced at a position other than the N terminus of the peptide to be translated.

In a non-limiting embodiment, examples of amino acids used in the peptide synthesis in the present invention include translatable amino acids represented by the following general formula (VI) or (VII).

(VI)

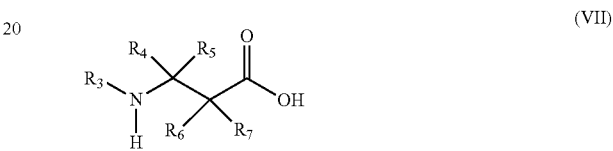

(VII)

In the formulae, $R_3$, $R_4$, and $R_5$ each independently are a hydrogen atom, an alkyl, an alkenyl, an alkynyl, an aryl, a heteroaryl, an aralkyl, or a cycloalkyl, each of which are optionally substituted; or R3 and R4, or R3 and R5, may form a ring together with an atom to which they are bonded. R6 and R7 each independently are a hydrogen atom or a methyl.

While not being limited to the following, either one of R4 and R5 may be a hydrogen atom or may form a ring together with R3, and in that case, the other one of R4 and R5 is an optionally substituted C1-6 alkyl, an optionally substituted C1-6 alkenyl, an optionally substituted C1-6 alkynyl, an optionally substituted aryl, an optionally substituted heteroaryl, an optionally substituted aralkyl, or an optionally substituted C3-7 cycloalkyl.

In a non-limiting embodiment, as amino acid analogs used in the peptide synthesis in the present invention, one or more amino acid analogs selected from the group consisting of azetidine-2-carboxylic acid (Aze(2)), n-butylglycine (nBuG), 3-pyridyl alanine (Ala(3-Pyr)), 2-amino-2-methyl-propanoic acid (α-aminoisobutyric acid; AIB), 3-aminopropanoic acid (β-alanine; β-Ala), D-alanine (D-Ala), and homophenylalanine (Hph), may be selected.

In a non-limiting embodiment, the present invention provides methods of synthesizing a peptide containing at least one amino acid, wherein the method comprises a step of deprotecting a protecting group of an amino acid having the protecting group and a translation step, the deprotecting and translation being performed in a cell-free translation system that comprises tRNA to which the amino acid having the protecting group has been linked; and the deprotecting and translation steps are performed in parallel.

The "amino acid having a protecting group" in the above-mentioned embodiment means an amino acid having a protecting group(s) on its main chain and/or side chain. While the amino acid is not limited as long as it is an amino acid that has such features, it is preferably an amino acid having a protecting group on the amino group of the amino acid main chain.

The term "performed in parallel" in the above-mentioned embodiment means performing, in a cell-free translation system comprising tRNA to which an amino acid comprising a protecting group has been linked, both of the step of deprotecting the protecting group of the amino acid and the step of peptide translation. As long as both the step of deprotecting the protecting group and the step of peptide translation are performed in the cell-free translation system, the deprotection step and the translation step may be performed such that the steps partially overlap with regard to time, or the steps may be performed simultaneously such that the steps coincide with regard to time. Alternatively, the deprotection step and the translation step may be performed independently from each other with regard to time.

The above-mentioned deprotection step may be started prior to the above-mentioned translation step, or the translation step may be initiated prior to the deprotection step. Alternatively, both steps can be initiated simultaneously. Furthermore, there is no particular limitation on the duration that the steps are performed in parallel, and examples may be 30 seconds, 1 minute, 5 minutes, 10 minutes, 20 minutes, 30 minutes, 60 minutes, 120 minutes, 180 minutes, or more.

In a non-limiting embodiment of the present invention, at the time when an amino acid linked to tRNA is added to a cell-free translation system, preferably the amino acid still retains its protecting group. Alternatively, the protecting group of the amino acid is preferably not deprotected before the amino acid linked to tRNA is added to a cell-free translation system.

In a non-limiting embodiment, for the step of deprotecting the protecting group of the amino acid in the above-mentioned peptide synthesis method, any deprotection methods may be used as long as the deprotection reaction proceeds under the conditions for translation. Furthermore, as long as the translation system is not damaged by operations performed for deprotection and reagents added for the deprotection reaction, or by debris of the protecting group discharged into the system by the deprotection reaction, any deprotection method may be used. However, even deprotection methods that damage the translation system can be used in a range that does not impair the effects of the present invention.

In a non-limiting embodiment, the peptide synthesis methods of the present invention may comprise the step of post-translationally modifying peptides (performing post-translational modification to peptides). In a limiting embodiment, the peptide synthesis methods of the present invention may comprise the step of cyclizing peptides by post-translational modification. The peptides prior to cyclization obtained by the peptide synthesis methods of the present invention may be a peptide in which amino acids which will be subjected to cyclization reaction are protected with protecting groups. In the present invention, for example, deprotection can be performed during post-translational modification. In that case, the deprotection condition under the above-mentioned translation condition is preferably orthogonal to a deprotection reaction condition used during the post-translational modification. In the present invention, for the deprotection condition under the translation condition, any deprotection methods may be used as long as they are methods with deprotection conditions orthogonal to the deprotection reaction conditions used during post-translational modification. Here, post-translational modification refers to chemical reactions that take place automatically after translation by actions other than the action of the ribosome, or chemical reactions that are made to take place by adding reagents that are different from the reagents for causing deprotection reactions to proceed under translation conditions, and such examples include cyclization reactions and deprotection reactions.

The step of deprotecting a protecting group of an amino acid in a cell-free translation system in the present invention can be understood as the step which does not include the deprotection reactions that take place spontaneously in the systems due to the effects of constituents originally included in the cell-free translation systems (for example, dithiothreitol (DTT)).

In a non-limiting embodiment, the above-mentioned peptide synthesis methods provide methods of synthesizing a peptide, wherein deprotection of the above-mentioned protecting group of amino acid is one or more deprotection selected from the group consisting of deprotection by enzymes, deprotection by reducing agents, and deprotection by photoreactions.

While not being limited to the following, enzymes used for the above-mentioned deprotection by enzymes are preferably hydrolytic enzymes (hydrolases), and more preferably penicillin amidohydrolases, esterases, or aminopeptidases.

Penicillin amidohydrolases in the present invention refer to the hydrolases classified as EC (Enzyme Commission numbers) 3.5.1.11. For the hydrolases classified as EC 3.5.1.11, their natural substrates are penicillin and water, and they are enzymes that catalyze the chemical reaction yielding carboxylic acid and penicillanic acid as the products. Furthermore, it is also known from long before that the enzymes do not hydrolyze ordinary peptide bonds, and the enzymes have specific hydrolytic activity towards, for example, phenylacetylamide bonds. For example, *Escherichia coli*-derived penicillin amidohydrolases may also be used. The amino acid sequences and nucleotide sequences of these penicillin amidohydrolases are known to those skilled in the art (www.ncbi.nlm.nih.gov/protein/?term=EC+3.5.1.11).

As long as penicillin amidohydrolases retain their functions, these penicillin amidohydrolases may be variants formed by altering their amino acids by genetic engineering, and it does not matter whether they have been chemically modified or not. EC numbers are numbers consisting of four sets of digits for systematically classifying enzymes according to their reaction mode, and are numbers for enzymes defined by the Enzyme Commission of the International Union of Biochemistry and Molecular Biology.

Esterases in the present invention are not particularly limited as long as they are enzymes which have an esterase activity, and those skilled in the art can appropriately select enzymes having an esterase activity. Examples of such enzymes include those classified as EC (Enzyme Commission numbers) 3.1.1.XX. Enzymes classified as EC 3.1.1.XX are enzymes that hydrolyze carboxylic acid esters to carboxylic acids and alcohols. While not being limited to the following, preferred examples include carboxylesterase classified as EC 3.1.1.1, and triacylglycerol lipase (also simply called lipase) classified as EC 3.1.1.3. For example, *E. coli*-derived or pig liver-derived esterases may also be used. The amino acid sequences and nucleotide sequences of these esterases are known to those skilled in the art (www.ncbi.nlm.nih.gov/protein/?term=EC+3.1.1).

As long as the esterases retain their functions, these esterases may be variants formed by altering their amino acids by genetic engineering, and it does not matter whether they have been chemically modified or not.

Aminopeptidases in the present invention are not particularly limited as long as they are enzymes which have an aminopeptidase activity, and those skilled in the art can appropriately select enzymes having an aminopeptidase activity. Examples of such enzymes include those classified as EC (Enzyme Commission numbers) 3.4.11.XX. Enzymes classified as EC 3.4.11.XX are enzymes that catalyze reactions that hydrolyze the peptide amino acid chain from the N terminus in a stepwise manner to produce amino acids. While not being limited to the following, preferred examples include leucine aminopeptidase classified as EC 3.4.11.1 and methionine aminopeptidase classified as EC 3.4.11.18. For example, bacteria-derived or pig kidney-derived aminopeptidases may also be used. The amino acid sequences and nucleotide sequences of these aminopeptidases are known to those skilled in the art (www.ncbi.nlm.nih.gov/protein/?term=EC+3.4.11).

As long as the aminopeptidases retain their functions, these aminopeptidases may be variants formed by altering their amino acids by genetic engineering, and it does not matter whether they have been chemically modified or not.

In a non-limiting embodiment, protecting groups which will be deprotected by the above-mentioned enzymes are preferably groups represented by the following general formula (I) or (II) which have the moiety X1 recognized by penicillin amidohydrolases:

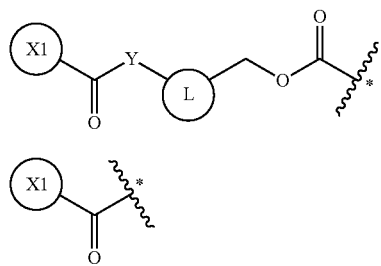

(I)

(II)

(wherein Y is NH or an oxygen atom; and L is a single bond (here, it represents a methylene group), an arylene, or a heteroarylene).

In the formula, X1 is a structure recognized by the enzyme penicillin amidohydrolases, and as long as an ester or amide bond represented by Y—C=O in formula (I) or an amide bond represented by *—C=O in formula (II) can be hydrolyzed as substrates of the penicillin amidohydrolases, the structure (X1) is not particularly limited. The protecting groups remaining after hydrolysis will be automatically deprotected from the amino acids.

Such structures can be appropriately selected by one skilled in the art from known techniques (Journal of Molecular Biology, Volume 284, Issue 2, 27 Nov. 1998, Pages 463-475, Annals New York Academy of Sciences, Volume 799, Enzyme Engineering XIII, Pages 659-669).

In a non-limiting embodiment, protecting groups which will be deprotected by the above-mentioned enzymes are preferably groups represented by the following general formula (III) which has the moiety X2 recognized by esterases:

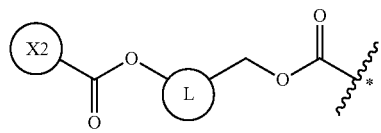

(III)

(wherein L is a single bond, an arylene, or a heteroarylene).

In the formula, X2 is a structure recognized by the enzyme esterases, and as long as an ester bond present between X2 and L in the formula can be hydrolyzed as substrates of esterases, the structure (X2) is not particularly limited. The protecting groups remaining after hydrolysis will be automatically deprotected from the amino acids. Esterases are known to have diverse substrate specificity depending on their types, and those skilled in the art can appropriately select suitable structures from known techniques.

In a non-limiting embodiment, protecting groups which will be deprotected by the above-mentioned enzymes are preferably groups represented by the following general formula (XII) which has the moiety X3 recognized by aminopeptidases:

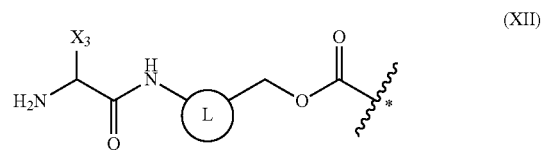

(XII)

(wherein L is a single bond, an arylene, or a heteroarylene).

In the formula, X3 is a structure recognized by the enzyme aminopeptidases, and as long as an amide bond in the formula may be hydrolyzed as substrates of aminopeptidases, the structure (X3) is not particularly limited. The protecting groups remaining after hydrolysis will be automatically deprotected from the amino acids. Such structures can be appropriately selected by one skilled in the art from known techniques.

In a non-limiting embodiment, the moiety X1 in formula (I) mentioned above is preferably the following general formula (IV) or 2-thienylmethyl:

(IV)

(wherein $R_1$ and $R_2$ each independently are a hydrogen atom, a hydroxyl, a fluoro, a chloro, a bromo, an amino, a nitro, or a methoxy).

Furthermore, preferred combinations of $R_1$ and $R_2$ include $R_1$=F and $R_2$=H; $R_1$=Cl and $R_2$=H; and $R_1$=Br and $R_2$=H. Furthermore, $R_1$ may be present in any of ortho-, meta-, or para-positions with respect to —$CHR_2$—, and is preferably present at the para-position.

In a non-limiting embodiment, the moiety X2 in formula (III) mentioned above is preferably an optionally substituted alkyl, an optionally substituted aralkyl, or an optionally substituted cycloalkyl, and particularly preferably a methyl, an ethyl, a benzyl, or an n-propyl.

In a non-limiting embodiment, the above-mentioned formula (XII) is preferably the following general formula (XIII).

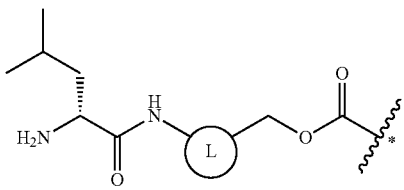

(XIII)

In a non-limiting embodiment, the protecting group that is deprotected by penicillin amidohydrolases, from among the above-mentioned enzymes, is preferably a 4-(2-(4-fluorophenyl)acetamide)benzyloxycarbonyl (F-Pnaz) group. The protecting group deprotected by esterases is preferably a 4-(propionyloxy)benzyloxycarbonyl (Etez) group. The protecting group deprotected by aminopeptidases is preferably an (S)-((4-(2-amino-4-methylpentanamide)benzyl)oxy)carbonyl (Leuz) group.

In a non-limiting embodiment, the ratio between the concentration of an enzyme to be mixed and the concentration of tRNA linked to an amino acid carrying the protecting group which will be deprotected by the enzyme is preferably 1:1000, 1:900, 1:800, 1:700, 1:600, 1:500, 1:400, 1:300, 1:200, 1:100, 1:90, 1:80, 1:70, 1:60, 1:50, 1:40, 1:30, 1:20, 1:10, or 1:1.

While not being limited to the following, a reducing agent to be used for the above-mentioned deprotection by a reducing agent is preferably tris(2-carboxyethyl) phosphine (TCEP). More preferably, as the protecting group deprotected by the above-mentioned reducing agent, a protecting group represented by the following general formula (V) or an azide group formed together with the amino group of a main chain (an azido group that masks the amino group of a main chain) may be used.

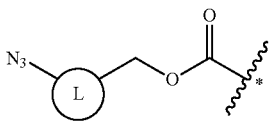

(V)

(wherein L is a single bond, an arylene, or a heteroarylene).

In a non-limiting embodiment, the protecting group that is deprotected by the above-mentioned reducing agents (preferably TCEP) is preferably a 4-azidobenzyloxycarbonyl group (Acbz) or an azidomethyloxycarbonyl group (Azoc).

In a non-limiting embodiment, the ratio between the concentration of the reducing agent to be mixed and the concentration of tRNA linked to an amino acid carrying the protecting group which will be deprotected by the reducing agents is preferably 5000:1, 4000:1, 3000:1, 2000:1, 1000:1, 900:1, 800:1, 700:1, 600:1, 500:1, 400:1, 300:1, 200:1, or 100:1.

While not being limited to the following, the above-mentioned deprotection by a photoreaction can be carried out by those skilled in the art by appropriately referring to known methods (Bioorganic & Medicinal Chemistry Letters, Volume 24, Issue 23, Nat. Commun. 7: 12501 doi: 10.1038/ncomms12501 (2016)).

In a non-limiting embodiment, the present invention provides methods of synthesizing a peptide, which comprise a step of deprotecting a protecting group of an amino acid having the protecting group by an enzyme or a reducing agent and a translation step, the deprotecting and translation being performed in a cell-free translation system that comprises a tRNA to which the amino acid having the protecting group has been linked.

In the above-mentioned embodiment, the step of deprotecting the protecting group of the amino acid and the peptide translation step may be carried out such that the steps partially overlap with regard to time, or the steps may be carried out simultaneously such that the steps coincide with regard to time. Alternatively, in the present invention, the deprotection step and the translation step may be carried out independently from each other with regard to time. When the steps are carried out independently, while not being limited to the following, the translation step is preferably initiated after deprotecting the protecting group of the amino acid in a cell-free translation system.

If a peptide cyclization reaction and such are further carried out after completing the peptide synthesis reaction in the present invention and during post-translational modification, protecting groups that are deprotected by reaction conditions orthogonal to the reaction conditions used for the post-translational modification are preferably used in the peptide synthesis reactions in the present invention.

More specifically, as a non-limiting embodiment, the present invention provides peptide synthesis methods, wherein protecting groups carried by amino acids are those deprotected by reaction conditions orthogonal to reaction conditions used for post-translational modification. Furthermore, the protecting group carried by the amino acid mentioned above is preferably orthogonal to a protecting group used in an initiation suppression (iSP) method.

In a non-limiting embodiment, the present invention provides peptide synthesis methods, wherein protecting groups carried by amino acids are those orthogonal to the protecting groups used in the Initiation Suppression (iSP) method.

For example, when performing a peptide cyclization reaction under reducing conditions during post-translational modification, deprotection condition by an enzyme, which is a reaction condition orthogonal to the reducing condition, may be used for the peptide synthesis of the present invention.

An "orthogonal" protecting group in the above-mentioned embodiment refers to a protecting group that is not affected substantially by deprotection reaction conditions for others. For example, when the other deprotection reactions are carried out under reducing conditions, a protecting group for which its deprotection reaction may progress under conditions other than reducing reactions (for example, enzyme reactions or photoreactions) is preferably selected as the protecting group orthogonal thereto. Furthermore, when other deprotection reactions are performed by enzyme reactions (esterases), a protecting group for which its deprotection reaction may progress by different enzyme reaction (for example, by penicillin amidohydrolases) can be selected as the orthogonal protecting group.

In a non-limiting embodiment, when introducing a desired amino acid other than methionine to the N terminus of the peptide to be translated, methods such as the following ones can be used (WO 2013/100132).

Initiation Suppression (iSP) Method

Although it is typical that methionine is translated as the translation initiation amino acid (N-terminal amino acid), by making to translate using a translation initiation tRNA aminoacylated with a different desired amino acid, the desired amino acid can be translated as a translation initiation amino acid (N-terminal amino acid). Tolerance for amino acid analogs is greater at the N terminus than in peptide chain elongation, and amino acid analogs having structures largely different from natural amino acids are known to be usable at the N terminus (NPL: J. Am. Chem. Soc. 2009 Apr. 15; 131(14): 5040-1. Translation initiation with initiator tRNA charged with exotic peptides. Goto, Y, Suga, H.).

While not being limited to the following, when using Cys or an amino acid analog carrying SH groups on its side chain as the N-terminal amino acid, the amino group of the main chain and/or the SH groups of the side chain of the amino acid preferably have protecting groups. It is more preferable that protecting groups for which their reactions progress under conditions orthogonal to the deprotection conditions in the peptide synthesis of the present invention are selected.

Another method of introducing a desired amino acid other than methionine as the translation initiation amino acid includes initiation read through (skipping of the initiation codon). Generally, proteins and peptides are translated beginning with methionine which is the translation initiation amino acid encoded as the AUC codon. On the other hand, initiation read through enables synthesis of translation products in which the amino acid encoded by the second or later codon is the N-terminal amino acid by not adding translation initiation methionyl-tRNA in the cell-free translation system, or by substituting the translation initiation amino acid to amino acid analogs having low translation efficiency.

Furthermore, another known method is the method of removing the N-terminal methionine of peptides by the action of enzymes such as peptide deformylases and methionine aminopeptidases (NPL: Meinnel, T., et al., Biochimie (1993) 75, 1061-1075, Methionine as translation start signal: A review of the enzymes of the pathway in *Escherichia coli*). A library in which the N-terminal amino acids have been randomized can be prepared by preparing a library of peptides starting from translation initiation methionine, and then removing the N-terminal methionine by making methionine aminopeptidase act on the peptides.

In a non-limiting embodiment, after completion of a peptide synthesis reaction in the present invention, peptide cyclization can further be performed during post-translational modification. In that case, a reactive site of an amino acid residue at the N-terminal side (herein after, it includes N-terminal carboxylic acid analogs, besides natural amino acid residues and an amino acid analog residues) and a reactive site in the side chain of an amino acid residue or an amino acid analog residue on the C-terminal side of the synthesized peptide can be linked to cyclize the peptide (WO 2013/100132). Examples of such methods include methods of obtaining cyclic compounds by amide bond formation between an amino acid residue at the N-terminal side, which has a reaction auxiliary group and an amino group on its side chain, and an amino acid residue or amino acid analog residue positioned closer to the C-terminal side than the amino acid residue at the N terminal side, which has an active ester (activated ester) group on its side chain; methods of obtaining cyclic compounds by amide bond formation between an amino group of an N-terminal amino acid residue having the amino group and an active ester group of an amino acid residue or amino acid analog residue having the active ester group on its side chain; and methods of forming a carbon-carbon bond between a reactive site of an N-terminal amino acid residue and a reactive site of an amino acid residue or amino acid analog residue having one reactive site on its side chain. Furthermore, the examples are not limited to those described above, and also include methods in which the placements of the functional groups are opposite of those described above, for example, an amide bond is formed between an active ester group of an amino acid residue at the N-terminal side, which has the active ester group, and an amino group in the amino acid residue at the C-terminal side, which has the amino group (which may have a reaction auxiliary group) on its side chain.

N-terminal carboxylic acid analogs in the present invention may be compounds carrying both an amino group and a carboxyl group, and the number of atoms between the two groups is three or more; various carboxylic acid derivatives that do not carry an amino group; peptides formed from two to four residues; and amino acids in which the main-chain amino group is chemically modified by amide bond formation with a carboxylic acid, and such. Furthermore, they may have a boric acid or borate ester portion which can be used for cyclization. Furthermore, they may be carboxylic acids having double-bond portions or triple-bond portions, or they may be carboxylic acids having ketone or halide. Portions other than the defined functional groups in these compounds are selected from (freely substituted with) a wide variety of groups such as optionally substituted alkyl groups, optionally substituted aralkyl groups, optionally substituted aryl groups, optionally substituted cycloalkyl groups, optionally substituted heteroaryl groups, optionally substituted alkenyl groups, and optionally substituted alkynyl groups.

A transfer RNA (tRNA) refers to an RNA which has a molecular weight of 25000 to 30000, consisting of 73 to 93 bases in chain length that contains a 3'-end CCA sequence, and is involved in discriminating codons. tRNA forms an ester bond through its 3'-end with the carboxy terminus of an amino acid, thereby forming an aminoacyl-tRNA. An aminoacyl-tRNA forms a ternary complex with polypeptide elongation factor (EF-Tu) and GTP, which is transferred to the ribosome. In the process of translation of the nucleotide sequence information of mRNA into an amino acid sequence in the ribosome, an anticodon in the sequence of aminoacyl-tRNA and a codon of mRNA forms a base pair, thereby discriminating the codons. tRNAs biosynthesized in cells contain covalently-modified bases, and the bases may influence the conformations of the tRNAs or the base pairing of anticodons and help the codon discrimination of tRNAs. tRNAs synthesized by common in vitro transcription are composed of the so-called nucleobases adenine, uracil, guanine, and cytosine, whereas tRNAs prepared from cells or chemically synthesized may contain modified bases such as their methylated forms, sulfur-containing derivatives, deaminated derivatives, and adenosine derivatives containing isopentenyl groups or threonine. When the pdCpA method or such is used, tRNAs may be those containing deoxy bases.

In a non-limiting embodiment, the aminoacyl-tRNAs used in the peptide synthesis of the present invention can be produced using methods such as the followings.

A template DNA encoding a desired tRNA sequence and having a T7, T3 or SP6 promoter located upstream thereof is provided and transcribed to synthesize tRNA using RNA polymerase compatible with the promoter, such as T7, T3 or SP6 RNA polymerase. Alternatively, tRNAs can also be extracted from cells and purified, and the generated tRNA of interest can be extracted by using a probe having a sequence complementary to the tRNA sequence. In this case, cells transformed with expression vectors for the tRNA of interest may be used as a source. The tRNA sequence of interest may also be synthesized chemically. For example, a tRNA lacking CA at the 3'-end CCA sequence thus obtained can be ligated to aminoacylated pdCpA or pCpA prepared separately with RNA ligase to obtain an aminoacyl-tRNA (pdCpA method, pCpA method).

For example, aminoacyl-tRNA for an amino acid represented by formula (VI) or (VII) can be prepared using pdCpA or pCpA linked to the amino acid represented by formula (VI) or (VII). The aminoacyl-tRNA is useful in preparing a peptide, a peptide-mRNA complex, and a library of peptide-mRNA complexes of the present invention. Therefore, the present invention relates to pdCpA or pCpA linked to an amino acid represented by formula (VI) or (VII). Specific examples of pdCpA or pCpA linked to an amino acid represented by formula (VI) or (VII) include the compound represented by the following formula (X) or (XI).

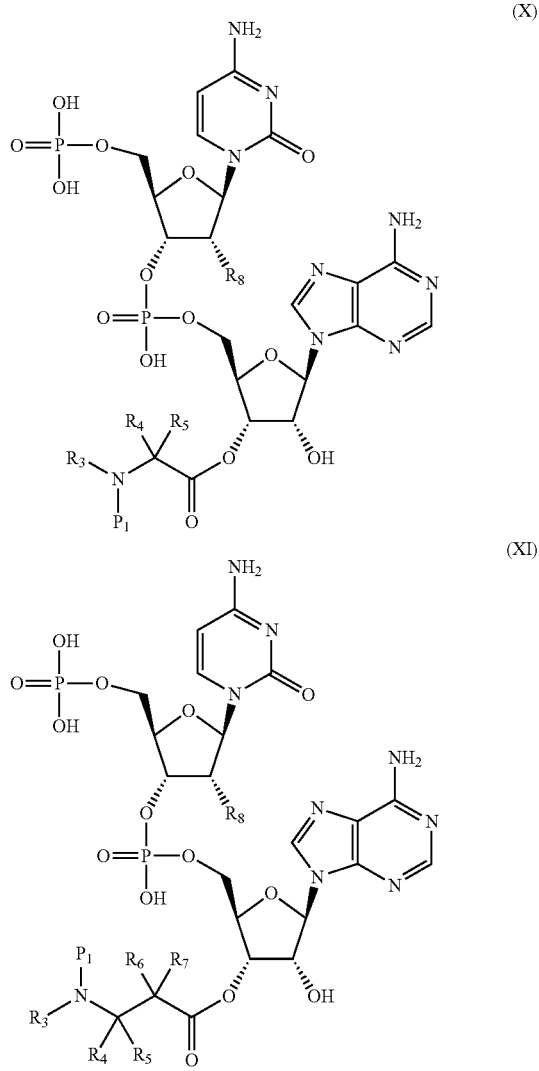

(wherein $R_3$ to $R_7$ and $P_1$ have the same meaning as $R_3$ to $R_7$ and $P_1$ in the formula (VIII) or (IX) described later and $R_8$ is a hydrogen atom or hydroxyl.)

Furthermore, the present invention relates to a tRNA aminoacylated with an amino acid represented by formula (VI) or (VII).

Alternatively, a full-length tRNA may be provided and aminoacylated by a flexizyme, which is a ribozyme capable of charging active esters of various amino acid analogs onto tRNAs.

In the present invention, ribosomal synthesis can be carried out, for example, by adding mRNA to a known cell-free translation system such as the PURE system mixed with protein factors necessary for translation in *E. coli* (methionyl tRNA transformylase, EF-G, RF1, RF2, RF3, RRF, IF1, IF2, IF3, EF-Tu, EF-Ts and ARS (necessary ones are selected from AlaRS, ArgRS, AsnRS, AspRS, CysRS, GlnRS, GluRS, GlyRS, HisRS, IleRS, LeuRS, LysRS, MetRS, PheRS, ProRS, SerRS, ThrRS, TrpRS, TyrRS and ValRS)), ribosome, amino acids, creatine kinase, myokinase, inorganic pyrophosphatase, nucleoside diphosphate kinase, *E. coli*-derived tRNA, creatine phosphate, potassium glutamate, HEPES-KOH (pH 7.6), magnesium acetate, spermidine, dithiothreitol, GTP, ATP, CTP, UTP and the like. Moreover, when adding T7 RNA polymerase in advance, coupled transcription and translation may be performed from a template DNA containing a T7 promoter. In this case, desired acylated tRNA population and amino acid analog population (e.g., F-Tyr) acceptable by ARS can be added to the system to ribosomally synthesize peptides containing the amino acid analog population (Kawakami T, et al. Ribosomal synthesis of polypeptoids and peptoid-peptide hybrids. J Am Chem Soc. 2008, 130, 16861-3; Kawakami T, et al. Diverse backbone-cyclized peptides via codon reprogramming. Nat Chem Biol. 2009, 5, 888-90). Alternatively, the translational incorporation efficiency of amino acid analogs may be enhanced by using variants of ribosome, EF-Tu, and the like (Dedkova L M, et al. Construction of modified ribosomes for incorporation of D-amino acids into proteins. Biochemistry. 2006, 45, 15541-51; Doi Y, et al. Elongation factor Tu mutants expand amino acid tolerance of protein biosynthesis system. J Am Chem Soc. 2007, 129, 14458-62; Park H S, et al. Expanding the genetic code of *Escherichia coli* with phosphoserine. Science. 2011, 333, 1151-4).

The cell-free translation system may include various systems as long as it can translate mRNAs into proteins. Examples include a combination of ribosomes extracted from cells as well as protein factors involved in translation, tRNAs, amino acids, energy sources such as ATPs and a regenerating system thereof. Furthermore, the cell-free translation system of the present invention can additionally contain an initiation factor, an elongation factor, a dissociation factor, aminoacyl-tRNA synthetase, and such. These factors can be obtained by purification from various cell extracts. Examples of cells for use in the purification of the factors can include prokaryotic cells and eukaryotic cells. Examples of the prokaryotic cells can include *E. coli* cells, extreme thermophile cells, and *Bacillus subtilis* cells. Those obtained using eukaryotic cells, such as yeast cells, wheat germs, rabbit reticulocytes, plant cells, insect cells, or animal cells, as a source are known.

Meanwhile, PURE system is a reconstituted cell-free translation system prepared by individually extracting and purifying protein factors necessary for translation in *E. coli*, energy-regenerating enzymes and ribosomes and mixing them with tRNAs, amino acids, ATPs, GTPs, and such. Since this system has a low content of impurities and is a reconstituted system, a system free from protein factors and amino acids to be excluded can be created easily ((i) Nat Biotechnol. 2001; 19: 751-5. Cell-free translation reconstituted with purified components. Shimizu Y, Inoue A, Tomari Y, Suzuki T, Yokogawa T, Nishikawa K, Ueda T; (ii) Methods Mol Biol. 2010; 607: 11-21. PURE technology. Shimizu Y, Ueda T.).

In a non-limiting embodiment, the present invention provides compounds represented by the following general formula (VIII) or (IX). These compounds carry the protecting group P1 on the main chain amino group of the amino acid:

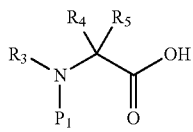
(VIII)

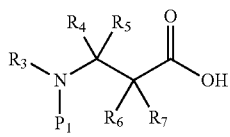
(IX)

(wherein $R_3$, $R_4$, and $R_5$ each independently are a hydrogen atom, an alkyl, an alkenyl, an alkynyl, an aryl, a heteroaryl, an aralkyl, or a cycloalkyl, and these groups are optionally substituted, or $R_3$ and $R_4$, or $R_3$ and R5 may form a ring together with an atom to which they are bonded; R6 and $R_7$ each independently are a hydrogen atom or a methyl; and P1 is a protecting group that is deprotected by an enzyme, a reducing agent, and/or a photoreaction).

While not being limited to the following, P1 in the formula is preferably a protecting group recognized by penicillin amidohydrolases, esterases, or aminopeptidases.

Specific examples of such P1 include protecting groups represented by the following general formula (I) or (II) which has the moiety X1 recognized by penicillin amidohydrolases; the following general formula (III) which has the moiety X2 recognized by esterases; or the following general formula (XII) which has the moiety X3 recognized by aminopeptidases.

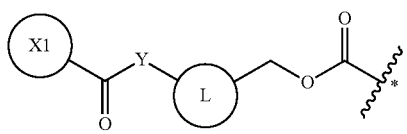
(I)

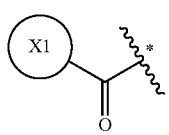
(II)

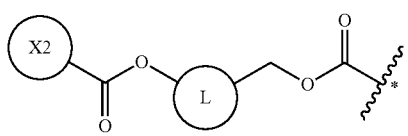
(III)

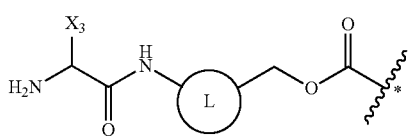
(XII)

(wherein Y is NH or an oxygen atom; and L is a single bond, an arylene, or a heteroarylene).

More specifically, $P_1$ in the formula is preferably $P_1$ in which the moiety X1 in the above-mentioned formula (I) is the following general formula (IV) or a 2-thienylmethyl, or the moiety X2 in the above-mentioned formula (III) is an optionally substituted alkyl, an optionally substituted aralkyl, or an optionally substituted cycloalkyl, and is particularly preferably a methyl, an ethyl, a benzyl, or a n-propyl:

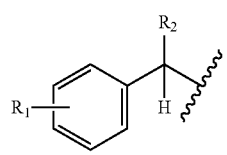
(IV)

(wherein $R_1$ and $R_2$ each independently are a hydrogen atom, a hydroxyl, a fluoro, a chloro, a bromo, an amino, a nitro, or a methoxy).

More specifically, the above-mentioned formula (XII) is preferably the following general formula (XIII).

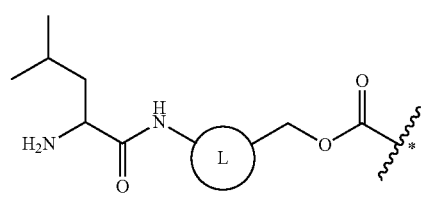
(XIII)

More specifically, such groups include a 4-(2-(4-fluorophenyl)acetamide)benzyloxy carbonyl (F-Pnaz) group:

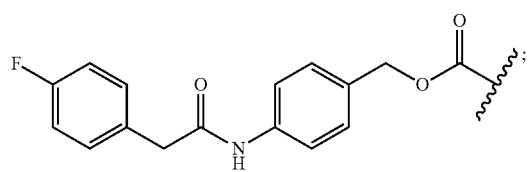 [SMILES: *C(=O)OCc1ccc(NC(=O)Cc2ccc(F)cc2)cc1]

a 4-(propionyloxy)benzyloxycarbonyl (Etez) group:

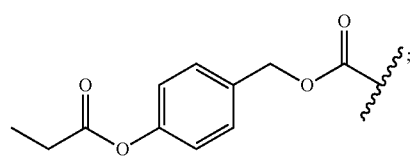 [SMILES: *C(=O)OCc1ccc(OC(=O)CC)cc1]

and
a (S)-((4-(2-amino-4-methylpentanamide)benzyl)oxy)carbonyl (Leuz) group:

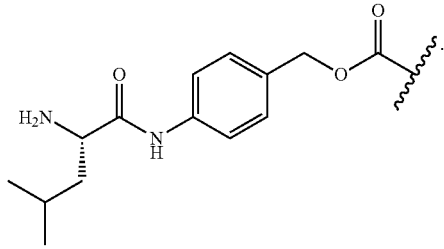 [SMILES: *C(=O)OCc1ccc(NC(=O)[C@@H](N)CC(C)C)cc1]

$P_1$ in the formula may be a protecting group represented by the following general formula (V) or an azide group formed together with the amino group of a main chain (an azide group that masks the amino group of a main chain):

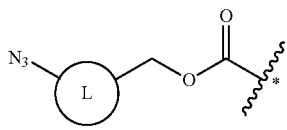

(V)

(wherein L is a single bond, an arylene, or a heteroarylene).

These protecting groups can be deprotected by reducing agents (preferably TCEP). More specifically, such protecting groups include, for example, a 4-azidobenzyloxycarbonyl group (Acbz) or an azidomethyloxycarbonyl group (Azoc).

In a non-limiting embodiment, the present invention provides compounds represented by the following general formula (X) or (XI). These compounds are formed by linking a compound represented by the general formula (VIII) or (IX) with pCpA or pdCpA:

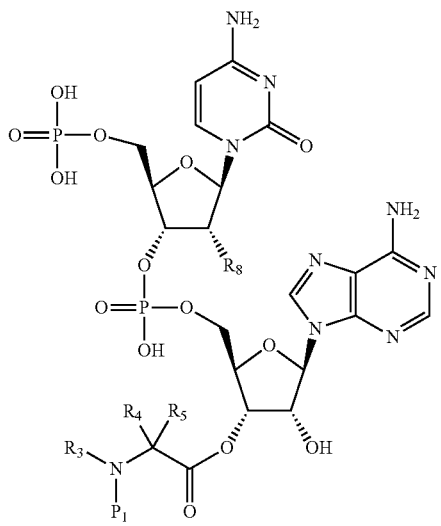

(X)

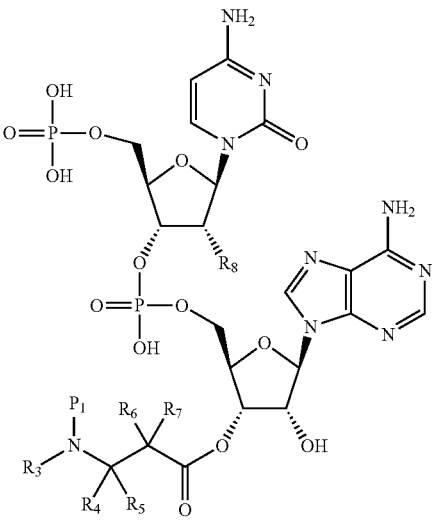

(XI)

(wherein $R_3$ to $R_7$ and $P_1$ have the same meaning as $R_3$ to $R_7$ and $P_1$ defined in formula (VIII) or (IX) mentioned above, and $R_8$ is a hydrogen atom or a hydroxyl).

Furthermore, the present invention relates to aminoacyl-tRNAs formed by linking the compound of the above-mentioned formula (X) or (XI) with a tRNA.

Furthermore, the present invention relates to aminoacyl-tRNAs formed by linking the compound of the above-mentioned formula (VIII) or (IX) with a tRNA.

The above-mentioned aminoacyl-tRNAs are useful in efficient translation of peptides comprising the amino acids in the present invention. The above-mentioned aminoacyl-tRNAs can be obtained by methods well known to those skilled in the art.

In a non-limiting embodiment, the present invention provides methods of synthesizing peptides, which comprise a step of deprotecting one or more types of constituents having protecting groups of cell-free translation systems and a translation step, the deprotecting and translation being performed in the cell-free translation systems, wherein the deprotecting and translation steps are performed in parallel. While not being limited to the following, enzymes or reducing agents are preferably used for the deprotection in the above-mentioned embodiments. The descriptions made above can be referred to appropriately for the types of enzymes and reducing agents, the types of protecting groups, the types of amino acids, and such used in this embodiment.

The "constituent of a cell-free translation system" in the above-mentioned embodiment is not limited as long as it is a constituent included in a cell-free translation system used when ribosomally synthesizing peptides comprising amino acids.

In a non-limiting embodiment, the present invention provides methods of producing a complex of a peptide which comprises one or more types of amino acid residues and has a cyclic portion and a nucleic acid which encodes the peptide, or producing a library comprising the complexes, the method comprising the steps of synthesizing the peptide(s) of the present invention and cyclizing the synthesized peptide(s). While not being limited to the following, the synthesized peptides are preferably cyclized by amide bonds, thioether bonds, disulfide bonds, ether bonds, ester bonds, thioester bonds, or carbon-carbon bonds.

mRNA Display

"Nucleic acid" in the present invention may include deoxyribonucleic acids (DNAs), ribonucleic acids (RNAs), or nucleotide derivatives having artificial bases. Peptide nucleic acids (PNAs) may also be included. Nucleic acids of the present invention may be any of these nucleic acids or hybrids thereof as long as they retain the genetic information of interest. More specifically, the nucleic acids according to the present invention also include DNA-RNA hybrid nucleotides, and chimeric nucleic acids in which different nucleic acids, such as DNA and RNA, are linked together to make a single strand.

In the present invention, nucleic acid libraries comprising these nucleic acids as templates such as display libraries can suitably be used.

The display library refers to a library in which peptides as phenotypes are associated with their peptide-encoding RNAs or DNAs as genotypes. The library is contacted with desired immobilized targets, and peptides binding to the targets can be enriched by washing away molecules unbound with the targets (panning). The gene information associated with the peptides selected through such a process can be analyzed to determine the sequences of the proteins bound to the targets. For example, a method using the nonspecific conjugation of an antibiotic puromycin, an aminoacyl-tRNA analog, to proteins during their mRNA translation elongation in the ribosome has been reported as mRNA display (Proc. Natl. Acad. Sci. USA. 1997; 94: 12297-302. RNA-peptide fusions for the in vitro selection of peptides and proteins. Roberts, R. W., Szostak, J. W.) or in vitro virus (FEBS Lett. 1997; 414: 405-8. In vitro virus: bonding of mRNA bearing puromycin at the 3'-terminal end to the C-terminal end of its encoded protein on the ribosome in vitro. Nemoto, N., Miyamoto-Sato, E., Husimi, Y, Yanagawa, H.).

By conjugating spacers such as puromycin to the 3'-ends of an mRNA library obtained by transcription from a DNA library containing a promoter such as T7 promoter, when these mRNAs are translated into proteins in cell-free translation systems, puromycin is mistakenly recognized as amino acid by the ribosome, and is incorporated into proteins. This causes the mRNA to be linked to the proteins encoded thereby, thus a library in which mRNAs are associated with their products can be obtained. This process, which does not involve the transformation of *E. coli* or the like, attains high efficiency and can construct a large-scale display library (1012 to 1014 types). cDNA is synthesized from the mRNA serving as a tag containing genetic information bound to the protein enriched and selected by panning, and then amplified by PCR. The amplified products can be sequenced to determine the sequence of the protein linked to the desired target substance. DNA libraries used as a template for the library can be obtained by mixing bases for sites where amino acid residues are not fixed and synthesizing. They can be synthesized as repetitions of triplets for mixture (N) of 4 types of bases A, T, G and C or as those in which the first and second letters in each codon is N and the third letter is mixture of two types of bases such as W, M, K, or S. There is another method in which the third base may be set to one type if types of amino acids introduced are reduced to 16 or fewer.

In addition to the mRNA display, the following libraries are known as display libraries using cell-free translation systems:

cDNA display in which peptide-encoding cDNAs are linked to peptide-puromycin complexes (Nucleic Acids Res. 2009; 37 (16): e108. cDNA display: a novel screening method for functional disulfide-rich peptides by solid-phase synthesis and stabilization of mRNA-protein fusions. Yamaguchi, J., Naimuddin, M., Biyani, M., Sasaki, T., Machida, M., Kubo, T., Funatsu, T., Husimi, Y, Nemoto, N.); ribosome display which utilizes characteristics that ribosome-translation product complexes during mRNA translation is relatively stable (Proc. Natl. Acad. Sci. USA. 1994; 91: 9022-6. An in vitro polysome display system for identifying ligands from very large peptide libraries. Mattheakis, L C., Bhatt, R R., Dower, W J.);

covalent display which utilizes characteristics that bacteriophage endonuclease P2A forms covalent bond with DNAs (Nucleic Acids Res. 2005; 33: e10. Covalent antibody display—an in vitro antibody—DNA library selection system. Reiersen, H., Lobersli, I., Loset, G A., Hvattum, E., Simonsen, B., Stacy, J E., McGregor, D., Fitzgerald, K., Welschof, M., Brekke, O H., Marvik, O J.); and CIS display which utilizes characteristics that a microbial plasmid replication initiator protein RepA binds to a replication origin ori (Proc. Natl. Acad. Sci. USA. 2004; 101: 2806-10. CIS display: In vitro selection of peptides from libraries of protein-DNA complexes. Odegrip, R., Coomber, D., Eldridge, B., Hederer, R., Kuhlman, P A., Ullman, C., FitzGerald, K., McGregor, D.). Also, in vitro compartmentalization is known in which a transcription-translation system is encapsulated into a water-in-oil emulsion or liposome per DNA molecule constituting a DNA library, and subjected to translation reaction (Nat. Biotechnol. 1998; 16: 652-6. Man-made cell-like compartments for molecular evolution. Tawfik, S, Griffiths, D.). The methods described above can be employed appropriately using known methods.

In the present invention, these nucleic acid libraries can be translated by using the above-described cell-free translation systems. When using the cell-free translation systems, a spacer-encoding sequence is preferably included downstream of the nucleic acid of interest. The spacer sequences include, but are not limited to, sequences containing glycine or serine. In addition, it is preferred that a linker formed by RNA, DNA, hexaethylene glycol (spc18) polymers (e.g., 5 polymers) or the like is contained between the nucleic acid library and a compound which is incorporated into a peptide during ribosomal translation such as puromycin or derivative thereof.

Screening/Production Methods for Cyclic Peptides Having Desired Activity

Examples of methods of producing peptide-nucleic acid complexes having desired activity include a production method comprising the following steps:

(i) ribosomally synthesizing noncyclic peptides having 9 to 13 natural amino acid and/or amino acid analog residues in total using the above-mentioned peptide synthesis method in the present invention and forming noncyclic peptide-nucleic acid complexes wherein in each complex a noncyclic peptide is linked to a nucleic acid sequence encoding the noncyclic peptide through a linker;

(ii) cyclizing the noncyclic peptides of the complexes ribosomally synthesized in step (i) by an amide bond or a carbon-carbon bond to form cyclic peptides in which a total number of natural amino acid and/or amino acid analog residues in a cyclic portion is 5 to 12; and (iii) contacting a library of the peptide-nucleic acid complexes having cyclic portions as obtained in step (ii)

with a target substance and selecting a complex having binding activity to the target substance.

Furthermore, peptides having desired activity can be produced from the complex selected by the above-mentioned steps.

Examples include a preparation method comprising the following steps:
(iv) obtaining sequence information of a peptide based on the nucleotide sequence of the complex selected in step (iii) above; and
(v) chemically synthesizing the peptide based on the sequence information obtained in step (iv) above.

In the above-mentioned production step, the noncyclic peptides may contain an α-hydroxycarboxylic acid, and an optionally protected natural amino acid and/or amino acid analog having an amino group at the side chain. The above preparation method may further comprise the step of forming a branched site by chemically reacting the α-hydroxycarboxylic acid with the natural amino acid and/or amino acid analog having an amino group at the side chain before or after step (ii) of forming the cyclic peptides. This step enables preparation of cyclic peptides having linear portions at various positions of the cyclic portion.

Here, natural amino acids and/or amino acid analogs removed by post-translational modification are not included in the total number of natural amino acids and/or amino acid analogs described in step (i) above and in the total number of natural amino acid and/or amino acid analog residues in the cyclic portion described in step (ii).

In the present production method, chemical modification for optimizing the aforementioned cyclic peptides may be carried out in step (ii) or step (v). In the present invention, the target substances are preferably in vivo molecules. The "in vivo molecule" in the present invention is not particularly limited as long as it is a molecule found in vivo. The in vivo molecule is preferably a molecule serving as a target in the treatment of a disease. Particularly, the in vivo molecule is preferably a molecule not having a cavity to which conventional small-molecule compounds having a molecular weight of less than 500 can bind, or an intracellular protein, nucleic acid, intracellular region of membrane protein or transmembrane domain of membrane protein inaccessible by high-molecular compounds such as antibodies.

Specific examples thereof include transcription factors such as STAT, AP1, CREB and SREBP; G-protein-coupled receptors (GPCRs) such as muscarinic acetylcholine receptors, cannabinoid receptors, GLP-1 receptors, and PTH receptors; cytokines and their receptors such as TNF, TNFR, IL-6 and IL-6R; ion channel receptors such as P2X receptors and nicotinic acetylcholine receptors; ion channels; transporters; and microRNAs such as miR-21 and miR206.

The cyclic portion may be formed by using, for example, the cyclization reaction mentioned above; and an amide bond or carbon-carbon bond can be formed by the cyclization reaction.

Also, a known technology, for example, a cell-free translation system can be used in the step of synthesizing the cyclic peptide-nucleic acid complexes. Specifically, the complexes can be prepared using the aforementioned methods.

In a non-limiting embodiment, the present invention provides use of a protecting group which is deprotected by an enzyme, a reducing agent, or a photoreaction in a peptide synthesis method, wherein the method comprises performing, in parallel, a step of deprotecting one or more types of protecting group-bearing constituents of a cell-free translation system and a translation step, the protecting and translation being performed in the cell-free translation system.

In a non-limiting embodiment, the present invention provides use of a protecting group which is deprotected by an enzyme, a reducing agent, or a photoreaction in a peptide synthesis method, wherein the method comprises performing, in parallel, a step of deprotecting a protecting group of an amino acid and a translation step, the protecting and translation being performed in a cell-free translation system that comprises a tRNA linked to the amino acid having the protecting group.

In a non-limiting embodiment, the present invention provides a protecting group for use in a peptide synthesis method, which protecting group is deprotected by an enzyme, a reducing agent, or a photoreaction, wherein the method comprises a step of deprotecting one or more types of protecting group-bearing constituents of a cell-free translation system and a translation step, the deprotecting and translation being performed in the cell-free translation system, wherein the deprotecting and translation steps are performed in parallel.

In a non-limiting embodiment, the present invention provides a protecting group for use in a peptide synthesis method, which protecting group is deprotected by an enzyme, a reducing agent, or a photoreaction, wherein the method comprises a step of deprotecting a protecting group of an amino acid and a translation step, the deprotecting and translation being performed in a cell-free translation system that comprises a tRNA linked to the amino acid comprising the protecting group, wherein the deprotecting and translation steps are performed in parallel.

All prior art references cited herein are incorporated by reference into this description.

EXAMPLES

The present invention will be further illustrated with reference to the following Examples but is not limited thereto.

The following abbreviations are used in the Examples.
DCM Dichloromethane
DIPEA N,N-diisopropylethylamine
DMF Dimethylformamide
DMSO Dimethylsulfoxide
DTT Dithiothreitol
FA Formic acid
TFA Trifluoroacetic acid
TFE Trifluoroethanol
THF Tetrahydrofuran
TCEP Tris(2-carboxyethyl)phosphine
NMP N-Methyl-2-pyrrolidone
DBU 1,8-Diazabicyclo[5.4.0]-7-undecene
HOAt 1-Hydroxybenzotriazole
DIC N,N-Diisopropylcarbodiimide
PGA Penicillin G acylase
Acbz 4-Azidobenzyloxycarbonyl group:

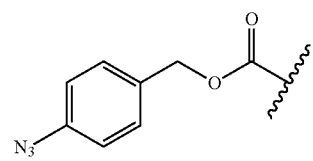 [SMILES: *C(=O)OCc1ccc(N=[N+]=[N-])cc1]

F-Pnaz 4-(2-(4-Fluorophenyl)acetamide)benzyloxycarbonyl group:

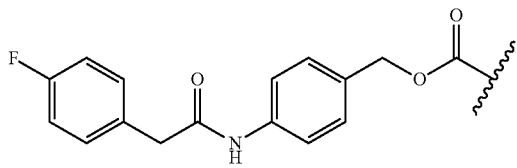 [SMILES: *C(=O)OCc1ccc(NC(=O)Cc2ccc(F)cc2)cc1]

Pen 4-Pentenoyl group
CH₂CN Cyanomethyl group
DMAP 4,4-Dimethylaminopyridine
Etez 4-(Propionyloxy)benzyloxycarbonyl group:

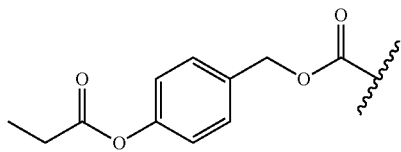 [SMILES: *C(=O)OCc1ccc(OC(=O)CC)cc1]

Leuz(S)-((4-(2-amino-4-methylpentanamide)benzyl)oxy) carbonyl group:

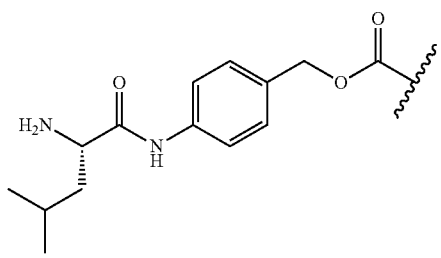 [SMILES: *C(=O)OCc1ccc(NC(=O)[C@@H](N)CC(C)C)cc1]

Furthermore, the LCMS analysis conditions are as follows.

Example 1 Synthesis of pCpA-Amino Acids Used for Cell-Free Translation Systems

Aminoacylated pCpAs (ts05, ts07, ts09, ts14, ts19, ts20, ts23, ts26, ts29, TS03, TS06, TS09, TS12, TS15, TS18, TS21, TS24, TS29, TS34, and TS37) were synthesized according to the following scheme.

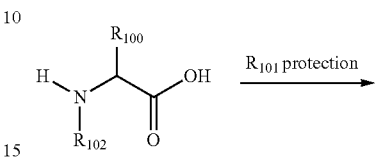

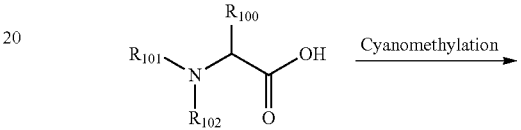

TABLE 1

| Fractionation Condition | Apparatus | Column (I.D. × Length (mm)) | Mobile phase | Gradient (A/B) | Flow rate (ml/min) | Column Temperature (° C.) | Wavelength |
|---|---|---|---|---|---|---|---|
| SQD FA05 | Acquity UPLC/SQD | Aldrich Ascentis Express C18 (2.1 × 50) | A) 0.1% FA, H2O B) 0.1% FA CH3CN | 95/5 => 0/100 (1.0 min) => 0/100 (0.4 min) | 1.0 | 35 | 210-400 nm PDA total |
| SMD method 1 | Shimadzu LCMS-2020 LC-30AD | Waters BEH C18 (2.1 × 50) | A) 0.1% FA, H2O B) 0.1% FA CH3CN | 90/10 => 5/95 (2.0 min) => 5/95 (0.6 min) | 0.7 | 45 | 190-600 nm PDA total |
| SMD method 2 | Nexera/ 2020 | Speed Core C18 (2.1 × 50) | A) 0.1% FA, H2O B) 0.1% FA CH3CN | 95/5 => 0/100 (1.5 min) => 0/100 (0.5 min) | 1.0 | 35 | 210-400 nm PDA total |
| SMD method 3 | Shimadzu LCMS-2020 LC-20AD | Shim-Pack XR-ODS (3.0 × 50) | A) 0.05% TFA, H2O B) 0.05% TFA CH3CN | 95/5 => 0/100 (2.2 min) => 5/95 (1.0 min) | 1.0 | 40 | 190-400 nm PDA total |

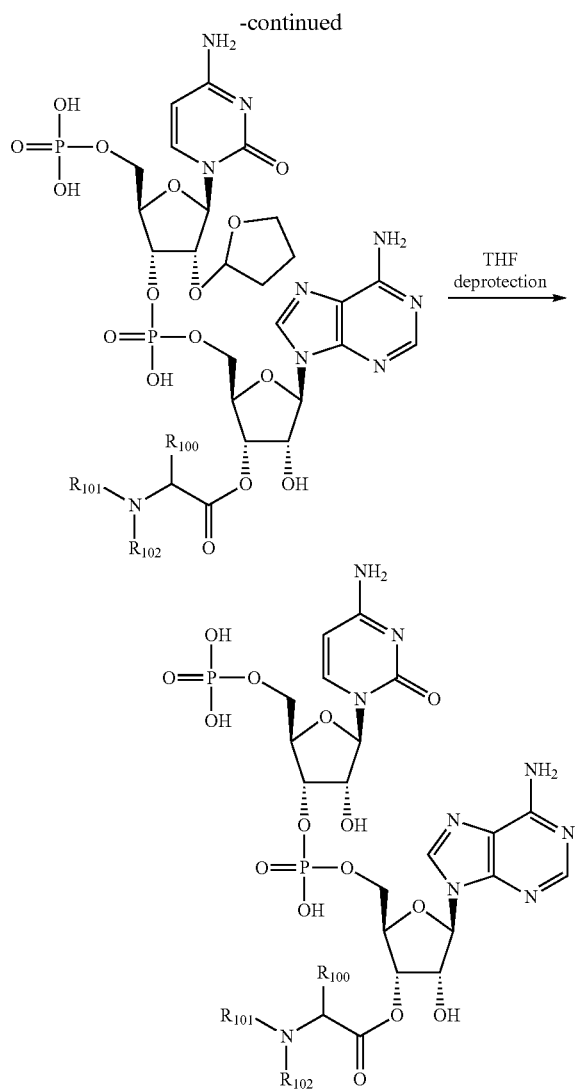

THF
deprotection
→

Synthesis of (S)-1-(((4-azidobenzyl)oxy)carbonyl) azetidine-2-carboxylic acid (Compound ts01, Acbz-Aze(2)-OH)

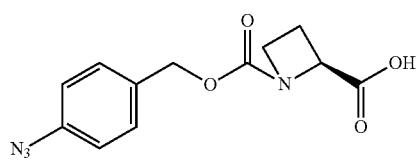 [SMILES: [N-]=[N+]=Nc1ccc(COC(=O)N2CC[C@H]2C(=O)O)cc1]

Under a nitrogen atmosphere, DMSO (5.0 mL) was added at room temperature to a mixture of (S)-azetidine-2-carboxylic acid (H-Aze(2)-OH) (50.6 mg, 0.50 mmol), n-butylglycine (H-nBuG-OH) (65.6 mg, 0.50 mmol), (S)-2-((((4-azidobenzyl)oxy)carbonyl)amino)-3-(pyridin-3-yl)propanoic acid (83.0 mg, 0.50 mmol), and 4-azidobenzyl (4-nitrophenyl)carbonate (566 mg, 1.80 mmol) synthesized by the method described in the literature (Bioconjugate Chem. 2008, 19, 714). After stirring at room temperature for five minutes, triethylamine (418 μL, 3.00 mmol) was added at room temperature. The reaction mixture was stirred at room temperature for 15 hours and then purified by reverse-phase silica gel column chromatography (0.1% aqueous formic acid solution/0.1% formic acid-acetonitrile solution) to give (S)-1-(((4-azidobenzyl)oxy)carbonyl) azetidine-2-carboxylic acid (Compound ts01, Acbz-Aze(2)-OH) (80.0 mg, 58%).

LCMS (ESI) m/z=275 (M−H)⁻

Retention time: 0.60 minutes (analysis condition SQDFA05)

Synthesis of N-(((4-azidobenzyl)oxy)carbonyl)-N-butylglycine (Compound ts02, Acbz-nBuG-OH)

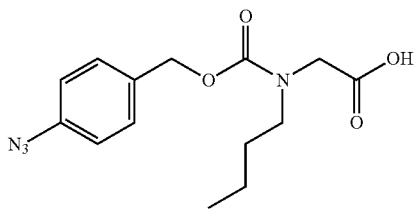 [SMILES: CCCCN(CC(=O)O)C(=O)OCc1ccc(N=[N+]=[N-])cc1]

Under a nitrogen atmosphere, DMSO (5.0 mL) was added at room temperature to a mixture of (S)-azetidine-2-carboxylic acid (H-Aze(2)-OH) (50.6 mg, 0.50 mmol), n-butylglycine (H-nBuG-OH) (65.6 mg, 0.50 mmol), (S)-2-((((4-azidobenzyl)oxy)carbonyl) amino)-3-(pyridin-3-yl)propanoic acid (83.0 mg, 0.50 mmol), and 4-azidobenzyl (4-nitrophenyl)carbonate (566 mg, 1.80 mmol) synthesized by the method described in the literature (Bioconjugate Chem. 2008, 19, 714). After stirring at room temperature for five minutes, triethylamine (418 μL, 3.00 mmol) was added at room temperature. The reaction mixture was stirred at room temperature for 15 hours and then purified by reverse-phase silica gel column chromatography (0.1% aqueous formic acid solution/0.1% formic acid-acetonitrile solution) to give N-(((4-azidobenzyl)oxy)carbonyl)-N-butylglycine (Compound ts02, Acbz-nBuG-OH) (70.0 mg, 46%).

LCMS (ESI) m/z=305 (M−H)⁻

Retention time: 0.77 minutes (analysis condition SQDFA05)

Synthesis of (S)-2-((((4-azidobenzyl)oxy)carbonyl) amino)-3-(pyridin-3-yl)propanoic acid (Compound ts03, Acbz-Ala(3-Pyr)-OH)

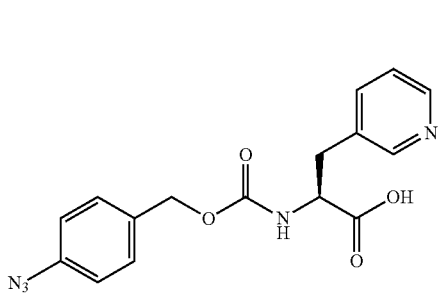 [SMILES: [N-]=[N+]=Nc1ccc(COC(=O)N[C@@H](Cc2cccnc2)C(=O)O)cc1]

Under a nitrogen atmosphere, DMSO (5.0 mL) was added at room temperature to a mixture of (S)-azetidine-2-carboxylic acid (H-Aze(2)-OH) (50.6 mg, 0.50 mmol), n-butylglycine (H-nBuG-OH) (65.6 mg, 0.50 mmol), (S)-2-((((4-azidobenzyl)oxy)carbonyl)amino)-3-(pyridin-3-yl)propanoic acid (83.0 mg, 0.50 mmol), and 4-azidobenzyl (4-nitrophenyl)carbonate (566 mg, 1.80 mmol) synthesized by the method described in the literature (Bioconjugate Chem. 2008, 19, 714). After stirring at room temperature for five minutes, triethylamine (418 µL, 3.00 mmol) was added at room temperature. The reaction mixture was stirred at room temperature for 15 hours and then purified by reverse-phase silica gel column chromatography (0.1% aqueous formic acid solution/0.1% formic acid-acetonitrile solution) to give (S)-2-((((4-azidobenzyl)oxy)carbonyl)amino)-3-(pyridin-3-yl)propanoic acid (Compound ts03, Acbz-Ala(3-Pyr)-OH) (105.0 mg, 62%).

LCMS (ESI) m/z=340 (M−H)⁻

Retention time: 0.43 minutes (analysis condition SQDFA05)

Synthesis of 2-(cyanomethyl) 1-(4-azidobenzyl) (S)-azetidine-1,2-dicarboxylate (Compound ts04, Acbz-Aze(2)-OCH₂CN)

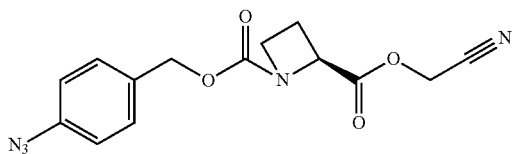 [SMILES: N#CCOC(=O)[C@@H]1CCN1C(=O)OCc1ccc(N=[N+]=[N-])cc1]

Under a nitrogen atmosphere, (S)-1-(((4-azidobenzyl)oxy)carbonyl)azetidine-2-carboxylic acid (Compound ts01, Acbz-Aze(2)-OH) (70.0 mg, 0.25 mmol) and N-ethyl-isopropylpropan-2-amine (DIPEA) (0.089 mL, 0.50 mmol) were dissolved in acetonitrile (507 µL). 2-Bromoacetonitrile (0.026 mL, 0.38 mmol) was added at 0° C., and this was stirred at room temperature for two hours. The reaction solution was concentrated to give 2-(cyanomethyl) 1-(4-azidobenzyl) (S)-azetidine-1,2-dicaroxylate (Compound ts04, Acbz-Aze(2)—OCH₂CN) as a crude product. The obtained crude product was dissolved in acetonitrile (2.00 mL), and was directly used in the next step.

LCMS (ESI) m/z=316 (M+H)⁺

Retention time: 0.72 minutes (analysis condition SQDFA05)

Synthesis of 1-(4-azidobenyl) 2-((2R,3S,4R,5R)-2-((((((2R,3S,4R,5R)-5-(4-amino-2-oxopyrimidin-1 (2H)-yl)-4-hydroxy-2-((phosphonooxy)methyl)tetrahydrofuran-3-yl)oxy) (hydroxy)phosphoryl)oxy) methyl)-5-(6-amino-9H-purin-9-yl)-4-hydroxy-tetrahydrofuran-3-yl) (2S)-azetidine-1,2-dicarboxylate (Compound ts05, Acbz-Aze(2)-pCpA)

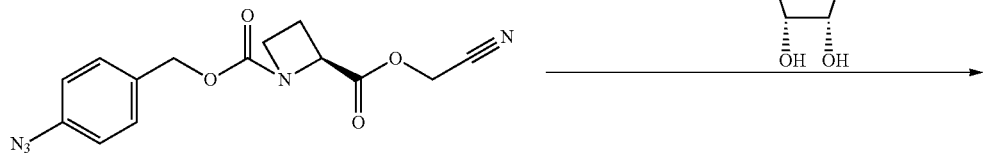

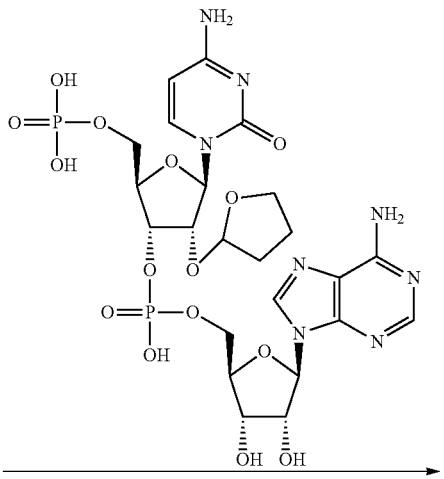

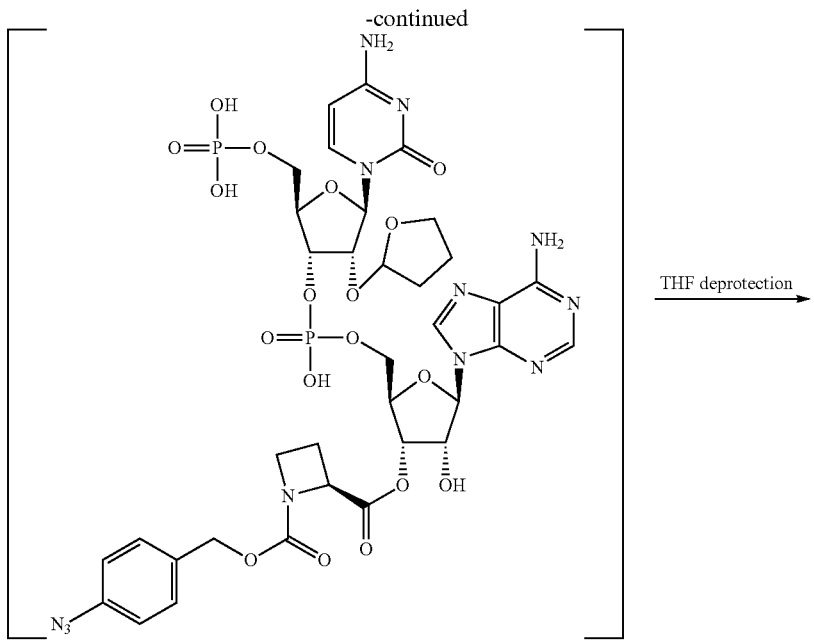

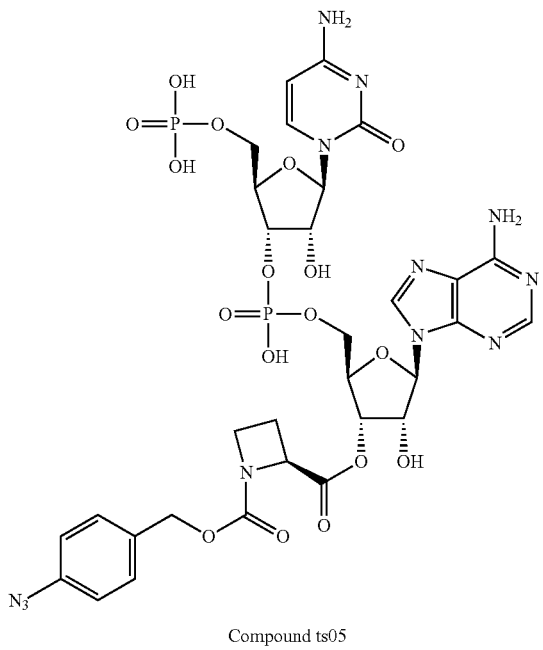

Compound ts05

((2R,3R,4R,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)-4-((tetrahydrofuran-2-yl)oxy)tetrahydrofuran-2-yl) methyl dihydrogenphosphate (Compound pc01) (85.0 mg, 0.117 mmol) was dissolved in Buffer A (40 mL), a solution of 2-(cyanomethyl) 1-(4-azidobenzyl) (S)-azetidine-1,2-dicaroxylate (Compound ts04, Acbz-Aze(2)—OCH₂CN) in acetonitrile (2.00 mL) was added to it, and this was stirred at room temperature for 90 minutes. The reaction solution was cooled to 0° C., and then trifluoroacetic acid (2 mL) was added to it. After stirring the reaction solution at 0° C. for 30 minutes, this was purified by reverse-phase silica gel column chromatography (0.05% aqueous trifluoroacetic acid solution/0.05% trifluoroacetic acid-acetonitrile) to give the titled compound (Compound ts05, Acbz-Aze(2)-pCpA) (6.0 mg, 8.5%).

LCMS (ESI) m/z=911 (M+H)⁺

Retention time: 0.43 minutes (analysis condition SQDFA05)

Buffer A was prepared as follows.

Acetic acid was added to an aqueous solution of N,N,N-trimethylhexadecan-1-aminium chloride (6.40 g, 20 mmol) and imidazole (6.81 g, 100 mmol) to give Buffer A of 20 mM N,N,N-trimethylhexadecan-1-aminium and 100 mM imidazole at pH 8 (1 L).

Synthesis of cyanomethyl N-(((4-azidobenzyl)oxy)carbonyl)-N-butylglycinate (Compound ts06, Acbz-nBuG-OCH₂CN)

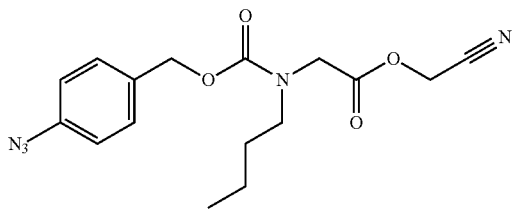 [SMILES: CCCCN(CC(=O)OCC#N)C(=O)OCc1ccc(N=[N+]=[N-])cc1]

Under a nitrogen atmosphere, N-(((4-azidobenzyl)oxy)carbonyl)-N-butylglycine (Compound ts02, Acbz-nBuG-OH) (70.0 mg, 0.23 mmol) and N-ethyl-isopropylpropan-2-amine (DIPEA) (0.080 mL, 0.46 mmol) were dissolved in acetonitrile (229 μL). 2-Bromoacetonitrile (0.023 mL, 0.34 mmol) was added at 0° C., and this was stirred at room temperature for two hours. The reaction solution was concentrated to give cyanomethyl N-(((4-azidobenzyl)oxy)carbonyl)-N-butylglycinate (Compound ts06, Acbz-nBuG-OCH₂CN) as a crude product. The obtained crude product was dissolved in acetonitrile (2.00 mL) and was directly used in the next step.

LCMS (ESI) m/z=346 (M+H)⁺

Retention time: 0.87 minutes (analysis condition SQDFA05)

Synthesis of (2R,3S,4R,5R)-2-(((((2R,3S,4R,5R)-5-(4-amino-2-oxopyrimidin-1(2H)-yl)-4-hydroxy-2-((phosphonooxy)methyl)tetrahydrofuran-3-yl)oxy)(hydroxy)phosphoryl)oxy) methyl)-5-(6-amino-9H-purin-9-yl)-4-hydroxytetrahydrofuran-3-yl)-N-(((4-azidobenzyl)oxy)carbonyl)-N-butylglycinate (Compound ts07, Acbz-nBuG-pCpA)

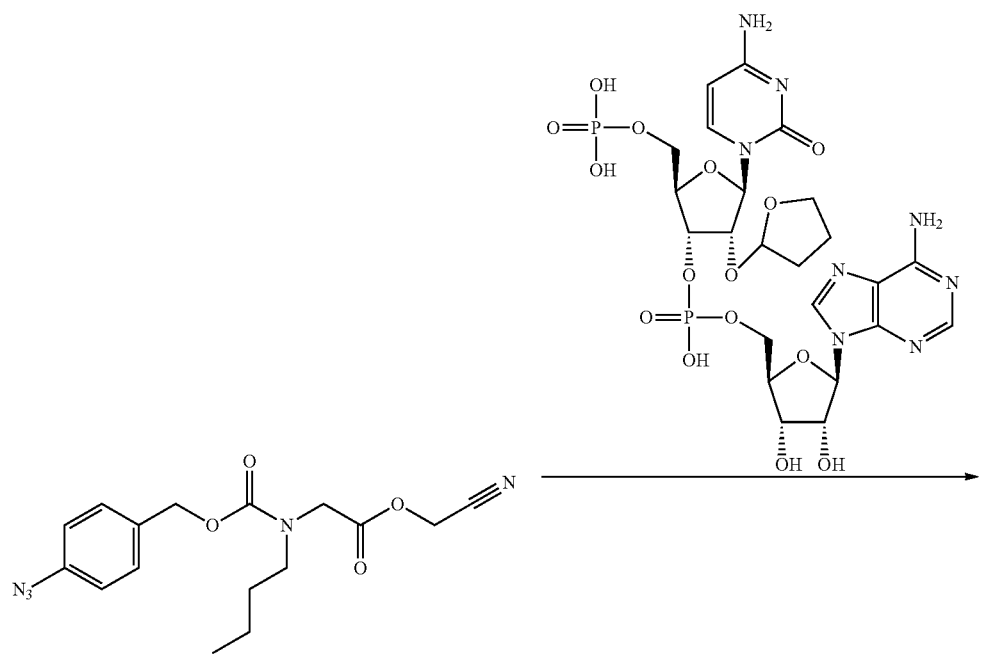

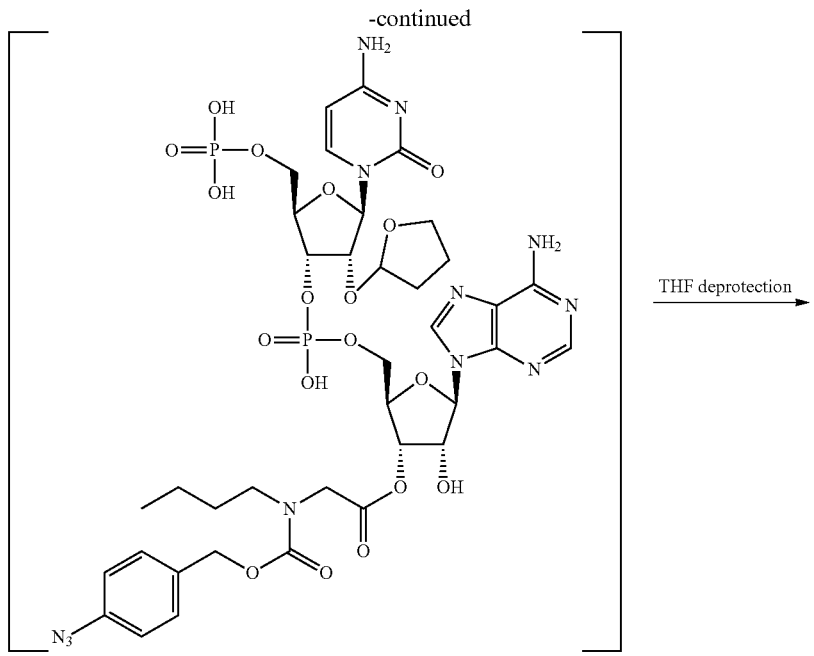

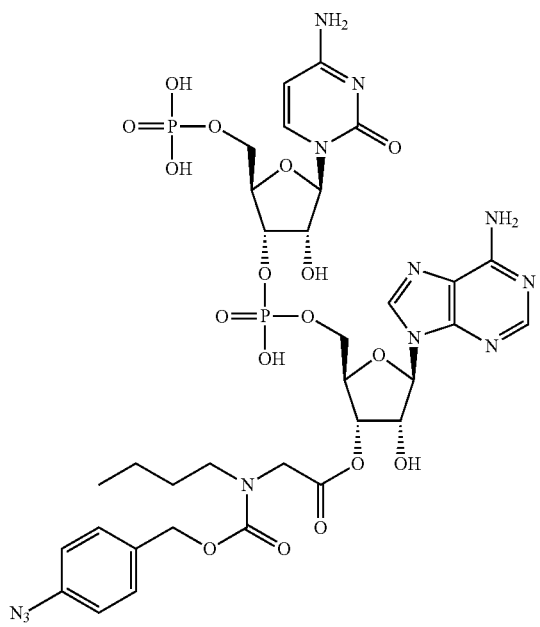

Compound ts07

((2R,3R,4R,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)-4-((tetrahydrofuran-2-yl)oxy)tetrahydrofuran-2-yl) methyl dihydrogenphosphate (Compound pc01) (85.0 mg, 0.117 mmol) was dissolved in Buffer A (40 mL). A solution of cyanomethyl N-(((4-azidobenzyl)oxy)carbonyl)-N-butylglycinate (Compound ts06, Acbz-nBuG-OCH$_2$CN) in acetonitrile (2.00 mL) was added to it, and this was stirred at room temperature for 90 minutes. The reaction solution was cooled to 0° C., and then trifluoroacetic acid (2 mL) was added to it. After stirring the reaction solution at 0° C. for 30 minutes, this was purified by reverse-phase silica gel column chromatography (0.05% aqueous trifluoroacetic acid solution/0.05% trifluoroacetic acid-acetonitrile) to give the titled compound (Compound ts07, Acbz-nBuG-pCpA) (16.0 mg, 21.8%).

LCMS (ESI) m/z=941 (M+H)$^+$

Retention time: 0.52 minutes (analysis condition SQDFA05)

Synthesis of cyanomethyl (S)-2-((((4-azidobenzyl)oxy)carbonyl)amino)-3-(pyridin-3-yl)propanoate (Compound ts08, Acbz-Ala(3-Pyr)-OCH₂CN)

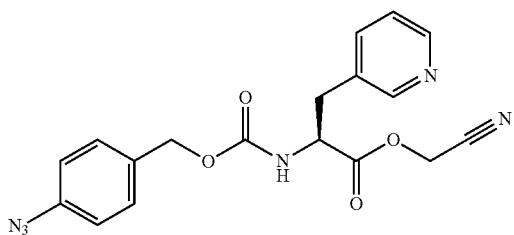 [SMILES: N#CCOC(=O)[C@H](Cc1cccnc1)NC(=O)OCc1ccc(N=[N+]=[N-])cc1]

Under a nitrogen atmosphere, (S)-2-((((4-azidobenzyl)oxy)carbonyl)amino)-3-(pyridin-3-yl)propanoic acid (Compound ts03, Acbz-Ala(3-Pyr)-OH) (80.0 mg, 0.23 mmol) and N-ethyl-isopropylpropan-2-amine (DIPEA) (0.082 mL, 0.47 mmol) were dissolved in acetonitrile (234 μL). 2-Bromoacetonitrile (0.024 mL, 0.35 mmol) was added at 0° C., and this was stirred at room temperature for two hours. The reaction solution was concentrated to give cyanomethyl (S)-2-((((4-azidobenzyl)oxy)carbonyl)amino)-3-(pyridin-3-yl)propanoate (Compound ts08, Acbz-Ala(3-Pyr)-OCH₂CN) as a crude product. The obtained crude product was dissolved in acetonitrile (2.00 mL) and was directly used in the next step.

LCMS (ESI) m/z=381 (M+H)⁺

Retention time: 0.51 minutes (analysis condition SQDFA05)

Synthesis of (2R,3S,4R,5R)-2-((((((2R,3S,4R,5R)-5-(4-amino-2-oxopyrimidin-1(2H)-yl)-4-hydroxy-2-((phosphonooxy)methyl)tetrahydrofuran-3-yl)oxy)(hydroxy)phosphoryl)oxy) methyl)-5-(6-amino-9H-purin-9-yl)-4-hydroxytetrahydrofuran-3-yl (2R)-2-((((4-azidobenzyl)oxy)carbonyl)amino)-3-(pyridin-3-yl)propanoate (Compound ts09, Acbz-Ala(3-Pyr)-pCpA)

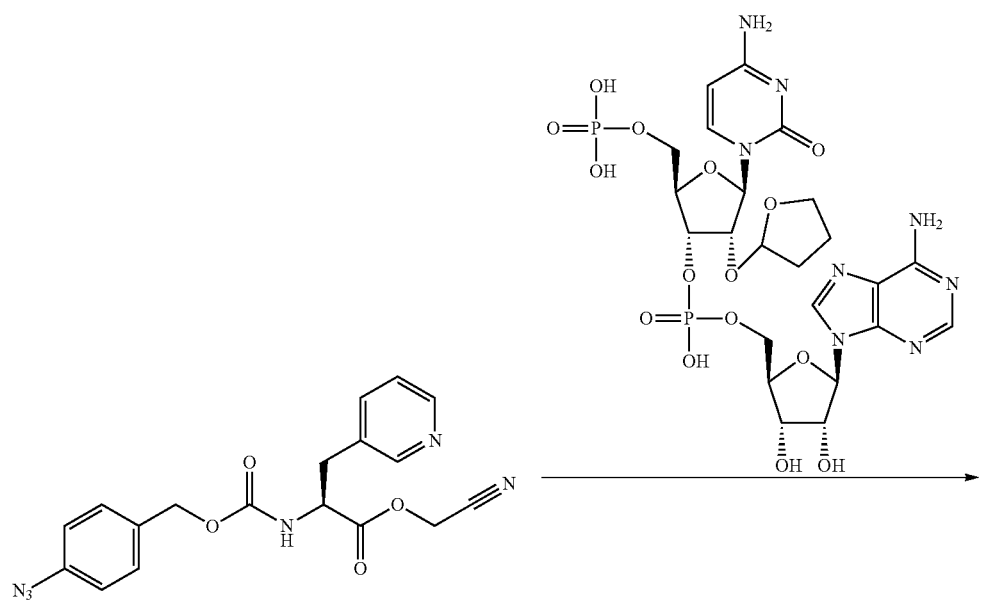

-continued

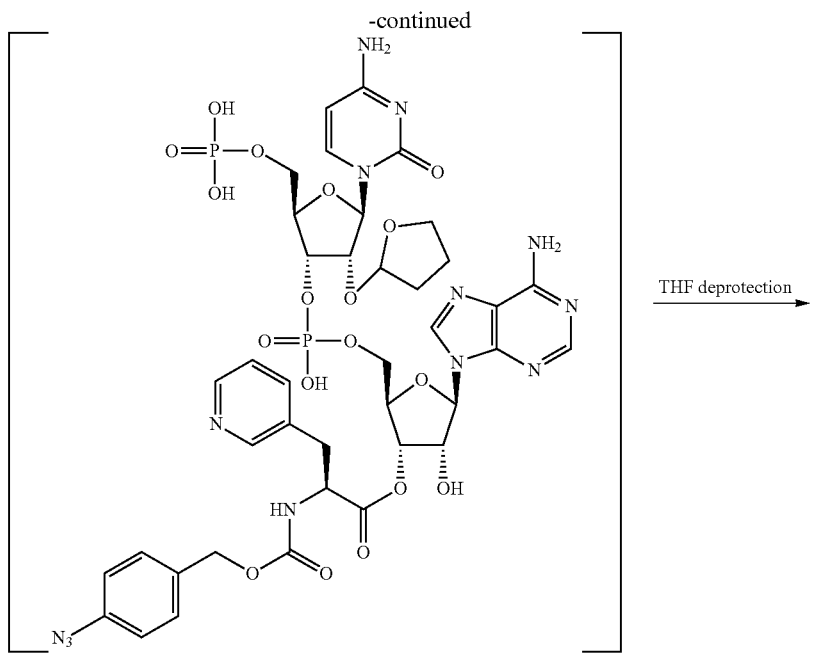

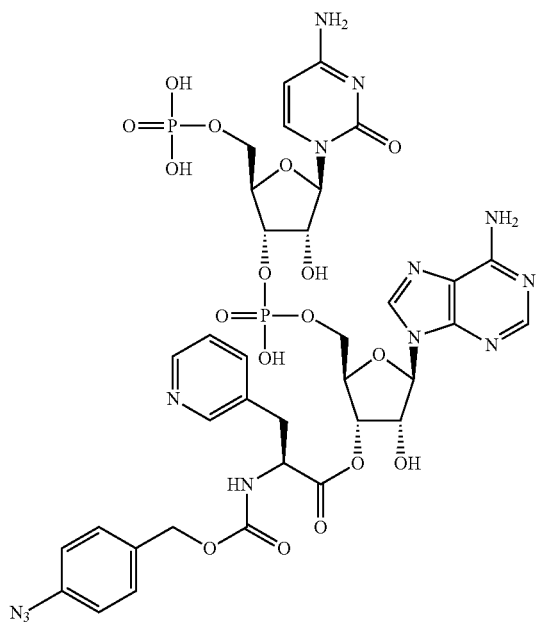

Compound ts09

((2R,3R,4R,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)-4-((tetrahydrofuran-2-yl)oxy)tetrahydrofuran-2-yl)methyl dihydrogenphosphate (Compound pc01) (85.0 mg, 0.117 mmol) was dissolved in Buffer A (40 mL), a solution of cyanomethyl (S)-2-((((4-azidobenzyl)oxy)carbonyl)amino)-3-(pyridin-3-yl)propanoate (Compound ts08, Acbz-Ala(3-Pyr)-OCH$_2$CN) in acetonitrile (2.00 mL) was added to it, and this was stirred at room temperature for 90 minutes. The reaction solution was cooled to 0° C., and then trifluoroacetic acid (2 mL) was added to it. After stirring the reaction solution at 0° C. for 30 minutes, this was purified by reverse-phase silica gel column chromatography (0.05% aqueous trifluoroacetic acid solution/0.05% trifluoroacetic acid-acetonitrile) to give the titled compound (Compound ts09, Acbz-Ala(3-Pyr)-pCpA) (10.0 mg, 13.1%).

LCMS (ESI) m/z=976 (M+H)$^+$

Retention time: 0.36 minutes (analysis condition SQDFA05)

Synthesis of 2-(4-fluorophenyl)-N-(4-(hydroxymethyl)phenyl)acetamide (Compound ts10)

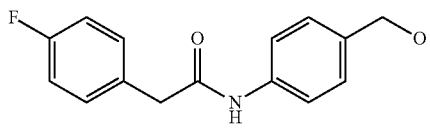 [SMILES: O=C(Cc1ccc(F)cc1)Nc1ccc(CO)cc1]

Under a nitrogen atmosphere, THF (9.7 mL) was added to a mixture of 2-(4-fluorophenyl)acetic acid (300 mg, 1.95 mmol), 4-aminophenylmethanol (264 mg, 2.14 mmol), and DMT-MM (646 mg, 2.34 mmol), and then this was stirred at 40° C. for two hours. The reaction solution was purified by reverse-phase silica gel column chromatography (0.1% aqueous formic acid solution/0.1% formic acid-acetonitrile) to give 2-(4-fluorophenyl)-N-(4-(hydroxymethyl)phenyl)acetamide (Compound ts10) (400.0 mg, 79.0%).

LCMS (ESI) m/z=260 (M+H)$^+$

Retention time: 0.55 minutes (analysis condition SQDFA05)

Synthesis of (4-nitrophenyl)-4-(2-(4-fluorophenyl)acetamide)benzyl carbonate (Compound ts11)

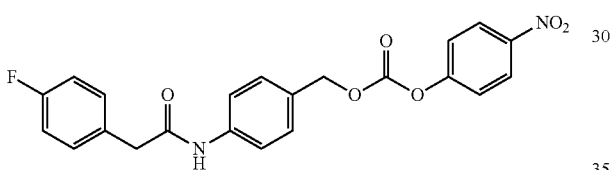

Under a nitrogen atmosphere, 2-(4-fluorophenyl)-N-(4-(hydroxymethyl)phenyl) acetamide (Compound ts10) (300 mg, 1.16 mmol) was dissolved in THF (1.00 mL). Pyridine (0.187 mL, 2.31 mmol) was added, and then the reaction solution was cooled to 0° C. To this reaction solution, a solution of 4-nitrophenylchloroformate (233 mg, 1.16 mmol) in THF (1.13 mL) was slowly added dropwise at 0° C., and then this was stirred at room temperature for two hours. The reaction solution was concentrated, and the obtained residue was washed using 3:1 hexane/ethyl acetate to give (4-nitrophenyl)-4-(2-(4-fluorophenyl)acetamide)benzyl carbonate (Compound ts11) (330.0 mg, 67.2%).

LCMS (ESI) m/z=425 (M+H)$^+$

Retention time: 0.84 minutes (analysis condition SQDFA05)

Synthesis of N-butyl-N-(((4-(2-(4-fluorophenyl)acetamide)benzyl)oxy)carbonyl)glycine (Compound ts12, F-Pnaz-nBuG-OH)

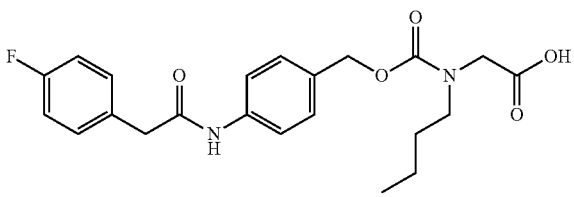 [SMILES: CCCCN(CC(=O)O)C(=O)OCc1ccc(NC(=O)Cc2ccc(F)cc2)cc1]

Under a nitrogen atmosphere, DMF (0.35 mL) was added at room temperature to a mixture of n-butylglycine (H-nBuG-OH) (46.4 mg, 0.35 mmol) and (4-nitrophenyl)-4-(2-(4-fluorophenyl)acetamide)benzyl carbonate (Compound ts11) (150 mg, 0.35 mmol). After stirring at room temperature for five minutes, triethylamine (113 μL, 0.81 mmol) was added at 0° C. The reaction mixture was stirred at room temperature for 15 hours, and then purified by reverse-phase silica gel column chromatography (0.1% aqueous formic acid solution/0.1% formic acid-acetonitrile solution) to give N-butyl-N-(((4-(2-(4-fluorophenyl)acetamide) benzyl)oxy)carbonyl)glycine (Compound ts12, F-Pnaz-nBuG-OH) (110.0 mg, 75%).

LCMS (ESI) m/z=415 (M−H)$^-$

Retention time: 0.72 minutes (analysis condition SQDFA05)

Synthesis of cyanomethyl N-butyl-N-(((4-(2-(4-fluorophenyl)acetamide)benzyl)oxy) carbonyl)glycinate (Compound ts13, F-Pnaz-nBuG-OCH$_2$CN)

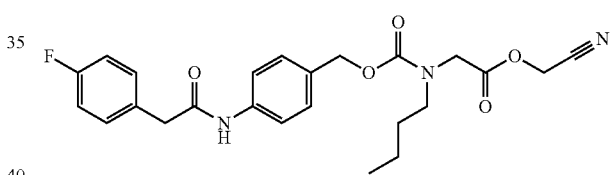

Under a nitrogen atmosphere, N-butyl-N-(((4-(2-(4-fluorophenyl)acetamide) benzyl)oxy)carbonyl)glycine (Compound ts12, F-Pnaz-nBuG-OH) (30.0 mg, 0.07 mmol) and N-ethyl-isopropylpropan-2-amine (DIPEA) (18.87 μL, 0.11 mmol) were dissolved in acetonitrile (180 μL), 2-bromoacetonitrile (4.83 μL, 0.34 mmol) was added at 0° C., and this was stirred at room temperature for two hours. The reaction solution was concentrated to give cyanomethyl N-butyl-N-(((4-(2-(4-fluorophenyl)acetamide)benzyl)oxy)carbonyl) glycinate (Compound ts13, F-Pnaz-nBuG-OCH$_2$CN) as a crude product. The obtained crude product was dissolved in acetonitrile (2.00 mL) and was directly used in the next step.

LCMS (ESI) m/z=456 (M+H)$^+$

Retention time: 0.81 minutes (analysis condition SQDFA05)

Synthesis of (2R,3S,4R,5R)-2-((((((2R,3S,4R,5R)-5-(4-amino-2-oxopyrimidin-1(2H)-yl)-4-hydroxy-2-((phosphonooxy)methyl)tetrahydrofuran-3-yl)oxy)(hydroxy)phosphoryl)oxy) methyl)-5-(6-amino-9H-purin-9-yl)-4-hydroxytetrahydrofuran-3-yl N-butyl-N-(((4-(2-(4-fluorophenyl)acetamide)benzyl)oxy)carbonyl)glycinate (Compound ts14, F-Pnaz-nBuG-pCpA)
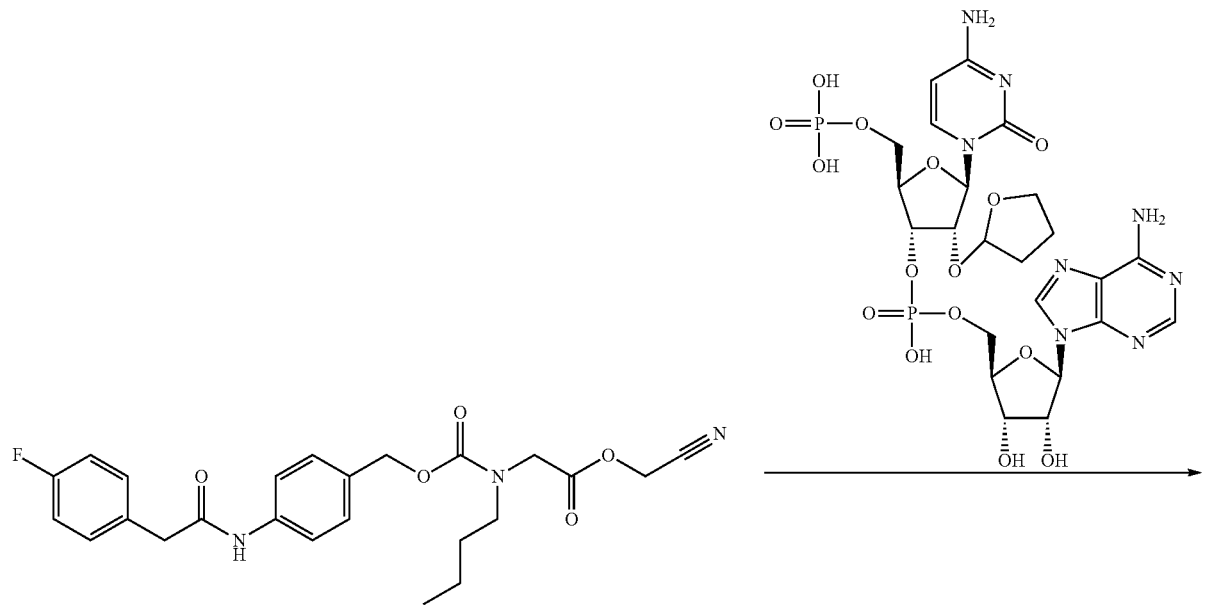
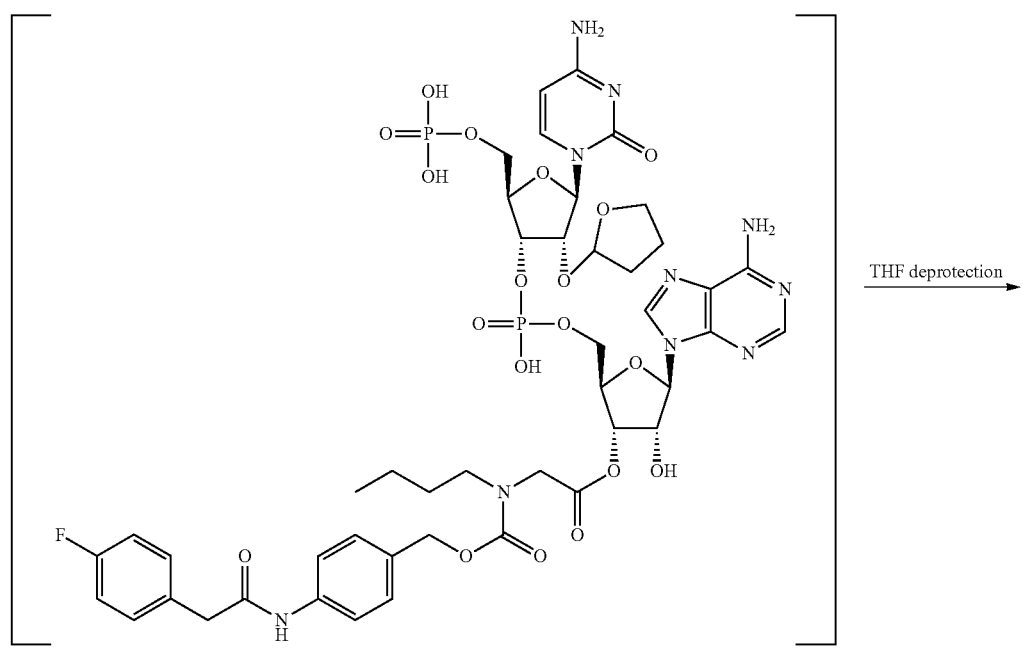

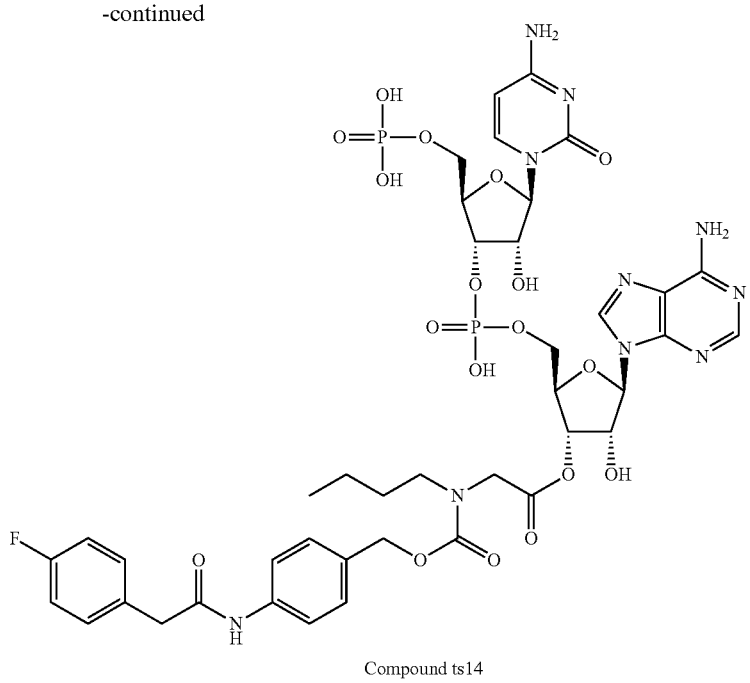

Compound ts14

((2R,3R,4R,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)-4-((tetrahydrofuran-2-yl)oxy)tetrahydrofuran-2-yl)methyl dihydrogenphosphate (Compound pc01) (104.0 mg, 0.144 mmol) was dissolved in Buffer A (40 mL), a solution of cyanomethyl N-butyl-N-(((4-(2-(4-fluorophenyl)acetamide)benzyl)oxy)carbonyl)glycinate (Compound ts13, F-Pnaz-nBuG-OCH₂CN) in acetonitrile (2.00 mL) was added to it, and this was stirred at room temperature for 60 minutes. The reaction solution was cooled to 0° C., and then trifluoroacetic acid (2 mL) was added to it. After stirring the reaction solution at 0° C. for 45 minutes, this was purified by reverse-phase silica gel column chromatography (0.05% aqueous trifluoroacetic acid solution/0.05% trifluoroacetic acid-acetonitrile) to give the titled compound (Compound ts14, F-Pnaz-nBuG-pCpA) (25.0 mg, 33.0%).

LCMS (ESI) m/z=1051 (M+H)⁺

Retention time: 0.53 minutes (analysis condition SQDFA05)

Synthesis of (S)-1-(((4-(2-(4-fluorophenyl)acetamide)benzyl)oxy)carbonyl)azetidin-2-carboxylic acid (Compound ts15, F-Pnaz-Aze(2)-OH)

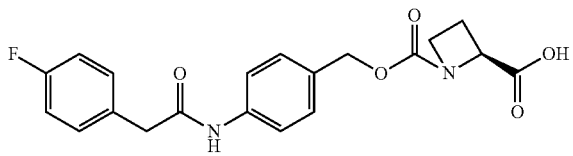 [SMILES: O=C(Cc1ccc(F)cc1)Nc1ccc(COC(=O)N2CC[C@H]2C(=O)O)cc1]

Under a nitrogen atmosphere, DMF (0.35 mL) was added at room temperature to a mixture of (S)-azetidine-2-carboxylic acid (H-Aze(2)-OH) (20.0 mg, 0.20 mmol) and (4-nitrophenyl)-4-(2-(4-fluorophenyl)acetamide)benzyl carbonate (Compound ts11) (101 mg, 0.24 mmol). After stirring at room temperature for five minutes, triethylamine (63.4 μL, 0.46 mmol) was added at 0° C. The reaction mixture was stirred at room temperature for 30 minutes, and then purified by reverse-phase silica gel column chromatography (0.1% aqueous formic acid solution/0.1% formic acid-acetonitrile solution) to give (S)-1-(((4-(2-(4-fluorophenyl)acetamide)benzyl)oxy)carbonyl)azetidin-2-carboxylic acid (Compound ts15, F-Pnaz-Aze(2)-OH) (66.0 mg, 86%).

LCMS (ESI) m/z=385 (M−H)⁻

Retention time: 0.60 minutes (analysis condition SQDFA05)

Synthesis of (S)-2-((((4-(2-(4-fluorophenyl)acetamide)benzyl))oxy)carbonyl)amino)-3-(pyridin-3-yl)propanoic acid (Compound ts16, F-Pnaz-Ala(3-Pyr)-OH)

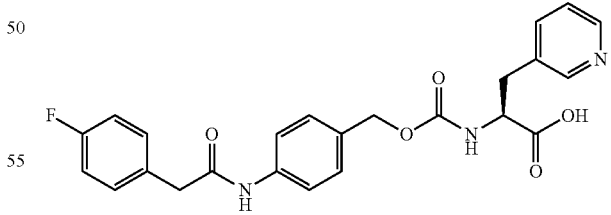

Under a nitrogen atmosphere, DMF (0.18 mL) was added at room temperature to a mixture of (S)-2-((((4-azidobenzyl)oxy)carbonyl)amino)-3-(pyridin-3-yl)propanoic acid (30.0 mg, 0.18 mmol) and (4-nitrophenyl)-4-(2-(4-fluorophenyl)acetamide)benzyl carbonate (Compound ts11) (92 mg, 0.22 mmol). After stirring at room temperature for five minutes, triethylamine (57.9 μL, 0.42 mmol) was added at 0° C. The reaction mixture was stirred at 35° C. for 30 minutes, and then purified by reverse-phase silica gel column chromatography (0.1% aqueous formic acid solution/0.1% formic acid-acetonitrile solution) to give (S)-2-((((4-(2-(4-fluorophenyl)acetamide)benzyl))oxy)carbonyl)amino)-3-(pyridin-3-yl)propanoic acid (Compound ts16, F-Pnaz-Ala(3-Pyr)-OH) (33.0 mg, 41%).

LCMS (ESI) m/z=452 (M+H)+

Retention time: 0.46 minutes (analysis condition SQDFA05)

Synthesis of 1-(4-(2-(4-fluorophenyl)acetamide)benzyl) 2-(cyanomethyl) (S)-azetidin-1,2-dicarboxylate (Compound ts17, F-Pnaz-Aze(2)-OCH₂CN)

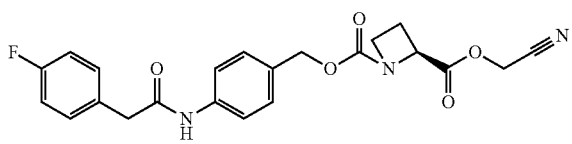 [SMILES: N#CCOC(=O)[C@@H]1CCN1C(=O)OCc1ccc(NC(=O)Cc2ccc(F)cc2)cc1]

Under a nitrogen atmosphere, (S)-1-(((4-(2-(4-fluorophenyl)acetamide)benzyl) oxy)carbonyl)azetidin-2-carboxylic acid (Compound ts15, F-Pnaz-Aze(2)-OH) (30.0 mg, 0.08 mmol) and N-ethyl-isopropylpropan-2-amine (DIPEA) (20.34 μL, 0.12 mmol) were dissolved in acetonitrile (194 μL), 2-bromoacetonitrile (6.24 μL, 0.09 mmol) was added at 0° C., and this was stirred at room temperature for three hours. The reaction solution was concentrated to give 1-(4-(2-(4-fluorophenyl)acetamide)benzyl) 2-(cyanomethyl) (S)-azetidin-1,2-dicarboxylate (Compound ts17, F-Pnaz-Aze(2)-OCH₂CN) as a crude product. The obtained crude product was dissolved in acetonitrile (2.00 mL) and was directly used in the next step.

LCMS (ESI) m/z=426 (M+H)+

Retention time: 0.70 minutes (analysis condition SQDFA05)

Synthesis of cyanomethyl (S)-2-((((4-(2-(4-fluorophenyl)acetamide)benzyl)oxy)carbonyl) amino)-3-(pyridin-3-yl)propanoate (Compound ts18, F-Pnaz-Ala(3-Pyr)-OCH₂CN)

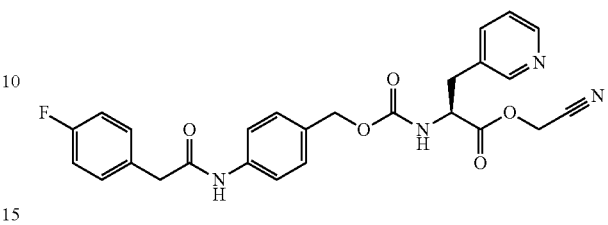

Under a nitrogen atmosphere, (S)-2-((((4-(2-(4-fluorophenyl)acetamide)benzyl) oxy)carbonyl)amino)-3-(pyridin-3-yl)propanoic acid (Compound ts16, F-Pnaz-Ala(3-Pyr)-OH) (30.0 mg, 0.07 mmol) and N-ethyl-isopropylpropan-2-amine (DIPEA) (17.41 μL, 0.10 mmol) were dissolved in acetonitrile (166 μL), 2-bromoacetonitrile (6.24 μL, 0.09 mmol) was added at 0° C., and this was stirred at room temperature for three hours. The reaction solution was concentrated, and the obtained residue was purified by normal-phase silica gel column chromatography (hexane/ethyl acetate) to give cyanomethyl (S)-2-((((4-(2-(4-fluorophenyl)acetamide)benzyl)oxy)carbonyl)amino)-3-(pyridin-3-yl)propanoate (Compound ts18, F-Pnaz-Ala(3-Pyr)-OCH₂CN) (14.0 mg, 43%).

LCMS (ESI) m/z=491 (M+H)+

Retention time: 0.52 minutes (analysis condition SQDFA05)

Synthesis of 1-(4-(2-(4-fluorophenyl)acetamide)benzyl) 2-((2R,3S,4R,5R)-2-((((((2R,3S, 4R,5R)-5-(4-amino-2-oxopyrimidin-1(2H)-yl)-4-hydroxy-2-((phosphonooxy) methyl) tetrahydrofuran-3-yl)oxy)(hydroxy)phosphoryl)oxy)methyl)-5-(6-amino-9H-purin-9-yl)-4-hydroxytetrahydrofuran-3-yl) (2S)-azetidin-1,2-dicarboxylate (Compound ts19, F-Pnaz-Aze(2)-pCpA)

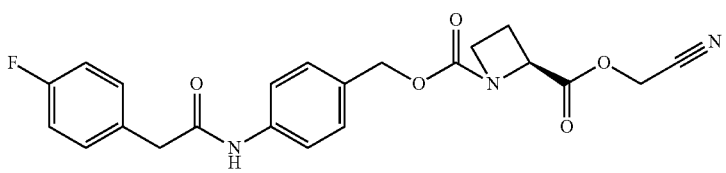

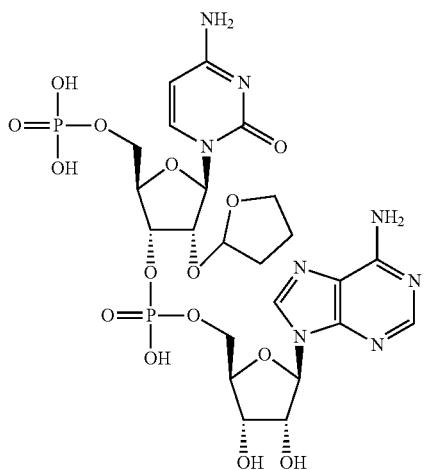

-continued

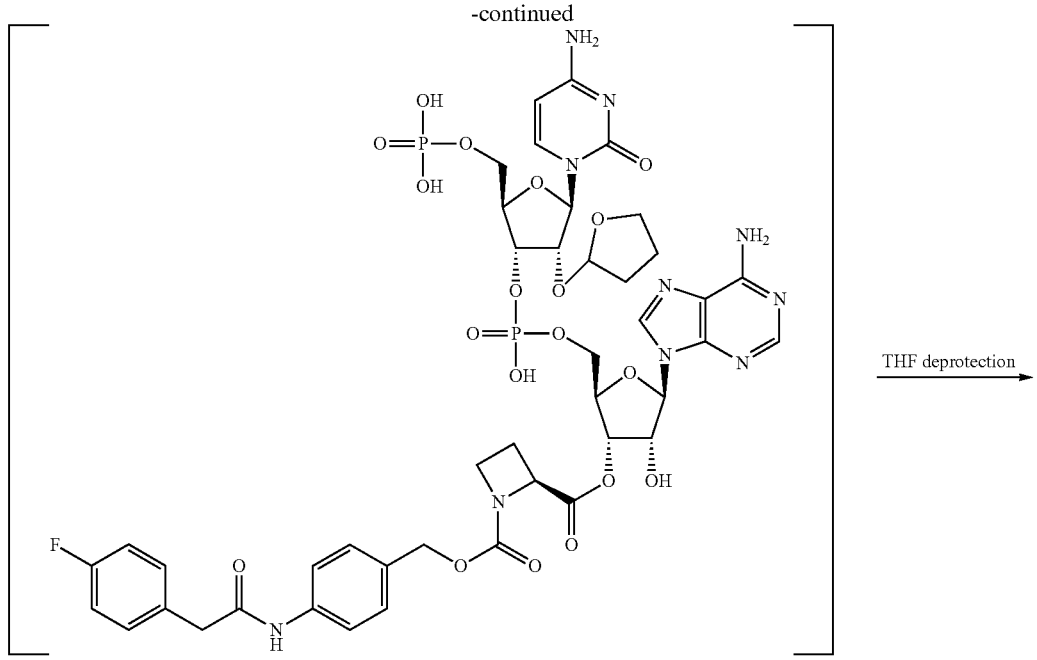

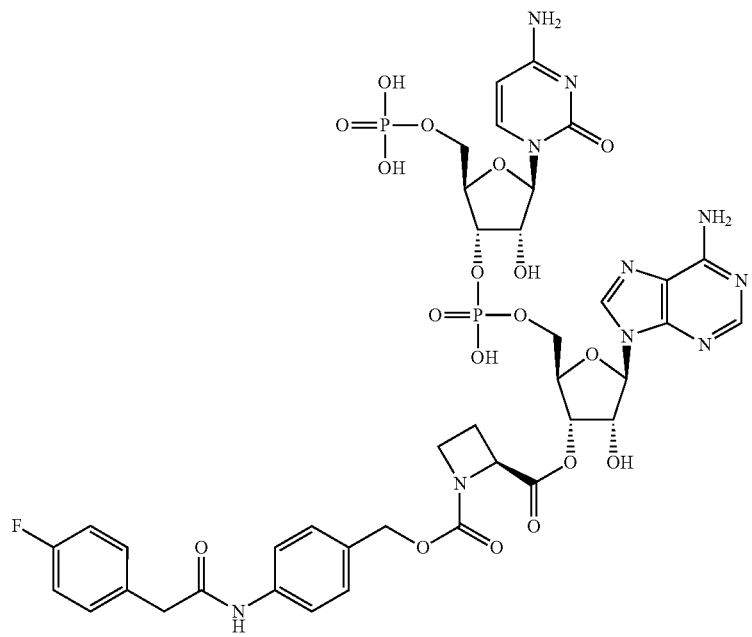

Compound ts19

((2R,3R,4R,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)-4-((tetrahydrofuran-2-yl)oxy)tetrahydrofuran-2-yl) methyl dihydrogenphosphate (Compound pc01) (113.0 mg, 0.156 mmol) was dissolved in Buffer A (40 mL), a solution of 1-(4-(2-(4-fluorophenyl)acetamide)benzyl) 2-(cyanomethyl) (S)-azetidin-1,2-dicarboxylate (Compound ts17, F-Pnaz-Aze(2)-OCH₂CN) in acetonitrile (2.00 mL) was added to it, and this was stirred at room temperature for 60 minutes. The reaction solution was cooled to 0° C., and then trifluoroacetic acid (2 mL) was added to it. After stirring the reaction solution at 0° C. for 45 minutes, the reaction solution was purified by reverse-phase silica gel column chromatography (0.05% aqueous trifluoroacetic acid solution/0.05% trifluoroacetic acid-acetonitrile) to give the titled compound (Compound ts19, F-Pnaz-Aze(2)-pCpA) (6.0 mg, 7.5%).

LCMS (ESI) m/z=1021 (M+H)⁺

Retention time: 0.45 minutes (analysis condition SQDFA05)

Synthesis of (2R,3S,4R,5R)-2-(((((2R,3S,4R,5R)-5-(4-amino-2-oxopyrimidin-1(2H)-yl)-4-hydroxy-2-((phosphonooxy)methyl)tetrahydrofuran-3-yl)oxy)(hydroxy)phosphoryl)oxy) methyl)-5-(6-amino-9H-purin-9-yl)-4-hydroxytetrahydrofuran-3-yl (2S)-2-((((4-(2-(4-fluorophenyl)acetamide)benzyl)oxy)carbonyl)amino)-3-(pyridin-3-yl)propanoate (Compound ts20, F-Pnaz-Ala(3-Pyr)-pCpA)
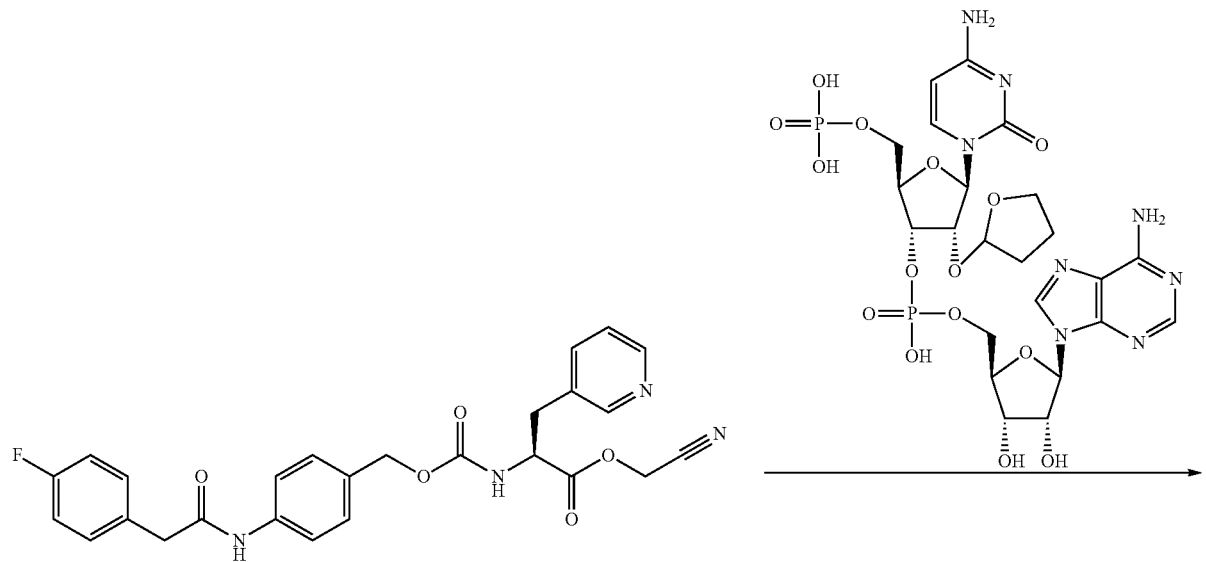
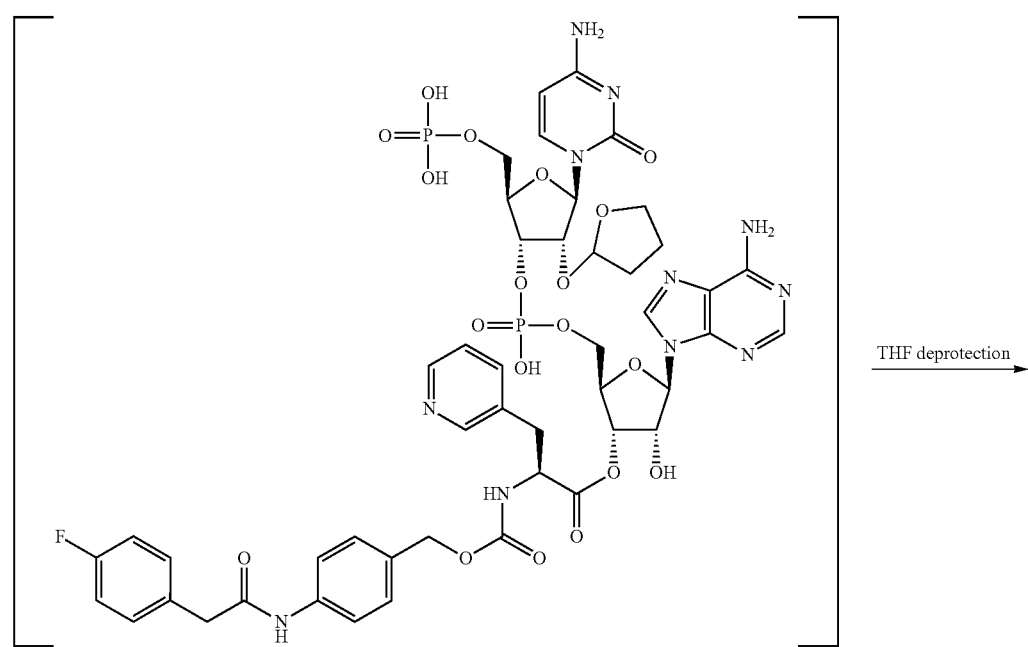

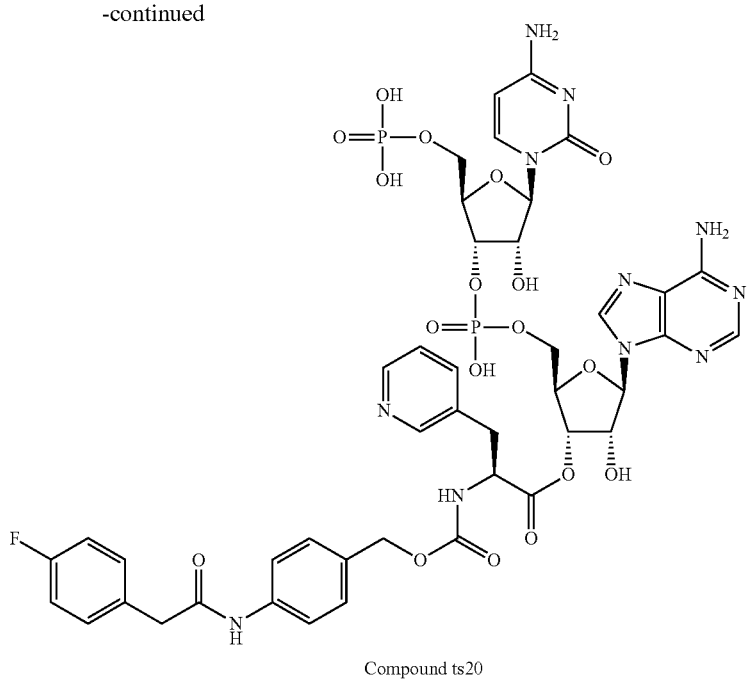

Compound ts20

((2R,3R,4R,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)-4-((tetrahydrofuran-2-yl)oxy)tetrahydrofuran-2-yl) methyl dihydrogenphosphate (Compound pc01) (41.0 mg, 0.057 mmol) was dissolved in Buffer A (15 mL), a solution of cyanomethyl (S)-2-((((4-(2-(4-fluorophenyl)acetamide) benzyl)oxy)carbonyl)amino)-3-(pyridin-3-yl)propanoate (Compound ts18, F-Pnaz-Ala(3-Pyr)-OCH$_2$CN) in acetonitrile (0.75 mL) was added to it, and this was stirred at room temperature for 60 minutes. The reaction solution was cooled to 0° C., and then trifluoroacetic acid (0.75 mL) was added to it. After stirring the reaction solution at 0° C. for 45 minutes, the reaction solution was purified by reverse-phase silica gel column chromatography (0.05% aqueous trifluoroacetic acid solution/0.05% trifluoroacetic acid-acetonitrile) to give the titled compound (Compound ts20, F-Pnaz-Ala(3-Pyr)-pCpA) (6.0 mg, 19.4%).

LCMS (ESI) m/z=1086 (M+H)$^+$

Retention time: 0.40 minutes (analysis condition SQDFA05)

Synthesis of (S)-1-(penta-4-enoyl)azetidine-2-carboxylic acid (Compound ts21, Pen-Aze(2)-OH)

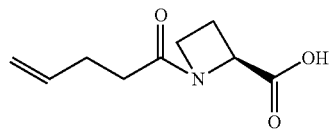

(S)-Azetidine-2-carboxylic acid (H-Aze(2)-OH) (4.00 g, 39.56 mmol) was dissolved in 1,4-dioxane (111 mL)/water (111 mL), then 2,5-dioxopyrrolidin-1-yl pent-4-enoate (23.4 g, 118.67 mmol) and sodium bicarbonate (6.65 g, 79.16 mmol) were added, and the reaction solution was stirred at 25° C. for 16 hours. After completion of the reaction, water was added to the reaction solution, this was washed with ethyl acetate, and a 1 M aqueous hydrochloric acid solution was added until the acidity of the aqueous layer reached pH 3. The resulting mixture was extracted with ethyl acetate, and the resulting organic layer was dried over anhydrous sodium sulfate, filtered, and then concentrated under reduced pressure. The resulting residue was purified by normal phase silica gel column chromatography (dichloromethane/methanol) to give (S)-1-(penta-4-enoyl)azetidine-2-carboxylic acid (Compound ts21, Pen-Aze(2)-OH) (6.30 g, 87%).

LCMS (ESI) m/z=184 (M+H)$^+$

Retention time: 1.03 minutes (analysis condition SMD method 2)

Synthesis of cyanomethyl (S)-1-(penta-4-enoyl) azetidine-2-carboxylate (Compound ts22, Pen-Aze(2)-OCH$_2$CN)

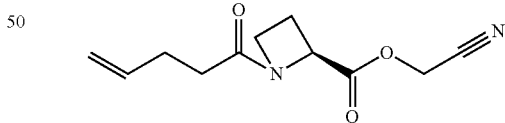

Under a nitrogen atmosphere, (S)-1-(penta-4-enoyl)azetidine-2-carboxylic acid (Compound ts21, Pen-Aze(2)-OH) (0.71 g, 3.88 mmol) and N-ethyl-isopropylpropan-2-amine (DIPEA) (1.00 g, 7.75 mmol) were dissolved in dichloromethane (16 mL), 2-bromoacetonitrile (1.86 g, 15.51 mmol) was added, and this was stirred at 25° C. for 16 hours. The reaction solution was concentrated, and the obtained residue was purified by normal-phase silica gel column chromatography (petroleum ether/ethyl acetate) to give cyanomethyl (S)-1-(penta-4-enoyl)azetidine-2-carboxylate (Compound ts22, Pen-Aze(2)-OCH$_2$CN) quantitatively.

LCMS (ESI) m/z=223 (M+H)$^+$

Retention time: 1.13 minutes (analysis condition SMD method 2)

Synthesis of (2R,3S,4R,5R)-2-((((((2R,3S,4R,5R)-5-(4-amino-2-oxopyrimidin-1(2H)-yl)-4-hydroxy-2-((phosphonooxy)methyl)tetrahydrofuran-3-yl)oxy)(hydroxy)phosphoryl)oxy) methyl)-5-(6-amino-9H-purin-9-yl)-4-hydroxytetrahydrofuran-3-yl (2S)-1-(penta-4-enoyl) azetidine-2-carboxylate (Compound ts23, Pen-Aze(2)-pCpA)

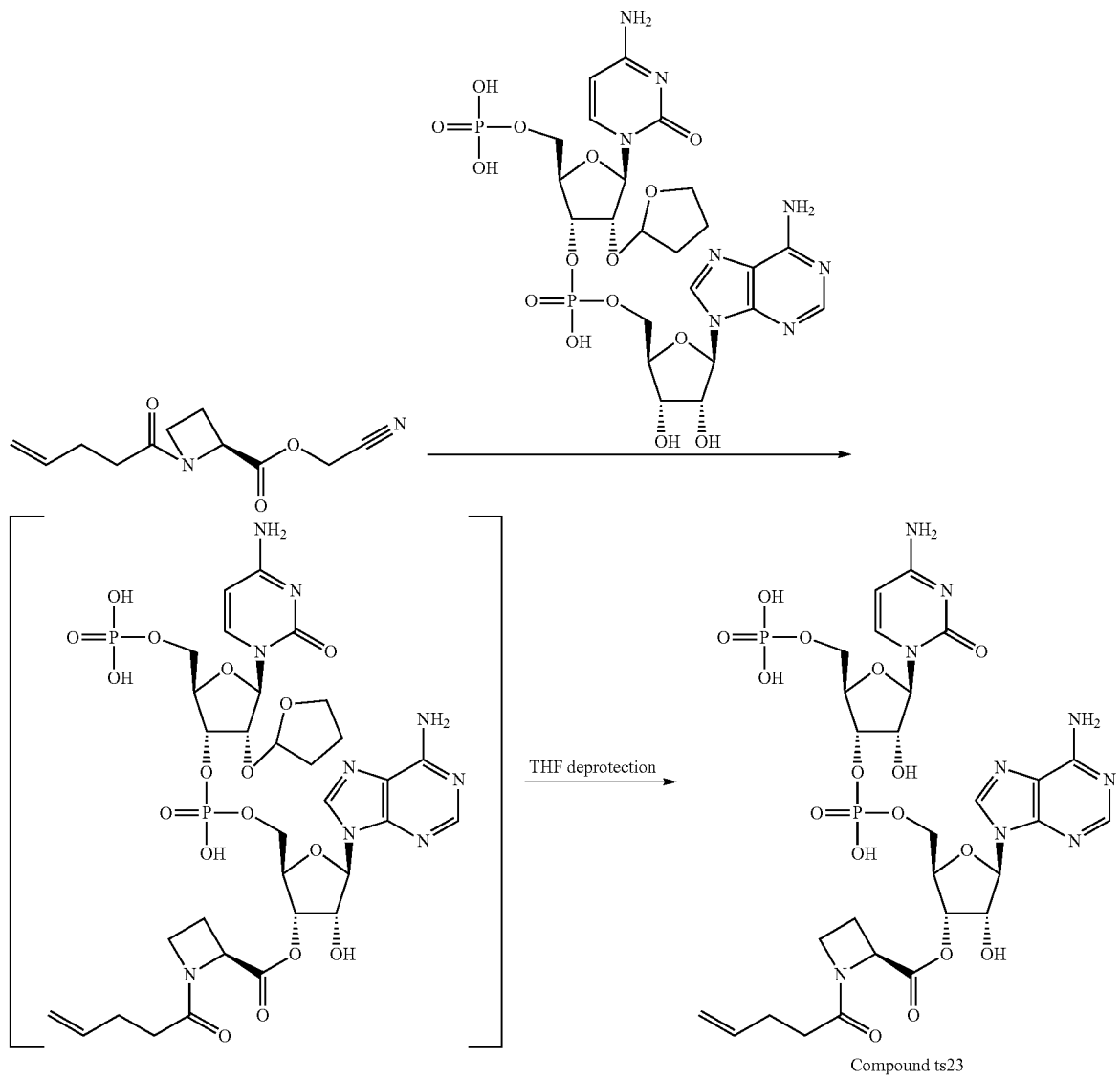

Compound ts23

((2R,3R,4R,5R)-5-(4-amino-2-oxopyrimidin-1(2H)-yl)-3-((((((2R,3S,4R,5R)-5-(6-amino-9H-purin-9-yl)-3,4-dihydroxytetrahydrofuran-2-yl)methoxy)(hydroxy)phosphoryl)oxy)-4-((tetrahydrofuran-2-yl)oxy)tetrahydrofuran-2-yl) methyl dihydrogenphosphate (Compound pc01) (800 mg, 1.11 mmol) was dissolved in Buffer A (200 mL). A solution of cyanomethyl (S)-1-(penta-4-enoyl)azetidine-2-carboxylate (Compound ts22, Pen-Aze(2)-OCH₂CN) (1.05 g, 4.71 mmol) in acetonitrile (6.00 mL) was added to it, and this was stirred at 25° C. for 60 minutes. Trifluoroacetic acid (4.60 mL) was added to this mixture at room temperature, and then this was lyophilized. The obtained residue was dissolved in water (50.0 mL), this was washed with ethyl acetate (100 mL), and then the aqueous layer was lyophilized. The obtained residue was purified by reverse-phase silica gel column chromatography (0.05% aqueous trifluoroacetic acid solution/0.05% trifluoroacetic acid-acetonitrile) to give the titled compound (Compound ts23, Pen-Aze (2)-pCpA) (20.0 mg, 2%).

LCMS (ESI) m/z=818 (M+H)⁺

Synthesis of N-butyl-N-(penta-4-enoyl)glycine (Compound ts24, Pen-nBuG-OH)

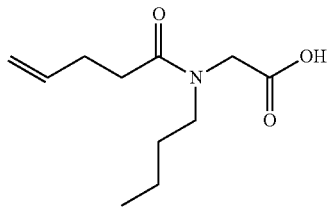

n-Butylglycine hydrochloride (H-nBuG-OH·HCl) (17.00 g, 7.62 mmol) was dissolved in 1,4-dioxane (150 mL)/water (150 mL), then the pH of this solution was adjusted to 7 using sodium carbonate. Then 2,5-dioxopyrrolidin-1-yl pent-4-enoate (20.0 g, 101.4 mmol) and sodium carbonate (7.00 g, 83.33 mmol) were added and the reaction solution was stirred at room temperature for 16 hours. After completion of the reaction, the reaction solution was washed with diethyl ether, and a 1 M aqueous hydrochloric acid solution was added until the acidity of the aqueous layer reached pH 2. The resulting mixture was extracted four times with DCM, and the obtained organic layer was dried over anhydrous sodium sulfate, filtered, and then concentrated under reduced pressure. Then, the resulting residue was purified by normal-phase silica gel column chromatography (ethyl acetate/ether) to give N-butyl-N-(penta-4-enoyl)glycine (Compound ts24, Pen-nBuG-OH) (7.00 g, 62%). LCMS (ESI) m/z=214 (M+H)$^+$ Retention time: 0.63 minutes (analysis condition SMD method 1)

Synthesis of cyanomethyl N-butyl-N-(penta-4-enoyl)glycinate (Compound ts25, Pen-nBuG-OCH$_2$CN)

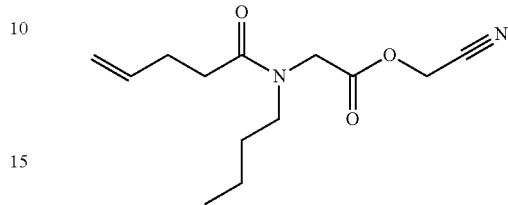

Under a nitrogen atmosphere, N-butyl-N-(penta-4-enoyl) glycine (Compound ts24, Pen-nBuG-OH) (3.80 g, 17.8 mmol) and N-ethyl-isopropylpropan-2-amine (DIPEA) (4.6 g, 35.6 mmol) were dissolved in dichloromethane (80 mL). 2-Bromoacetonitrile (8.54 g, 71.2 mmol) was added, and this was stirred at room temperature for 16 hours. The reaction solution was concentrated, and the obtained residue was purified by normal-phase silica gel column chromatography (petroleum ether/ethyl acetate) to give cyanomethyl N-butyl-N-(penta-4-enoyl)glycinate (Compound ts25, Pen-nBuG-OCH$_2$CN) (2.8 g, 64%).

LCMS (ESI) m/z=253 (M+H)$^+$

Retention time: 1.40 minutes (analysis condition SMD method 3)

Synthesis of (2R,3S,4R,5R)-2-((((((2R,3S,4R,5R)-5-(4-amino-2-oxopyrimidin-1(2H)-yl)-4-hydroxy-2-((phosphonooxy)methyl)tetrahydrofuran-3-yl)oxy)(hydroxy)phosphoryl)oxy) methyl)-5-(6-amino-9H-purin-9-yl)-4-hydroxytetrahydrofuran-3-yl N-butyl-N-(penta-4-enoyl)glycinate (Compound ts26, Pen-nBuG-pCpA)

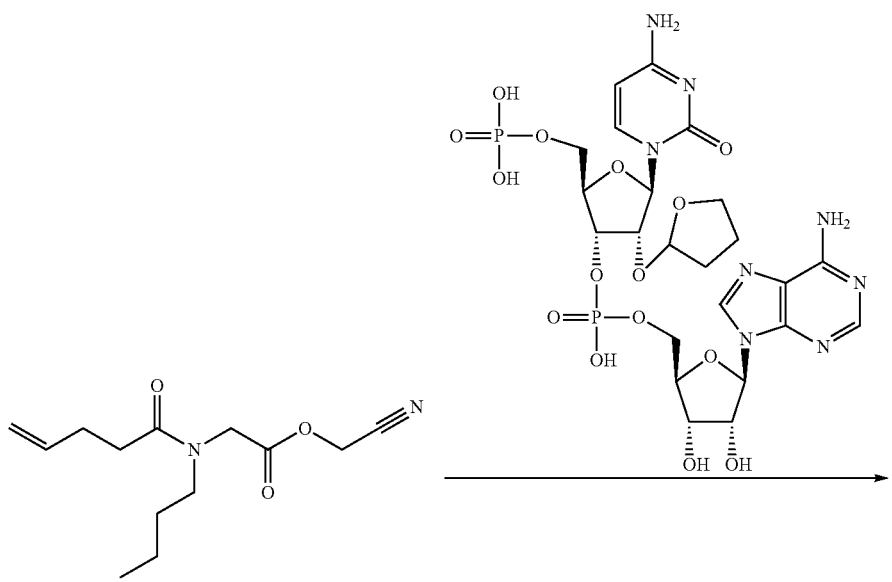

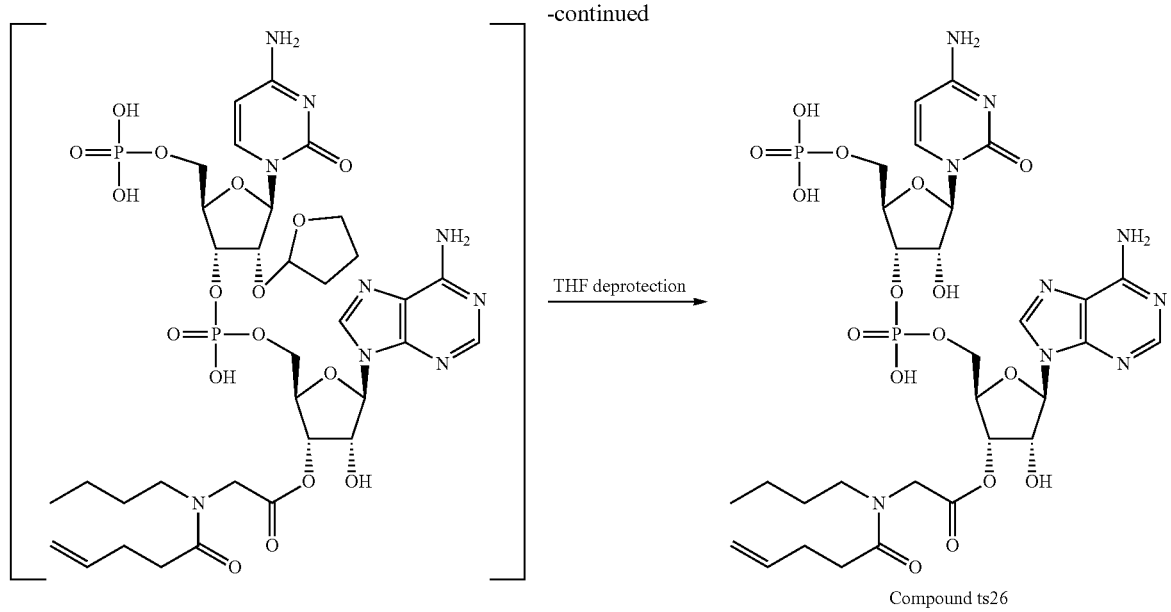

Compound ts26

((2R,3R,4R,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)-4-((tetrahydrofuran-2-yl)oxy)tetrahydrofuran-2-yl) methyl dihydrogenphosphate (Compound pc01) (400 mg, 0.55 mmol) was dissolved in Buffer A (100 mL). A solution of cyanomethyl N-butyl-N-(penta-4-enoyl)glycinate (Compound ts25, Pen-nBuG-OCH$_2$CN) (558 mg, 2.22 mmol) in THF (4 mL) was added to it, and this was stirred at room temperature for two hours. Trifluoroacetic acid (2.30 mL) was added to this mixture at room temperature, and then this was lyophilized. The obtained residue was purified by reverse-phase silica gel column chromatography (0.05% aqueous trifluoroacetic acid solution/0.05% trifluoroacetic acid-acetonitrile) to give the titled compound (Compound ts26, Pen-nBuG-pCpA) (65 mg, 14%).

LCMS (ESI) m/z=848 (M+H)$^+$

Retention time: 1.25 minutes (analysis condition SMD method 3)

Synthesis of (S)-2-(penta-4-enamide)-3-(pyridin-3-yl)propanoic acid (Compound ts27, Pen-Ala(3-Pyr)-OH)

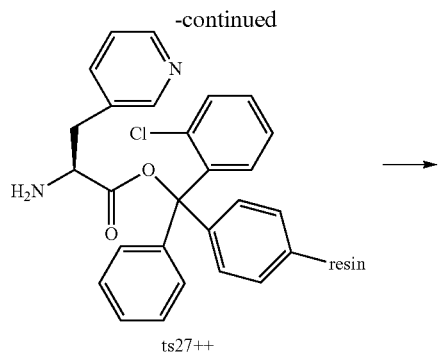

ts27++

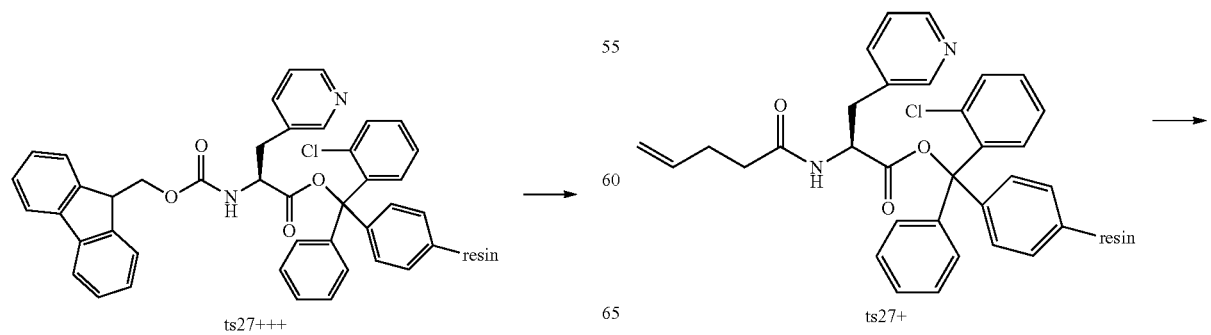

ts27+++           ts27+

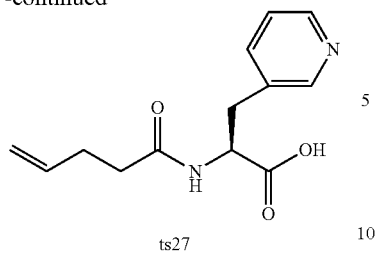

ts27

A 2-chlorotrityl resin (1.60 mmol/g, 3.21 g) was added to DCM (20 mL), and the resin was swollen by shaking for ten minutes. After removing DCM, a solution of (S)-2-((((9H-fluoren-9-yl)methoxy)carbonyl)amino)-3-(pyridin-3-yl)propanoic acid (Fmoc-Ala(3-Pyr)-OH) (2.00 g, 5.15 mmol) and N-ethyl-isopropylpropan-2-amine (DIPEA) (1.33 g, 10.3 mmol) in DCM (33 mL) was added, this was shaken at room temperature for 30 minutes. Then, MeOH (2.78 mL) was added and this was shaken for another hour. DCM solution was removed, and then the resin was washed twice with DCM (15 mL) to obtain Compound ts27+++. To the obtained Compound ts27+++, a 2% DBU-DMF solution (20 mL) was added, this was shaken at room temperature for 15 minutes. Then, the solution was removed, and the resin was washed five times with DMF (20 mL) to obtain Compound ts27++(2.35 g, 5.14 mmol). A solution of 4-pentenoic acid (2.06 g, 20.6 mmol), HOAt (2.10 g, 15.4 mmol), and DIC (3.24 g, 25.7 mmol) in DMF (20 mL) was added to the obtained Compound ts27++, and this was shaken at room temperature overnight. The solution was removed, and the resin was washed four times with DMF (20 mL) and four times with DCM (20 mL) to obtain Compound 27+(2.76 g, 5.12 mmol). DCM (30 mL) was added to the obtained Compound 27+, and the resin was swollen by shaking this for 15 minutes. After removing DCM, TFE (50 mL)/DCM (50 mL) was added and this was shaken at room temperature for 2.5 hours to cleave Compound ts27 from the resin. The cleavage solution TFE-DCM (100 mL) was removed, and then the resin was further washed twice with TFE (30 mL)/DCM (30 mL). This washing solution (total 60 mL) and the above-mentioned cleavage solution (100 mL) were mixed, the solvents were distilled off using an evaporator, and the obtained residue was purified by reverse-phase silica gel column chromatography (0.1% aqueous formic acid solution/0.1% formic acid-acetonitrile solution) to give (S)-2-(penta-4-enamide)-3-(pyridin-3-yl)propanoic acid (Compound ts27, Pen-Ala(3-Pyr)-OH) (564 mg, 44%).

LCMS (ESI) m/z=247 (M−H)⁻

Retention time: 0.33 minutes (analysis condition SQDFA05)

Synthesis of cyanomethyl (S)-2-(penta-4-enamide)-3-(pyridin-3-yl)propanoate (Compound ts28, Pen-Ala(3-Pyr)-OCH$_2$CN)

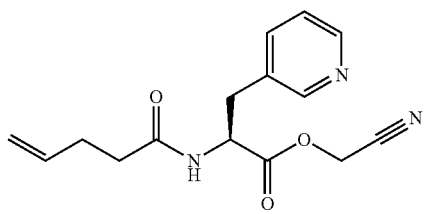 [SMILES: C=CCCC(=O)N[C@@H](Cc1cccnc1)C(=O)OCC#N]

Under a nitrogen atmosphere, (S)-2-(penta-4-enamide)-3-(pyridin-3-yl)propanoic acid (Compound ts27, Pen-Ala(3-Pyr)-OH) (100 mg, 0.40 mmol) and N-ethyl-isopropylpropan-2-amine (DIPEA) (106 μL, 0.60 mmol) were dissolved in DMF (1.00 mL), 2-bromoacetonitrile (28.1 μL, 0.40 mmol) was added at room temperature, this was stirred at room temperature for 30 minutes, and then N-ethyl-isopropylpropan-2-amine (DIPEA) (35 μL, 0.20 mmol) and 2-bromoacetonitrile (8.43 μL, 0.12 mmol) were added again. After stirring at room temperature for ten minutes, saturated aqueous ammonium chloride solution was added, and this was extracted using MTBE. The resulting organic layer was washed with saturated saline solution and dried over anhydrous sodium sulfate. Then the solvent was distilled off using an evaporator to give cyanomethyl (S)-2-(penta-4-enamide)-3-(pyridin-3-yl)propanoate (Compound ts28, Pen-Ala(3-Pyr)-OCH$_2$CN) as a crude product. The obtained crude product was dissolved in acetonitrile (0.57 mL) and was directly used in the next step. LCMS (ESI) m/z=288 (M+H)⁺

Retention time: 0.40 minutes (analysis condition SQDFA05)

Synthesis of (2R,3S,4R,5R)-2-((((((2R,3S,4R,5R)-5-(4-amino-2-oxopyrimidin-1(2H)-yl)-4-hydroxy-2-((phosphonooxy)methyl)tetrahydrofuran-3-yl)oxy)(hydroxy)phosphoryl)oxy) methyl)-5-(6-amino-9H-purin-9-yl)-4-hydroxytetrahydrofuran-3-yl (2S)-2-(penta-4-enamide)-3-(pyridin-3-yl)propanoate (Compound ts29, Pen-Ala(3-Pyr)-pCpA)

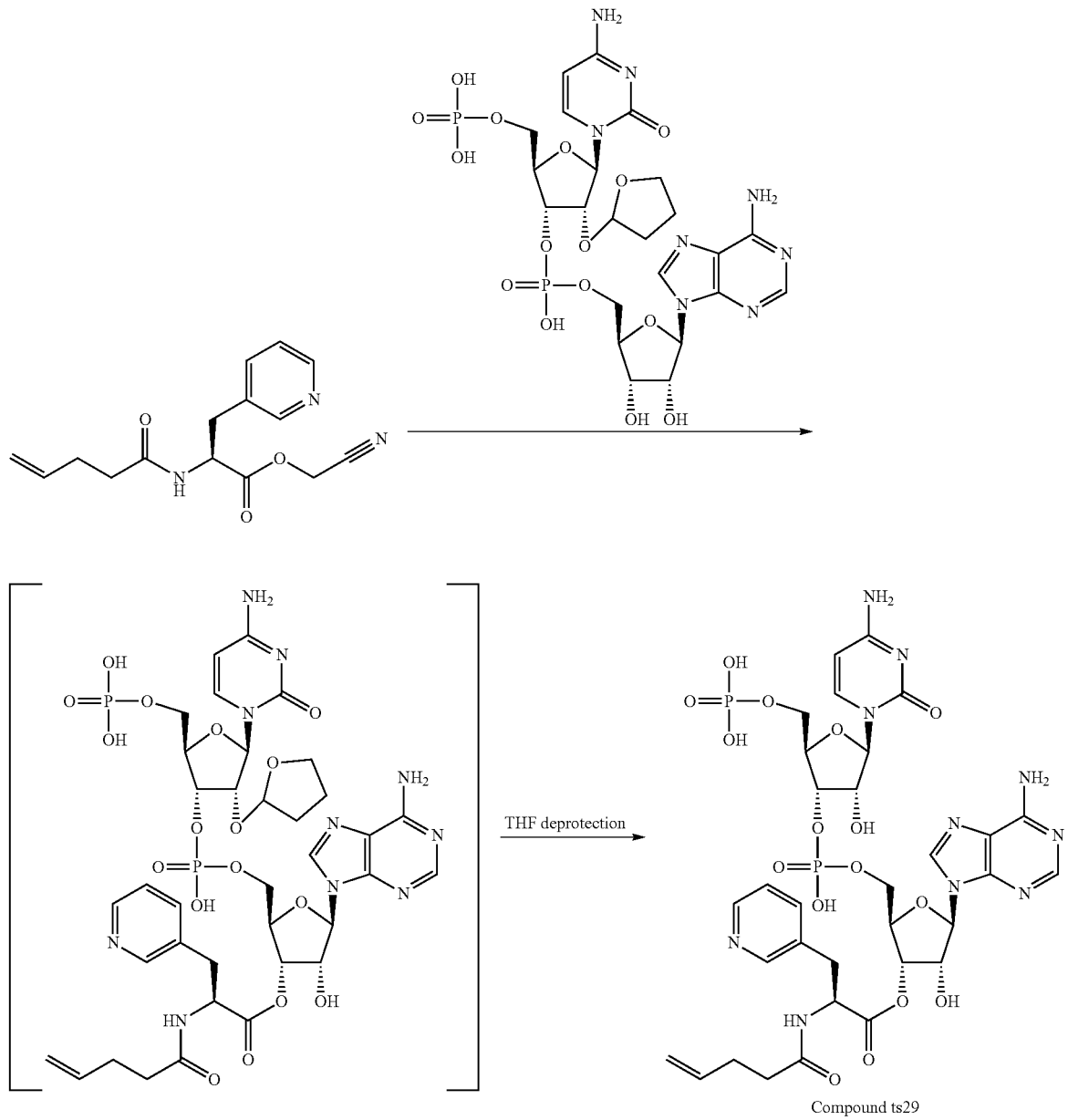

Compound ts29

((2R,3R,4R,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)-4-((tetrahydrofuran-2-yl)oxy)tetrahydrofuran-2-yl) methyl dihydrogenphosphate (Compound pc01) (59.2 mg, 0.082 mmol) was dissolved in Buffer A (17 mL), a solution of cyanomethyl (S)-2-(penta-4-enamide)-3-(pyridin-3-yl) propanoate (Compound ts28, Pen-Ala(3-Pyr)-OCH₂CN) in acetonitrile (0.57 mL) was added to it, and this was stirred at room temperature for 60 minutes. Acetic acid (17 mL) was added to the reaction solution, and after stirring this for one hour, this was purified by reverse-phase silica gel column chromatography (0.05% aqueous trifluoroacetic acid solution/0.05% trifluoroacetic acid-acetonitrile) to give the titled compound (Compound ts29, Pen-Ala(3-Pyr)-pCpA) (14.8 mg, 20.5%).

LCMS (ESI) m/z=896 (M+H)$^+$

Retention time: 0.39, 0.41 minutes (analysis condition SMD method 2)

81

Synthesis of N-(((4-azidobenzyl)oxy)carbonyl)-L-alanine (Compound TS01, Acbz-Ala-OH)

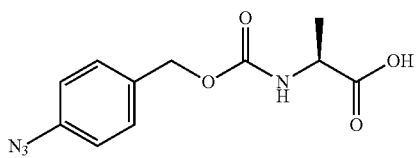

Under a nitrogen atmosphere, DMF (1.0 mL) was added at room temperature to a mixture of L-alanine (H-Ala-OH) (44.5 mg, 0.50 mmol), and 4-azidobenzyl (4-nitrophenyl) carbonate (157 mg, 0.50 mmol) synthesized by the method described in the literature (Bioconjugate Chem. 2008, 19, 714). After stirring at 0° C. for five minutes, triethylamine (174 µL, 1.25 mmol) was added at 0° C. The reaction mixture was stirred at room temperature for 72 hours and then purified by reverse-phase silica gel column chromatography (0.1% aqueous formic acid solution/0.1% formic acid-acetonitrile solution) to give N-(((4-azidobenzyl)oxy) carbonyl)-L-alanine (Compound TS01, Acbz-Ala-OH) (113.6 mg, 86%).

LCMS (ESI) m/z=263 (M−H)⁻

Retention time: 0.61 minutes (analysis condition SQDFA05)

82

Synthesis of cyanomethyl (((4-azidobenzyl)oxy) carbonyl)-L-alaninate (Compound TS02, Acbz-Ala-OCH₂CN)

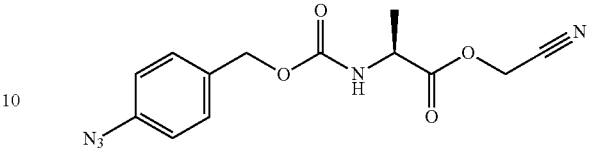

Under a nitrogen atmosphere, N-(((4-azidobenzyl)oxy) carbonyl)-L-alanine (Compound TS01, Acbz-Ala-OH) (174.0 mg, 0.66 mmol) and N-ethyl-isopropylpropan-2-amine (DIPEA) (0.172 mL, 0.99 mmol) were dissolved in acetonitrile (1315 µL). 2-Bromoacetonitrile (0.067 mL, 0.99 mmol) was added at 0° C., and this was stirred at room temperature for 18 hours. The reaction solution was concentrated to give cyanomethyl (((4-azidobenzyl)oxy)carbonyl)-L-alaninate (Compound TS02, Acbz-Ala-OCH₂CN) as a crude product. The obtained crude product was dissolved in acetonitrile (2.00 mL) and was directly used in the next step.

LCMS (ESI) m/z=302 (M+H)⁻

Retention time: 0.71 minutes (analysis condition SQDFA05)

Synthesis of (2R,3S,4R,5R)-2-((((((2R,3S,4R,5R)-5-(4-amino-2-oxopyrimidin-1(2H)-yl)-4-hydroxy-2-((phosphonooxy)methyl)tetrahydrofuran-3-yl)oxy)(hydroxy)phosphoryl)oxy) methyl)-5-(6-amino-9H-purin-9-yl)-4-hydroxytetrahydrofuran-3-yl (((4-azidobenzyl)oxy) carbonyl)-L-alaninate (Compound TS03, Acbz-Ala-pCpA)

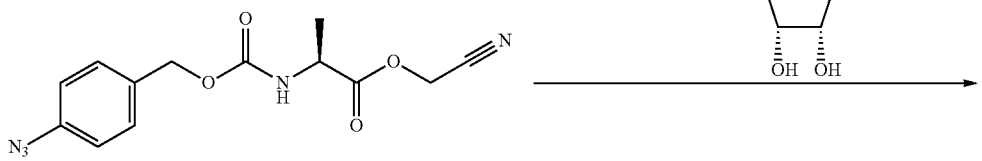
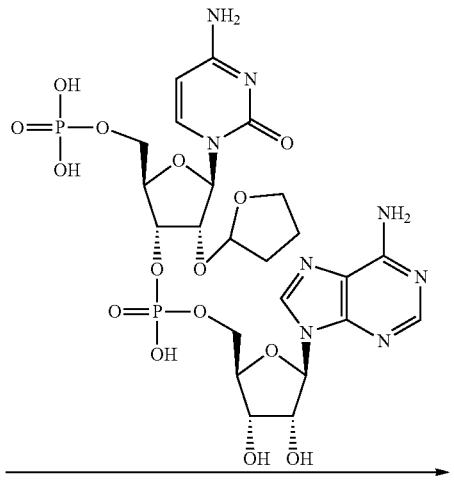

-continued

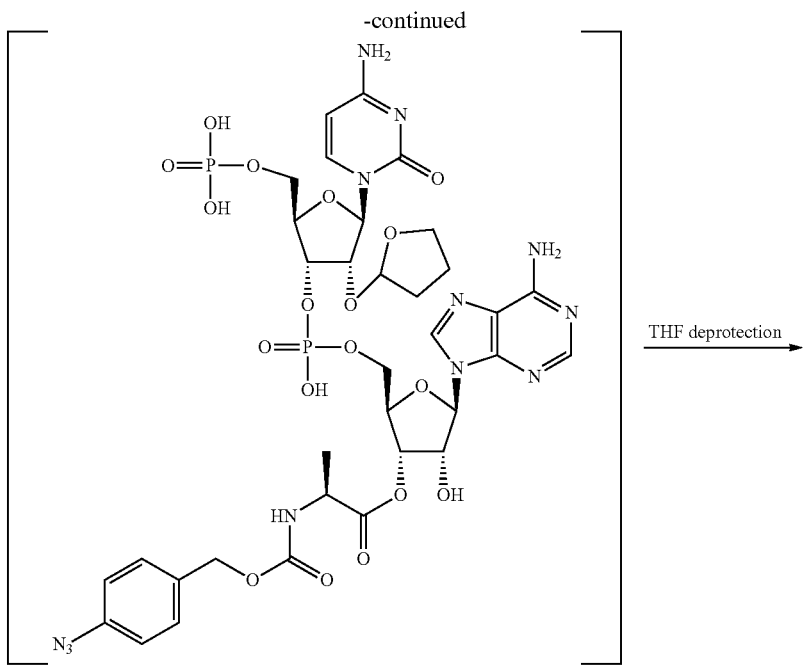

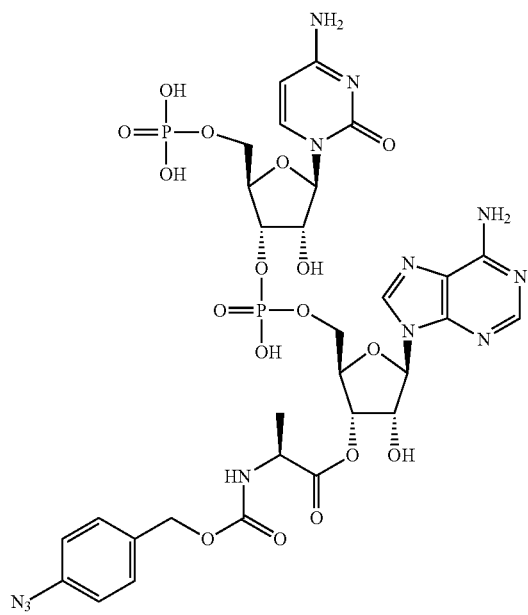

Compound TS03

((2R,3R,4R,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)-4-((tetrahydrofuran-2-yl)oxy)tetrahydrofuran-2-yl) methyl dihydrogenphosphate (Compound pc01) (60.2 mg, 0.083 mmol) was dissolved in Buffer A (40 mL). A solution of cyanomethyl (((4-azidobenzyl)oxy)carbonyl)-L-alaninate (Compound TS02, Acbz-Ala-OCH$_2$CN) in acetonitrile (1.25 mL) was added to it, and this was stirred at room temperature for 90 minutes. The reaction solution was cooled to 0° C., and then trifluoroacetic acid (1.25 mL) was added to it. After stirring the reaction solution at 0° C. for 30 minutes, this was purified by reverse-phase silica gel column chromatography (0.05% aqueous trifluoroacetic acid solution/0.05% trifluoroacetic acid-acetonitrile) to give the titled compound (Compound TS03, Acbz-Ala-pCpA) (36.3 mg, 48.5%).

LCMS (ESI) m/z=899 (M+H)$^+$

Retention time: 0.44 minutes (analysis condition SQDFA05)

Synthesis of (((4-(2-(4-fluorophenyl)acetamide)benzyl)oxy)carbonyl)-L-alanine (Compound TS04, F-Pnaz-Ala-OH)

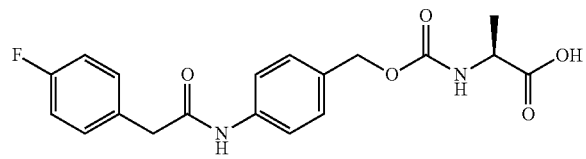 [SMILES: C[C@H](NC(=O)OCc1ccc(NC(=O)Cc2ccc(F)cc2)cc1)C(=O)O]

Under a nitrogen atmosphere, DMSO (1.12 mL) was added at room temperature to a mixture of L-alanine (H-Ala-OH) (30.0 mg, 0.34 mmol) and (4-nitrophenyl)-4-(2-(4-fluorophenyl)acetamide)benzyl carbonate (Compound ts11) (143 mg, 0.34 mmol). After stirring at room temperature for five minutes, triethylamine (94.0 µL, 0.67 mmol) was added at 0° C. The reaction mixture was stirred at room temperature for 40 hours and then purified by reverse-phase silica gel column chromatography (0.1% aqueous formic acid solution/0.1% formic acid-acetonitrile solution) to give (((4-(2-(4-fluorophenyl)acetamide)benzyl)oxy) carbonyl)-L-alanine (Compound TS04, F-Pnaz-Ala-OH) (78.6 mg, 62%).

LCMS (ESI) m/z=373 (M+H)⁻

Retention time: 0.62 minutes (analysis condition SQDFA05)

Synthesis of cyanomethyl (((4-(2-(4-fluorophenyl)acetamide)benzyl)oxy)carbonyl)-L-alaninate (Compound TS05, F-Pnaz-Ala-OCH₂CN)

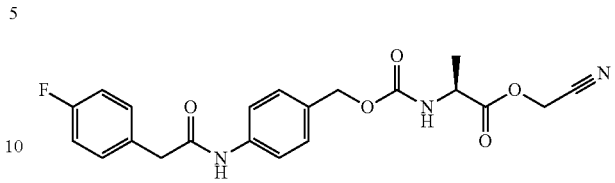

Under a nitrogen atmosphere, (((4-(2-(4-fluorophenyl)acetamide)benzyl)oxy) carbonyl)-L-alanine (Compound TS04, F-Pnaz-Ala-OH) (31.1 mg, 0.08 mmol) and N-ethyl-isopropylpropan-2-amine (DIPEA) (29.0 µL, 0.17 mmol) were dissolved in acetonitrile (415 µL). 2-Bromoacetonitrile (57.9 µL, 0.83 mmol) was added at 0° C., and this was stirred at room temperature for two hours. The reaction solution was concentrated to give cyanomethyl (((4-(2-(4-fluorophenyl)acetamide)benzyl)oxy)carbonyl)-L-alaninate (Compound TS05, F-Pnaz-Ala-OCH₂CN) as a crude product. The obtained crude product was dissolved in acetonitrile (0.75 mL) and was directly used in the next step.

LCMS (ESI) m/z=412 (M+H)⁻

Retention time: 0.71 minutes (analysis condition SQDFA05)

Synthesis of (2R,3S,4R,5R)-2-((((((2R,3S,4R,5R)-5-(4-amino-2-oxopyrimidin-1(2H)-yl)-4-hydroxy-2-((phosphonooxy)methyl)tetrahydrofuran-3-yl)oxy)(hydroxy)phosphoryl)oxy) methyl)-5-(6-amino-9H-purin-9-yl)-4-hydroxytetrahydrofuran-3-yl (((4-(2-(4-fluorophenyl) acetamide)benzyl)oxy)carbonyl)-L-alaninate (Compound TS06, F-Pnaz-Ala-pCpA)

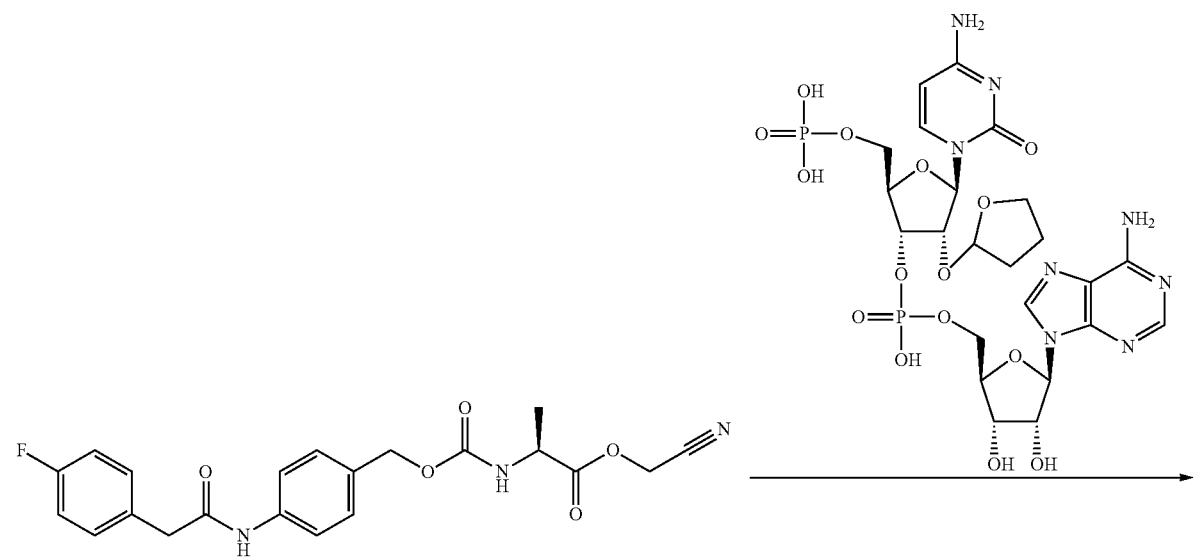

-continued

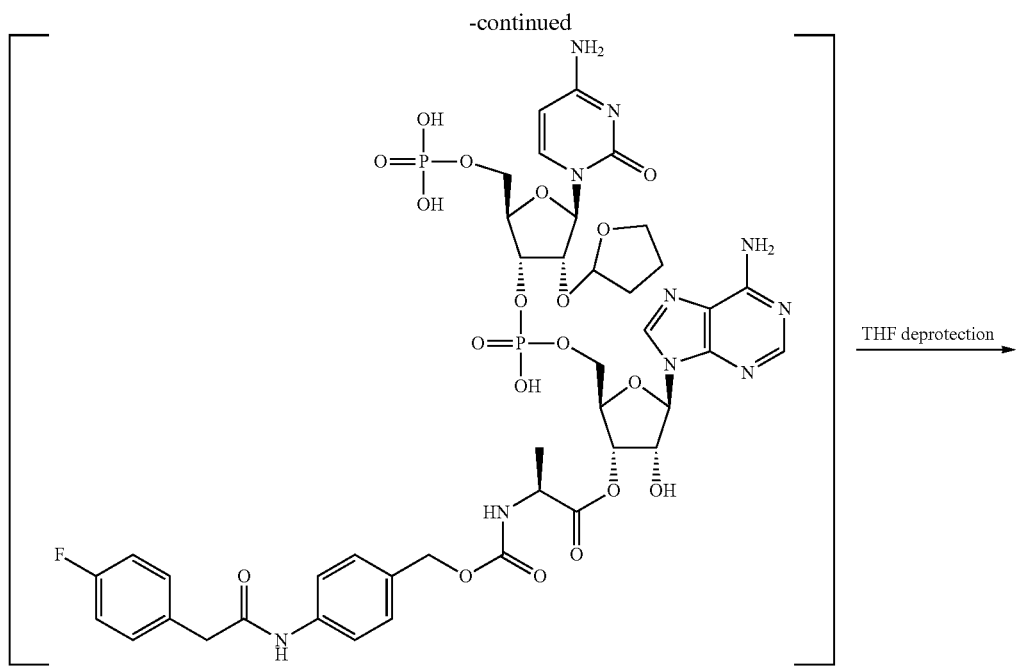

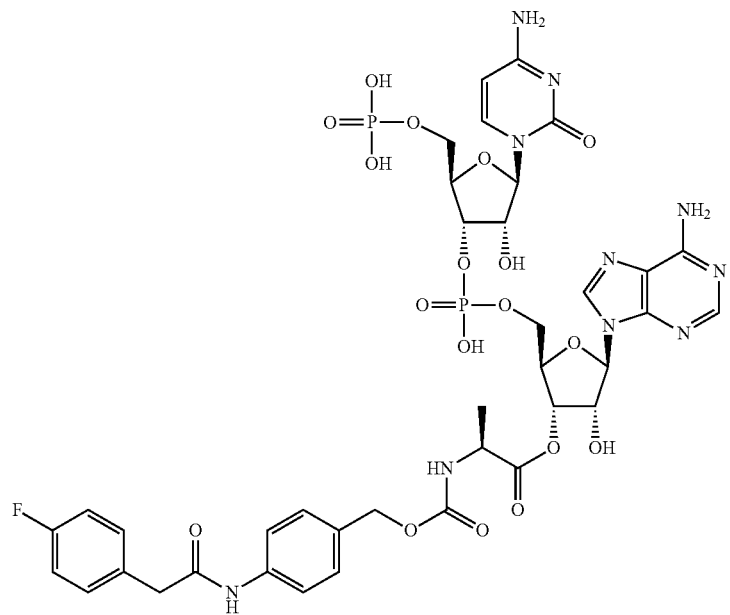

Compound TS06

(((2R,3R,4R,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)-4-((tetrahydrofuran-2-yl)oxy)tetrahydrofuran-2-yl)methyl dihydrogenphosphate (Compound pc01) (30.0 mg, 0.042 mmol) was dissolved in Buffer A (22.5 mL). A solution of cyanomethyl (((4-(2-(4-fluorophenyl)acetamide)benzyl)oxy)carbonyl)-L-alaninate (Compound TS05, F-Pnaz-Ala-OCH$_2$CN) in acetonitrile (0.75 mL) was added to it, and this was stirred at room temperature for 120 minutes. The reaction solution was cooled to 0° C., and then trifluoroacetic acid (0.75 mL) was added to it. After stirring the reaction solution at 0° C. for 30 minutes, this was purified by reverse-phase silica gel column chromatography (0.05% aqueous trifluoroacetic acid solution/0.05% trifluoroacetic acid-acetonitrile) to give the titled compound (Compound TS06, F-Pnaz-Ala-pCpA) (7.9 mg, 18.7%).

LCMS (ESI) m/z=1007 (M+H)⁻

Retention time: 0.47 minutes (analysis condition SQDFA05)

Synthesis of 2-((((4-azidobenzyl)oxy)carbonyl)amino)-2-methylpropanoic acid (Compound TS07, Acbz-AIB-OH)

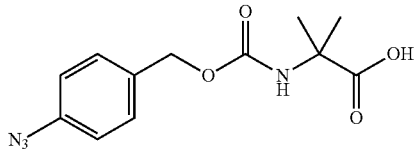 [SMILES: CC(C)(NC(=O)OCc1ccc(N=[N+]=[N-])cc1)C(=O)O]

Under a nitrogen atmosphere, DMSO (1.59 mL) was added at room temperature to a mixture of 2-amino-2-methylpropanoic acid (H-AIB-OH) (32.8 mg, 0.32 mmol), and 4-azidobenzyl (4-nitrophenyl)carbonate (100 mg, 0.32 mmol) synthesized by the method described in the literature (Bioconjugate Chem. 2008, 19, 714). After stirring at 0° C. for five minutes, triethylamine (127 μL, 0.73 mmol) was added at 0° C. The reaction mixture was stirred at room temperature for 15 hours and then purified by reverse-phase silica gel column chromatography (0.1% aqueous formic acid solution/0.1% formic acid-acetonitrile solution) to give 2-((((4-azidobenzyl)oxy)carbonyl)amino)-2-methylpropanoic acid (Compound TS07, Acbz-AIB-OH) (8.0 mg, 9%).

LCMS (ESI) m/z=277 (M−H)−

Retention time: 0.64 minutes (analysis condition SQDFA05)

Synthesis of cyanomethyl 2-((((4-azidobenzyl)oxy)carbonyl)amino)-2-methylpropanoate (Compound TS08, Acbz-AIB-OCH$_2$CN)

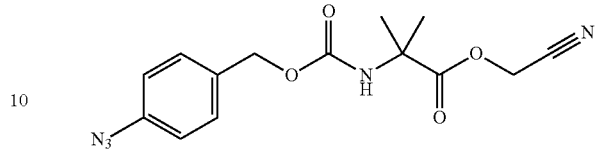

Under a nitrogen atmosphere, 2-((((4-azidobenzyl)oxy)carbonyl)amino)-2-methylpropanoic acid (Compound TS07, Acbz-AIB-OH) (7.0 mg, 0.03 mmol) and N-ethyl-isopropylpropan-2-amine (DIPEA) (8.80 μL, 0.06 mmol) were dissolved in acetonitrile (126 μL). 2-Bromoacetonitrile (2.54 μL, 0.04 mmol) was added at 0° C., and this was stirred at room temperature for three hours. The reaction solution was concentrated to give cyanomethyl 2-((((4-azidobenzyl)oxy)carbonyl)amino)-2-methylpropanoate (Compound TS08, Acbz-AIB-OCH$_2$CN) as a crude product. The obtained crude product was dissolved in acetonitrile (0.75 mL) and was directly used in the next step.

LCMS (ESI) m/z=316 (M+H)−

Retention time: 0.74 minutes (analysis condition SQDFA05)

Synthesis of (2R,3S,4R,5R)-2-((((((2R,3S,4R,5R)-5-(4-amino-2-oxopyrimidin-1(2H)-yl)-4-hydroxy-2-((phosphonooxy)methyl)tetrahydrofuran-3-yl)oxy)(hydroxy)phosphoryl)oxy) methyl)-5-(6-amino-9H-purin-9-yl)-4-hydroxytetrahydrofuran-3-yl 2-((((4-azidobenzyl)oxy) carbonyl)amino)-2-methylpropanoate (Compound TS09, Acbz-AIB-pCpA)

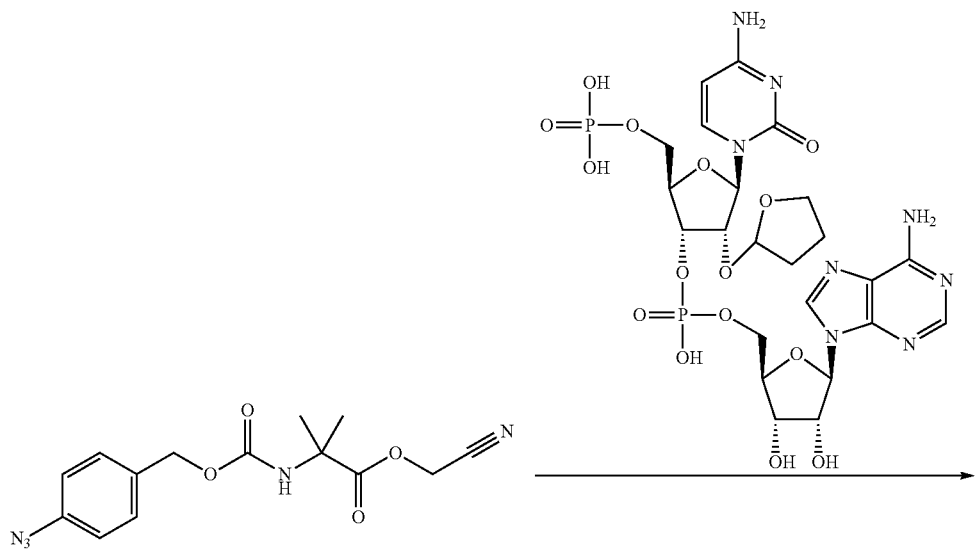

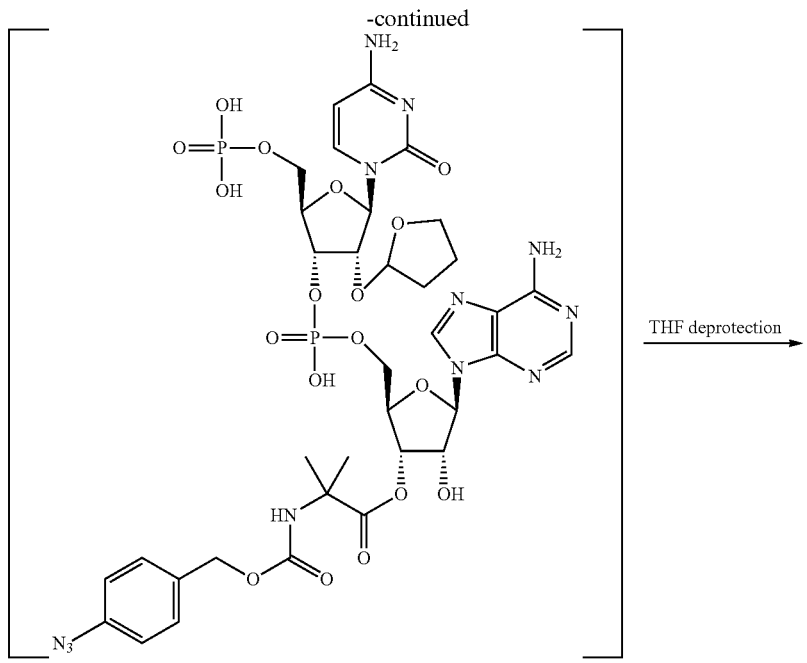

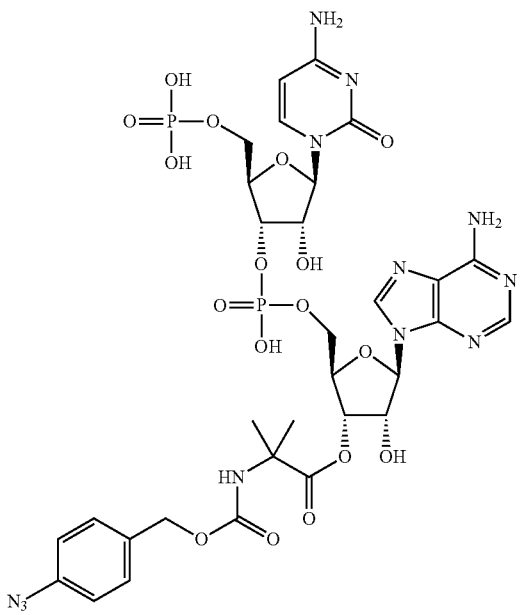

Compound TS09

((2R,3R,4R,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)-4-((tetrahydrofuran-2-yl)oxy)tetrahydrofuran-2-yl) methyl dihydrogenphosphate (Compound pc01) (31.9 mg, 0.044 mmol) was dissolved in Buffer A (15 mL). A solution of cyanomethyl 2-((((4-azidobenzyl)oxy)carbonyl)amino)-2-methylpropanoate (Compound TS08, Acbz-AIB-OCH$_2$CN) in acetonitrile (0.75 mL) was added to it, and this was stirred at room temperature for 120 minutes. The reaction solution was cooled to 0° C., and then trifluoroacetic acid (0.75 mL) was added to it. After stirring the reaction solution at 0° C. for 30 minutes, this was purified by reverse-phase silica gel column chromatography (0.05% aqueous trifluoroacetic acid solution/0.05% trifluoroacetic acid-acetonitrile) to give the titled compound (Compound TS09, Acbz-AIB-pCpA) (1.8 mg, 8.9%).

LCMS (ESI) m/z=1007 (M+H)⁻

Retention time: 0.47 minutes (analysis condition SQDFA05)

Synthesis of 2-((((4-(2-(4-fluorophenyl)acetamide) benzyl)oxy)carbonyl)amino)-2-methylpropanoic acid (Compound TS10, F-Pnaz-AIB-OH)

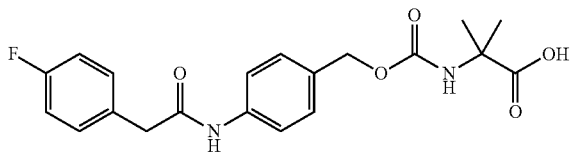 [SMILES: CC(C)(NC(=O)OCc1ccc(NC(=O)Cc2ccc(F)cc2)cc1)C(=O)O]

Under a nitrogen atmosphere, DMSO (1.00 mL) was added at room temperature to a mixture of 2-amino-2-methylpropanoic acid (H-AIB-OH) (12.9 mg, 0.13 mmol), and (4-nitrophenyl)-4-(2-(4-fluorophenyl)acetamide)benzyl carbonate (Compound ts11) (106 mg, 0.25 mmol). After stirring at room temperature for five minutes, triethylamine (40.1 µL, 0.29 mmol) was added at room temperature. The reaction mixture was stirred at 50° C. for 15 hours and then purified by reverse-phase silica gel column chromatography (0.1% aqueous formic acid solution/0.1% formic acid-acetonitrile solution) to give 2-((((4-(2-(4-fluorophenyl)acetamide)benzyl)oxy)carbonyl)amino)-2-methylpropanoic acid (Compound TS10, F-Pnaz-AIB-OH) (21.0 mg, 43%).

LCMS (ESI) m/z=387 (M+H)⁻

Retention time: 0.63 minutes (analysis condition SQDFA05)

Synthesis of cyanomethyl 2-((((4-(2-(4-fluorophenyl)acetamide)benzyl)oxy)carbonyl) amino)-2-methylpropanoate (Compound TS11, F-Pnaz-AIB-OCH₂CN)

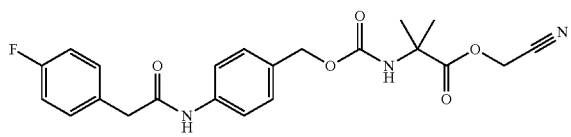

Under a nitrogen atmosphere, 2-((((4-(2-(4-fluorophenyl) acetamide)benzyl) oxy)carbonyl)amino)-2-methylpropanoic acid (Compound TS10, F-Pnaz-AIB-OH) (20.0 mg, 0.05 mmol) and N-ethyl-isopropylpropan-2-amine (DIPEA) (14.39 µL, 0.08 mmol) were dissolved in acetonitrile (257 µL). 2-Bromoacetonitrile (5.18 µL, 0.08 mmol) was added at 0° C., and this was stirred at room temperature for 24 hours. The reaction solution was concentrated to give cyanomethyl 2-((((4-(2-(4-fluorophenyl)acetamide)benzyl)oxy) carbonyl)amino)-2-methylpropanoate (Compound TS11, F-Pnaz-AIB-OCH₂CN) as a crude product. The obtained crude product was dissolved in acetonitrile (1.50 mL) and was directly used in the next step.

LCMS (ESI) m/z=426 (M+H)⁻

Retention time: 0.71 minutes (analysis condition SQDFA05)

Synthesis of (2R,3S,4R,5R)-2-(((((2R,3S,4R,5R)-5-(4-amino-2-oxopyrimidin-1(2H)-yl)-4-hydroxy-2-((phosphonooxy)methyl)tetrahydrofuran-3-yl)oxy)(hydroxy)phosphoryl)oxy) methyl)-5-(6-amino-9H-purin-9-yl)-4-hydroxytetrahydrofuran-3-yl 2-((((4-(2-(4-fluoro-phenyl)acetamide)benzyl)oxy)carbonyl) amino)-2-methylpropanoate (Compound TS12, F-Pnaz-AIB-pCpA)

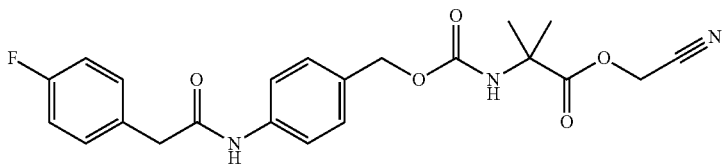 [SMILES: CC(C)(NC(=O)OCc1ccc(NC(=O)Cc2ccc(F)cc2)cc1)C(=O)OCC#N]

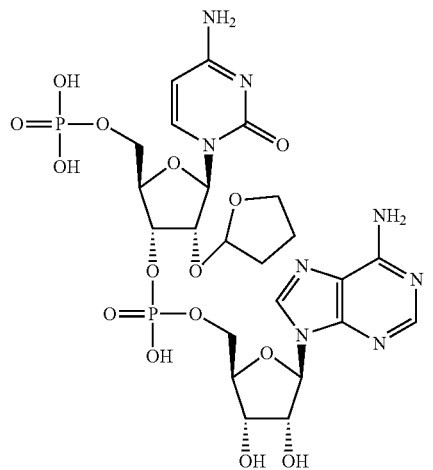

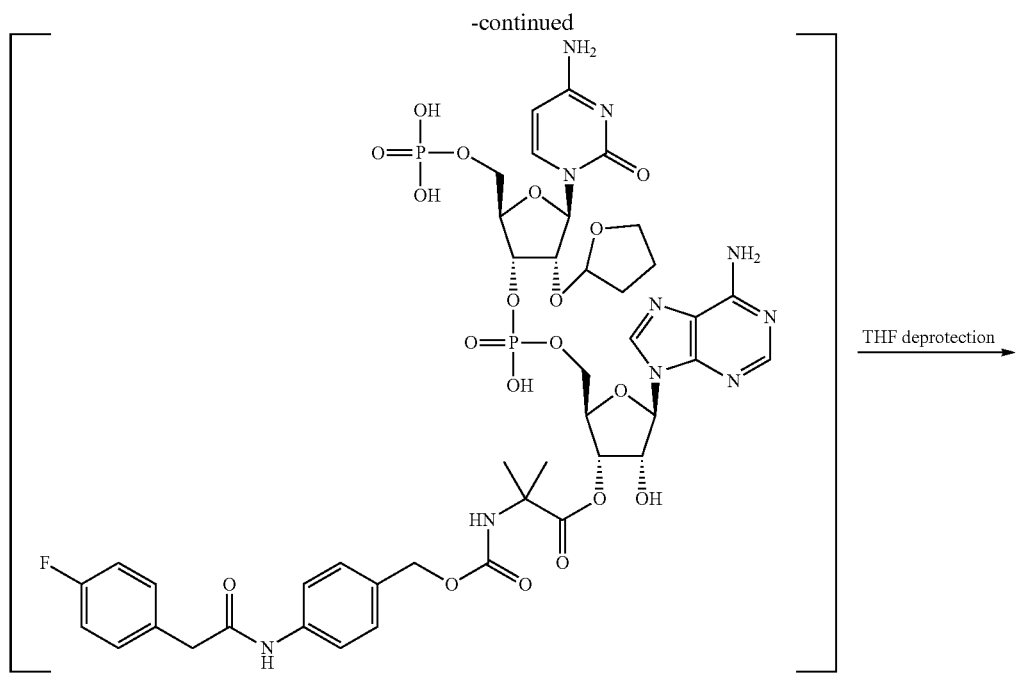

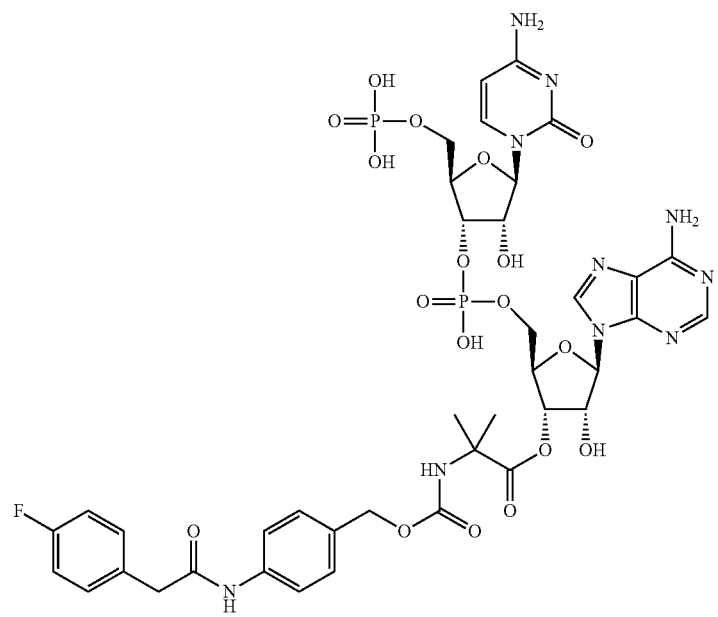

Compound TS12

((2R,3R,4R,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)-4-((tetrahydrofuran-2-yl)oxy)tetrahydrofuran-2-yl) methyl dihydrogenphosphate (Compound pc01) (74.4 mg, 0.103 mmol) was dissolved in Buffer A (30.0 mL). A solution of cyanomethyl 2-(((((4-(2-(4-fluorophenyl)acetamide)benzyl)oxy)carbonyl)amino)-2-methylpropanoate (Compound TS11, F-Pnaz-AIB-OCH$_2$CN) in acetonitrile (1.50 mL) was added to it, and this was stirred at room temperature for 120 minutes. The reaction solution was cooled to 0° C., and then trifluoroacetic acid (1.50 mL) was added to it. After stirring the reaction solution at 0° C. for 30 minutes, this was purified by reverse-phase silica gel column chromatography (0.05% aqueous trifluoroacetic acid solution/0.05% trifluoroacetic acid-acetonitrile) to give the titled compound (Compound TS12, F-Pnaz-AIB-pCpA) (7.3 mg, 13.9%).

LCMS (ESI) m/z=1021 (M+H)⁻

Retention time: 0.46 minutes (analysis condition SQDFA05)

Synthesis of 2-((((4-azidobenzyl)oxy)carbonyl)amino)propanoic acid (Compound TS13, Acbz-β-Ala-OH)

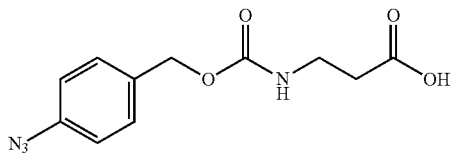 [SMILES: [N-]=[N+]=Nc1ccc(COC(=O)NCCC(=O)O)cc1]

Under a nitrogen atmosphere, DMSO (1.59 mL) was added at room temperature to a mixture of 3-amino propanoic acid (28.4 mg, 0.32 mmol) and 4-azidobenzyl (4-nitrophenyl)carbonate (100 mg, 0.32 mmol) synthesized by the method described in the literature (Bioconjugate Chem. 2008, 19, 714). After stirring at 0° C. for five minutes, triethylamine (127 μL, 0.73 mmol) was added at 0° C. The reaction mixture was stirred at room temperature for 15 hours and then purified by reverse-phase silica gel column chromatography (0.1% aqueous formic acid solution/0.1% formic acid-acetonitrile solution) to give 2-((((4-azidobenzyl)oxy)carbonyl)amino)propanoic acid (Compound TS13, Acbz-β-Ala-OH) (60.0 mg, 71.4%).

LCMS (ESI) m/z=263 (M−H)⁻

Retention time: 0.58 minutes (analysis condition SQDFA05)

Synthesis of cyanomethyl 3-((((4-azidobenzyl)oxy)carbonyl)amino)propanoate (Compound TS14, Acbz-β-Ala-OCH₂CN)

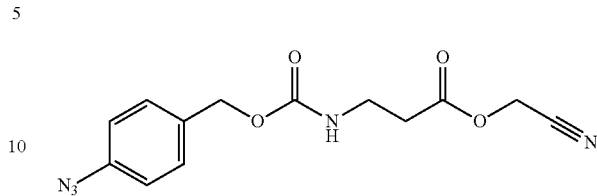

Under a nitrogen atmosphere, 2-((((4-azidobenzyl)oxy)carbonyl)amino)propanoic acid (Compound TS13, Acbz-β-Ala-OH) (60.0 mg, 0.23 mmol) and N-ethyl-isopropylpropan-2-amine (DIPEA) (79.0 μL, 0.45 mmol) were dissolved in acetonitrile (1.14 mL). 2-Bromoacetonitrile (23.0 μL, 0.34 mmol) was added at 0° C., and this was stirred at room temperature for three hours. The reaction solution was concentrated to give cyanomethyl 3-((((4-azidobenzyl)oxy)carbonyl)amino)propanoate (Compound TS14, Acbz-β-Ala-OCH₂CN) as a crude product. The obtained crude product was dissolved in acetonitrile (2.50 mL) and was directly used in the next step.

LCMS (ESI) m/z=302 (M+H)⁻

Retention time: 0.69 minutes (analysis condition SQDFA05)

Synthesis of (2R,3S,4R,5R)-2-((((((2R,3S,4R,5R)-5-(4-amino-2-oxopyrimidin-1(2H)-yl)-4-hydroxy-2-((phosphonooxy)methyl)tetrahydrofuran-3-yl)oxy)(hydroxy)phosphoryl)oxy)methyl)-5-(6-amino-9H-purin-9-yl)-4-hydroxytetrahydrofuran-3-yl 3-((((4-azidobenzyl)oxy)carbonyl)amino)propanoate (Compound TS15, Acbz-β-Ala-pCpA)

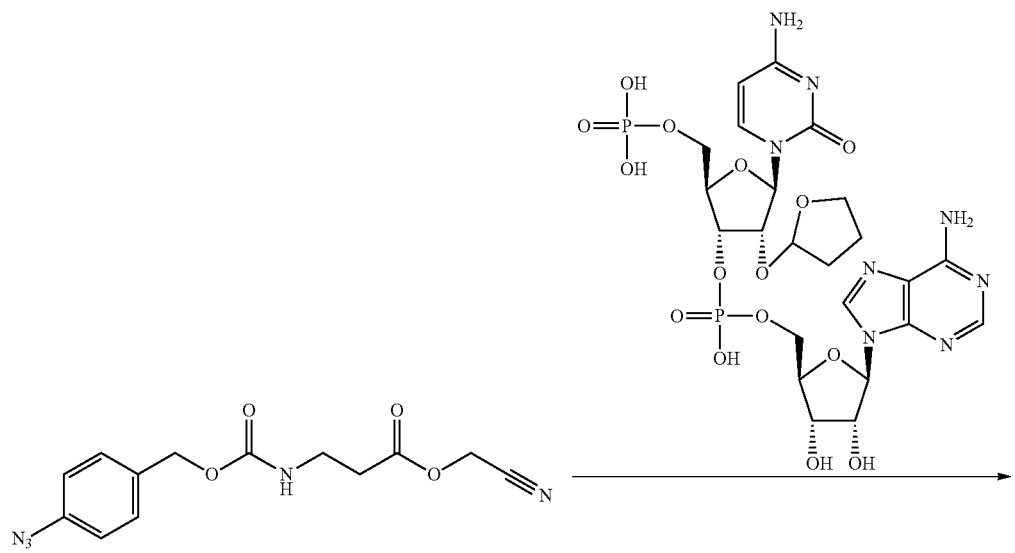

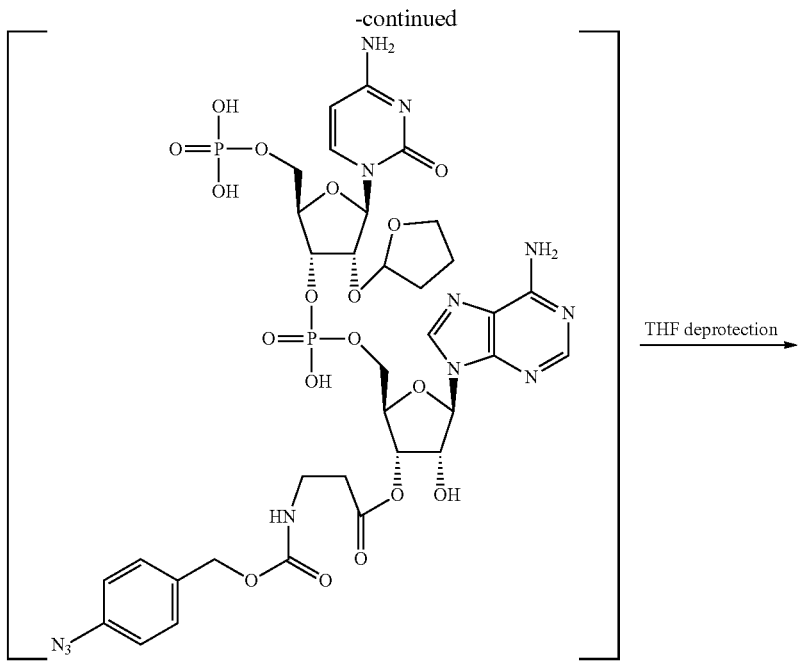

→ THF deprotection

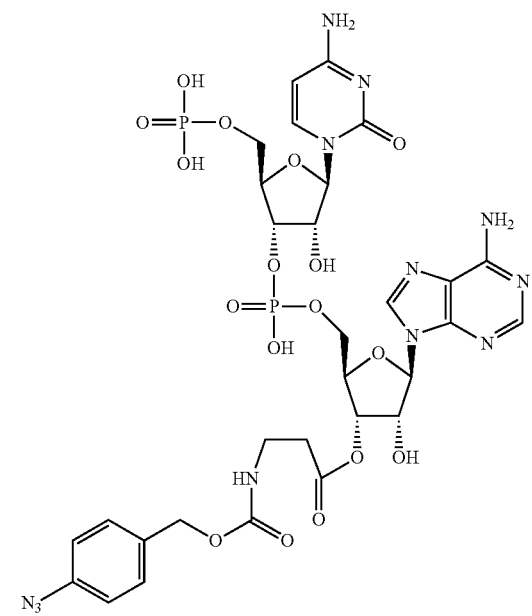

Compound TS15

((2R,3R,4R,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)-4-((tetrahydrofuran-2-yl)oxy)tetrahydrofuran-2-yl) methyl dihydrogenphosphate (Compound pc01) (31.9 mg, 0.044 mmol) was dissolved in Buffer A (50 mL). A solution of cyanomethyl 3-((((4-azidobenzyl)oxy)carbonyl)amino)propanoate (Compound TS14, Acbz-β-Ala-OCH$_2$CN) in acetonitrile (2.50 mL) was added to it, and this was stirred at room temperature for 30 minutes. The reaction solution was cooled to 0° C., and then trifluoroacetic acid (2.50 mL) was added to it. After stirring the reaction solution at 0° C. for 30 minutes, this was purified by reverse-phase silica gel column chromatography (0.05% aqueous trifluoroacetic acid solution/0.05% trifluoroacetic acid-acetonitrile) to give the titled compound (Compound TS15, Acbz-β-Ala-pCpA) (30.0 mg, 33.7%).

LCMS (ESI) m/z=897 (M+H)$^-$

Retention time: 0.42 minutes (analysis condition SQDFA05)

101
Synthesis of 3-((((4-(2-(4-fluorophenyl)acetamide)benzyl)oxy)carbonyl)amino)propanoic acid (Compound TS16, F-Pnaz-β-Ala-OH)

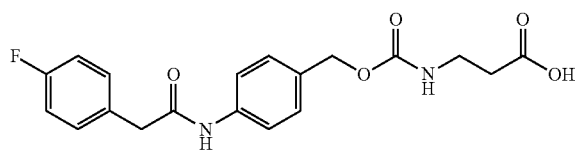 [SMILES: O=C(O)CCNC(=O)OCc1ccc(NC(=O)Cc2ccc(F)cc2)cc1]

Under a nitrogen atmosphere, DMSO (1.00 mL) was added at room temperature to a mixture of 3-amino propanoic acid (22.3 mg, 0.25 mmol) and (4-nitrophenyl)-4-(2-(4-fluorophenyl)acetamide)benzyl carbonate (Compound ts11) (111 mg, 0.26 mmol). After stirring at room temperature for five minutes, triethylamine (80.1 μL, 0.58 mmol) was added at room temperature. The reaction mixture was stirred at room temperature for 15 hours and then purified by reverse-phase silica gel column chromatography (0.1% aqueous formic acid solution/0.1% formic acid-acetonitrile solution) to give 3-((((4-(2-(4-fluorophenyl)acetamide)benzyl)oxy)carbonyl)amino)propanoic acid (Compound TS16, F-Pnaz-β-Ala-OH) (57.0 mg, 60.9%).

LCMS (ESI) m/z=373 (M+H)⁻

Retention time: 0.58 minutes (analysis condition SQDFA05)

102
Synthesis of cyanomethyl 3-((((4-(2-(4-fluorophenyl)acetamide)benzyl)oxy)carbonyl)amino) propanoate (Compound TS17, F-Pnaz-β-Ala-OCH$_2$CN)

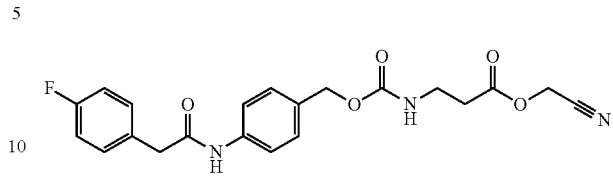

Under a nitrogen atmosphere, 3-((((4-(2-(4-fluorophenyl) acetamide)benzyl)oxy) carbonyl)amino)propanoic acid (Compound TS16, F-Pnaz-β-Ala-OH) (20.0 mg, 0.05 mmol) and N-ethyl-isopropylpropan-2-amine (DIPEA) (14.93 μL, 0.09 mmol) were dissolved in acetonitrile (107 μL). 2-Bromoacetonitrile (5.37 μL, 0.08 mmol) was added at 0° C., and this was stirred at room temperature for 90 minutes. The reaction solution was concentrated to give cyanomethyl 3-((((4-(2-(4-fluorophenyl) acetamide) benzyl)oxy)carbonyl)amino) propanoate (Compound TS17, F-Pnaz-β-Ala-OCH$_2$CN) as a crude product. The obtained crude product was dissolved in acetonitrile (1.50 mL) and was directly used in the next step. LCMS (ESI) m/z=412 (M+H)⁻

Retention time: 0.67 minutes (analysis condition SQDFA05)

Synthesis of (2R,3S,4R,5R)-2-((((((2R,3S,4R,5R)-5-(4-amino-2-oxopyrimidin-1(2H)-yl)-4-hydroxy-2-((phosphonooxy)methyl)tetrahydrofuran-3-yl)oxy)(hydroxy)phosphoryl)oxy) methyl)-5-(6-amino-9H-purin-9-yl)-4-hydroxytetrahydrofuran-3-yl 3-((((4-(2-(4-fluorophenyl)acetamide)benzyl)oxy)carbonyl)amino)propanoate (Compound TS18, F-Pnaz-β-Ala-pCpA)

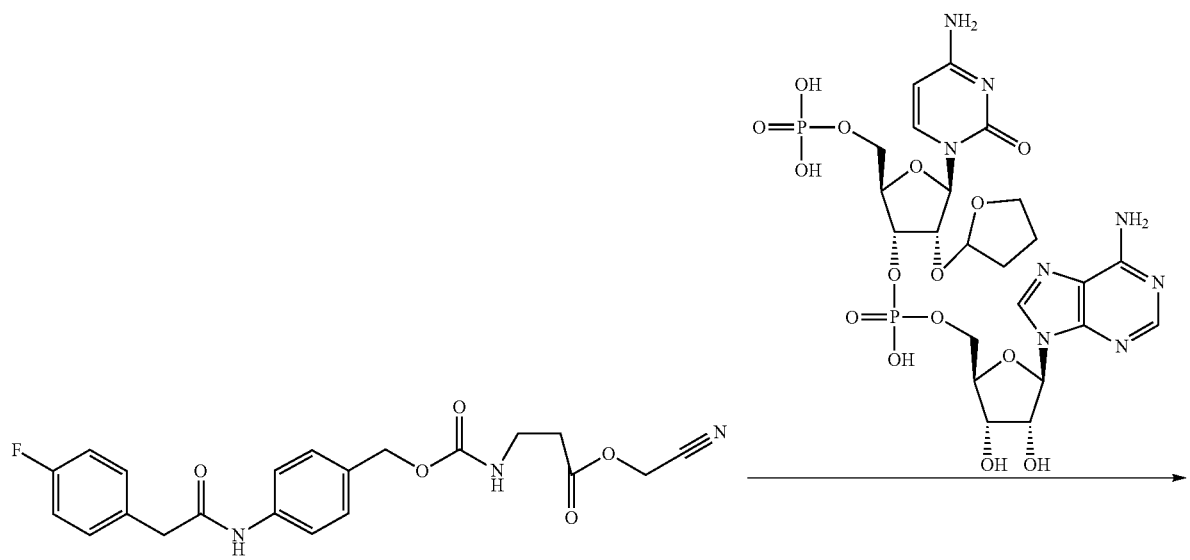

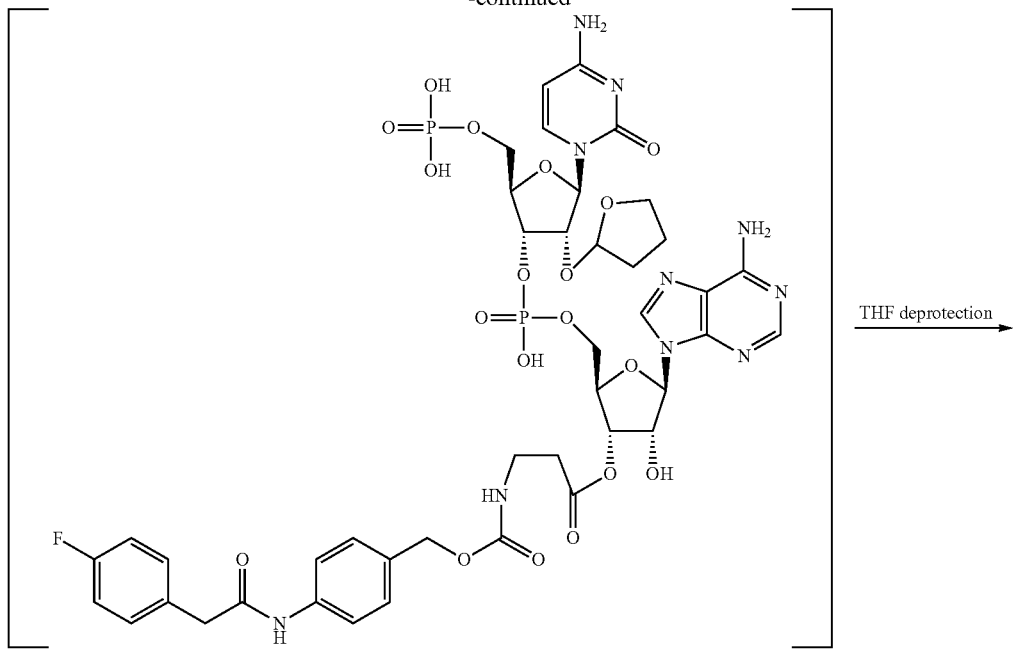

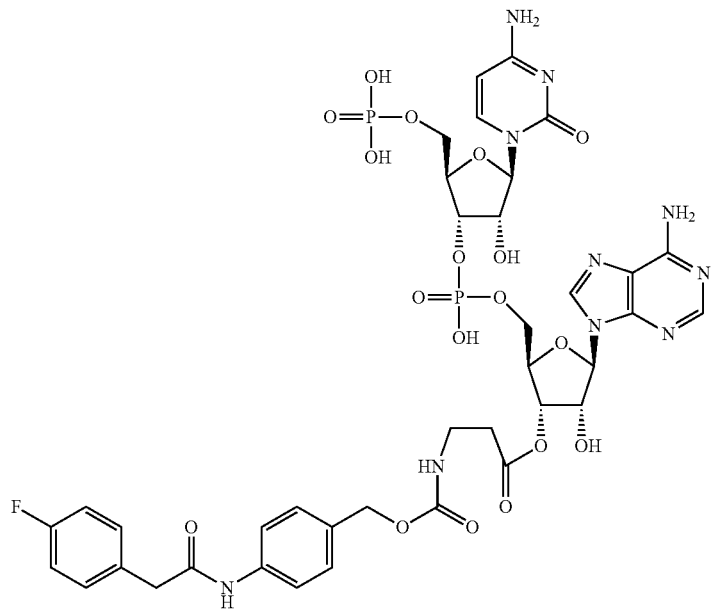

Compound TS18

((2R,3R,4R,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)-4-((tetrahydrofuran-2-yl)oxy)tetrahydrofuran-2-yl) methyl dihydrogenphosphate (Compound pc01) (48.9 mg, 0.068 mmol) was dissolved in Buffer A (30 mL), a solution of cyanomethyl 3-(((((4-(2-(4-fluorophenyl)acetamide)benzyl) oxy)carbonyl)amino)propanoate (Compound TS17, F-Pnaz-β-Ala-OCH₂CN) in acetonitrile (1.50 mL) was added to it, and this was stirred at room temperature for 30 minutes. The reaction solution was cooled to 0° C., and then trifluoroacetic acid (1.50 mL) was added to it. After stirring the reaction solution at 0° C. for 30 minutes, this was purified by reverse-phase silica gel column chromatography (0.05% aqueous trifluoroacetic acid solution/0.05% trifluoroacetic acid-acetonitrile) to give the titled compound (Compound TS18, F-Pnaz-β-Ala-pCpA) (8.6 mg, 17.6%).

LCMS (ESI) m/z=1007 (M+H)⁻

Retention time: 0.44 minutes (analysis condition SQDFA05)

Synthesis of N-(((4-azidobenzyl)oxy)carbonyl)-D-alanine (Compound TS19, Acbz-D-Ala-OH)

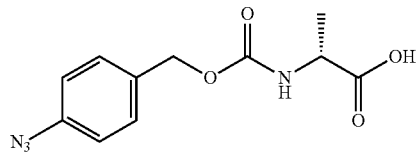 [SMILES: C[C@@H](NC(=O)OCc1ccc(N=[N+]=[N-])cc1)C(=O)O]

Under a nitrogen atmosphere, DMF (1.0 mL) was added at room temperature to a mixture of D-alanine (H-D-Ala-OH) (44.5 mg, 0.50 mmol), and 4-azidobenzyl (4-nitrophenyl)carbonate (157 mg, 0.50 mmol) synthesized by the method described in the literature (Bioconjugate Chem. 2008, 19, 714). After stirring at 0° C. for five minutes, triethylamine (174 μL, 1.25 mmol) was added at 0° C. The reaction mixture was stirred at room temperature for 72 hours and then purified by reverse-phase silica gel column chromatography (0.1% aqueous formic acid solution/0.1% formic acid-acetonitrile solution) to give N-(((4-azidobenzyl)oxy)carbonyl)-D-alanine (Compound TS19, Acbz-D-Ala-OH) (119.1 mg, 90%).

LCMS (ESI) m/z=263 (M−H)⁻

Retention time: 0.61 minutes (analysis condition SQDFA05)

Synthesis of cyanomethyl (((4-azidobenzyl)oxy)carbonyl)-D-alaninate (Compound TS20, Acbz-D-Ala-OCH₂CN)

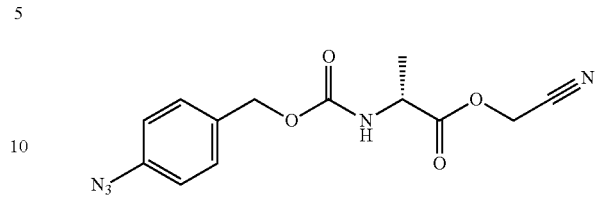

Under a nitrogen atmosphere, N-(((4-azidobenzyl)oxy)carbonyl)-D-alanine (Compound TS19, Acbz-D-Ala-OH) (79.0 mg, 0.3 mmol) and N-ethyl-isopropylpropan-2-amine (DIPEA) (0.079 mL, 0.45 mmol) were dissolved in acetonitrile (600 μL). 2-Bromoacetonitrile (0.030 mL, 0.45 mmol) was added at 0° C., and this was stirred at room temperature for 18 hours. The reaction solution was concentrated to give cyanomethyl (((4-azidobenzyl)oxy)carbonyl)-D-alaninate (Compound TS20, Acbz-D-Ala-OCH₂CN) as a crude product. The obtained crude product was dissolved in acetonitrile (2.00 mL) and was directly used in the next step.

LCMS (ESI) m/z=302 (M+H)⁻

Retention time: 0.71 minutes (analysis condition SQDFA05)

Synthesis of (2R,3S,4R,5R)-2-((((((2R,3S,4R,5R)-5-(4-amino-2-oxopyrimidin-1(2H)-yl)-4-hydroxy-2-((phosphonooxy)methyl)tetrahydrofuran-3-yl)oxy)(hydroxy)phosphoryl)oxy) methyl)-5-(6-amino-9H-purin-9-yl)-4-hydroxytetrahydrofuran-3-yl (((4-azidobenzyl)oxy) carbonyl)-D-alaninate (Compound TS21, Acbz-D-Ala-pCpA)

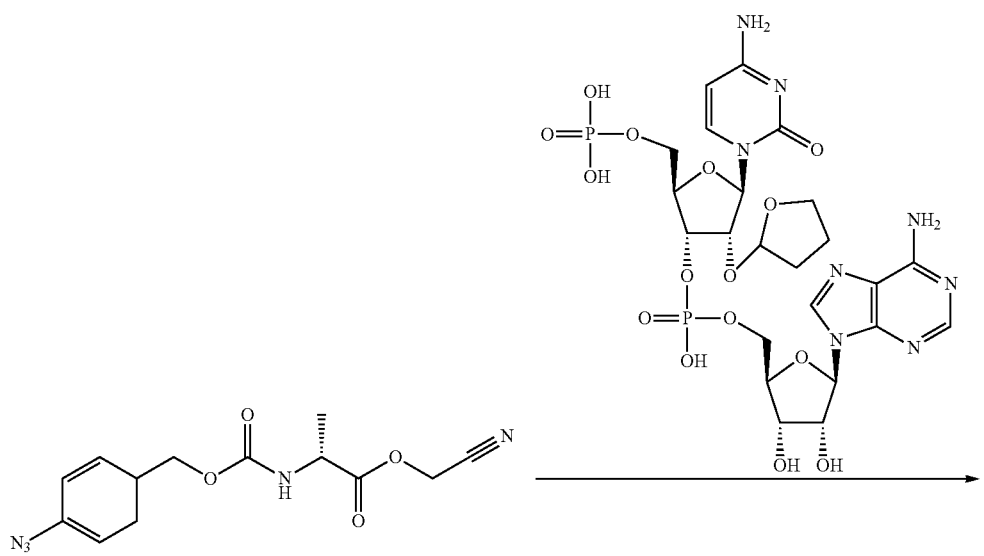

-continued

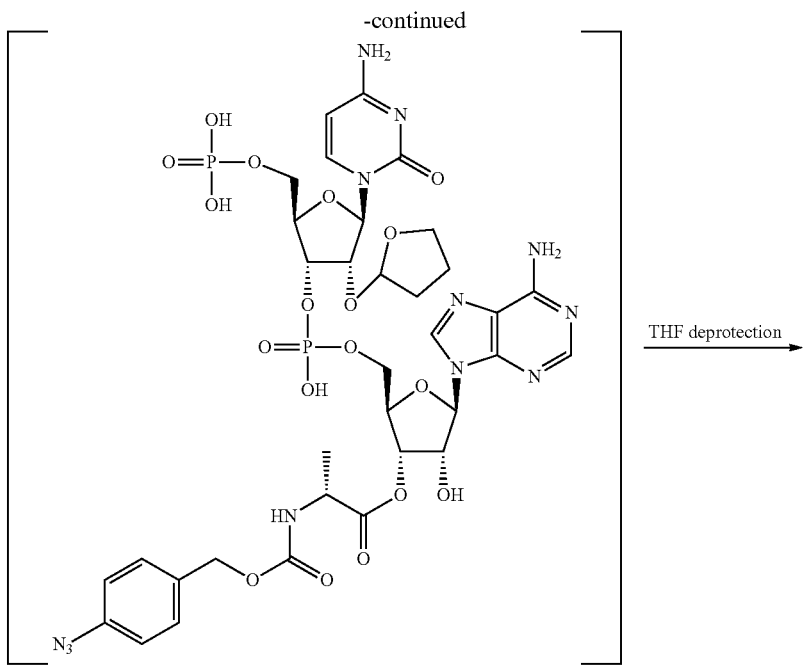

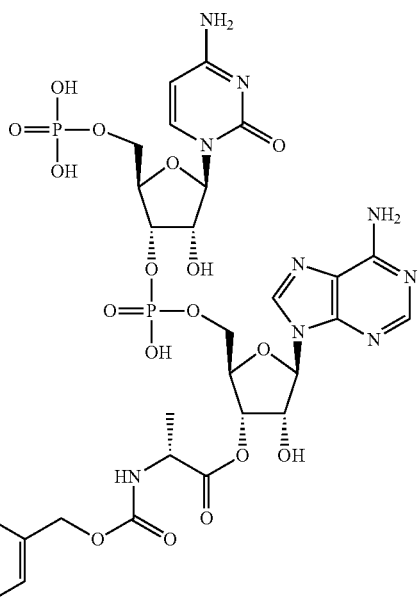

Compound TS21

(((2R,3R,4R,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)-4-((tetrahydrofuran-2-yl)oxy)tetrahydrofuran-2-yl)methyl dihydrogenphosphate (Compound pc01) (108 mg, 0.15 mmol) was dissolved in Buffer A (72 mL). A solution of cyanomethyl (((4-azidobenzyl)oxy)carbonyl)-D-alaninate (Compound TS20, Acbz-D-Ala-OCH$_2$CN) in acetonitrile (2.25 mL) was added to it, and this was stirred at room temperature for 90 minutes. The reaction solution was cooled to 0° C., and then trifluoroacetic acid (2.25 mL) was added to it. After stirring the reaction solution at 0° C. for 30 minutes, this was purified by reverse-phase silica gel column chromatography (0.05% aqueous trifluoroacetic acid solution/0.05% trifluoroacetic acid-acetonitrile) to give the titled compound (Compound TS21, Acbz-D-Ala-pCpA) (56.3 mg, 41.7%).

LCMS (ESI) m/z=899 (M+H)$^+$

Retention time: 0.44 minutes (analysis condition SQDFA05)

Synthesis of (((4-(2-(4-fluorophenyl)acetamide)benzyl)oxy)carbonyl)-D-alanine (Compound TS22, F-Pnaz-D-Ala-OH)

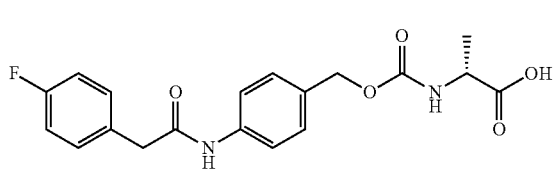 [SMILES: C[C@@H](NC(=O)OCc1ccc(NC(=O)Cc2ccc(F)cc2)cc1)C(=O)O]

Under a nitrogen atmosphere, DMSO (3.74 mL) was added at room temperature to a mixture of D-alanine (H-D-Ala-OH) (100 mg, 1.12 mmol) and (4-nitrophenyl)-4-(2-(4-fluorophenyl)acetamide)benzyl carbonate (Compound ts11) (476 mg, 1.12 mmol). After stirring at room temperature for five minutes, triethylamine (3134, 2.25 mmol) was added at 0° C. The reaction mixture was stirred at room temperature for 20 hours and then purified by reverse-phase silica gel column chromatography (0.1% aqueous formic acid solution/0.1% formic acid-acetonitrile solution) to give (((4-(2-(4-fluorophenyl)acetamide)benzyl)oxy)carbonyl)-D-alanine (Compound TS22, F-Pnaz-D-Ala-OH) (366 mg, 87%).

LCMS (ESI) m/z=373 (M+H)⁻

Retention time: 0.62 minutes (analysis condition SQDFA05)

Synthesis of cyanomethyl (((4-(2-(4-fluorophenyl)acetamide)benzyl)oxy)carbonyl)-D-alaninate (Compound TS23, F-Pnaz-D-Ala-OCH₂CN)

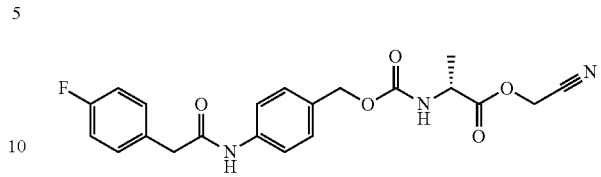

Under a nitrogen atmosphere, (((4-(2-(4-fluorophenyl)acetamide)benzyl)oxy) carbonyl)-D-alanine (Compound TS22, F-Pnaz-D-Ala-OH) (366 mg, 0.98 mmol) and N-ethyl-isopropylpropan-2-amine (DIPEA) (341 μL, 1.95 mmol) were dissolved in acetonitrile (4.88 mL). 2-Bromoacetonitrile (661 μL, 9.77 mmol) was added at 0° C., this was stirred at room temperature for two hours, and then purified by reverse-phase silica gel column chromatography (0.1% aqueous formic acid solution/0.1% formic acid-acetonitrile solution) to give cyanomethyl (((4-(2-(4-fluorophenyl)acetamide)benzyl)oxy)carbonyl)-D-alaninate (Compound TS23, F-Pnaz-D-Ala-OCH₂CN) (390 mg, 97%).

LCMS (ESI) m/z=412 (M+H)⁻

Retention time: 0.71 minutes (analysis condition SQDFA05)

Synthesis of (2R,3S,4R,5R)-2-((((((2R,3S,4R,5R)-5-(4-amino-2-oxopyrimidin-1(2H)-yl)-4-hydroxy-2-((phosphonooxy)methyl)tetrahydrofuran-3-yl)oxy)(hydroxy)phosphoryl)oxy) methyl)-5-(6-amino-9H-purin-9-yl)-4-hydroxytetrahydrofuran-3-yl (((4-(2-(4-fluorophenyl) acetamide)benzyl)oxy)carbonyl)-D-alaninate (Compound TS24, F-Pnaz-D-Ala-pCpA)

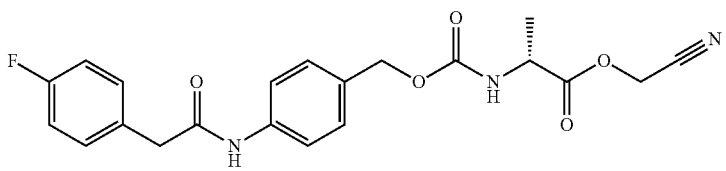

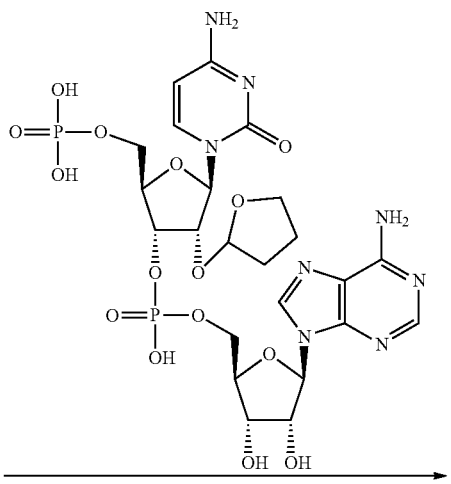

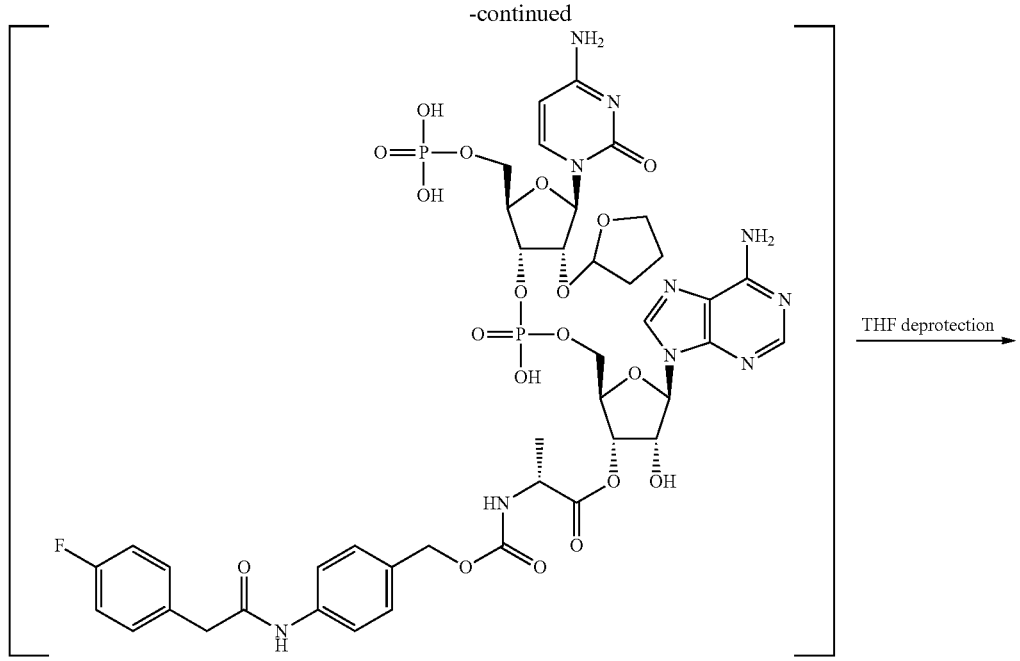

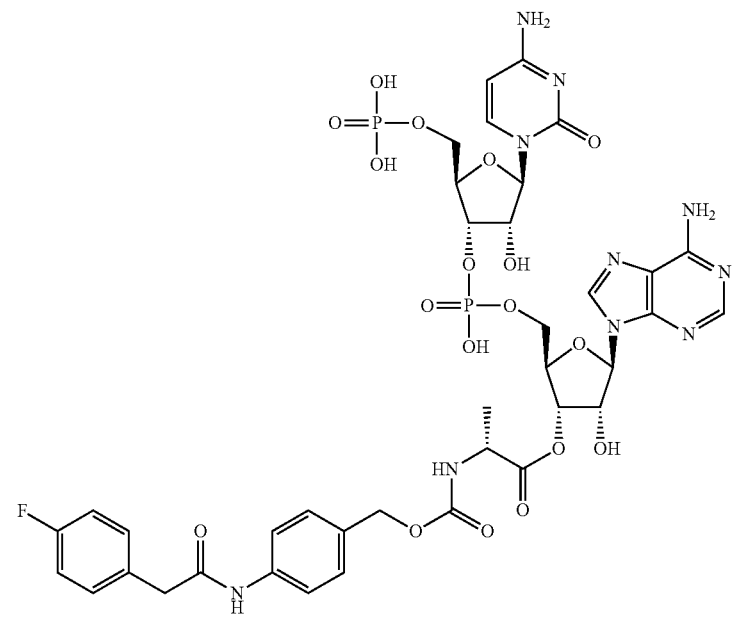

Compound TS24

((2R,3R,4R,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)-4-((tetrahydrofuran-2-yl)oxy)tetrahydrofuran-2-yl) methyl dihydrogenphosphate (Compound pc01) (80.0 mg, 0.083 mmol) was dissolved in Buffer A (45 mL). A solution of cyanomethyl (((4-(2-(4-fluorophenyl)acetamide)benzyl)oxy)carbonyl)-D-alaninate (Compound TS23, F-Pnaz-D-Ala-OCH$_2$CN) (68.7 mg, 0.17 mmol) in acetonitrile (1.50 mL) was added to it, and this was stirred at room temperature for 120 minutes. The reaction solution was cooled to 0° C., and then trifluoroacetic acid (1.50 mL) was added to it. After stirring the reaction solution at 0° C. for 30 minutes, this was purified by reverse-phase silica gel column chromatography (0.05% aqueous trifluoroacetic acid solution/0.05% trifluoroacetic acid-acetonitrile) to give the titled compound (Compound TS24, F-Pnaz-D-Ala-pCpA) (19.7 mg, 23.5%).

LCMS (ESI) m/z=1007 (M+H)$^-$

Retention time: 0.47 minutes (analysis condition SQDFA05)

Synthesis of 4-(hydroxymethyl)phenyl propionate (Compound TS25)

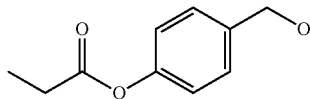

Under a nitrogen atmosphere, DCM (5.00 mL) was added to a mixture of 4-(hydroxymethyl)phenol (124 mg, 1.00 mmol) and DMAP (12.2 mg, 0.10 mmol), this was stirred. Triethylamine (307 μL, 2.20 mmol), and then propionic anhydride (128 μL, 1.00 mmol) was added at room temperature and stirred for 15 minutes. The reaction solution was concentrated, and the obtained residue was purified by normal-phase silica gel column chromatography (hexane/ethyl acetate) to give 4-(hydroxymethyl)phenyl propionate (Compound TS25) (97.0 mg, 54.0%).

LCMS (ESI) m/z=179 (M+H)⁻

Retention time: 0.51 minutes (analysis condition SQDFA05)

Synthesis of 4-((((4-nitrophenoxy)carbonyl)oxy)methyl)phenyl propionate (Compound TS26)

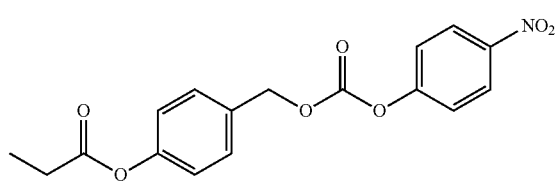 [SMILES: CCC(=O)Oc1ccc(COC(=O)Oc2ccc([N+](=O)[O-])cc2)cc1]

Under a nitrogen atmosphere, a mixture of 4-(hydroxymethyl)phenyl propionate (Compound TS25) (97.0 mg, 0.54 mmol) and 4-nitrophenyl chloroformate (108 mg, 0.54 mmol) was dissolved in DCM (1.00 mL), and this was cooled to 0° C. Pyridine (0.052 mL, 0.65 mmol) was added to this solution, and then this was stirred at room temperature for one hour. The reaction solution was concentrated, and the obtained residue was purified by normal-phase silica gel column chromatography (hexane/ethyl acetate) to give 4-((((4-nitrophenoxy)carbonyl)oxy)methyl)phenyl propionate (Compound TS26) (82.0 mg, 44.1%).

LCMS (ESI) m/z=346 (M+H)⁺

Retention time: 0.86 minutes (analysis condition SQDFA05)

Synthesis of (S)-4-phenyl-2-((((4-(propionyloxy)benzyl)oxy)carbonyl)amino)butanoic acid (Compound TS27, Etez-Hph-OH)

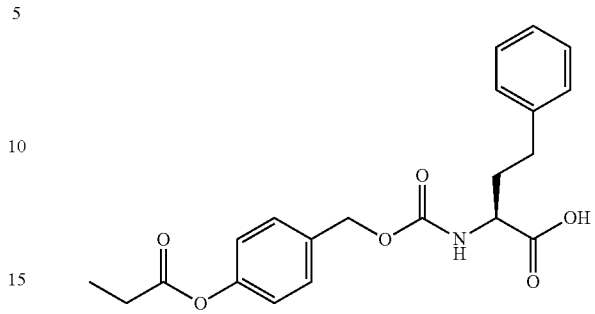

Under a nitrogen atmosphere, DMSO (1.19 mL) was added at room temperature to a mixture of homophenylalanine (H-Hph-OH) (42.6 mg, 0.24 mmol) and 4-((((4-nitrophenoxy)carbonyl)oxy)methyl)phenyl propionate (Compound TS26) (82.0 mg, 0.24 mmol). After stirring at room temperature for five minutes, triethylamine (76.0 μL, 0.55 mmol) was added at room temperature. The reaction mixture was stirred at room temperature for 4 hours and then purified by reverse-phase silica gel column chromatography (0.1% aqueous formic acid solution/0.1% formic acid-acetonitrile solution) to give (S)-4-phenyl-2-((((4-(propionyloxy)benzyl)oxy)carbonyl)amino)butanoic acid (Compound TS27, Etez-Hph-OH) (46.0 mg, 50%).

LCMS (ESI) m/z=384 (M+H)⁻

Retention time: 0.75 minutes (analysis condition SQDFA05)

Synthesis of cyanomethyl (S)-4-phenyl-2-((((4-(propionyloxy)benzyl)oxy)carbonyl)amino) butanoate (Compound TS28, Etez-Hph-OCH₂CN)

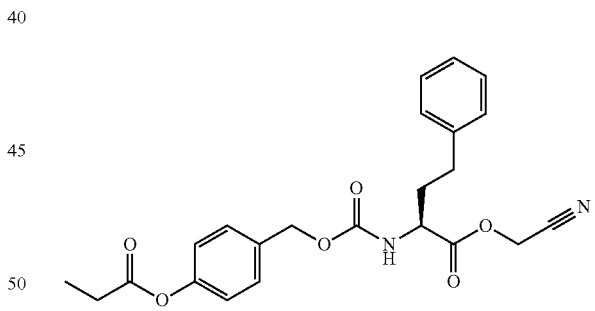

Under a nitrogen atmosphere, (S)-4-phenyl-2-((((4-(propionyloxy)benzyl)oxy)carbonyl)amino)butanoic acid (Compound TS27, Etez-Hph-OH) (46.0 mg, 0.12 mmol) and N-ethyl-isopropylpropan-2-amine (DIPEA) (33.0 μL, 0.19 mmol) were dissolved in acetonitrile (200 μL). 2-Bromoacetonitrile (11.0 μL, 0.17 mmol) was added at room temperature, and this was stirred overnight. The reaction solution was concentrated to give cyanomethyl (S)-4-phenyl-2-((((4-(propionyloxy)benzyl)oxy)carbonyl)amino)butanoate (Compound TS28, Etez-Hph-OCH₂CN) as a crude product. The obtained crude product was dissolved in acetonitrile (3.00 mL) and was directly used in the next step.

LCMS (ESI) m/z=423 (M+H)⁻

Retention time: 0.84 minutes (analysis condition SQDFA05)

Synthesis of (2R,3S,4R,5R)-2-((((((2R,3S,4R,5R)-5-(4-amino-2-oxopyrimidin-1(2H)-yl)-4-hydroxy-2-((phosphonooxy)methyl)tetrahydrofuran-3-yl)oxy)(hydroxy)phosphoryl)oxy) methyl)-5-(6-amino-9H-purin-9-yl)-4-hydroxytetrahydrofuran-3-yl (2S)-4-phenyl-2-((((4-(propionyloxy)benzyl)oxy)carbonyl)amino)butanoate (Compound TS29, Etez-Hph-pCpA)
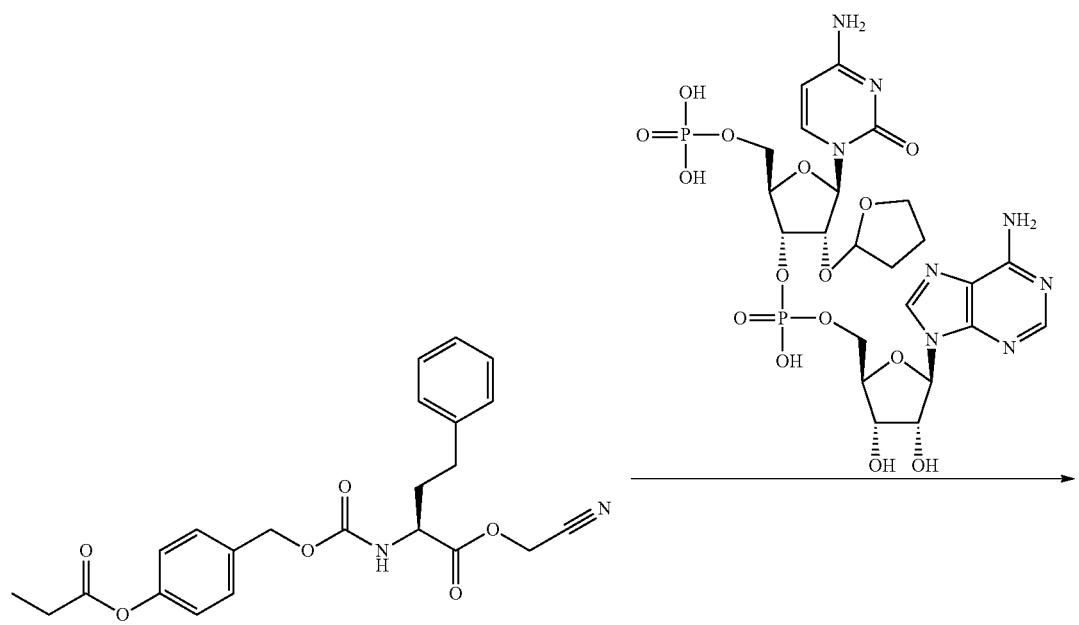
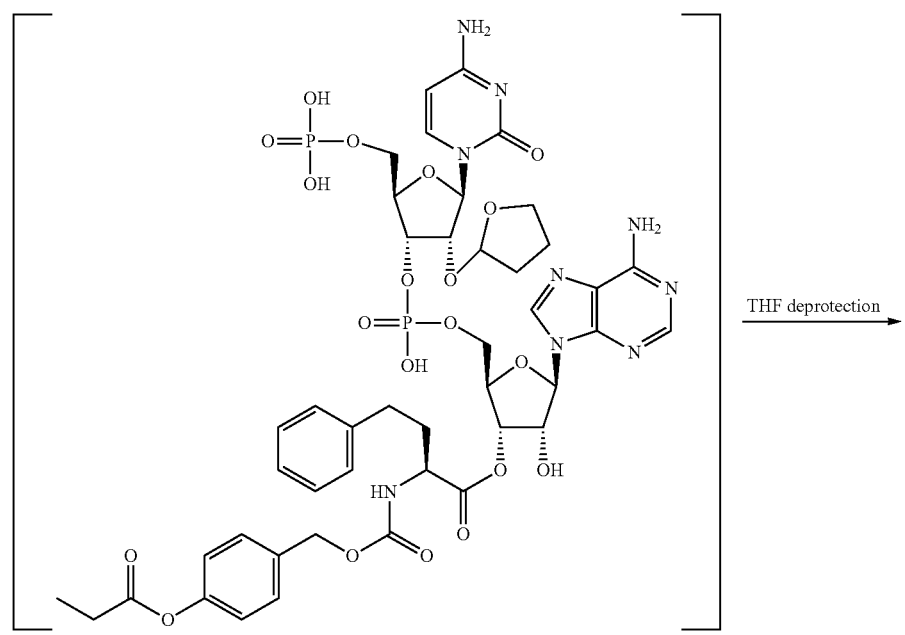
THF deprotection

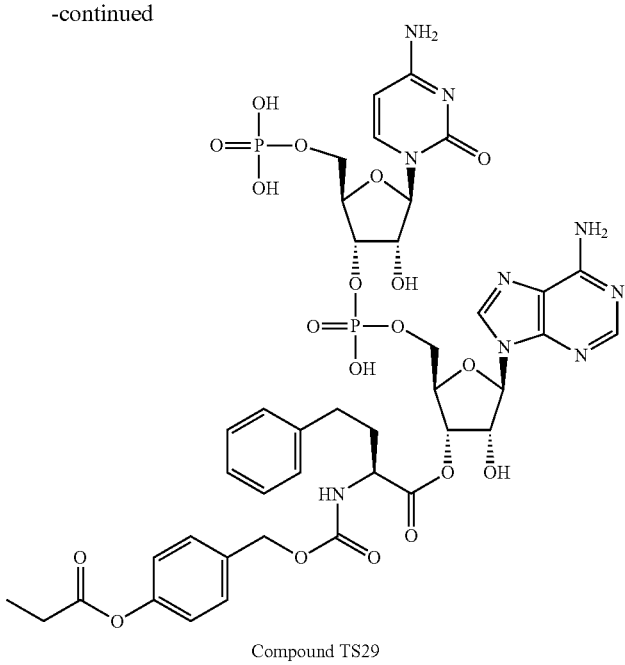

Compound TS29

((2R,3R,4R,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)-4-((tetrahydrofuran-2-yl)oxy)tetrahydrofuran-2-yl) methyl dihydrogenphosphate (Compound pc01) (72.2 mg, 0.10 mmol) was dissolved in Buffer A (60.0 mL). A solution of cyanomethyl (S)-4-phenyl-2-(((((4-(propionyloxy)benzyl)oxy)carbonyl)amino)butanoate (Compound TS28, Etez-Hph-OCH₂CN) in acetonitrile (3.00 mL) was added to it, and this was stirred at room temperature for 60 minutes. The reaction solution was cooled to 0° C., and then trifluoroacetic acid (3.00 mL) was added to it. After stirring the reaction solution at 0° C. for 30 minutes, this was purified by reverse-phase silica gel column chromatography (0.05% aqueous trifluoroacetic acid solution/0.05% trifluoroacetic acid-acetonitrile) to give the titled compound (Compound TS29, Etez-Hph-pCpA) (16.4 mg, 16.1%).

LCMS (ESI) m/z=1018 (M+H)⁻
Retention time: 0.54 minutes (analysis condition SQDFA05)

Synthesis of tert-butyl(S)-(1-((4-(hydroxymethyl)phenyl)amino)-4-methyl-1-oxopentan-2-yl)carbamate (Compound TS30)

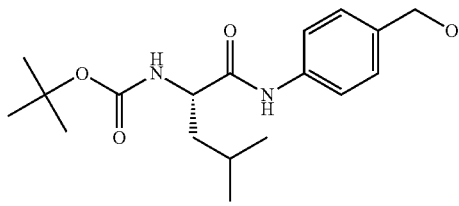 [SMILES: CC(C)C[C@H](NC(=O)OC(C)(C)C)C(=O)Nc1ccc(CO)cc1]

Under a nitrogen atmosphere, DCM (2.00 mL) was added to a mixture of (tert-butoxycarbonyl)-L-leucine (231 mg, 1.00 mmol) and 4-aminophenyl methanol (123 mg, 1.00 mmol) and stirred. Then, ethyl 2-ethoxyquinolin-1(2H)-carboxylate (272 mg, 1.10 mmol) was added at room temperature, and this was stirred for another hour. The reaction solution was purified by reverse-phase silica gel column chromatography (0.1% aqueous formic acid solution/0.1% formic acid-acetonitrile) to give tert-butyl (S)-(1-((4-(hydroxymethyl)phenyl) amino)-4-methyl-1-oxopentan-2-yl)carbamate (Compound TS30) (285.0 mg, 85.0%).
LCMS (ESI) m/z=335 (M+H)⁻
Retention time: 0.66 minutes (analysis condition SQDFA05)

Synthesis of tert-butyl (S)-(4-methyl-1-((4-((((4-nitrophenoxy)carbonyl)oxy)methyl)phenyl) amino)-1-oxopentan-2-yl)carbamate (Compound TS31)

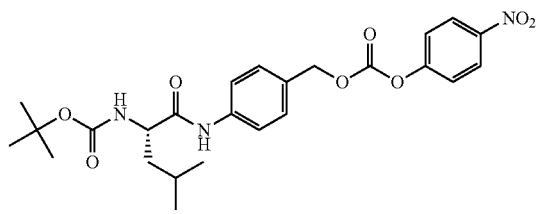 [SMILES: CC(C)C[C@H](NC(=O)OC(C)(C)C)C(=O)Nc1ccc(COC(=O)Oc2ccc([N+](=O)[O-])cc2)cc1]

Under a nitrogen atmosphere, a mixture of tert-butyl (S)-(1-((4-(hydroxymethyl) phenyl)amino)-4-methyl-1-oxopentan-2-yl)carbamate (Compound TS30) (168 mg, 0.50 mmol) and 4-nitrophenylchloroformate (101 mg, 0.50 mmol) were dissolved in DCM (2.00 mL). After this was cooled to 0° C., pyridine (0.049 mL, 0.60 mmol) was added, and this was stirred at room temperature for one hour. After adding DCM (3.5 mL) to the reaction solution, the organic layer was washed twice with water (2 mL) and then concentrated to give the reaction product tert-butyl (S)-(4-methyl-1-((4-((((4-nitrophenoxy) carbonyl)oxy)methyl) phenyl)amino)-1-oxopentan-2-yl)carbamate (Compound TS31) (250.0 mg, 100%).
LCMS (ESI) m/z=502 (M+H)⁺
Retention time: 0.91 minutes (analysis condition SQDFA05)

119

Synthesis of (S)-2-((((4-((S)-2-((tert-butoxycarbonyl)amino)-4-methylpentanamide)benzyl) oxy)carbonyl)amino)-4-phenylbutanoic acid (Compound TS32, Boc-Leuz-Hph-OH)

120

Synthesis of cyanomethyl (S)-2-((((4-((S)-2-((tert-butoxycarbonyl)amino)-4-methylpentanamide)benzyl)oxy)carbonyl)amino)-4-phenylbutanoate (Compound TS33, Boc-Leuz-Hph-OCH₂CN)

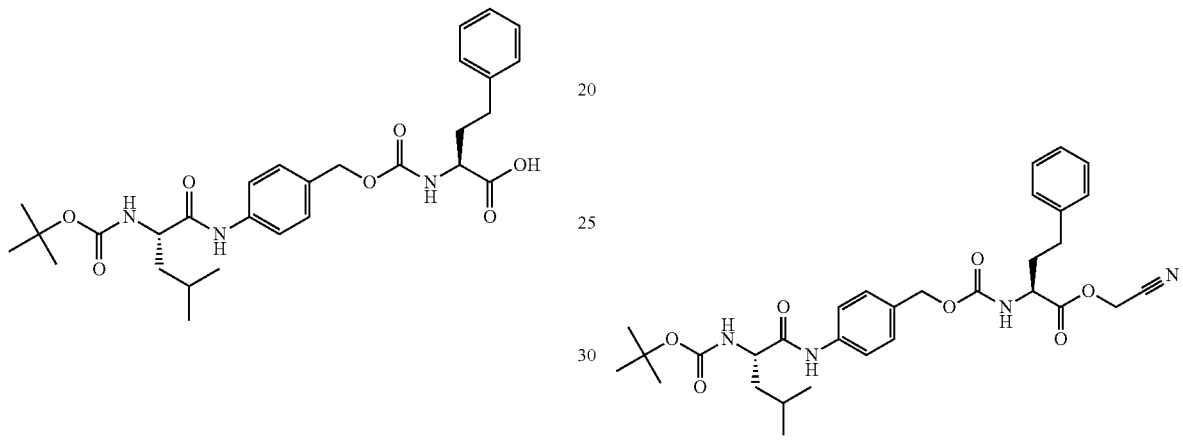

Under a nitrogen atmosphere, DMSO (0.50 mL) was added at room temperature to a mixture of homophenylalanine (H-Hph-OH) (22.4 mg, 0.13 mmol) and tert-butyl (S)-(4-methyl-1-((4-((((4-nitrophenoxy)carbonyl)oxy)methyl)phenyl)amino)-1-oxopentan-2-yl)carbamate (Compound TS31) (62.7 mg, 0.13 mmol). After stirring at room temperature for five minutes, triethylamine (40.0 µL, 0.29 mmol) was added at room temperature. The reaction mixture was stirred at room temperature for three hours and then purified by reverse-phase silica gel column chromatography (0.1% aqueous formic acid solution/0.1% formic acid-acetonitrile solution) to give (S)-2-((((4-((S)-2-((tert-butoxycarbonyl)amino)-4-methylpentanamide)benzyl)oxy)carbonyl)amino)-4-phenylbutanoic acid (Compound TS32, Boc-Leuz-Hph-OH) (37.0 mg, 55%).

LCMS (ESI) m/z=540 (M+H)⁻

Retention time: 0.84 minutes (analysis condition SQDFA05)

Under a nitrogen atmosphere, (S)-2-((((4-((S)-2-((tert-butoxycarbonyl)amino)-4-methylpentanamide)benzyl)oxy)carbonyl)amino)-4-phenylbutanoic acid (Compound TS32, Boc-Leuz-Hph-OH) (14.0 mg, 0.03 mmol) and N-ethylisopropylpropan-2-amine (DIPEA) (7.0 µL, 0.04 mmol) were dissolved in acetonitrile (50 µL). 2-Bromoacetonitrile (2.5 µL, 0.04 mmol) was added at room temperature, and this was stirred at 35° C. for one hour. The reaction solution was concentrated to give cyanomethyl (S)-2-((((4-((S)-2-((tert-butoxycarbonyl)amino)-4-methylpentanamide)benzyl)oxy)carbonyl)amino)-4-phenylbutanoate (Compound TS33, Boc-Leuz-Hph-OCH₂CN) as a crude product. The obtained crude product was dissolved in acetonitrile (0.75 mL) and was directly used in the next step.

LCMS (ESI) m/z=1074 (M+H)⁻

Retention time: 0.46 minutes (analysis condition SQDFA05)

Synthesis of (2R,3S,4R,5R)-2-((((((2R,3S,4R,5R)-5-(4-amino-2-oxopyrimidin-1(2H)-yl)-4-hydroxy-2-((phosphonooxy)methyl)tetrahydrofuran-3-yl)oxy)(hydroxy)phosphoryl) oxy)methyl)-5-(6-amino-9H-purin-9-yl)-4-hydroxytetrahydrofuran-3-yl (2S)-2-((((4-((R)-2-amino-4-methylpentanamide)benzyl)oxy)carbonyl)amino)-4-phenylbutanoate (Compound TS34, Leuz-Hph-pCpA)
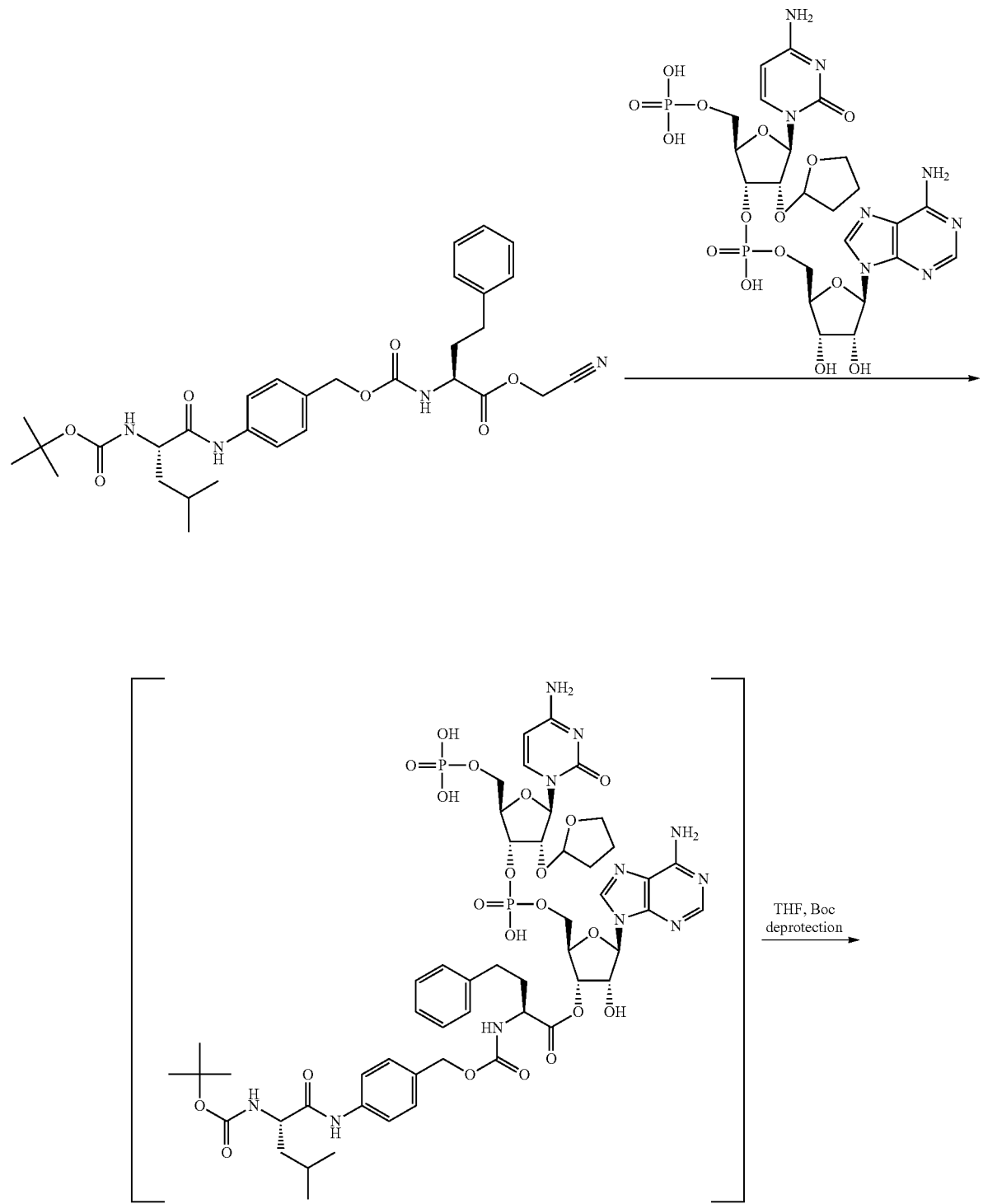

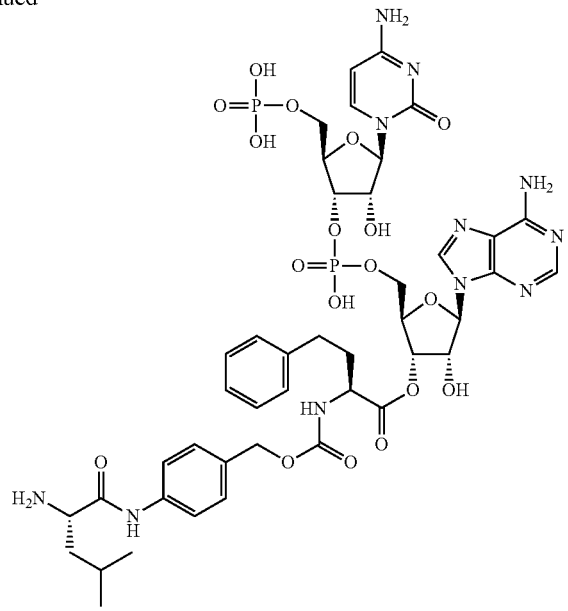

Compound TS34

((2R,3R,4R,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)-4-((tetrahydrofuran-2-yl)oxy)tetrahydrofuran-2-yl) methyl dihydrogenphosphate (Compound pc01) (27.1 mg, 0.04 mmol) was dissolved in Buffer A (15.0 mL). A solution of cyanomethyl (S)-2-(((((4-((S)-2-((tert-butoxycarbonyl)amino)-4-methylpentanamide)benzyl) oxy)carbonyl)amino)-4-phenylbutanoate (Compound TS33, Boc-Leuz-Hph-OCH$_2$CN) in acetonitrile (0.75 mL) was added to it, and this was stirred at room temperature for 60 minutes. After cooling the reaction solution to 0° C., trifluoroacetic acid (3.00 mL) was added to it and the reaction solution was stirred at 0° C. for 60 minutes. Trifluoroacetic acid (4.50 mL) was added further and stirred at room temperature for 45 minutes and then the reaction solution was purified by reverse-phase silica gel column chromatography (0.05% aqueous trifluoroacetic acid solution/0.05% trifluoroacetic acid-acetonitrile) to give the titled compound (Compound TS34, Leuz-Hph-pCpA) (2.0 mg, 7.4%).

LCMS (ESI) m/z=1074 (M+H)⁻

Retention time: 0.46 minutes (analysis condition SQDFA05)

Synthesis of (S)-2-(((((4-azidobenzyl)oxy)carbonyl)amino)-4-phenylbutanoic acid (Compound TS35, Acbz-Hph-OH)

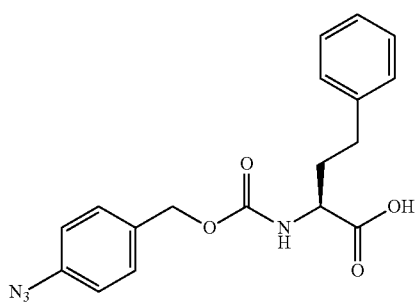 [SMILES: [N-]=[N+]=Nc1ccc(COC(=O)N[C@@H](CCc2ccccc2)C(=O)O)cc1]

Under a nitrogen atmosphere, DMSO (2.0 mL) was added at room temperature to a mixture of homophenylalanine (H-Hph-OH) (54.0 mg, 0.30 mmol) and 4-azidobenzyl (4-nitrophenyl)carbonate (99.0 mg, 0.32 mmol) synthesized by the method described in the literature (Bioconjugate Chem. 2008, 19, 714). After stirring at room temperature for five minutes, triethylamine (966.0 μL, 0.69 mmol) was added at room temperature. The reaction mixture was stirred at room temperature for 15 hours and then purified by reverse-phase silica gel column chromatography (0.1% aqueous formic acid solution/0.1% formic acid-acetonitrile solution) to give (S)-2-((((4-azidobenzyl)oxy)carbonyl)amino)-4-phenylbutanoic acid (Compound TS35, Acbz-Hph-OH) (33.0 mg, 31%).

LCMS (ESI) m/z=353 (M−H)⁻

Retention time: 0.82 minutes (analysis condition SQDFA05)

Synthesis of cyanomethyl (S)-2-((((4-azidobenzyl)oxy)carbonyl)amino)-4-phenylbutanoate (Compound TS36, Acbz-Hph-OCH$_2$CN)

Under a nitrogen atmosphere, (S)-2-((((4-azidobenzyl)oxy)carbonyl)amino)-4-phenylbutanoic acid (Compound TS35, Acbz-Hph-OH) (35.0 mg, 0.10 mmol) and N-ethylisopropylpropan-2-amine (DIPEA) (0.035 mL, 0.20 mmol) were dissolved in acetonitrile (500 μL). 2-Bromoacetonitrile (0.013 mL, 0.20 mmol) was added at room temperature, and this was stirred at room temperature for four hours. The reaction solution was concentrated to give cyanomethyl (S)-2-((((4-azidobenzyl)oxy)carbonyl)amino)-4-phenylbutanoate (Compound TS36, Acbz-Hph-OCH$_2$CN) as a crude product. The obtained crude product was dissolved in acetonitrile (3.00 mL) and was directly used in the next step.

LCMS (ESI) m/z=392 (M+H)⁻

Retention time: 0.91 minutes (analysis condition SQDFA05)

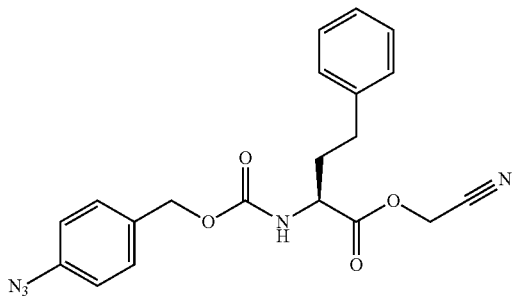 [SMILES: N#CCOC(=O)[C@H](CCc1ccccc1)NC(=O)OCc1ccc(N=[N+]=[N-])cc1]

Synthesis of (2R,3S,4R,5R)-2-((((((2R,3S,4R,5R)-5-(4-amino-2-oxopyrimidin-1(2H)-yl)-4-hydroxy-2-((phosphonooxy)methyl)tetrahydrofuran-3-yl)oxy)(hydroxy)phosphoryl) oxy)methyl)-5-(6-amino-9H-purin-9-yl)-4-hydroxytetrahydrofuran-3-yl (2S)-2-((((4-azidobenzyl)oxy)carbonyl)amino)-4-phenylbutanoate (Compound TS37, Acbz-Hph-pCpA)

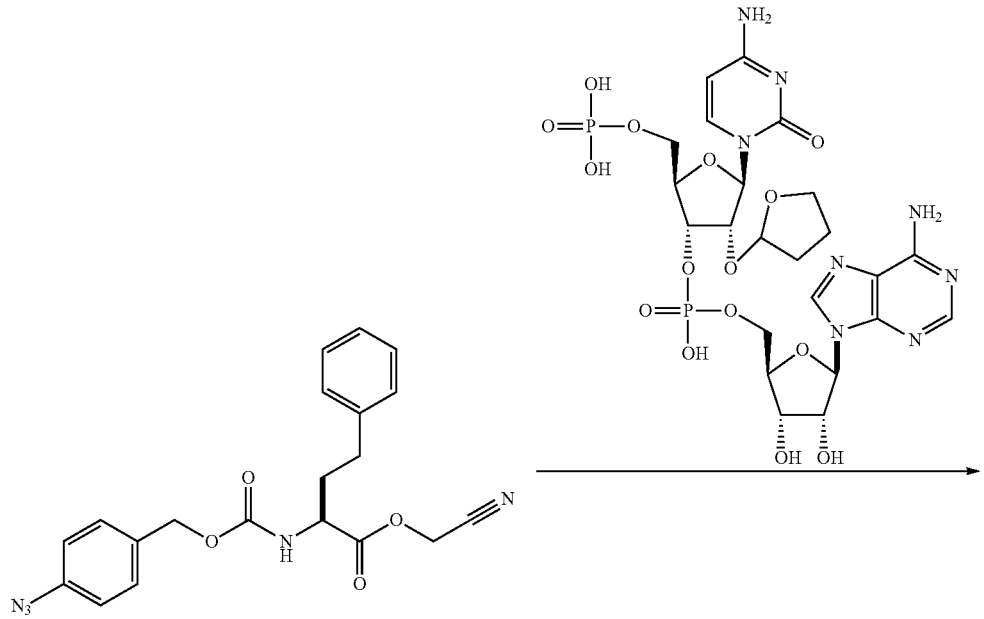

-continued

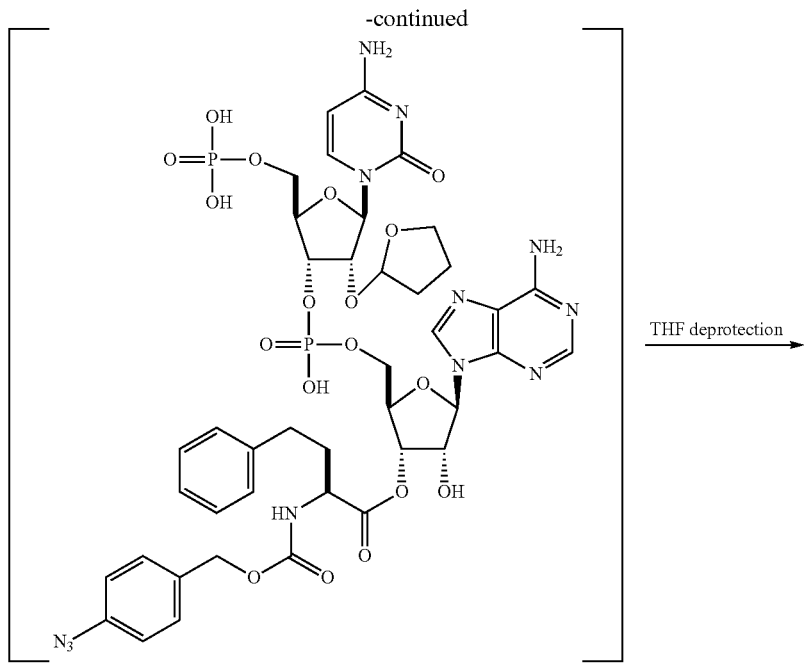

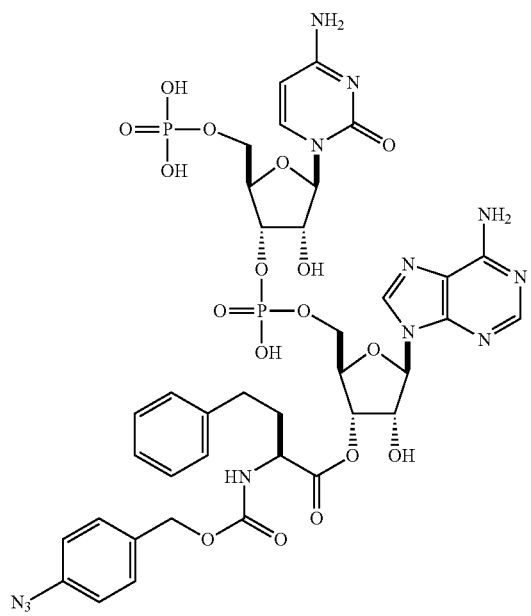

Compound TS37

((2R,3R,4R,5R)-5-(4-amino-2-oxopyrimidin-1(2H)-yl)-3-(((((2R,3S,4R,5R)-5-(6-amino-9H-purin-9-yl)-3,4-dihydroxytetrahydrofuran-2-yl)methoxy)(hydroxy)phosphoryl)oxy)-4-((tetrahydrofuran-2-yl)oxy)tetrahydrofuran-2-yl) methyl dihydrogenphosphate (Compound pc01) (72.0 mg, 0.10 mmol) was dissolved in Buffer A (60 mL). A solution of cyanomethyl (S)-2-((((4-azidobenzyl)oxy)carbonyl)amino)-4-phenylbutanoate (Compound TS36, Acbz-Hph-OCH$_2$CN) in acetonitrile (3.00 mL) was added to it, and this was stirred at room temperature for 120 minutes. The reaction solution was cooled to 0° C., and then trifluoroacetic acid (3.00 mL) was added to it. After stirring the reaction solution at 0° C. for 30 minutes, this was purified by reverse-phase silica gel column chromatography (0.05% aqueous trifluoroacetic acid solution/0.05% trifluoroacetic acid-acetonitrile) to give the titled compound (Compound TS37, Acbz-Hph-pCpA) (27.0 mg, 27%).

LCMS (ESI) m/z=987 (M+H)$^-$

Retention time: 0.62 minutes (analysis condition SQDFA05)

Example 2 Synthesis of Aminoacylated tRNA

The following tRNAGluUAG(-CA) was prepared by the ordinary method. Sequence Number TR-1 (SEQ ID NO: 1) tRNAGluUAG(-CA) RNA sequence:

GUCCCCUUCGUCUAGAGGCCCAGGACACCGCCCUUAGACGGCGGUAACA

GGGGUUCGAAUCCCCUAGGGGACGC

The following tRNAGluACG(-CA) was prepared by the ordinary method. Sequence Number TR-2 (SEQ ID NO: 9) tRNAGluACG(-CA) RNA sequence:

GUCCCCUUCGUCUAGAGGCCCAGGACACCGCCCUACGACGGCGGUAACA

GGGGUUCGAAUCCCCUAGGGGACGC

Synthesis of Aminoacylated-tRNA Using Aminoacylated pCpA: Part 1

10× Ligation buffer (500 mM HEPES-KOH pH 7.5, 200 mM MgCl$_2$) (4 µL), 10 mM ATP (4 µL), and nuclease free water (5.6 µL) were added to 50 µM transcribed tRNA-GluUAG(-CA) (Sequence Number TR-1) (20 µL), this was heated at 95° C. for two minutes and then left to stand at room temperature for five minutes to perform refolding of tRNA. 2.4 µL of 10 units/4 T4 RNA ligase (New England Biolabs) and 4 µL of a 2.5 mM solution of aminoacylated pCpA (ts05, ts07, ts09, ts14, ts19, ts20, ts23, ts26, or ts29) in DMSO were added, and ligation reaction was carried out at 16° C. for 45 minutes. 0.3 M Sodium acetate and 62.5 mM iodine (solution in water:THF=1:1) were added to the ligation reaction solution, this was left to stand at room temperature for ten minutes to perform deprotection of the pentenoyl group. Then, phenol-chloroform extraction was carried out, and aminoacylated tRNA (Compounds AAtR-1, 2, 3, 4, 5, 6, 7, 8, or 9) was collected by ethanol precipitation. (This operation was not performed for ts05, ts07, ts09, ts14, ts19, and ts20 in which their protecting groups are not pentenoyl.) The collected aminoacylated tRNA (Compound AAtR-1, 2, 3, 4, 5, 6, 7, 8, or 9) was dissolved in 1 mM sodium acetate immediately prior to addition to the translation mixture.

Aze(2)-tRNAGluUAG (SEQ ID NO: 2)

Compound AAtR-1 nBuG-tRNAGluUAG (SEQ ID NO: 2)

Compound AAtR-2

Ala(3-Pyr)-tRNAGluUAG (SEQ ID NO: 2)

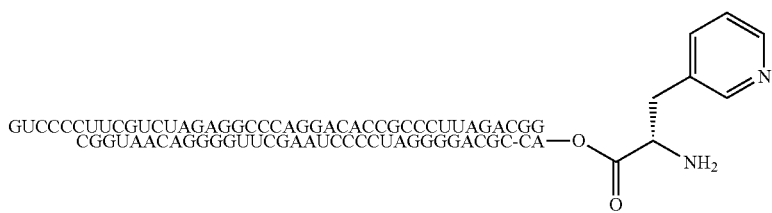

Compound AAtR-3

Acbz-Aze(2)-tRNAGluUAG (SEQ ID NO: 2)

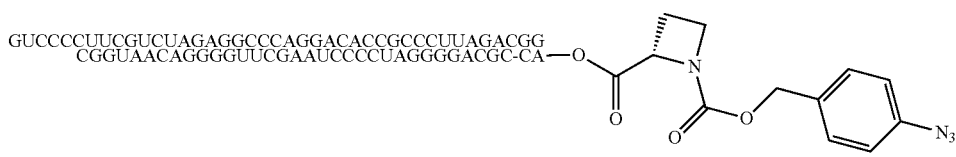

Compound AAtR-4

Acbz-nBuG-tRNAGluUAG (SEQ ID NO: 2)

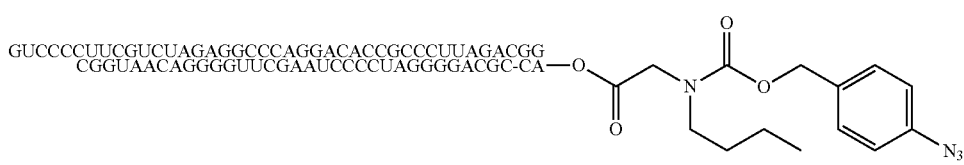

Compound AAtR-5

-continued

Acbz-Ala(3-Pyr)-tRNAGluUAG (SEQ ID NO: 2)

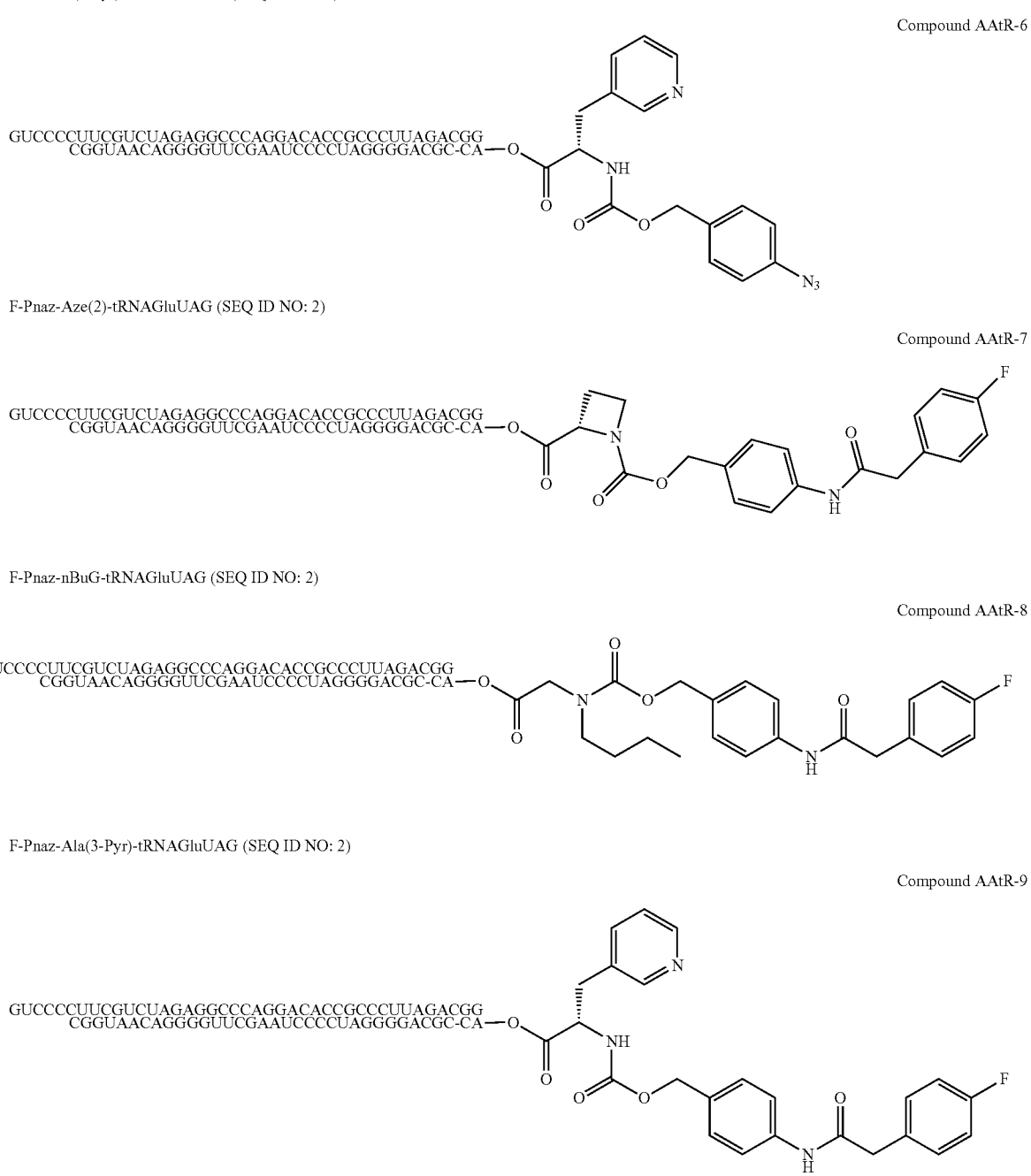

Compound AAtR-6

F-Pnaz-Aze(2)-tRNAGluUAG (SEQ ID NO: 2)

Compound AAtR-7

F-Pnaz-nBuG-tRNAGluUAG (SEQ ID NO: 2)

Compound AAtR-8

F-Pnaz-Ala(3-Pyr)-tRNAGluUAG (SEQ ID NO: 2)

Compound AAtR-9

Synthesis of Aminoacylated-tRNA Using Aminoacylated pCpA: Part 2

10× Ligation buffer (500 mM HEPES-KOH pH 7.5, 200 mM MgCl$_2$) (4 μL), 10 mM ATP (4 μL), and nuclease free water (5.6 μL) were added to 50 μM transcribed tRNA-GluUAG(-CA) (Sequence Number TR-1) (20 μL), this was heated at 95° C. for two minutes and then left to stand at room temperature for five minutes to perform refolding of the tRNA. 2.4 μL of 10 units/4 T4 RNA ligase (New England Biolabs) and 4 μL of a 2.5 mM solution of aminoacylated pCpA (TS03, TS06, TS09, TS12, TS15, TS18, TS21, TS24, TS29, or TS37) in DMSO were added, and ligation reaction was carried out at 16° C. for 45 minutes. 0.3 M Sodium acetate and 0.5 M aqueous TCEP solution (adjusted to pH 7, 4 μL) were added to the ligation reaction solution, this was left to stand at room temperature for ten minutes to perform deprotection of the Acbz group. Then, phenol-chloroform extraction was carried out, and aminoacylated tRNA was collected by ethanol precipitation. (This deprotection operation was not performed for TS06, TS12, TS18, TS24, and TS29 in which their protecting groups are not Acbz.) The collected aminoacylated tRNA (any one of Compounds AAtR-10 to AAtR-14, and AAtR-16 to AAtR-20) was dissolved in 1 mM sodium acetate immediately prior to addition to the translation mixture.

Ala-tRNAGluUAG (SEQ ID NO: 2)
Compound AAtR-10
AIB-tRNAGluUAG (SEQ ID NO: 2)
Compound AAtR-11
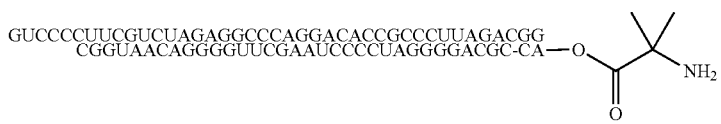
β-Ala-tRNAGluUAG (SEQ ID NO: 2)
Compound AAtR-12
D-Ala-tRNAGluUAG (SEQ ID NO: 2)
Compound AAtR-13
Hph-tRNAGluUAG (SEQ ID NO: 2)
Compound AAtR-14
F-Pnaz-Ala-tRNAGluUAG (SEQ ID NO: 2)
Compound AAtR-16
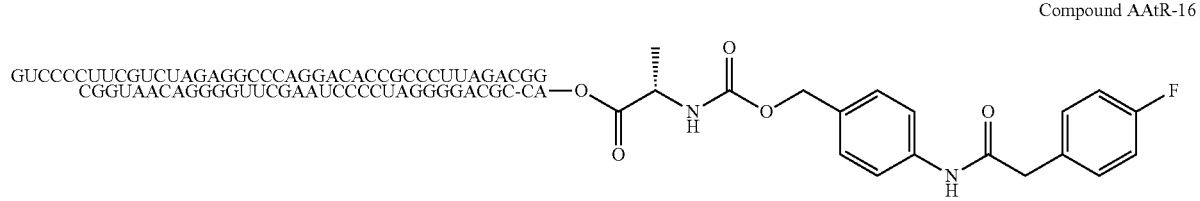
F-Pnaz-AIB-tRNAGluUAG (SEQ ID NO: 2)
Compound AAtR-17
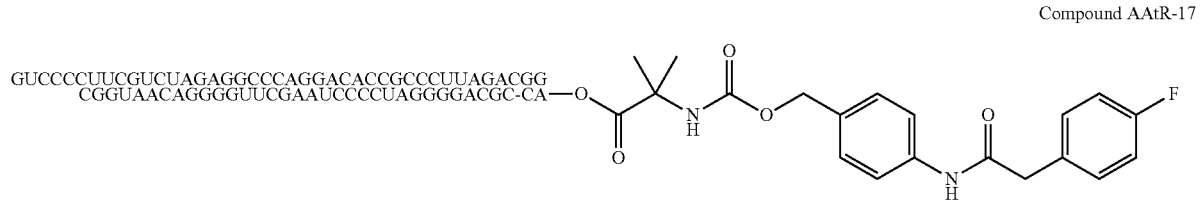
F-Pnaz-β-Ala-tRNAGluUAG (SEQ ID NO: 2)
Compound AAtR-18
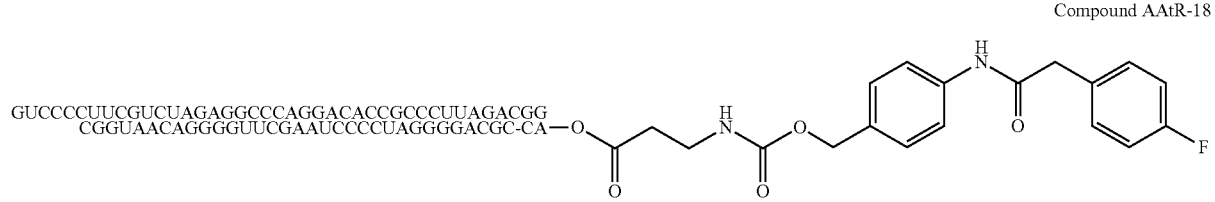

-continued

F-Pnaz-D-Ala-tRNAGluUAG (SEQ ID NO: 2)

Compound AAtR-19

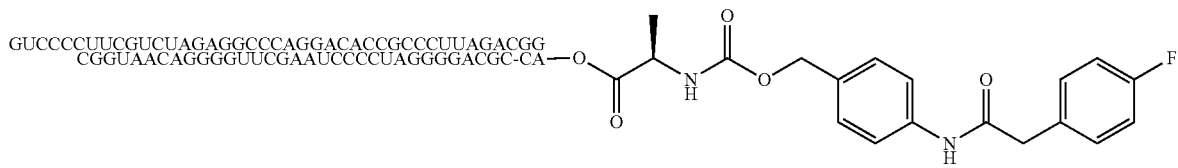

GUCCCCUUCGUCUAGAGGCCCAGGACACCGCCCUUAGACGG
CGGUAACAGGGGUUCGAAUCCCCUAGGGGACGC-CA

Etez-Hph-tRNAGluUAG (SEQ ID NO: 2)

Compound AAtR-20

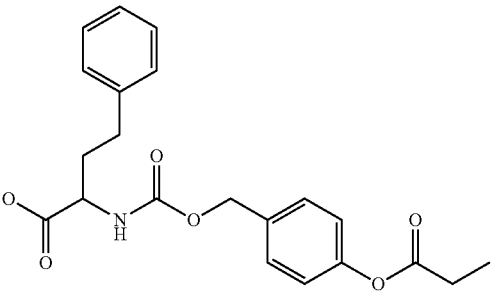

GUCCCCUUCGUCUAGAGGCCCAGGACACCGCCCUUAGACGG
CGGUAACAGGGGUUCGAAUCCCCUAGGGGACGC-CA

Synthesis of Aminoacylated-tRNA Using Aminoacylated pCpA: Part 3

10× Ligation buffer (500 mM HEPES-KOH pH 7.5, 200 mM MgCl$_2$) (4 μL), 10 mM ATP (4 μL), and nuclease free water (5.6 μL) were added to 50 μM transcribed tRNA-GluUAG(-CA) (Sequence Number TR-2) (20 μL), this was heated at 95° C. for two minutes and then left to stand at room temperature for five minutes to perform refolding of the tRNA. 2.4 μL of 10 units/4 T4 RNA ligase (New England Biolabs) and 4 μL of a 2.5 mM solution of aminoacylated pCpA (TS34 or TS37) in DMSO were added, and ligation reaction was carried out at 16° C. for 45 minutes. 0.3 M Sodium acetate and 0.5 M aqueous TCEP solution (adjusted to pH 7, 4 μL) were added to the ligation reaction solution, this was left to stand at room temperature for ten minutes to perform deprotection of the Acbz group. Then, phenol-chloroform extraction was carried out, and aminoacylated tRNA was collected by ethanol precipitation. (This deprotection operation was not performed for TS34 in which its protecting group is not Acbz.) The collected aminoacylated tRNA (Compound AAtR-15 or AAtR-21) was dissolved in 1 mM sodium acetate immediately prior to addition to the translation mixture.

Hph-tRNaGluACG (SEQ ID NO: 10)

Compound AAtR-15

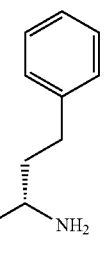

GUCCCCUUCGUCUAGAGGCCCAGGACACCGCCCUACGACGG
CGGUAACAGGGGUUCGAAUCCCCUAGGGGACGC-CA

-continued

Leuz-Hph-tRNAGluACG (SEQ ID NO: 10)

Compound AAtR-21

GUCCCCUUCGUCUAGAGGCCCAGGACACCGCCCUACGACGG
CGGUAACAGGGGUUCGAAUCCCCUAGGGGACGC-CA—O

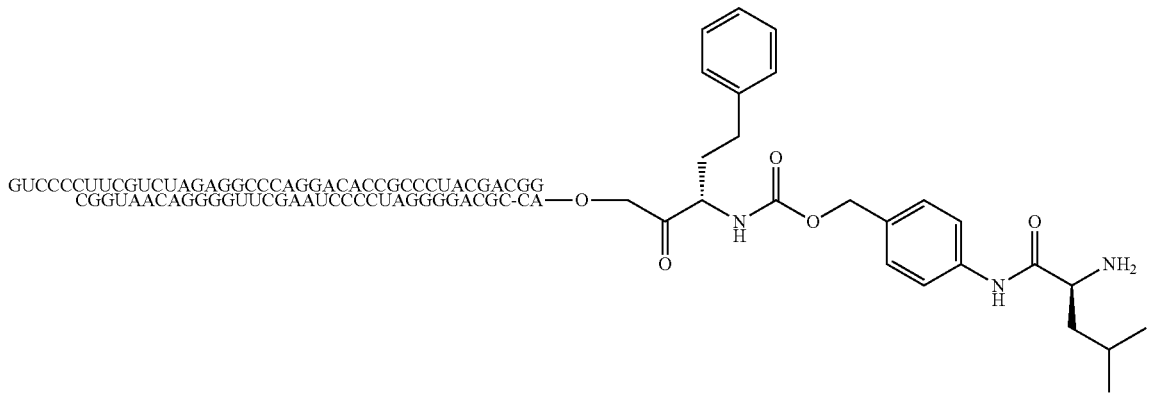

Next, experiments were performed to confirm how translation efficiency of an amino acid and product purity are affected in translation elongation reaction by using the present method. Specifically, the same peptide compounds containing the same amino acids were ribosomally synthesized, mass spectrometry were used for comparison and confirmation of product purities, and radioisotope-labeled species were used for comparison and confirmation of translation efficiencies.

Example 3 Peptide Ribosomal Synthesis

Ribosomal synthesis was performed. The translation system used was PURE system, an *E. coli*-derived reconstituted cell-free protein synthesis system. Specifically, the synthesis was carried out as follows: 1 µM template mRNA and 250 µM each of amino acids, Ala, Phe, Gly, Lys, Met, Pro, Arg, Ser, and Val, were added to a cell-free translation solution (1% (v/v) RNasein Ribonuclease inhibitor (Promega, N2111), 1 mM GTP, 1 mM ATP, 20 mM creatine phosphate, 50 mM HEPES-KOH (pH 7.6), 100 mM potassium acetate, 6 mM magnesium acetate, 2 mM spermidine, 1 mM dithiothreitol, 1.5 mg/mL *E. coli* MRE600 (RNase-negative)-derived tRNA (Roche), 0.1 mM 10-HCO—H4 folate, 4 µg/ml creatine kinase, 3 µg/ml myokinase, 2 units/mL inorganic pyrophosphatase, 1.1 µg/mL nucleoside diphosphate kinase, 0.6 µM methionyl-tRNA transformylase, 0.26 µM EF-G, 0.24 µM RF2, 0.17 µM RF3, 0.5 µM RRF, 2.7 µM IF1, 0.4 µM IF2, 1.5 µM IF3, 40 µM EF-Tu, 44 µM EF-Ts, 1.2 µM ribosome, 0.73 µM AlaRS, 0.03 µM ArgRS, 0.38 µM AsnRS, 0.13 µM AspRS, 0.02 µM CysRS, 0.06 µM GlnRS, 0.23 µM GluRS, 0.09 µM GlyRS, 0.02 µM HisRS, 0.4 µM IleRS, 0.04 µM LeuRS, 0.11 µM LysRS, 0.03 µM MetRS, 0.68 µM PheRS, 0.16 µM ProRS, 0.04 µM SerRS, 0.09 µM ThrRS, 0.03 µM TrpRS, 0.02 µM TyrRS, 0.02 µM ValRS (self-prepared proteins were basically prepared as His-tagged proteins)), 10 µM aminoacylated tRNA Glu were added to the translation solution mixture, and this was incubated at 37° C. for one hour.

Detection by Mass Spectrometry: Part 1

MALDI-TOF MS was used for mass spectrometric analyses of the peptides ribosomally synthesized in the cell-free translation system. Specifically, a solution was prepared by adding 1 µM template mRNA (R-1) and Ala, Phe, Gly, Lys, Met, Pro, Arg, Ser, and Val as each amino acid (each at a final concentration of 250 µM) to the above-described cell-free translation system, nine types of the prepared 10 µM aminoacylated tRNAs (AAtR-1, AAtR-2, AAtR-3, AAtR-4, AAtR-5, AAtR-6, AAtR-7, AAtR-8, and AAtR-9) were respectively added, and incubated at 37° C. for 60 minutes. For the translation system using Acbz-protected aminoacylated tRNAs (AAtR-4, AAtR-5, and AAtR-6), tris(2-carboxyethyl)phosphine (TCEP) (reducing agent; at a final concentration of 10 mM) was added as the deprotecting reagent, and for the system using F-Pnaz-protected aminoacylated tRNAs (AAtR-7, AAtR-8, and AAtR-9), penicillin G acylase (PGA (=penicillin amidohydrolase); final concentration of 1 µM; SIGMA) was added as the deprotecting reagent. The obtained translation reaction products were purified with SPE C-TIP (Nikkyo Technos) and analyzed by MALDI-TOF MS. The translated products were identified by measuring MALDI-TOF MS spectra using α-cyano-4-hydroxycinnamic acid as the matrix.

Figures 1, 2:
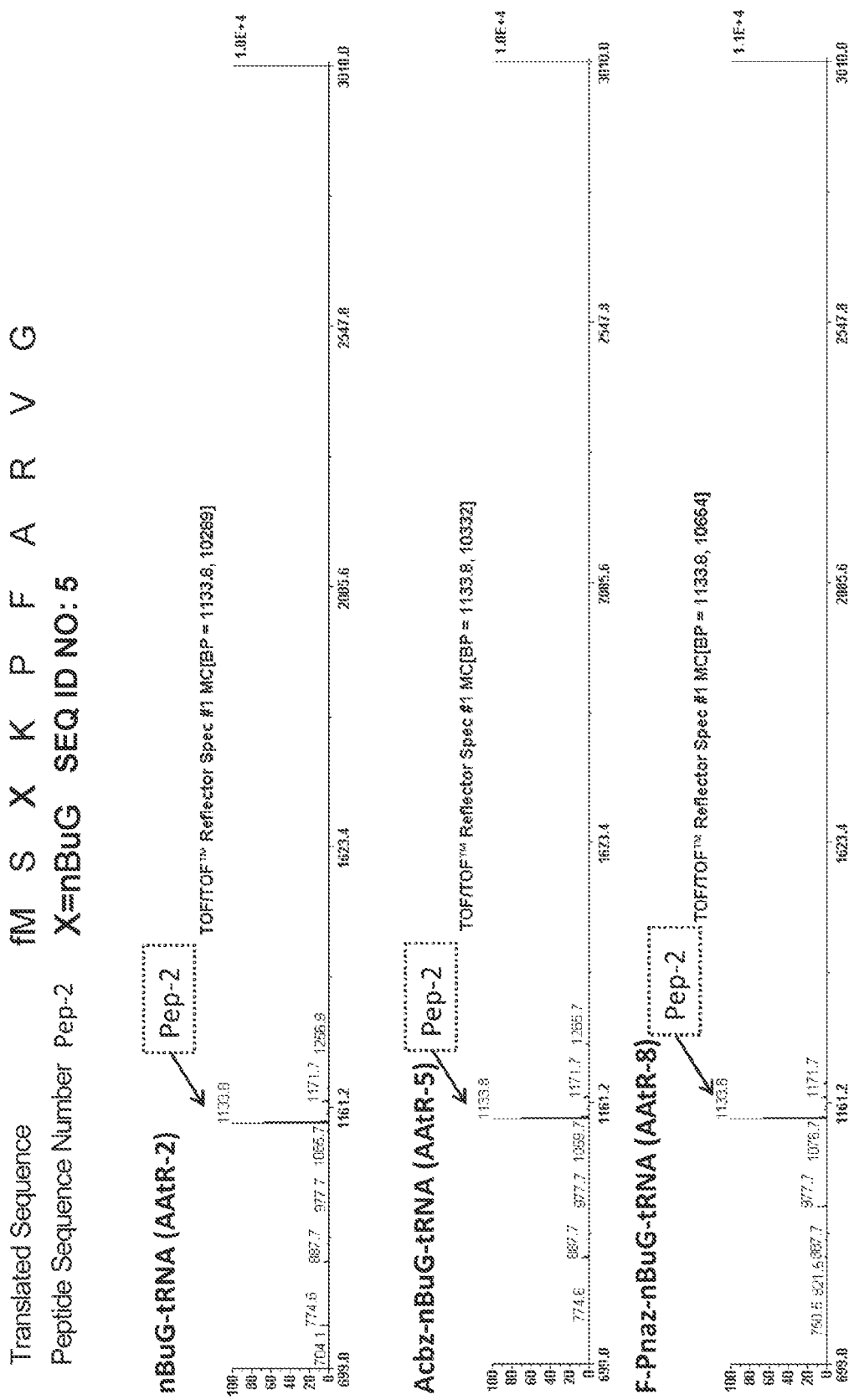
Figures 1, 2, 3:
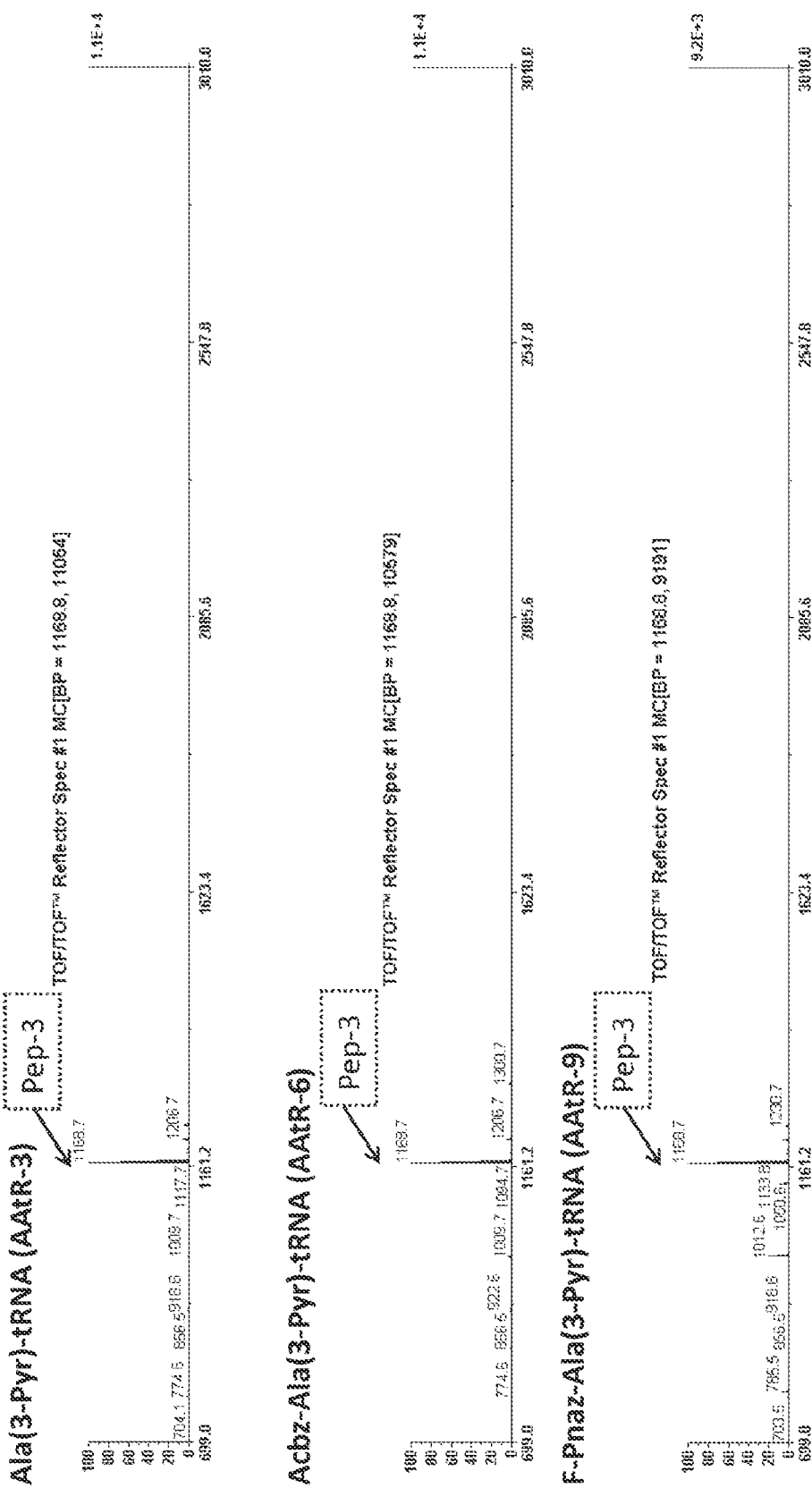

As a result, the products of interest shown in Table 2 were confirmed to be translated as the major products for all of the translated products (AAtR-4, AAtR-5, and AAtR-6) obtained by deprotecting the Acbz-protected aminoacylated tRNAs in the translation system using TCEP, and the translated products (AAtR-7, AAtR-8, and AAtR-9) obtained by deprotecting the F-Pnaz-protected aminoacylated tRNAs in the translation system using PGA (FIGS. 1-1, 1-2, and 1-3).

Detection by Mass Spectrometry: Part 2

MALDI-TOF MS was used for mass spectrometric analyses of the peptides ribosomally synthesized in the cell-free translation system. Specifically, a solution was prepared by adding 1 µM template mRNA (R-1) and Ala, Phe, Gly, Lys, Met, Pro, Arg, Ser, and Val as each amino acid (each at a final concentration of 250 µM) to the above-described cell-free translation system, eight types of the prepared 10 µM aminoacylated tRNAs (AAtR-10 to AAtR-13 and AAtR-16 to AAtR-19) were respectively added, and incubated at 37° C. for 60 minutes. To the F-Pnaz-protected aminoacylated tRNAs (AAtR-16 to AAtR-19), PGA (final concentration of 1 µM, SIGMA) was added as the deprotecting reagent. The obtained translation reaction products were purified with SPE C-TIP (Nikkyo Technos) and analyzed by MALDI-TOF MS. The translated products were identified by measuring MALDI-TOF MS spectra using α-cyano-4-hydroxycinnamic acid as the matrix.

As a result, when translated products were obtained by deprotecting the F-Pnaz-protected aminoacylated tRNAs in the translation system using PGA, the translation was confirmed to give the products of interest shown in Table 2 as the major products, in a similar manner to conventional methods (FIGS. 1-4, 1-5, 1-6, and 1-7).

Detection by Mass Spectrometry: Part 3

MALDI-TOF MS was used for mass spectrometric analyses of the peptides ribosomally synthesized in the cell-free translation system. Specifically, a solution was prepared by adding 1 μM template mRNA (R-1) and Ala, Phe, Gly, Lys, Met, Pro, Arg, Ser, and Val as each amino acid (each at a final concentration of 250 μM) to the above-described cell-free translation system, two types of the prepared 10 μM aminoacylated tRNAs (AAtR-14 and AAtR-20) were respectively added, and incubated at 37° C. for 60 minutes. For the Etez-protected aminoacylated tRNA (AAtR-20), CHIRAZYME L-2 CB (lipase; final concentration of 1 mg/mL; Roche Diagnostics) was added as the deprotecting reagent. The obtained translation reaction products were purified with SPE C-TIP (Nikkyo Technos) and analyzed by MALDI-TOF MS. The translated products were identified by measuring MALDI-TOF MS spectra using α-cyano-4-hydroxycinnamic acid as the matrix.

As a result, when translated products were obtained by deprotecting the Etez-protected aminoacylated tRNA in the translation system using lipase, the translation was confirmed to give the product of interest shown in Table 2 as the major product, in a similar manner to conventional methods (FIG. 1-8).

Detection by Mass Spectrometry: Part 4

MALDI-TOF MS was used for mass spectrometric analyses of the peptides ribosomally synthesized in the cell-free translation system. Specifically, a solution was prepared by adding 1 μM template mRNA (R-1) and Ala, Phe, Gly, Lys, Met, Pro, Leu, Ser, and Val as each amino acid (each at a final concentration of 250 μM) to the above-described cell-free translation system, two types of the prepared 10 μM aminoacylated tRNAs (AAtR-15 and AAtR-21) were respectively added, and incubated at 37° C. for 60 minutes. For the Leuz-protected aminoacylated tRNA (AAtR-21), Aminopeptidase (leucine aminopeptidase; final concentration of 1 mg/mL; SIGMA) was added as the deprotecting reagent. The obtained translation reaction products were purified with SPE C-TIP (Nikkyo Technos) and analyzed by MALDI-TOF MS. The translated products were identified by measuring MALDI-TOF MS spectra using α-cyano-4-hydroxycinnamic acid as the matrix.

As a result, when translated products were obtained by deprotecting the Leuz-protected aminoacylated tRNA in the translation system using leucine aminopeptidase, the translation was confirmed to give the product of interest shown in Table 2 as the major product, in a similar manner to conventional methods (FIG. 1-9).

mRNA (Sequence Number R-1) to be used as a template was synthesized from the template DNA (Sequence Number D-1) by in vitro transcription reaction using RiboMAX Large Scale RNA production System T7 (Promega, P1300) and purified with RNeasy Mini kit (Qiagen).

Template DNA Sequence Number D-1
(SEQ ID NO: 3)
DNA sequence:
GGCGTAATACGACTCACTATAGGGTTAACTTTAAGAAGGAGATATACAT
ATGAGTCTAAAGCCGTTTGCTCGTGTTGGTTAAGCTTCG Template mRNA Sequence Number R-1
(SEQ ID NO: 4)
RNA sequence:
GGGUUAACUUUAAGAAGGAGAUAUACAUAUGAGUCUAAAGCCGUUUGCU
CGUGUUGGUUAAGCUUCG Peptide sequence
(SEQ ID NO: 5)
fMetSer[Xaa]LysProPheAlaArgValGly (SEQ ID NO: 11)
fMetSerLeuLysProPheAla[Xaa]ValGly

TABLE 2

| Aminoacyl-tRNAGlu (Compound number) | Peptide sequence number (Sequence ID No) | Peptide sequence | MS theoretical value | MS measured value [M + H]+ |
|---|---|---|---|---|
| Aze(2) (AAtR-1, AAtR-4, AAtR-7) | Pep-1 (SEQ ID No: 5) | fMetSerAze(2)LysProPheAlaArgValGly | 1102.6 | 1103.5 |
| nBuG (AAtR-2, AAtR-5, AAtR-8) | Pep-2 (SEQ ID No: 5) | fMetSernBuGLysProPheAlaArgValGly | 1132.6 | 1133.5 |
| Ala(3-Pyr) AAtR-3, AAtR-6, AAtR-9) | Pep-3 (SEQ ID No: 5) | fMetSerAla(3-Pyr)LysProPheAlaArgValGly | 1167.6 | 1168.5 |
| Ala (AAtR-10, AAtR-16) | Pep-7 (SEQ ID No: 5) | fMetSerAlaLysProPheAlaArgValGly | 1091.6 | 1091.8 |
| AIB (AAtR-11, AAtR-17) | Pep-8 (SEQ ID No: 5) | fMetSerAIBLysProPheAlaArgValGly | 1105.6 | 1105.7 |
| β-Ala (AAtR-12, AAtR-18) | Pep-9 (SEQ ID No: 5) | fMetSerβ-AlaLysProPheAlaArgValGly | 1091.6 | 1091.7 |

TABLE 2-continued

| Aminoacyl-tRNAGlu (Compound number) | Peptide sequence number (Sequence ID No) | Peptide sequence | MS theoretical value | MS measured value [M + H]+ |
|---|---|---|---|---|
| D-Ala (AAtR-13, AAtR-19) | Pep-10 (SEQ ID No: 5) | fMetSerD-AlaLysProPheAlaArgValGly | 1091.6 | 1091.7 |
| Hph (AAtR-14, AAtR-20) | Pep-11 (SEQ ID No: 5) | fMetSerHphLysProPheAlaArgValGly | 1181.6 | 1181.8 |
| Hph (AAtR-15, AAtR-21) | Pep-12 (SEQ ID No: 11) | fMetSerLeuLysProPheAlaHphValGly | 1138.6 | 1138.8 |

Detection by Electrophoresis: Part 1

For detection of peptides into which a cysteine or a cysteine analog was ribosomally introduced at the N terminus, radioisotope-labeled aspartic acid was used to perform peptide translation experiments. Specifically, a solution was prepared by adding 1 μM template mRNA (R-1D) and Ala, Phe, Gly, Lys, Met, Pro, Arg, Ser, and Val as each amino acid (each at a final concentration of 250 μM), and $^{14}$C-aspartic acid (final concentration of 37 μM, Moravek Biochemicals, MC139) to the above-described cell-free translation system, nine types of the prepared 10 μM aminoacylated tRNAs (AAtR-1, AAtR-2, AAtR-3, AAtR-4, AAtR-5, AAtR-6, AAtR-7, AAtR-8, and AAtR-9) were respectively added, and this was left to stand at 37° C. for one hour. For the translation system using Acbz-protected aminoacylated tRNAs (AAtR-4, AAtR-5, and AAtR-6), TCEP (final concentration of 10 mM) was added as the deprotecting reagent, and for the translation system using F-Pnaz-protected aminoacylated tRNAs (AAtR-7, AAtR-8, and AAtR-9), PGA (final concentration of 1 μM, SIGMA) was added as the deprotecting reagent.

After an equivalent amount of 2× sample buffer (TEFCO, cat No. 06-323) was added to the obtained translation reaction solution, this was heated at 95° C. for three minutes, and then subjected to electrophoresis (16% Peptide-PAGE mini, TEFCO, TB-162). The electrophoresed gel was dried using a Clear Dry Quick Dry Starter KIT (TEFCO, 03-278), light-exposed for 24 hours to an Imaging Plate (GE Healthcare, 28-9564-75), subjected to detection using a bioanalyzer system (Typhoon FLA 7000, GE Healthcare), and analyzed using ImageQuantTL (GE Healthcare).

As a result, the products of interest shown in Table 3 were confirmed to be synthesized with higher translation efficiency for all of the translated products (AAtR-4, AAtR-5, and AAtR-6) obtained by deprotecting the Acbz-protected aminoacylated tRNAs in the translation system using TCEP, and the translated products (AAtR-7, AAtR-8, and AAtR-9) obtained by deprotecting the F-Pnaz-protected aminoacylated tRNAs to in the translation system using PGA, in comparison to the cases when aminoacylated tRNAs (AAtR-1, AAtR-2, and AAtR-3) prepared outside the translation system were respectively used (FIG. 2-1).

Detection by Electrophoresis: Part 2

For detection of peptides into which a cysteine or a cysteine analog was ribosomally introduced at the N terminus, radioisotope-labeled aspartic acid was used to perform peptide translation experiments. Specifically, a solution was prepared by adding 1 μL template mRNA (R-1D) and Ala, Phe, Gly, Lys, Met, Pro, Arg, Ser, and Val as each amino acid (each at a final concentration of 250 μM), and $^{14}$C-aspartic acid (final concentration of 37 μM, Moravek Biochemicals, MC139) to the above-described cell-free translation system, eight types of the prepared 10 μM aminoacylated tRNAs (AAtR-10 to AAtR-13, and AAtR-16 to AAtR-19) were respectively added, and this was left to stand at 37° C. for one hour. For the F-Pnaz-protected aminoacylated tRNAs (AAtR-16 to AAtR-19), PGA (final concentration of 1 μM, SIGMA) was added as the deprotecting reagent.

After an equivalent amount of 2× sample buffer (TEFCO, cat No. 06-323) was added to the obtained translation reaction solution, this was heated at 95° C. for three minutes, and then subjected to electrophoresis (16% Peptide-PAGE mini, TEFCO, TB-162). The electrophoresed gel was dried using a Clear Dry Quick Dry Starter KIT (TEFCO, 03-278), light-exposed for 24 hours to an Imaging Plate (GE Healthcare, 28-9564-75), subjected to detection using a bioanalyzer system (Typhoon FLA 7000, GE Healthcare), and analyzed using ImageQuantTL (GE Healthcare).

As a result, the products of interest shown in Table 3 were confirmed to be synthesized with higher translation efficiency for the translated products (AAtR-16 to AAtR-19) obtained by deprotecting the F-Pnaz-protected aminoacylated tRNAs in the translation system using PGA, in comparison to the cases when aminoacylated tRNAs (AAtR-10 to AAtR-13) prepared outside the translation system were respectively used (FIG. 2-2).

Detection by Electrophoresis: Part 3

For detection of peptides into which a cysteine or a cysteine analog was ribosomally introduced at the N terminus, radioisotope-labeled aspartic acid was used to perform peptide translation experiments. Specifically, a solution was prepared by adding 1 μM template mRNA (R-1D) and Ala, Phe, Gly, Lys, Met, Pro, Arg, Ser, and Val as each amino acid (each at a final concentration of 250 μM), and $^{14}$C-aspartic acid (final concentration of 37 μM, Moravek Biochemicals, MC139) to the above-described cell-free translation system, two types of the prepared 10 μM aminoacylated tRNAs (AAtR-14 and AAtR-20) were respectively added, and this was left to stand at 37° C. for one hour. For the Etez-protected aminoacylated tRNA (AAtR-20), CHIRAZYME L-2 CB (lipase; final concentration of 1 mg/mL, Roche Diagnostics) was added as the deprotecting reagent.

After an equivalent amount of 2× sample buffer (TEFCO, cat No. 06-323) was added to the obtained translation reaction solution, this was heated at 95° C. for three minutes, and then subjected to electrophoresis (16% Peptide-PAGE mini, TEFCO, TB-162). The electrophoresed gel was dried using a Clear Dry Quick Dry Starter KIT (TEFCO, 03-278), light-exposed for 24 hours to an Imaging Plate (GE Healthcare, 28-9564-75), subjected to detection using a bioanalyzer system (Typhoon FLA 7000, GE Healthcare), and analyzed using ImageQuantTL (GE Healthcare).

As a result, the product of interest shown in Table 3 was confirmed to be synthesized with higher translation efficiency for the translated product (AAtR-20) obtained by deprotecting the Etez-protected aminoacylated tRNA in the translation system using lipase, in comparison to the case when aminoacylated tRNA (AAtR-14) prepared outside the translation system was used (FIG. 2-3).

Detection by Electrophoresis: Part 4

For detection of peptides into which a cysteine or a cysteine analog was ribosomally introduced at the N terminus, radioisotope-labeled aspartic acid was used to perform peptide translation experiments. Specifically, a solution was prepared by adding 1 µM template mRNA (R-1D) and Ala, Phe, Gly, Lys, Met, Pro, Leu, Ser, and Val as each amino acid (each at a final concentration of 250 µM), and $^{14}$C-aspartic acid (final concentration of 37 µM, Moravek Biochemicals, MC139) to the above-described cell-free translation system, two types of the prepared 10 µM aminoacylated tRNAs (AAtR-15 and AAtR-21) were respectively added, and this was left to stand at 37° C. for one hour. For the Leuz-protected aminoacylated tRNA (AAtR-21), Aminopeptidase (final concentration of 1 mg/mL, SIGMA) was added as the deprotecting reagent.

After an equivalent amount of 2× sample buffer (TEFCO, cat No. 06-323) was added to the obtained translation reaction solution, this was heated at 95° C. for three minutes, and then subjected to electrophoresis (16% Peptide-PAGE mini, TEFCO, TB-162). The electrophoresed gel was dried using a Clear Dry Quick Dry Starter KIT (TEFCO, 03-278), light-exposed for 24 hours to an Imaging Plate (GE Healthcare, 28-9564-75), subjected to detection using a bioanalyzer system (Typhoon FLA 7000, GE Healthcare), and analyzed using ImageQuantTL (GE Healthcare).

Figures 1, 2:
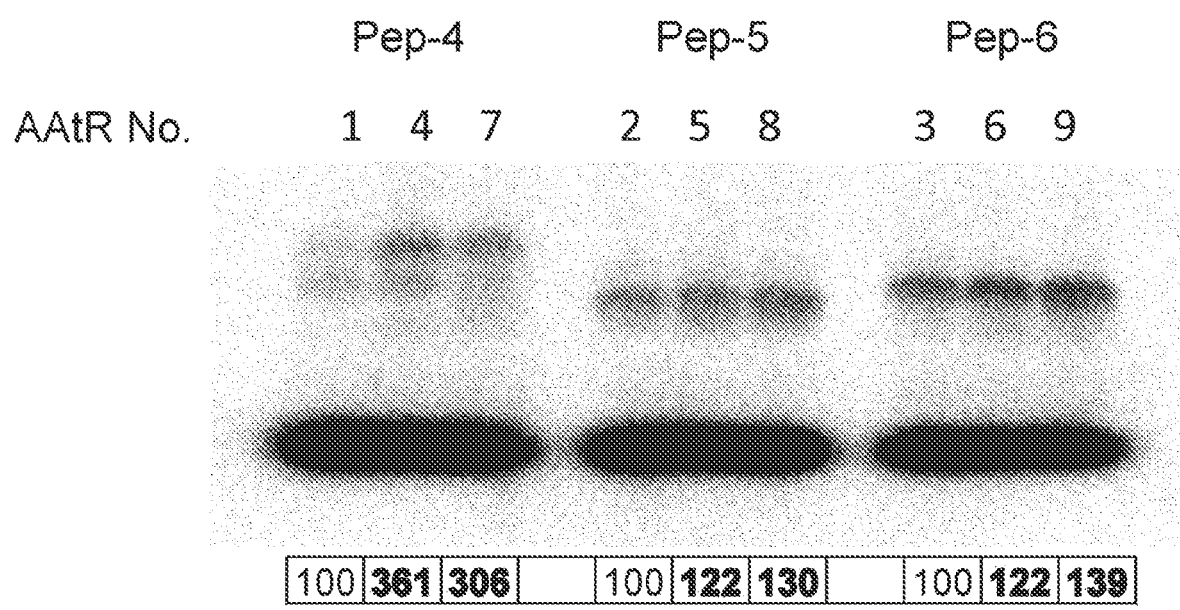
Figure 2:
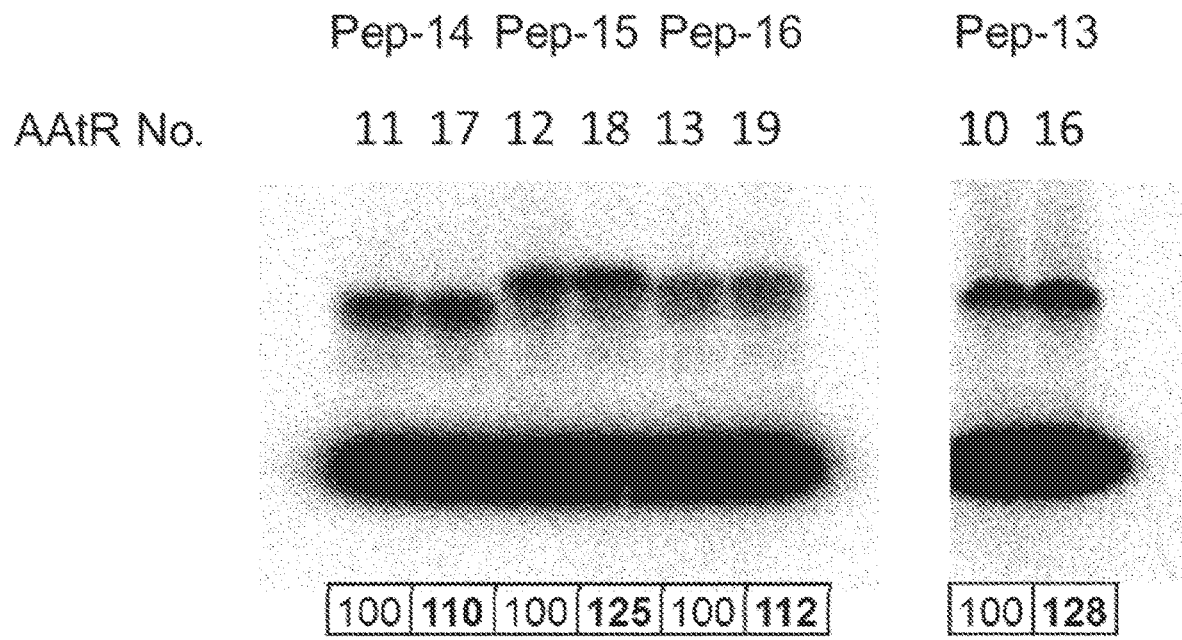
Figures 2, 3:
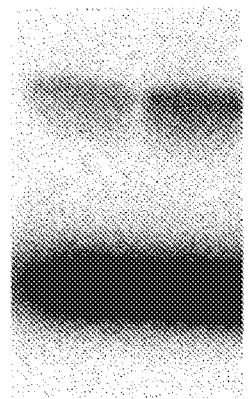
Figures 2, 3, 4:
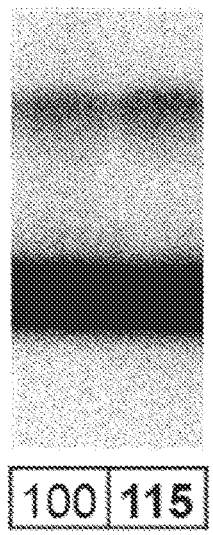

As a result, the product of interest shown in Table 3 was confirmed to be synthesized with higher translation efficiency for the translated product (AAtR-21) obtained by deprotecting the Leuz-protected aminoacylated tRNA in the translation system using leucine aminopeptidase, in comparison to the case when aminoacylated tRNA (AAtR-15) prepared outside the translation system was used (FIG. 2-4).

mRNA (Sequence Number R-1D) to be used as a template was synthesized from the template DNA (Sequence Number D-1D) by in vitro transcription reaction using RiboMAX Large Scale RNA production System T7 (Promega, P1300) and purified with RNeasy Mini kit (Qiagen).

```
Template DNA Sequence Number D-1D
                                        (SEQ ID NO: 6)
DNA sequence:
GGCGTAATACGACTCACTATAGGGTTAACTTTAAGAAGGAGATATACAT
ATGAGTCTAAAGCCGTTTGCTCGTGTTGGTGACGACGACTAAGCTTCG Template mRNA Sequence Number R-1D
                                        (SEQ ID NO: 7)
RNA sequence:
GGGUUAACUUUAAGAAGGAGAUAUACAUAUGAGUCUAAAGCCGUUUGCU
CGUGUUGGUGACGACGACUAAGCUUCG Peptide sequence
                                        (SEQ ID NO: 8)
fMetSer[Xaa]LysProPheAlaArgValGlyAspAspAsp (SEQ ID NO: 12)
fMetSerLeuLysProPheAla[Xaa]ValGlyAspAspAsp
```

TABLE 3

| Aminoacyl-tRNAGlu (Compound number) | Peptide sequence number (Sequence ID No) | Peptide sequence |
|---|---|---|
| Aze(2) (AAtR-1, AAtR-4, AAtR-7) | Pep-4 (SEQ ID NO: 8) | fMetSerAze(2)LysProPheAlaArgValGlyAspAspAsp |
| nBuG (AAtR-2, AAtR-5, AAtR-8) | Pep-5 (SEQ ID NO: 8) | fMetSernBuGLysProPheAlaArgValGlyAspAspAsp |
| Ala(3-Pyr) (AAtR-3, AAtR-6, AAtR-9) | Pep-6 (SEQ ID NO: 8) | fMetSerAla(3-Pyr)LysProPheAlaArgValGlyAspAspAsp |
| Ala (AAtR-10, AAtR-16) | Pep-13 (SEQ ID NO: 8) | fMetSerAlaLysProPheAlaArgValGlyAspAspAsp |
| AIB (AAtR-11, AAtR-17) | Pep-14 (SEQ ID NO: 8) | fMetSerAIBLysProPheAlaArgValGlyAspAspAsp |
| β-Ala (AAtR-12, AAtR-18) | Pep-15 (SEQ ID NO: 8) | fMetSerβ-AlaLysProPheAlaArgValGlyAspAspAsp |
| D-Ala (AAtR-13, AAtR-19) | Pep-16 (SEQ ID NO: 8) | fMetSerD-AlaLysProPheAlaArgValGlyAspAspAsp |

TABLE 3-continued

| Aminoacyl-tRNAGlu (Compound number) | Peptide sequence number (Sequence ID No) | Peptide sequence |
|---|---|---|
| Hph (AAtR-14, AAtR-20) | Pep-17 (SEQ ID NO: 8) | fMetSerHphLysProPheAlaArgValGlyAspAspAsp |
| Hph (AAtR-15, AAtR-21) | Pep-18 (SEQ ID NO: 12) | fMetSerLeuLysProPheAlaHphValGlyAspAspAsp |

INDUSTRIAL APPLICABILITY

The present invention has provided techniques for efficiently synthesizing peptides comprising one or more amino acids. Methods of the present invention comprise a step of deprotecting a protecting group of an amino acid linked to a tRNA and a step of translating peptide from a template nucleic acid, and these steps are performed in parallel in a cell-free translation system. The present invention is useful in screening and synthesizing middle-molecular-weight compounds such as amino acid-containing cyclic peptides, which are expected as candidate substances for pharmaceuticals.

The invention claimed is:

1. A method of synthesizing a peptide, wherein the method comprises a step of deprotecting a protecting group of an amino acid having the protecting group on the amino group that forms a peptide bond and a translation step, in a cell-free translation system that comprises tRNA to which the amino acid having the protecting group is linked, wherein the deprotecting and translation steps are performed in parallel, wherein the protecting group is

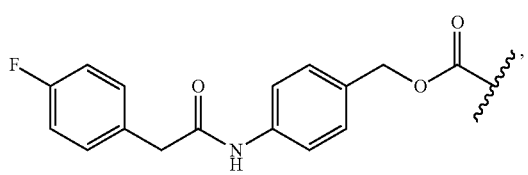 [SMILES: *C(=O)OCc1ccc(NC(=O)Cc2ccc(F)cc2)cc1 ; "."]

and wherein the protecting group is deprotected by a penicillin amidohydrolase.

2. The method of claim 1, wherein the amino acid is an amino acid analog.

3. The method of claim 2, wherein the amino acid analog is one or more types of translatable amino acid analogs selected from the group consisting of cyclic amino acid-containing N-alkyl amino acids, aliphatic amino acids, aromatic amino acids, β-amino acids, D-amino acids, and α,α-dialkylamino acids.

4. The method of claim 3, wherein the amino acid analog is represented by the following general formula (VI) or (VII):

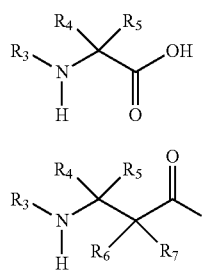

wherein $R_3$, $R_4$, and $R_5$ each independently are a hydrogen atom, an alkyl, an alkenyl, an alkynyl, an aryl, a heteroaryl, an aralkyl, or a cycloalkyl group, each of which are substituted or unsubstituted; or $R_3$ and $R_4$, or $R_3$ and $R_5$, form a ring together with an atom to which they are bonded; and $R_6$ and $R_7$ each independently are a hydrogen atom or a methyl.

5. The method of claim 4, wherein the alkyl, alkenyl, alkynyl, aryl, heteroaryl, aralkyl, or cycloalkyl group is unsubstituted.

6. The method of claim 4, wherein in formula (VI), $R_4$ or $R_5$ is

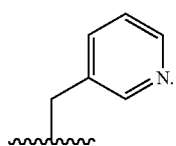

7. The method of claim 1, further comprising a post-translational modification, wherein the protecting group is deprotected by a reaction condition orthogonal to the reaction condition used for the post-translational modification.

8. The method of claim 7, wherein the translation step comprises using a protecting group in an initiation suppression (iSP) method, and wherein the protecting group of claim 7 is orthogonal to the protecting group used in the initiation suppression (iSP) method.

9. The method of claim 6, wherein the amino acid having the protecting group is represented by the following general formula (VIII),

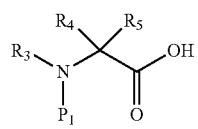

wherein $R_3$, $R_4$, and $R_5$ each independently are a hydrogen atom, an alkyl, an alkenyl, an alkynyl, an aryl, a heteroaryl, an aralkyl, or a cycloalkyl group, each of which is substituted or unsubstituted; or $R_3$ and $R_4$, or $R_3$ and $R_5$, form a ring together with an atom to which they are bonded; and $P_1$ is the protecting group represented by a group

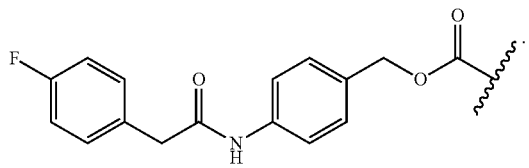

10. The method of claim 9, further comprising a post-translational modification, wherein the protecting group $P_1$ is deprotected by a reaction condition orthogonal to the reaction condition used for the post-translational modification.

11. The method of claim 10, wherein the translation step comprises using a protecting group in an initiation suppression (iSP) method, and wherein the protecting group $P_1$ is orthogonal to the protecting group used in the initiation suppression (iSP) method.

12. The method of claim 9, wherein the tRNA to which the amino acid having the protecting group is linked is formed by linking the compound of the general formula (VIII) with a tRNA.

13. The method of claim 9, wherein the tRNA to which the amino acid having the protecting group is linked is formed by linking a compound of the following general formula (X) with a tRNA:

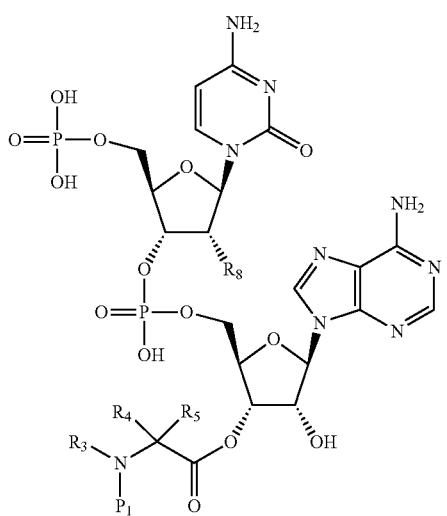 (X)

wherein each of $R_3$ to $R_5$ and $P_1$ is as defined in claim 9, and $R_8$ is a hydrogen atom or a hydroxyl.

14. The method of claim 9, wherein the amino acid is an amino acid analog.

15. The method of claim 14, wherein the amino acid analog is one or more types of translatable amino acid analogs selected from the group consisting of cyclic amino acid-containing N-alkyl amino acids, aliphatic amino acids, aromatic amino acids, D-amino acids, and α,α-dialkylamino acids.

16. The method of claim 9, wherein the alkyl, alkenyl, alkynyl, aryl, heteroaryl, aralkyl, or cycloalkyl group is unsubstituted.

17. The method of claim 9, wherein in formula (VIII), $R_4$ or $R_5$ is

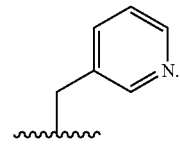 [SMILES: *Cc1cccnc1]

* * * * *

SEQUENCE LISTING

```
<160> NUMBER OF SEQ ID NOS: 12

<210> SEQ ID NO 1
<211> LENGTH: 74
<212> TYPE: RNA
<213> ORGANISM: Artificial sequence
<220> FEATURE:
<223> OTHER INFORMATION: tRNAGluUAG(-CA)

<400> SEQUENCE: 1 gucccuucg ucuagaggcc caggacaccg cccuuagacg gcgguaacag ggguucgaau     60
ccccuagggg acgc                                                     74

<210> SEQ ID NO 2
<211> LENGTH: 76
<212> TYPE: RNA
<213> ORGANISM: Artificial sequence
<220> FEATURE:
<223> OTHER INFORMATION: tRNAGluUAG

<400> SEQUENCE: 2 gucccuucg ucuagaggcc caggacaccg cccuuagacg gcgguaacag ggguucgaau     60
ccccuagggg acgcca                                                   76

<210> SEQ ID NO 3
<211> LENGTH: 88
<212> TYPE: DNA
<213> ORGANISM: Artificial sequence
<220> FEATURE:
<223> OTHER INFORMATION: template DNA D-1

<400> SEQUENCE: 3
ggcgtaatac gactcactat agggttaact ttaagaagga gatatacata tgagtctaaa   60
gccgtttgct cgtgttggtt aagcttcg                                      88

<210> SEQ ID NO 4
<211> LENGTH: 67
<212> TYPE: RNA
<213> ORGANISM: Artificial sequence
<220> FEATURE:
<223> OTHER INFORMATION: template mRNA R-1
```

<400> SEQUENCE: 4
ggguuaacuu uaagaaggag auauacauau gagucuaaag ccguuugcuc guguuggu ua 60 agcuucg 67

<210> SEQ ID NO 5
<211> LENGTH: 10
<212> TYPE: PRT
<213> ORGANISM: Artificial sequence
<220> FEATURE:
<223> OTHER INFORMATION: Pep-1, Pep-2, Pep-3, Pep-7, Pep-8, Pep-9,
      Pep-10, Pep-11
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MISC_FEATURE
<222> LOCATION: (3)..(3)
<223> OTHER INFORMATION: Xaa = Aze(2), nBuG, Ala(3-Pyr), Ala, AIB,
      beta-Ala, D-Ala, or Hph

<400> SEQUENCE: 5

Met Ser Xaa Lys Pro Phe Ala Arg Val Gly
1               5                   10

<210> SEQ ID NO 6
<211> LENGTH: 97
<212> TYPE: DNA
<213> ORGANISM: Artificial sequence
<220> FEATURE:
<223> OTHER INFORMATION: template DNA D-1D

<400> SEQUENCE: 6
ggcgtaatac gactcactat agggttaact ttaagaagga gatatacata tgagtctaaa    60
gccgtttgct cgtgttggtg acgacgacta agcttcg                             97

<210> SEQ ID NO 7
<211> LENGTH: 76
<212> TYPE: RNA
<213> ORGANISM: Artificial sequence
<220> FEATURE:
<223> OTHER INFORMATION: template mRNA R-1D

<400> SEQUENCE: 7 gggu uaacuu uaagaaggag auauacauau gagucuaaag ccguuugcuc guguugguga   60
cgacgacuaa gcuucg                                                    76

<210> SEQ ID NO 8
<211> LENGTH: 13
<212> TYPE: PRT
<213> ORGANISM: Artificial sequence
<220> FEATURE:
<223> OTHER INFORMATION: Pep-4, Pep-5, Pep-6, Pep-13, Pep-14, Pep-15,
      Pep-16, Pep-17
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MISC_FEATURE
<222> LOCATION: (3)..(3)
<223> OTHER INFORMATION: Xaa = Aze(2), nBuG, Ala(3-Pyr), Ala, AIB,
      beta-Ala, D-Ala, or Hph

<400> SEQUENCE: 8

Met Ser Xaa Lys Pro Phe Ala Arg Val Gly Asp Asp Asp

```
<210> SEQ ID NO 9
<211> LENGTH: 74
<212> TYPE: RNA
<213> ORGANISM: Artificial Sequence
<220> FEATURE:
<223> OTHER INFORMATION: tRNAGluACG(-CA)

<400> SEQUENCE: 9
guccccuucg ucuagaggcc caggacaccg cccuacgacg gcgguaacag ggguucgaau    60
ccccuagggg acgc                                                     74

<210> SEQ ID NO 10
<211> LENGTH: 76
<212> TYPE: RNA
<213> ORGANISM: Artificial Sequence
<220> FEATURE:
<223> OTHER INFORMATION: tRNAGluACG

<400> SEQUENCE: 10
guccccuucg ucuagaggcc caggacaccg cccuacgacg gcgguaacag ggguucgaau    60
ccccuagggg acgcca                                                   76

<210> SEQ ID NO 11
<211> LENGTH: 10
<212> TYPE: PRT
<213> ORGANISM: Artificial Sequence
<220> FEATURE:
<223> OTHER INFORMATION: Pep-12
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MISC_FEATURE
<222> LOCATION: (8)..(8)
<223> OTHER INFORMATION: Xaa = Hph

<400> SEQUENCE: 11

Met Ser Leu Lys Pro Phe Ala Xaa Val Gly
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Pep-18
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MISC_FEATURE
<222> LOCATION: (8)..(8)
<223> OTHER INFORMATION: Xaa = Hph

<400> SEQUENCE: 12

Met Ser Leu Lys Pro Phe Ala Xaa Val Gly Asp Asp Asp
1               5                   10
```